US012752006B2

(12) United States Patent
Contrastano et al.

(10) Patent No.: US 12,752,006 B2
(45) Date of Patent: Oct. 6, 2026

(54) BCMA CHIMERIC ANTIGEN RECEPTORS

(71) Applicant: Regeneron Pharmaceuticals, Inc., Tarrytown, NY (US)

(72) Inventors: Shannon Grande Contrastano, Auburndale, MA (US); Emily G. Kuiper, Arlington, MA (US)

(73) Assignee: Regeneron Pharmaceuticals, Inc., Tarrytown, NY (US)

(*) Notice: Subject to any disclaimer, the term of this patent is extended or adjusted under 35 U.S.C. 154(b) by 661 days.

(21) Appl. No.: 18/023,232

(22) PCT Filed: Aug. 24, 2021

(86) PCT No.: PCT/US2021/047290

§ 371 (c)(1),
(2) Date: Feb. 24, 2023

(87) PCT Pub. No.: WO2022/046730

PCT Pub. Date: Mar. 3, 2022

(65) Prior Publication Data

US 2023/0310604 A1 Oct. 5, 2023

Related U.S. Application Data

(60) Provisional application No. 63/069,784, filed on Aug. 25, 2020.

(51) Int. Cl.

| | |
|---|---|
| ***A61K 40/31*** | (2025.01) |
| ***A61K 40/11*** | (2025.01) |
| ***A61K 40/42*** | (2025.01) |
| ***A61P 35/00*** | (2006.01) |
| ***C07K 16/28*** | (2006.01) |
| ***C12N 15/86*** | (2006.01) |

(52) U.S. Cl.

CPC .............. *A61K 40/31* (2025.01); *A61K 40/11* (2025.01); *A61K 40/4215* (2025.01); *A61P 35/00* (2018.01); *C07K 16/2878* (2013.01); *C12N 15/86* (2013.01); *A61K 2239/22* (2023.05); *A61K 2239/28* (2023.05); *A61K 2239/48* (2023.05); *C07K 2317/622* (2013.01); *C12N 2740/15043* (2013.01)

(58) Field of Classification Search

CPC .... A61K 40/31; A61K 40/11; A61K 40/4215; A61K 2239/22; A61K 2239/28; A61K 2239/48; A61K 2039/5156; A61K 35/17; A61K 2039/5158; A61P 35/00; C07K 16/2878; C07K 2317/622; C07K 14/7051; C07K 2317/56; C07K 2317/565; C07K 2317/73; C07K 2319/03; C07K 14/70517; C07K 14/70521; C07K 2319/02; C12N 15/86; C12N 2740/15043; C12N 2510/00; C12N 2830/50

See application file for complete search history.

(56) References Cited

FOREIGN PATENT DOCUMENTS

| | | | |
|---|---|---|---|
| JP | 2017-522882 | A | 8/2017 |
| WO | 2016/014789 | A2 | 1/2016 |
| WO | 2018/026819 | A2 | 2/2018 |
| WO | 2019/241426 | A1 | 12/2019 |
| WO | 2022/261346 | A2 | 12/2022 |

OTHER PUBLICATIONS

African Journal of Biotechnology, 10(79):18294-18302, 2011 (Year: 2011).*
Annu. Rev. Biophys. Biophys. Chem., 16: 139-159, 1987 (Year: 1987).*
J. Immunol. Methods, 251(1-2): 137-149, 2001 (Year: 2001).*
European Office Action for Application No. 21862543.2, dated Sep. 4, 2024, 17 pages.
Written Opinion for Application No. PCT/US2021/047290, dated Nov. 12, 2021, 3 pages.

* cited by examiner

*Primary Examiner* — Nelson B Moseley, II
*Assistant Examiner* — Josephine K Darpolor
(74) *Attorney, Agent, or Firm* — McCarter & English, LLP; Marcie B. Clarke; Dylan M. Blumenthal

(57) ABSTRACT

The disclosure provides improved compositions for adoptive T cell therapies for B cell related conditions.

24 Claims, 11 Drawing Sheets

Specification includes a Sequence Listing.

BCMA CHIMERIC ANTIGEN RECEPTORS

CROSS REFERENCE TO RELATED APPLICATIONS

This application is a U.S. national stage application filed under 35 U.S.C. § 371 of International Patent Application No. PCT/US2021/047290, accorded an international filing date of Aug. 24, 2021, which claims the benefit under 35 U.S.C. § 119(e) of U.S. Provisional Application No. 63/069,784, filed Aug. 25, 2020, each of which is incorporated by reference herein in its entirety.

STATEMENT REGARDING SEQUENCE LISTING

The Sequence Listing associated with this application is provided in text format in lieu of a paper copy and is hereby incorporated by reference into the specification. The name of the text file containing the Sequence Listing is REPLACEMENT_01/31/2023.txt. The text file is 98,807 bytes, created on Jan. 31, 2023, and is being submitted electronically via EFS-Web.

BACKGROUND

Technical Field

The present invention generally relates to improved compositions and methods for treating B cell related conditions. More particularly, the invention relates to improved chimeric antigen receptors (CARs) comprising human anti-B cell maturation antigen (anti-BCMA) antibodies or antigen binding fragments thereof, immune effector cells genetically modified to express these CARs, and use of these compositions to effectively treat B cell related conditions.

Description of the Related Art

Several significant diseases involve B lymphocytes, i.e., B cells. Malignant transformation of B cells leads to cancers including, but not limited to lymphomas, e.g., multiple myeloma and non-Hodgkins' lymphoma. Abnormal B cell physiology can also lead to development of autoimmune diseases including, but not limited to systemic lupus erythematosus (SLE).

The large majority of patients having B cell malignancies, including non-Hodgkin's lymphoma (NHL) and multiple myeloma (MM), are significant contributors to cancer mortality. The response of B cell malignancies to various forms of treatment is mixed. Traditional methods of treating B cell malignancies, including chemotherapy, radiotherapy, and therapeutic antibodies have provided limited success.

More recently, attempts to treat B cell malignancies through the use of therapeutic antibodies or chimeric antigen receptors (CARs) which target BCMA have been met with promising but limited success. Indeed, not all patients are cured or experience complete remission when treated with these therapies. One difficulty in developing such treatments is that the therapeutic efficacy of a given antigen binding domain used in a therapeutic antibody or CAR is unpredictable. For example, if the antigen binding domain binds too strongly, the CAR T cells induce massive cytokine release resulting in a potentially fatal immune reaction deemed a "cytokine storm," and if the antigen binding domain binds too weakly, the CAR T cells do not display sufficient therapeutic efficacy in clearing cancer cells. Moreover, some CARs display prohibitive levels of antigen-independent signaling which causes T cell dysfunction (sometimes called T cell exhaustion), thus limiting efficacy.

Accordingly, there remains a substantial need to identify improved anti-BCMA CARs having improved efficacy while limiting antigen-independent signaling and T cell dysfunction.

BRIEF SUMMARY

The disclosure generally provides improved vectors, antibodies, antibody fragments, and chimeric antigen receptors (CARs) for generating T cell therapies and methods of using the same. Particularly, the disclosure provides improved anti-BCMA antibodies, antibody fragments, and chimeric antigen receptors (CARs). More particularly, the disclosure provides improved human anti-BCMA antibodies, antibody fragments, or CARs.

In one aspect of the disclosure, a chimeric antigen receptor (CAR) is provided, comprising: a) an extracellular domain comprising an anti-BCMA (B cell maturation antigen) antibody or antigen binding fragment thereof that binds one or more epitopes of a human BCMA polypeptide comprising variable light chain CDRL1, CDRL2, and CDRL3 regions within a variable light chain amino acid sequence as set forth in SEQ ID NOs: 7, 15, 23, 31, 39, or 47, and variable heavy chain CDRH1, CDRH2, and CDRH3 regions within a variable heavy chain amino acid sequence as set forth in SEQ ID NOs: 8, 16, 24, 32, 40, or 48; b) a transmembrane domain; c) one or more intracellular co-stimulatory signaling domains; and d) a primary signaling domain.

In in another aspect, a chimeric antigen receptor (CAR) is provided, comprising: a) an extracellular domain comprising an anti-BCMA (B cell maturation antigen) antibody or antigen binding fragment thereof that binds one or more epitopes of a human BCMA polypeptide comprising: variable light chain CDRL1, CDRL2, and CDRL3 sequences set forth in SEQ ID NOs: 1-3, 9-11, 17-19, 25-27, 33-35, or 41-43 and variable heavy chain CDRH1, CDRH2, and CDRH3 sequences set forth in SEQ ID NOs: 4-6, 12-14, 20-22, 28-30, 36-38, or 44-46; b) a transmembrane domain; c) one or more intracellular co-stimulatory signaling domains; and d) a primary signaling domain.

In various embodiments, the variable light chain amino acid sequence is set forth in SEQ ID NO: 7, and/or the variable heavy chain amino acid sequence is set forth in SEQ ID NO: 8. In various embodiments, the variable light chain amino acid sequence is set forth in SEQ ID NO: 15, and/or the variable heavy chain amino acid sequence is set forth in SEQ ID NO: 16. In various embodiments, the variable light chain amino acid sequence is set forth in SEQ ID NO: 23, and/or the variable heavy chain amino acid sequence is set forth in SEQ ID NO: 24. In various embodiments, the variable light chain amino acid sequence is set forth in SEQ ID NO: 31, and/or the variable heavy chain amino acid sequence is set forth in SEQ ID NO: 32. In various embodiments, the variable light chain amino acid sequence is set forth in SEQ ID NO: 39, and/or the variable heavy chain amino acid sequence is set forth in SEQ ID NO: 40. In various embodiments, the variable light chain amino acid sequence is set forth in SEQ ID NO: 47, and/or the variable heavy chain amino acid sequence is set forth in SEQ ID NO: 48.

In various embodiments, the anti-BCMA antibody or antigen binding fragment is selected from the group consisting of: a Camel Ig, Ig NAR, Fab fragments, Fab' fragments, F(ab)'2 fragments, F(ab)'3 fragments, Fv, single chain Fv antibody ("scFv"), bis-scFv, (scFv) 2, minibody, diabody, triabody, tetrabody, disulfide stabilized Fv protein ("dsFv"), and single-domain antibody (sdAb, Nanobody). In some embodiments, the anti-BCMA antibody or antigen binding fragment is an scFv.

In various embodiments, the anti-BCMA antibody or antigen binding fragment thereof comprises one or more light chain CDRs as set forth in any one of SEQ ID NOs: 1-3 and/or one or more heavy chain CDRs as set forth in any one of SEQ ID NOs: 4-6. In some embodiments, the anti-BCMA antibody or antigen binding fragment thereof comprises one or more light chain CDRs as set forth in any one of SEQ ID NOs: 9-11 and/or one or more heavy chain CDRs as set forth in any one of SEQ ID NOs: 12-14. In some embodiments, the anti-BCMA antibody or antigen binding fragment thereof comprises one or more light chain CDRs as set forth in any one of SEQ ID NOs: 17-19 and/or one or more heavy chain CDRs as set forth in any one of SEQ ID NOs: 20-22. In some embodiments, the anti-BCMA antibody or antigen binding fragment thereof comprises one or more light chain CDRs as set forth in any one of SEQ ID NOs: 25-27 and/or one or more heavy chain CDRs as set forth in any one of SEQ ID NOs: 28-30. In some embodiments, the anti-BCMA antibody or antigen binding fragment thereof comprises one or more light chain CDRs as set forth in any one of SEQ ID NOs: 33-35 and/or one or more heavy chain CDRs as set forth in any one of SEQ ID NOs: 36-38. In some embodiments, the anti-BCMA antibody or antigen binding fragment thereof comprises one or more light chain CDRs as set forth in any one of SEQ ID NOs: 41-43 and/or one or more heavy chain CDRs as set forth in any one of SEQ ID NOs: 44-46.

In various embodiments, the anti-BCMA antibody or antigen binding fragment thereof comprises a variable light chain comprising an amino acid sequence having at least 85%, 90%, 95%, 96%, 97%, 98%, or 99% identity to a variable light chain amino acid sequence as set forth in any one of SEQ ID NOs: 7, 15, 23, 31, 39, or 47 and/or a variable heavy chain comprising an amino acid sequence having at least 85%, 90%, 95%, 96%, 97%, 98%, or 99% identity to a variable heavy chain amino acid sequence as set forth in any one of SEQ ID NOs: 8, 16, 24, 32, 40, or 48. In some embodiments, the anti-BCMA antibody or antigen binding fragment thereof comprises a variable light chain comprising an amino acid sequence having at least 85%, 90%, 95%, 96%, 97%, 98%, or 99% identity to a variable light chain amino acid sequence as set forth in SEQ ID NO: 7 and/or a variable heavy chain comprising an amino acid sequence having at least 85%, 90%, 95%, 96%, 97%, 98%, or 99% identity to a variable heavy chain amino acid sequence as set forth in SEQ ID NO: 8. In some embodiments, the anti-BCMA antibody or antigen binding fragment thereof comprises a variable light chain comprising an amino acid sequence having at least 85%, 90%, 95%, 96%, 97%, 98%, or 99% identity to a variable light chain amino acid sequence as set forth in SEQ ID NO: 15 and/or a variable heavy chain comprising an amino acid sequence having at least 85%, 90%, 95%, 96%, 97%, 98%, or 99% identity to a variable heavy chain amino acid sequence as set forth in SEQ ID NO: 16. In some embodiments, the anti-BCMA antibody or antigen binding fragment thereof comprises a variable light chain comprising an amino acid sequence having at least 85%, 90%, 95%, 96%, 97%, 98%, or 99% identity to a variable light chain amino acid sequence as set forth in SEQ ID NO: 23 and/or a variable heavy chain comprising an amino acid sequence having at least 85%, 90%, 95%, 96%, 97%, 98%, or 99% identity to a variable heavy chain amino acid sequence as set forth in SEQ ID NO: 24. In some embodiments, the anti-BCMA antibody or antigen binding fragment thereof comprises a variable light chain comprising an amino acid sequence having at least 85%, 90%, 95%, 96%, 97%, 98%, or 99% identity to a variable light chain amino acid sequence as set forth in SEQ ID NO: 31 and/or a variable heavy chain comprising an amino acid sequence having at least 85%, 90%, 95%, 96%, 97%, 98%, or 99% identity to a variable heavy chain amino acid sequence as set forth in SEQ ID NO: 32. In some embodiments, the anti-BCMA antibody or antigen binding fragment thereof comprises a variable light chain comprising an amino acid sequence having at least 85%, 90%, 95%, 96%, 97%, 98%, or 99% identity to a variable light chain amino acid sequence as set forth in SEQ ID NO: 39 and/or a variable heavy chain comprising an amino acid sequence having at least 85%, 90%, 95%, 96%, 97%, 98%, or 99% identity to a variable heavy chain amino acid sequence as set forth in SEQ ID NO: 40. In some embodiments, the anti-BCMA antibody or antigen binding fragment thereof comprises a variable light chain comprising an amino acid sequence having at least 85%, 90%, 95%, 96%, 97%, 98%, or 99% identity to a variable light chain amino acid sequence as set forth in SEQ ID NO: 31 and/or a variable heavy chain comprising 47an amino acid sequence having at least 85%, 90%, 95%, 96%, 97%, 98%, or 99% identity to a variable heavy chain amino acid sequence as set forth in SEQ ID NO: 48.

In various embodiments, the anti-BCMA antibody or antigen binding fragment thereof comprises a variable light chain sequence as set forth in any one of SEQ ID NOs: 7, 15, 23, 31, 39, or 47 and/or a variable heavy chain sequence as set forth in any one of SEQ ID NOs: 8, 16, 24, 32, 40, or 48. In some embodiments, the anti-BCMA antibody or antigen binding fragment thereof comprises a variable light chain sequence as set forth in SEQ ID NO: 7 and/or a variable heavy chain sequence as set forth in SEQ ID NO: 8. In some embodiments, the anti-BCMA antibody or antigen binding fragment thereof comprises a variable light chain sequence as set forth in SEQ ID NO: 15 and/or a variable heavy chain sequence as set forth in SEQ ID NO: 16. In some embodiments, the anti-BCMA antibody or antigen binding fragment thereof comprises a variable light chain sequence as set forth in SEQ ID NO: 23 and/or a variable heavy chain sequence as set forth in SEQ ID NO: 24. In some embodiments, the anti-BCMA antibody or antigen binding fragment thereof comprises a variable light chain sequence as set forth in SEQ ID NO: 31 and/or a variable heavy chain sequence as set forth in SEQ ID NO: 32. In some embodiments, the anti-BCMA antibody or antigen binding fragment thereof comprises a variable light chain sequence as set forth in SEQ ID NO: 39 and/or a variable heavy chain sequence as set forth in SEQ ID NO: 40. In some embodiments, the anti-BCMA antibody or antigen binding fragment thereof comprises a variable light chain sequence as set forth in SEQ ID NO: 47 and/or a variable heavy chain sequence as set forth in SEQ ID NO: 48.

In particular embodiments, the antibody or antigen binding fragment thereof is an scFv and the variable light chain is positioned c-terminal to that of the variable heavy chain. In particular embodiments, the antibody or antigen binding fragment thereof is an scFv and the variable heavy chain is positioned c-terminal to that of the variable light chain.

In various embodiments, the CAR transmembrane domain is isolated from a polypeptide selected from the group consisting of: alpha or beta chain of the T-cell receptor, CDδ, CD3ε, CDγ, CD3ζ, CD4, CD5, CD8α, CD9, CD 16, CD22, CD27, CD28, CD33, CD37, CD45, CD64, CD80, CD86, CD 134, CD137, CD152, CD154, and PD1. In some embodiments, the transmembrane domain is isolated from a polypeptide selected from the group consisting of: CD8α; CD4, CD45, PD1, and CD152. In some embodiments, the transmembrane domain is isolated from CD8a. In some embodiments, the transmembrane domain is isolated from PD1. In some embodiments, the transmembrane domain is isolated from CD152.

In various embodiments, the one or more CAR co-stimulatory signaling domains are isolated from a co-stimulatory molecule selected from the group consisting of: TLR1, TLR2, TLR3, TLR4, TLR5, TLR6, TLR7, TLR8, TLR9, TLR10, CARD11, CD2, CD7, CD27, CD28, CD30, CD40, CD54 (ICAM), CD83, CD134 (OX40), CD137 (4-1BB), CD278 (ICOS), DAP10, LAT, NKD2C, SLP76, TRIM, and ZAP70. In some embodiments, one or more co-stimulatory signaling domains are isolated from a co-stimulatory molecule selected from the group consisting of: CD28, CD134, and CD137. In some embodiments, the one or more co-stimulatory signaling domains is isolated from CD28. In some embodiments, the one or more co-stimulatory signaling domains is isolated from CD134. In some embodiments, the one or more co-stimulatory signaling domains is isolated from CD137.

In various embodiments, the primary signaling domain isolated from a polypeptide selected from the group consisting of: FcRγ, FcRβ, CD3γ, CD3ε, CD3ζ, CD35, CD22, CD79a, CD79b, and CD66d. In some embodiments, the primary signaling domain isolated from a CD3ζ.

In various embodiments, the CAR further comprises a hinge region polypeptide. In some embodiments, the hinge region polypeptide comprises a hinge region of CD8a. In some embodiments, the hinge region polypeptide comprises a hinge region of PD1. In some embodiments, the hinge region polypeptide comprises a hinge region of CD152.

In various embodiments, the CAR further comprises a spacer region. In some embodiments, the spacer region polypeptide comprises CH2 and CH3 regions of IgG1, IgG2, IgG4, or IgD.

In various embodiments, the CAR further comprising a signal peptide.

In various embodiments, the CAR comprises an amino acid sequence as set forth in any one of SEQ ID NOs: 50, 52, 54, 56, 58, 60, 62, 64, 66, and 68. In some embodiments, the CAR comprises an amino acid sequence as set forth in SEQ ID NO: 50. In some embodiments, the CAR comprises an amino acid sequence as set forth in SEQ ID NO: 52. In some embodiments, the CAR comprises an amino acid sequence as set forth in SEQ ID NO: 54. In some embodiments, the CAR comprises an amino acid sequence as set forth in SEQ ID NO: 56. In some embodiments, the CAR comprises an amino acid sequence as set forth in SEQ ID NO: 58. In some embodiments, the CAR comprises an amino acid sequence as set forth in SEQ ID NO: 60. In some embodiments, the CAR comprises an amino acid sequence as set forth in SEQ ID NO: 62. In some embodiments, the CAR comprises an amino acid sequence as set forth in SEQ ID NO: 64. In some embodiments, the CAR comprises an amino acid sequence as set forth in SEQ ID NO: 66. In some embodiments, the CAR comprises an amino acid sequence as set forth in SEQ ID NO: 68.

In various embodiments, the CAR comprises a polypeptide comprising the amino acid sequence of any one of the CAR contemplated herein.

In another aspect of the disclosure, a polynucleotide is provided encoding any one of the CARs or polypeptides contemplated herein. In some embodiments, the polynucleotide comprises a polynucleotide sequence having at least 90%, 95%, 96%, 97%, 98%, or 99% identity to a polynucleotide sequence as set forth in any one of SEQ ID NO: 49, 51, 53, 55, 57, 59, 61, 63, 65, and 67. In some embodiments, the polynucleotide comprises a polynucleotide sequence as set forth in any one of SEQ ID NO: 49, 51, 53, 55, 57, 59, 61, 63, 65, and 67.

In another aspect of the disclosure, a vector is provided comprising any one of the polynucleotides contemplated herein. In some embodiments, the vector is an expression vector. In some embodiments, the vector is an episomal vector. In some embodiments, the vector is a viral vector. In some embodiments, the vector is a retroviral vector. In some embodiments, the vector is a lentiviral vector. In some embodiments, the lentiviral vector is selected from the group consisting essentially of: human immunodeficiency virus 1 (HIV-1); human immunodeficiency virus 2 (HIV-2), visna-maedi virus (VMV) virus; caprine arthritis-encephalitis virus (CAEV); equine infectious anemia virus (EIAV); feline immunodeficiency virus (FIV); bovine immune deficiency virus (BIV); and simian immunodeficiency virus (SIV).

In particular embodiments, the vector further comprises a left (5') retroviral LTR, a Psi (Ψ) packaging signal, a central polypurine tract/DNA flap (cPPT/FLAP), a retroviral export element; a promoter operably linked to any one of the polynucleotides contemplated herein; and a right (3') retroviral LTR. In some embodiments, the vector further comprises a heterologous polyadenylation sequence. In some embodiments, the vector further comprises a hepatitis B virus posttranscriptional regulatory element (HPRE) or woodchuck post-transcriptional regulatory element (WPRE). In some embodiments, the promoter of the 5' LTR is replaced with a heterologous promoter. In some embodiments, the heterologous promoter is a cytomegalovirus (CMV) promoter, a Rous Sarcoma Virus (RSV) promoter, or a Simian Virus 40 (SV40) promoter. In some embodiments, the 5' LTR or 3' LTR is a lentivirus LTR. In some embodiments, the 3' LTR comprises one or more modifications. In some embodiments, the 3' LTR comprises one or more deletions. In some embodiments, the 3' LTR is a self-inactivating (SIN) LTR. In some embodiments, the polyadenylation sequence is a bovine growth hormone polyadenylation or signal rabbit β-globin polyadenylation sequence. In some embodiments, the polynucleotide comprises an optimized Kozak sequence. In some embodiments, the promoter operably linked to the polynucleotide is selected from the group consisting of: a cytomegalovirus immediate early gene promoter (CMV), an elongation factor 1 alpha promoter (EF1-α), a phosphoglycerate kinase-1 promoter (PGK), a ubiquitin-C promoter (UBQ-C), a cytomegalovirus enhancer/chicken beta-actin promoter (CAG), polyoma enhancer/herpes simplex thymidine kinase promoter (MC1), a beta actin promoter (β-ACT), a simian virus 40 promoter (SV40), and a myeloproliferative sarcoma virus enhancer, negative control region deleted, d1587rev primer-binding site substituted (MND) U3 promoter.

In another aspect of the disclosure, a cell is provided that expresses any one of the CARs or polypeptides contemplated herein. In some embodiments, the cell comprises any one of the polynucleotides contemplated herein or any one of the vectors contemplated herein. In some embodiments, the cell is a genetically engineered host cell. In some embodiments, the cell is a hematopoietic cell. In some embodiments, the cell is a hematopoietic stem or progenitor cell. In some embodiments, the cell is a CD34+ hematopoietic stem or progenitor cell. In some embodiments, the cell is an immune effector cell. In some embodiments, the cell is a T-cell. In some embodiments, the cell is a $CD3^+$, $CD4^+$, and/or $CD8^+$ cell. In some embodiments, the cell is a cytotoxic T lymphocytes (CTLs), a tumor infiltrating lymphocytes (TILs), or a helper T cell. In some embodiments, the T-cell is a αβ-T cell. In some embodiments, the T-cell is a γδ-T cell. In some embodiments, the host cell is a natural killer (NK) cell. In some embodiments, the natural killer cell is a natural killer T (NKT) cell. In some embodiments, the cell is a macrophage.

In various embodiments, the immune effector cell is transduced with any one of the vectors contemplated herein and is activated and stimulated in the presence of an inhibitor of the PI3K pathway, thereby maintaining proliferation of the transduced immune effector cells compared to the proliferation of transduced immune effector cells that were activated and stimulated in the absence of the inhibitor of the PI3K pathway. In some embodiments, the immune effector cell activated and stimulated in the presence of the inhibitor of PI3K pathway has increased expression of i) one or more markers selected from the group consisting of: CD62L, CD127, CD197, and CD38 or ii) all of the markers CD62L, CD127, CD197, and CD38 compared to an immune effector cell activated and stimulated in the absence of the inhibitor of PI3K pathway. In some embodiments, the immune effector cell activated and stimulated in the presence of the inhibitor of PI3K pathway has increased expression of i) one or more markers selected from the group consisting of: CD62L, CD127, CD27, and CD8 or ii) all of the markers CD62L, CD127, CD27, and CD8 compared to an immune effector cell activated and stimulated in the absence of the inhibitor of PI3K pathway. In some embodiments, the PI3K inhibitor is ZSTK474.

In various embodiments, the cell or progeny thereof display high IFNγ release in co-culture with BCMA expressing cells. In some embodiments, the cell or progeny thereof display similar or higher IFNγ release in co-culture with BCMA expressing cells compared to the same cell except that the CAR comprises an extracellular domain comprising a murine derived anti-BCMA scFv. In some embodiments, the co-cultured BCMA expressing cells are Daudi cells, HT1080.BCMA cells, and/or RPMI-8226 cells. In some embodiments, the cell or progeny thereof, display high IFNγ release in co-culture with low BCMA expressing cells. In some embodiments, the low BCMA expressing cells have at least 5-fold less surface BCMA expression compared to Daudi, HT1080.BCMA, and/or RPMI-8226 cells. In some embodiments, the low BCMA expressing cells have at least 10-fold less surface BCMA expression compared to HT1080.BCMA cells. In some embodiments, the low BCMA expressing cells have at least 10-fold less surface BCMA expression compared to RPMI-8226 cells. In some embodiments, the low BCMA expressing cells are RL and/or Toledo cells. In some embodiments, the CAR T cells display higher IFNγ release in co-culture with low antigen density cells compared to the same CAR T cell except that the CAR comprises an extracellular domain comprising a murine derived anti-BCMA scFv. In some embodiments, the cell displays low antigen independent signaling. In some embodiments, the cell displays low antigen independent signaling compared to the same CAR T cell except that the CAR comprises an extracellular domain comprising a murine derived anti-BCMA scFv.

In another aspect of the disclosure, a composition is provided comprising any one of the cells contemplated herein and a physiologically acceptable excipient.

In another aspect of the disclosure, a method of generating an immune effector cell comprising a CAR or polypeptide contemplated herein is provided, comprising introducing into an immune effector cell any one of the vectors contemplated herein. In some embodiments, the method further comprises stimulating the immune effector cell and inducing the cell to proliferate by contacting the cell with antibodies that bind CD3 and antibodies that bind to CD28; thereby generating a population of immune effector cells. In some embodiments, the immune effector cell is stimulated and induced to proliferate before introducing the vector. In some embodiments, the immune effector cells comprise T lymphocytes. In some embodiments, the immune effector cells comprise NK cells. In some embodiments, the immune effector cell is activated and stimulated in the presence of the inhibitor of PI3K pathway has increased expression of i) one or more markers selected from the group consisting of: CD62L, CD127, CD197, and CD38 or ii) all of the markers CD62L, CD127, CD197, and CD38 compared to an immune effector cell activated and stimulated in the absence of the inhibitor of PI3K pathway. In some embodiments, the immune effector cell is activated and stimulated in the presence of the inhibitor of PI3K pathway has increased expression of i) one or more markers selected from the group consisting of: CD62L, CD127, CD27, and CD8 or ii) all of the markers CD62L, CD127, CD27, and CD8 compared to an immune effector cell activated and stimulated in the absence of the inhibitor of PI3K pathway. In some embodiments, the PI3K inhibitor is ZSTK474.

In another aspect of the disclosure, a method of treating a B cell related condition in a subject in need thereof is provided, comprising administering to the subject a therapeutically effect amount of any one of the compositions provided herein. In some embodiments, the B cell related condition is a cancer. In some embodiments, the cancer is a solid cancer. In some embodiments, the cancer is a liquid cancer. In some embodiments, the cancer is a hematological malignancy. In some embodiments, the B cell related condition is multiple myeloma (MM), non-Hodgkin's lymphoma (NHL), B cell proliferations of uncertain malignant potential, lymphomatoid granulomatosis, post-transplant lymphoproliferative disorder, an immunoregulatory disorder, rheumatoid arthritis, myasthenia gravis, idiopathic thrombocytopenia purpura, anti-phospholipid syndrome, Chagas' disease, Grave's disease, Wegener's granulomatosis, poly-arteritis nodosa, Sjogren's syndrome, pemphigus vulgaris, scleroderma, multiple sclerosis, anti-phospholipid syndrome, ANCA associated vasculitis, Goodpasture's disease, Kawasaki disease, autoimmune hemolytic anemia, and rapidly progressive glomerulonephritis, heavy-chain disease, primary or immunocyte-associated amyloidosis, or monoclonal gammopathy of undetermined significance. In some embodiments, the B cell related condition is a B cell malignancy. In some embodiments, the B cell malignancy is multiple myeloma (MM) or non-Hodgkin's lymphoma (NHL). In some embodiments, the MM is selected from the group consisting of: overt multiple myeloma, smoldering multiple myeloma, plasma cell leukemia, non-secretory myeloma, IgD myeloma, osteosclerotic myeloma, solitary plasmacytoma of bone, and extramedullary plasmacytoma. In some embodiments, the NHL is selected from the group consisting of: Burkitt lymphoma, chronic lymphocytic leukemia/small lymphocytic lymphoma (CLL/SLL), diffuse large B-cell lymphoma, follicular lymphoma, immunoblastic large cell lymphoma, precursor B-lymphoblastic lymphoma, and mantle cell lymphoma. In some embodiments, the B cell related condition is a plasma cell malignancy. In some embodiments, the B cell related condition is an autoimmune disease. In some embodiments, the autoimmune disease is systemic lupus erythematosus. In some embodiments, the B cell related condition is rheumatoid arthritis. In some embodiments, the B cell related condition is idiopathic thrombocytopenia purpura, or myasthenia gravis, or autoimmune hemolytic anemia.

In another aspect of the disclosure, a method for ameliorating at one or more symptoms associated with a cancer expressing BCMA in a subject is provided, comprising administering to the subject an amount of any one of the compositions provided herein sufficient to ameliorate at least one symptom associated with cancer cells that express BCMA. In some embodiments, the one or more symptoms ameliorated are selected from the group consisting of: weakness, fatigue, shortness of breath, easy bruising and bleeding, frequent infections, enlarged lymph nodes, distended or painful abdomen, bone or joint pain, fractures, unplanned weight loss, poor appetite, night sweats, persistent mild fever, and decreased urination.

In another aspect of the disclosure, a method for decreasing the number of cells expressing BCMA in a subject is provided, comprising administering to the subject an amount of any one of the compositions contemplated herein sufficient to decrease the number of cells that express BCMA compared to the number of the cells that express BCMA prior to the administration.

In another aspect of the disclosure, an antibody or antigen binding fragment thereof that binds one or more epitopes of a human BCMA polypeptide is provided, comprising: variable light chain CDRL1, CDRL2, and CDRL3 regions within a variable light chain amino acid sequence as set forth in SEQ ID NOs: 7, 15, 23, 31, 39, or 47, and/or variable heavy chain CDRH1, CDRH2, and CDRH3 regions within a variable heavy chain amino acid sequence as set forth in SEQ ID NOs: 8, 16, 24, 32, 40, or 48. In some embodiments, the antibody or antigen binding fragment comprises variable light chain CDRL1, CDRL2, and CDRL3 sequences set forth in any one of SEQ ID NOs: 1-3, 9-11, 17-19, 25-27, 33-35, or 41-43 and/or variable heavy chain CDRH1, CDRH2, and CDRH3 sequences set forth in SEQ ID NOs: 4-6, 12-14, 20-22, 28-30, 36-38, or 44-46.

In particular embodiments, the antibody or antigen binding fragment is selected from the group consisting of: a Camel Ig, Ig NAR, Fab fragments, Fab' fragments, F(ab)'2 fragments, F(ab)'3 fragments, Fv, single chain Fv antibody ("scFv"), bis-scFv, (scFv) 2, minibody, diabody, triabody, tetrabody, disulfide stabilized Fv protein ("dsFv"), and single-domain antibody (sdAb, Nanobody). In some embodiments, the antibody or antigen binding fragment is an scFv.

In some embodiments, the antibody or antigen binding fragment thereof comprises one or more light chain CDRs as set forth in any one of SEQ ID NOs: 1-3 and/or one or more heavy chain CDRs as set forth in any one of SEQ ID NOs: 4-6. In some embodiments, the antibody or antigen binding fragment thereof comprises one or more light chain CDRs as set forth in any one of SEQ ID NOs: 9-11 and/or one or more heavy chain CDRs as set forth in any one of SEQ ID NOs: 12-14. In some embodiments, the antibody or antigen binding fragment thereof comprises one or more light chain CDRs as set forth in any one of SEQ ID NOs: 17-19 and/or one or more heavy chain CDRs as set forth in any one of SEQ ID NOs: 20-22. In some embodiments, the antibody or antigen binding fragment thereof comprises one or more light chain CDRs as set forth in any one of SEQ ID NOs: 25-27 and/or one or more heavy chain CDRs as set forth in any one of SEQ ID NOs: 28-30. In some embodiments, the antibody or antigen binding fragment thereof comprises one or more light chain CDRs as set forth in any one of SEQ ID NOs: 33-35 and/or one or more heavy chain CDRs as set forth in any one of SEQ ID NOs: 36-38. In some embodiments, the antibody or antigen binding fragment thereof comprises one or more light chain CDRs as set forth in any one of SEQ ID NOs: 41-43 and/or one or more heavy chain CDRs as set forth in any one of SEQ ID NOs: 44-46.

In various embodiments, the antibody or antigen binding fragment thereof comprises a variable light chain comprising an amino acid sequence having at least 85%, 90%, 95%, 96%, 97%, 98%, or 99% identity to a variable light chain amino acid sequence as set forth in any one of SEQ ID NOs: 7, 15, 23, 31, 39, or 47 and/or a variable heavy chain comprising an amino acid sequence having at least 85%, 90%, 95%, 96%, 97%, 98%, or 99% identity to a variable heavy chain amino acid sequence as set forth in any one of SEQ ID NOs: 8, 16, 24, 32, 40, or 48. In some embodiments, the antibody or antigen binding fragment thereof comprises a variable light chain comprising an amino acid sequence having at least 85%, 90%, 95%, 96%, 97%, 98%, or 99% identity to a variable light chain amino acid sequence as set forth in SEQ ID NO: 7 and/or a variable heavy chain comprising an amino acid sequence having at least 85%, 90%, 95%, 96%, 97%, 98%, or 99% identity to a variable heavy chain amino acid sequence as set forth in SEQ ID NO: 8. In some embodiments, the antibody or antigen binding fragment thereof comprises a variable light chain comprising an amino acid sequence having at least 85%, 90%, 95%, 96%, 97%, 98%, or 99% identity to a variable light chain amino acid sequence as set forth in SEQ ID NO: 15 and/or a variable heavy chain comprising an amino acid sequence having at least 85%, 90%, 95%, 96%, 97%, 98%, or 99% identity to a variable heavy chain amino acid sequence as set forth in SEQ ID NO: 16. In some embodiments, the antibody or antigen binding fragment thereof comprises a variable light chain comprising an amino acid sequence having at least 85%, 90%, 95%, 96%, 97%, 98%, or 99% identity to a variable light chain amino acid sequence as set forth in SEQ ID NO: 23 and/or a variable heavy chain comprising an amino acid sequence having at least 85%, 90%, 95%, 96%, 97%, 98%, or 99% identity to a variable heavy chain amino acid sequence as set forth in SEQ ID NO: 24. In some embodiments, the antibody or antigen binding fragment thereof comprises a variable light chain comprising an amino acid sequence having at least 85%, 90%, 95%, 96%, 97%, 98%, or 99% identity to a variable light chain amino acid sequence as set forth in SEQ ID NO: 31 and/or a variable heavy chain comprising an amino acid sequence having at least 85%, 90%, 95%, 96%, 97%, 98%, or 99% identity to a variable heavy chain amino acid sequence as set forth in SEQ ID NO: 32. In some embodiments, the antibody or antigen binding fragment thereof comprises a variable light chain comprising an amino acid sequence having at least 85%, 90%, 95%, 96%, 97%, 98%, or 99% identity to a variable light chain amino acid sequence as set forth in SEQ ID NO: 39 and/or a variable heavy chain comprising an amino acid sequence having at least 85%, 90%, 95%, 96%, 97%, 98%, or 99% identity to a variable heavy chain amino acid sequence as set forth in SEQ ID NO: 40. In some embodiments, the antibody or antigen binding fragment thereof comprises a variable light chain comprising an amino acid sequence having at least 85%, 90%, 95%, 96%, 97%, 98%, or 99% identity to a variable light chain amino acid sequence as set forth in SEQ ID NO: 47 and/or a variable heavy chain comprising an amino acid sequence having at least 85%, 90%, 95%, 96%, 97%, 98%, or 99% identity to a variable heavy chain amino acid sequence as set forth in SEQ ID NO: 48.

In various embodiments, the antibody or antigen binding fragment thereof comprises a variable light chain sequence as set forth in any one of SEQ ID NOs: 7, 15, 23, 31, 39, or 47 and/or a variable heavy chain sequence as set forth in any one of SEQ ID NOs: 8, 16, 24, 32, 40, or 48. In some embodiments, the antibody or antigen binding fragment thereof comprises a variable light chain sequence as set forth in SEQ ID NO: 7 and/or a variable heavy chain sequence as set forth in SEQ ID NO: 8. In some embodiments, the antibody or antigen binding fragment thereof comprises a variable light chain sequence as set forth in SEQ ID NO: 15 and/or a variable heavy chain sequence as set forth in SEQ ID NO: 16. In some embodiments, the antibody or antigen binding fragment thereof comprises a variable light chain sequence as set forth in SEQ ID NO: 23 and/or a variable heavy chain sequence as set forth in SEQ ID NO: 24. In some embodiments, the antibody or antigen binding fragment thereof comprises a variable light chain sequence as set forth in SEQ ID NO: 31 and/or a variable heavy chain sequence as set forth in SEQ ID NO: 32. In some embodiments, the antibody or antigen binding fragment thereof comprises a variable light chain sequence as set forth in SEQ ID NO: 39 and/or a variable heavy chain sequence as set forth in SEQ ID NO: 40. In some embodiments, the antibody or antigen binding fragment thereof comprises a variable light chain sequence as set forth in SEQ ID NO: 47 and/or a variable heavy chain sequence as set forth in SEQ ID NO: 48.

In particular embodiments, the antibody or antigen binding fragment thereof is an scFv and the variable light chain is positioned c-terminal to that of the variable heavy chain. In particular embodiments, the antibody or antigen binding fragment thereof is an scFv and the variable heavy chain is positioned c-terminal to that of the variable light chain.

BRIEF DESCRIPTION OF SEVERAL VIEWS OF THE DRAWINGS

FIGS. 3A-31 show the amount of IFNγ released from anti-BCMA CAR T cells either alone (FIGS. 3A, 3D, and 3G) or in co-culture for 24 hours with BCMA negative Rhabdomyosarcoma (RD) cells (FIG. 3B) or HT1080 cells (FIGS. 3E and 3H) compared to BCMA expressing Daudi cells (FIG. 3C) or HT.1080.BCMA cells (FIGS. 3F and 3I).

FIG. 5 shows cytotoxicity of T cells expressing a comparator CAR, CAR1, or CAR5 against BCMA expressing HT.1080 cells over time.

FIG. 6 shows BCMA antigen expression/density on HT.1080, RL, Toledo, Daudi, RPMI-8226, and HT.1080.BCMA cancer cells.

FIG. 7A) or HT1080-nucRed.BCMA cells which express BCMA (antigen dependent proliferation; FIG. 7B).

BRIEF DESCRIPTION OF THE SEQUENCE IDENTIFIERS

Figure 1:
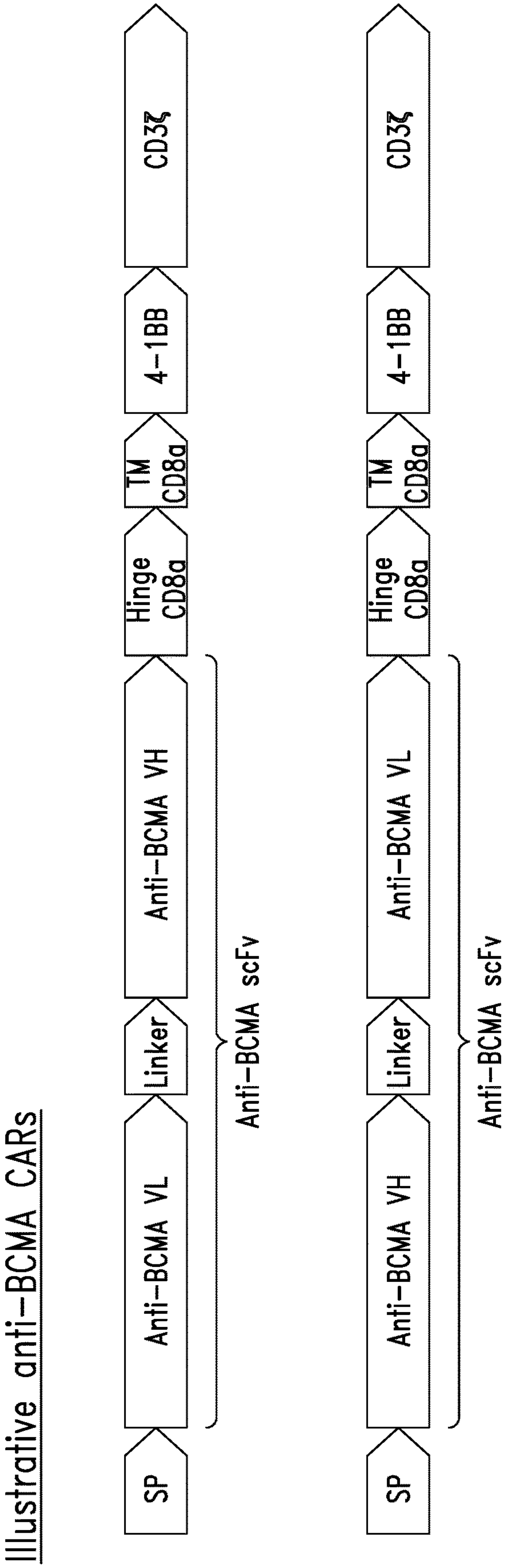
FIG. 1 show illustrative schematics of anti-BCMA CAR constructs.

SEQ ID NOs: 1-48 set forth amino acid sequences of exemplary light chain CDR sequences, heavy chain CDR sequences, variable light chains, and variable heavy chains for anti-BCMA CARs contemplated herein.

SEQ ID NOs: 49-68 set forth polynucleotide and amino acid sequences of exemplary BCMA CAR constructs contemplated herein. 1

SEQ ID NO: 69 sets forth the amino acid sequence of human BCMA.

SEQ ID NO: 71-81 sets forth the amino acid sequence of various linkers.

SEQ ID NOs: 82-106 sets forth the amino acid sequence of protease cleavage sites and self-cleaving polypeptide cleavage sites.

In the foregoing sequences, X, if present, refers to any amino acid or the absence of an amino acid.

DETAILED DESCRIPTION a. Overview

The invention generally relates to improved compositions and methods for treating B cell related conditions. Particularly, the invention relates to improved human anti-BCMA antibodies, CARs, and CAR T cells for treating B cell related conditions (e.g., cancer).

As used herein, the term "B cell related conditions" relates to conditions involving inappropriate B cell activity and B cell malignancies. In particular embodiments, the disclosure relates to improved adoptive cell therapy of B cell related conditions using genetically modified immune effector cells. Genetic approaches offer a potential means to enhance immune recognition and elimination of cancer cells.

One promising strategy is to genetically engineer immune effector cells to express chimeric antigen receptors (CARs) that redirect cytotoxicity toward cancer cells. However, the potential therapeutic efficacy of any CAR involves a delicate balance among several components of the CAR, including, but not limited to selecting the right structural domains (e.g., hinge or transmembrane domains), selecting the right signaling or co-stimulatory domains (e.g., 4-1BB or CD3), and selecting the right antigen-binding domain. For example, preferably, the antigen-binding domain binds an antigen that is expressed on cancer cells and has relatively low (or absent) expression on non-cancer cells. Moreover, the binding can't be too strong or too weak, lest you get either no signaling or too much signaling.

Recent attempts to treat B cell malignancies by targeting B cell maturation antigen (BCMA, also known as CD269 or tumor necrosis factor receptor superfamily, member 17; TNFRSF17) through the use of therapeutic antibodies or chimeric antigen receptors (CARs) which target BCMA have been met with promising but limited success. Indeed, although many patients experience a measurable therapeutic benefit not previously seen in these patient populations, not all patients receiving these therapies experience complete remission and many relapse. Accordingly, there remains a significant unmet need in these patient populations for improved therapeutics, including improve anti-BCMA antibodies and/or CARs (including CAR T therapies).

BCMA is a member of the tumor necrosis factor receptor superfamily (see, e.g., Thompson et al., *J. Exp. Medicine,* 192 (1): 129-135, 2000, and Mackay et al., *Annu. Rev. Immunol,* 21:231-264, 2003. BCMA binds B-cell activating factor (BAFF) and a proliferation inducing ligand (APRIL) (see, e.g., Mackay et al., 2003 and Kalled et al., *Immunological Reviews,* 204:43-54, 2005). Among nonmalignant cells, BCMA has been reported to be expressed mostly in plasma cells and subsets of mature B-cells (see, e.g., Laabi et al., *EMBO J.,* 77 (1): 3897-3904, 1992; Laabi et al., *Nucleic Acids Res.,* 22 (7): 1147-1154, 1994; Kalled et al., 2005; O'Connor et al., *J. Exp. Medicine,* 199 (1): 91-97, 2004; and Ng et al., *J. Immunol.,* 73 (2): 807-817, 2004. Mice deficient in BCMA are healthy and have normal numbers of B cells, but the survival of long-lived plasma cells is impaired (see, e.g., O'Connor et al., 2004; Xu et al., *Mol. Cell. Biol,* 21 (12): 4067-4074, 2001; and Schiemann et al., *Science,* 293 (5537): 2 111-21 14, 2001). BCMA RNA has been detected universally in multiple myeloma cells and in other lymphomas, and BCMA protein has been detected on the surface of plasma cells from multiple myeloma patients by several investigators (see, e.g., Novak et al., *Blood,* 103 (2): 689-694, 2004; Neri et al., *Clinical Cancer Research,* 73 (19): 5903-5909, 2007; Bellucci et al., *Blood,* 105 (10): 3945-3950, 2005; and Moreaux et al., *Blood,* 703 (8): 3148-3157, 2004.

Accordingly, the improved compositions and methods of adoptive cell therapy disclosed herein, provide genetically modified immune effector cells (e.g., CAR T cells) that target cells expressing BCMA and have human derived antigen binding domains, display improved cytokine release, and/or low antigen independent signaling. In particular embodiments, a CAR comprising a human anti-BCMA antibody or antigen binding fragment, a transmembrane domain, and one or more intracellular signaling domains is provided. In further embodiments, the improved CAR T cells display high IFNγ release in co-culture with low antigen density cells.

In one embodiment, an immune effector cell is genetically modified to express a CAR contemplated herein is provided. T cells expressing a CAR are referred to herein as CAR T cells or CAR modified T cells.

In various embodiments, the genetically modified immune effector cells contemplated herein, are administered to a patient with a B cell related condition, e.g., an autoimmune disease associated with B cells or a B cell malignancy.

In other embodiments, improved anti-BCMA antibodies or fragments thereof are provided.

The practice of the invention will employ, unless indicated specifically to the contrary, conventional methods of chemistry, biochemistry, organic chemistry, molecular biology, microbiology, recombinant DNA techniques, genetics, immunology, and cell biology that are within the skill of the art, many of which are described below for the purpose of illustration. Such techniques are explained fully in the literature. See, e.g., Sambrook, et al., *Molecular Cloning: A Laboratory Manual* (3rd Edition, 2001); Sambrook, et al., *Molecular Cloning: A Laboratory Manual* (2nd Edition, 1989); Maniatis et al., *Molecular Cloning: A Laboratory Manual* (1982); Ausubel et al., *Current Protocols in Molecular Biology* (*John Wiley and Sons, updated* July 2008); *Short Protocols in Molecular Biology: A Compendium of Methods from Current Protocols in Molecular Biology*, Greene Pub. Associates and Wiley-Interscience; Glover, *DNA Cloning: A Practical Approach*, vol. I & II (IRL Press, Oxford, 1985); Anand, *Techniques for the Analysis of Complex Genomes*, (Academic Press, New York, 1992); *Transcription and Translation* (B. Hames & S. Higgins, Eds., 1984); Perbal, *A Practical Guide to Molecular Cloning* (1984); *Harlow and Lane, Antibodies*, (Cold Spring Harbor Laboratory Press, Cold Spring Harbor, N.Y., 1998) *Current Protocols in Immunology Q.* E. Coligan, A. M. Kruisbeek, D. H. Margulies, E. M. Shevach and W. Strober, eds., 1991); *Annual Review of Immunology*; as well as monographs in journals such as Advances in Immunology.

B. Definitions

Prior to setting forth this disclosure in more detail, it may be helpful to an understanding thereof to provide definitions of certain terms to be used herein.

Unless defined otherwise, all technical and scientific terms used herein have the same meaning as commonly understood by those of ordinary skill in the art to which the invention belongs. Although any methods and materials similar or equivalent to those described herein can be used in the practice or testing of particular embodiments, preferred embodiments of compositions, methods and materials are described herein. For the purposes of the present disclosure, the following terms are defined below.

The articles "a," "an," and "the" are used herein to refer to one or to more than one (i.e., to at least one, or to one or more) of the grammatical object of the article. By way of example, "an element" means one element or one or more elements.

The use of the alternative (e.g., "or") should be understood to mean either one, both, or any combination thereof of the alternatives.

The term "and/or" should be understood to mean either one, or both of the alternatives.

As used herein, the term "about" or "approximately" refers to a quantity, level, value, number, frequency, percentage, dimension, size, amount, weight or length that varies by as much as 15%, 10%, 9%, 8%, 7%, 6%, 5%, 4%, 3%, 2% or 1% to a reference quantity, level, value, number, frequency, percentage, dimension, size, amount, weight or length. In one embodiment, the term "about" or "approximately" refers a range of quantity, level, value, number, frequency, percentage, dimension, size, amount, weight or length±15%, ±10%, ±9%, ±8%, ±7%, ±6%, ±5%, ±4%, ±3%, ±2%, or ±1% about a reference quantity, level, value, number, frequency, percentage, dimension, size, amount, weight or length.

In one embodiment, a range, e.g., 1 to 5, about 1 to 5, or about 1 to about 5, refers to each numerical value encompassed by the range. For example, in one non-limiting and merely illustrative embodiment, the range "1 to 5" is equivalent to the expression 1, 2, 3, 4, 5; or 1.0, 1.5, 2.0, 2.5, 3.0, 3.5, 4.0, 4.5, or 5.0; or 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or 5.0.

As used herein, the term "substantially" refers to a quantity, level, value, number, frequency, percentage, dimension, size, amount, weight or length that is 80%, 85%, 90%, 91%, 92%, 93%, 94%, 95%, 96%, 97%, 98%, 99% or higher compared to a reference quantity, level, value, number, frequency, percentage, dimension, size, amount, weight or length. In one embodiment, "substantially the same" refers to a quantity, level, value, number, frequency, percentage, dimension, size, amount, weight or length that produces an effect, e.g., a physiological effect, that is approximately the same as a reference quantity, level, value, number, frequency, percentage, dimension, size, amount, weight or length.

Throughout this specification, unless the context requires otherwise, the words "comprise", "comprises" and "comprising" will be understood to imply the inclusion of a stated step or element or group of steps or elements but not the exclusion of any other step or element or group of steps or elements. By "consisting of" is meant including, and limited to, whatever follows the phrase "consisting of." Thus, the phrase "consisting of" indicates that the listed elements are required or mandatory, and that no other elements may be present. By "consisting essentially of" is meant to include any elements listed after the phrase and limited to other elements that do not interfere with or contribute to the activity or action specified in the disclosure for the listed elements. Thus, the phrase "consisting essentially of" indicates that the listed elements are required or mandatory, but that no other elements are present that materially affect the activity or action of the listed elements.

Reference throughout this specification to "one embodiment," "an embodiment," "a particular embodiment," "a related embodiment," "a certain embodiment," "an additional embodiment," or "a further embodiment" or combinations thereof means that a particular feature, structure or characteristic described in connection with the embodiment is included in at least one embodiment. Thus, the appearances of the foregoing phrases in various places throughout this specification are not necessarily all referring to the same embodiment. Furthermore, the particular features, structures, or characteristics may be combined in any suitable manner in one or more embodiments. It is also understood that the positive recitation of a feature in one embodiment, serves as a basis for excluding the feature in a particular embodiment.

Additional definitions are set forth throughout this disclosure.

C. Human Anti-BCMA Antibodies

In particular embodiments, an antibody or antigen binding fragment thereof that binds human BCMA is provided.

The term "antibody" refers to a binding agent that is a polypeptide comprising at least a light chain or heavy chain immunoglobulin variable region or fragment thereof which specifically recognizes and binds one or more epitopes of an antigen, such as a peptide, lipid, polysaccharide, or nucleic acid containing an antigenic determinant, such as those recognized by an immune cell.

The term "antibody" encompasses any naturally-occurring, recombinant, modified or engineered immunoglobulin or immunoglobulin-like structure or antigen-binding fragment or portion thereof, or derivative thereof, as further described elsewhere herein. Thus, the term refers to an immunoglobulin molecule that specifically binds to a target antigen, and includes, for instance, chimeric, humanized, fully human, and bispecific antibodies. An intact antibody will generally comprise at least two full-length heavy chains and two full-length light chains, but in some instances can include fewer chains such as antibodies naturally occurring in camelids which can comprise only heavy chains. Antibodies can be derived solely from a single source, or can be "chimeric," that is, different portions of the antibody can be derived from two different antibodies. Antibodies, or antigen-binding portions thereof, can be produced in hybridomas, by recombinant DNA techniques, or by enzymatic or chemical cleavage of intact antibodies.

The term "antigen binding fragment" or "antigen binding portion" refers to one or more fragments of an antibody that retain the ability to specifically bind to an antigen (e.g., BCMA). Antigen binding fragments include, but are not limited to, any naturally occurring, enzymatically obtainable, synthetic, or genetically engineered polypeptide or glycoprotein that specifically binds an antigen to form a complex. In some embodiments, an antigen-binding portion of an antibody may be derived, e.g., from full antibody molecules using any suitable standard techniques such as proteolytic digestion or recombinant genetic engineering techniques involving the manipulation and expression of DNA encoding antibody variable and optionally constant domains. In a preferred embodiment, the antigen binding fragment is a single chain variable fragment (svFv).

A "Single-chain Fv" or "scFv" antibody fragments comprise the VH and VL domains of antibody, wherein these domains are present in a single polypeptide chain and in either orientation (e.g., VL-VH or VH-VL). For example, in some embodiments, the scFv variable light chain is positioned c-terminal to that of the variable heavy chain. In some embodiments, the scFv variable heavy chain is positioned c-terminal to that of the variable light chain. Generally, the scFv polypeptide further comprises a polypeptide linker between the VH and VL domains which enables the scFv to form the desired structure for antigen binding. For a review of scFv, see, e.g., Pluckthün, in The Pharmacology of Monoclonal Antibodies, vol. 113, Rosenburg and Moore eds., (Springer-Verlag, New York, 1994), pp. 269-315.

An "isolated antibody or antigen binding fragment thereof" refers to an antibody or antigen binding fragment thereof which has been identified and separated and/or recovered from a component of its natural environment.

An "antigen (Ag)" broadly includes any molecules comprising an antigenic determinant within a binding region(s) to which an antibody or a fragment specifically binds. In particular embodiments, an "antigen (Ag)" refers to a compound, composition, or substance that can stimulate the production of antibodies or a T cell response in an animal, including compositions (such as one that includes a cancer-specific protein) that are injected or absorbed into an animal. An antigen reacts with the products of specific humoral or cellular immunity, including those induced by heterologous antigens, such as the disclosed antigens. In particular embodiments, the target antigen is an epitope of a BCMA polypeptide (e.g., a human BCMA polypeptide).

An antigen can be a single-unit molecule (such as a protein monomer or a fragment) or a complex comprised of multiple components. An antigen provides an epitope, e.g., a molecule or a portion of a molecule, or a complex of molecules or portions of molecules, capable of being bound by a selective binding agent, such as an antigen-binding protein (including, e.g., an antibody). Thus, a selective binding agent may specifically bind to an antigen that is formed by two or more components in a complex. In some embodiments, the antigen is capable of being used in an animal to produce antibodies capable of binding to that antigen. An antigen can possess one or more epitopes that are capable of interacting with different antigen-binding proteins, e.g., antibodies.

An "epitope" or "antigenic determinant" refers to the region of an antigen to which a binding agent binds. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5, about 9, or about 8-10 amino acids in a unique spatial conformation.

The terms "specific binding affinity" or "specifically binds" or "specifically bound" or "specific binding" or "specifically targets" as used herein, describe binding of an anti-BCMA antibody or antigen binding fragment thereof (or a CAR comprising the same) to BCMA (e.g., human BCMA) at greater binding affinity than background binding. A binding domain (or a CAR comprising a binding domain or a fusion protein containing a binding domain) "specifically binds" to a BCMA if it binds to or associates with BCMA with an affinity or $K_a$ (i.e., an equilibrium association constant of a particular binding interaction with units of 1/M) of, for example, greater than or equal to about $10^5$ $M^{-1}$. In certain embodiments, a binding domain (or a fusion protein thereof) binds to a target with a $K_a$ greater than or equal to about $10^6$ $M^{-1}$, $10^7$ $M^{-1}$, $10^8$ $M^{-1}$, $10^9$ $M^{-1}$, $10^{10}$ $M^{-1}$, $10^{11}$ $M^{-1}$, $10^{12}$ $M^{-1}$, or $10^{13}$ $M^{-1}$. "High affinity" binding domains (or single chain fusion proteins thereof) refers to those binding domains with a $K_a$ of at least $10^7$ $M^{-1}$, at least $10^8$ $M^{-1}$, at least $10^9$ $M^{-1}$, at least $10^{10}$ $M^{-1}$, at least $10^{11}$ $M^{-1}$, at least $10^{12}$ $M^{-1}$, at least $10^{13}$ $M^{-1}$, or greater.

Alternatively, affinity may be defined as an equilibrium dissociation constant ($K_d$) of a particular binding interaction with units of M (e.g., $10^{-5}$ M to $10^{13}$ $M^{-1}$, or less). Affinities of binding domain polypeptides and CAR proteins according to the present disclosure can be readily determined using conventional techniques, e.g., by competitive ELISA (enzyme-linked immunosorbent assay), or by binding association, or displacement assays using labeled ligands, or using a surface-plasmon resonance device such as the Biacore T100, which is available from Biacore, Inc., Piscataway, NJ, or optical biosensor technology such as the EPIC system or EnSpire that are available from Corning and Perkin Elmer respectively (see also, e.g., Scatchard et al. (1949) Ann. N.Y. Acad. Sci. 51:660; and U.S. Pat. Nos. 5,283,173; 5,468,614, or the equivalent).

In one embodiment, the affinity of specific binding is about 2 times greater than background binding, about 5 times greater than background binding, about 10 times greater than background binding, about 20 times greater than background binding, about 50 times greater than background binding, about 100 times greater than background binding, or about 1000 times greater than background binding or more.

In particular embodiments, the extracellular binding domain of a CAR comprises an antibody or antigen binding fragment thereof. In the context of a CAR, an "antibody" refers to a binding agent that is a polypeptide comprising at least a light chain or heavy chain immunoglobulin variable region which specifically recognizes and binds an epitope of an antigen, such as a peptide, lipid, polysaccharide, or nucleic acid containing an antigenic determinant, such as those recognized by an immune cell.

As would be understood by the skilled person and as described elsewhere herein, a complete antibody comprises two heavy chains and two light chains. Each heavy chain consists of a variable region and a first, second, and third constant region, while each light chain consists of a variable region and a constant region.

Light and heavy chain variable regions contain a "framework" region interrupted by three hypervariable regions, also called "complementarity-determining regions" or "CDRs." The CDRs can be defined or identified by conventional methods, such as by sequence according to Kabat et al (Wu, TT and Kabat, E. A., *J Exp Med.* 132(2):211-50, (1970); Borden, P. and Kabat E. A., PNAS, 84:2440-2443 (1987); (see, Kabat et al., *Sequences of Proteins of Immunological Interest*, U.S. Department of Health and Human Services, 1991, which is hereby incorporated by reference), or by structure according to Chothia et al (Chothia, C. and Lesk, A. M., *J Mol. Biol.,* 196 (4): 901-917 (1987), Chothia, C. et al, *Nature,* 342:877-883 (1989)).

Other boundaries defining CDRs overlapping with the Kabat CDRs have been described by Padlan (1995) *FASEB J.* 9:133-139 and MacCallum (1996) *J. Mol. Biol.* 262 (5): 732-45. Still other CDR boundary definitions may not strictly follow one of the herein systems, but will nonetheless overlap with the Kabat CDRs, although they may be shortened or lengthened in light of prediction or experimental findings that particular residues or groups of residues or even entire CDRs do not significantly impact antigen-binding. For example, the CDRs of an antibody can be determined according to the AbM numbering scheme, which refers AbM hypervariable regions, which represent a compromise between the Kabat CDRs and Chothia structural loops, and are used by Oxford Molecular's AbM antibody modeling software (Oxford Molecular Group, Inc.).

Additionally, the CDRs of an antibody can be determined according to the IMGT numbering system as described in Lefranc M-P, (1999) *The Immunologist* 7:132-136 and Lefranc M-P et al., (1999) *Nucleic Acids Res* 27:209-212.

Still other methods of CDR determination are disclosed in MacCallum R M et al., (1996) *J Mol Biol* 262:732-745. See also, e.g., Martin A. "Protein Sequence and Structure Analysis of Antibody Variable Domains," in Antibody Engineering, Kontermann and Dübel, eds., Chapter 31, pp. 422-439, Springer-Verlag, Berlin (2001). Proprietary and publicly available programs are known to those skilled in the art which can be used to determine CDRs base on any of the CDR definitions described herein, for example, ab Ysis (abysis.org/abysis/) and IMGT/V-QUEST (imgt.org/IMGT_vquest).

Illustrative examples of rules for predicting light chain CDRs include: CDRL1 starts at about residue 24, is preceded by a Cys, is about 10-17 residues, and is followed by a Trp (typically Trp-Tyr-Gln, but also, Trp-Leu-Gln, Trp-Phe-Gln, Trp-Tyr-Leu); CDRL2 starts about 16 residues after the end of CDRL1, is generally preceded by Ile-Tyr, but also, Val-Tyr, Ile-Lys, Ile-Phe, and is 7 residues; and CDRL3 starts about 33 residues after the end of CDRL2, is preceded by a Cys, is 7-11 residues, and is followed by Phe-Gly-XXX-Gly (SEQ ID NO: 108) (XXX is any amino acid).

Illustrative examples of rules for predicting heavy chain CDRs include: CDRH1 starts at about residue 26, is preceded by Cys-XXX-XXX-XXX (SEQ ID NO: 109), is 10-12 residues and is followed by a Trp (typically Trp-Val, but also, Trp-Ile, Trp-Ala); CDRH2 starts about 15 residues after the end of CDRH1, is generally preceded by Leu-Glu-Trp-Ile-Gly (SEQ ID NO: 110), or a number of variations, is 16-19 residues, and is followed by Lys/Arg-Leu/Ile/Val/Phe/Thr/Ala-Thr/Ser/Ile/Ala, AbM definition ends 7 residues earlier; and CDRH3 starts about 33 residues after the end of CDRH2, is preceded by Cys-XXX-XXX (typically Cys-Ala-Arg), is 3 to 25 residues, and is followed by Trp-Gly-XXX-Gly (SEQ ID NO: 111).

Accordingly, in certain embodiments, the instant disclosure provides an isolated antibody, antigen binding fragment thereof, that specifically binds to human BCMA protein and comprises a heavy chain variable region comprising the CDRL1, CDRL2, and CDRL3 region amino acid sequences set forth within variable light chain SEQ ID NOs: 7, 15, 23, 31, 39, or 47 and/or the CDRH1, CDRH2, and CDRH3 region amino acid sequences set forth within variable heavy chain SEQ ID NO: 8, 16, 24, 32, 40, or 48 wherein each CDR is defined in accordance with the Kabat definition, Chothia definition, the combination of the Kabat definition and the Chothia definition, the IMGT definition, the AbM definition, or the contact definition of a CDR. In some embodiments, the CDRs are defined in accordance with the Kabat definition. In some embodiments, the CDRs are defined in accordance with the Chothia definition. In some embodiments, the CDRs are defined in accordance with the AbM definition. In some embodiments, the CDRs are defined in accordance with the IMGT definition. In some embodiments, the CDRs are defined in accordance with the contact definition. In some embodiments, the CDRs are defined by a combination of any one of the above-mentioned CDR definitions.

Illustrative examples of light chain CDRs that are suitable for the antibodies, or antigen binding fragments thereof, contemplated herein include, but are not limited to the CDR sequences set forth in SEQ ID NOs: 1-3, 9-11, 17-19, 25-27, 33-35, or 41-43. Illustrative examples of heavy chain CDRs that are suitable for the antibodies, or antigen binding fragments thereof, contemplated herein include, but are not limited to the CDR sequences set forth in SEQ ID NOs: 4-6, 12-14, 20-22, 28-30, 36-38, or 44-46.

References to "$V_H$" or "VH" refer to the variable region of an immunoglobulin heavy chain, including that of an antibody, Fv, scFv, dsFv, Fab, or other antibody fragment as disclosed herein. References to "VL" or "VL" refer to the variable region of an immunoglobulin light chain, including that of an antibody, Fv, scFv, dsFv, Fab, or other antibody fragment as disclosed herein.

In particular embodiments, the antigen-specific binding domain is a scFv that binds a human BCMA polypeptide. Illustrative examples of variable heavy chains that are suitable for the antibodies or antigen binding fragments thereof contemplated herein include, but are not limited to the amino acid sequences set forth in SEQ ID NO: 8, 16, 24, 32, 40, and 48. Illustrative examples of variable light chains that are suitable for the antibodies or antigen binding fragments thereof contemplated herein include, but are not limited to the amino acid sequences set forth in SEQ ID NO: 7, 15, 23, 31, 39 and 47.

BCMA-specific binding domains provided herein also comprise one, two, three, four, five, or six CDRs. Such CDRs may be human or nonhuman CDRs or altered nonhuman CDRs selected from CDRL1, CDRL2 and CDRL3 of the light chain and CDRH1, CDRH2 and CDRH3 of the heavy chain. In certain embodiments, a BCMA-specific binding domain comprises (a) a light chain variable region that comprises a light chain CDRL1, a light chain CDRL2, and a light chain CDRL3, and (b) a heavy chain variable region that comprises a heavy chain CDRH1, a heavy chain CDRH2, and a heavy chain CDRH3. In preferred embodiments, the CDRs are human CDRs.

Illustrative examples of light chain CDRs that are suitable for the antibodies or antigen binding fragments thereof contemplated herein include, but are not limited to the CDR sequences set forth in SEQ ID NOs: 1-3, 9-11, 17-19, 25-27, 33-35 or 41-43. Illustrative examples of heavy chain CDRs that are suitable for the antibodies or antigen binding fragments thereof contemplated herein include, but are not limited to the CDR sequences set forth in SEQ ID NOs: 4-6, 12-14, 20-22, 28-30, 36-38, or .44-46.

In various embodiment, the antibody or antigen binding fragment thereof comprises one or more CDR sequences substantially similar to CDRH1, CDRH2, CDRH3, CDRL1, CDRL2, and/or CDRL3 as compared to a corresponding CDR region. For example, the antibody or antigen binding fragment thereof may include one or more CDR sequences (e.g., SEQ ID NOs: 1-6, 9-14, 17-22, 25-30, 33-38, or 41-46) each containing up to 1, 2, 3, 4, or 5 amino acid residue variations as compared to the corresponding CDR region in any one of SEQ ID NOs: 1-6, 9-14, 17-22, 25-30, 33-38, or 41-46.

As used herein, the phrase "amino acid variations" or "amino acid changes" or "changes in amino acid residues" refers to one or more amino acid differences compared to a reference sequence and includes amino acid modifications, substitutions, insertions, and/or deletions.

In one embodiment, the antibody or antigen binding fragment thereof comprises at least three CDRs selected from the following, optionally comprising up to 3 amino acid changes, for example 1, 2, or 3 amino acid changes for each of the CDRs: CDRL1: SEQ ID NO: 1; CDRL2: SEQ ID NO: 2; CDRL3: SEQ ID NO: 3; CDRH1: SEQ ID NO: 4; CDRH2: SEQ ID NO: 5; and CDRH3: SEQ ID NO: 6.

In one embodiment, the antibody or antigen binding fragment thereof comprises at least three CDRs selected from the following, optionally comprising up to 3 amino acid changes, for example 1, 2, or 3 amino acid changes for each of the CDRs: CDRL1: SEQ ID NO: 9; CDRL2: SEQ ID NO: 10; CDRL3: SEQ ID NO: 11; CDRH1: SEQ ID NO: 12; CDRH2: SEQ ID NO: 13; and CDRH3: SEQ ID NO: 14.

In one embodiment, the antibody or antigen binding fragment thereof comprises at least three CDRs selected from the following, optionally comprising up to 3 amino acid changes, for example 1, 2, or 3 amino acid changes for each of the CDRs: CDRL1: SEQ ID NO: 17; CDRL2: SEQ ID NO: 18; CDRL3: SEQ ID NO: 19; CDRH1: SEQ ID NO: 20; CDRH2: SEQ ID NO: 21; and CDRH3: SEQ ID NO: 22.

In one embodiment, the antibody or antigen binding fragment thereof comprises at least three CDRs selected from the following, optionally comprising up to 3 amino acid changes, for example 1, 2, or 3 amino acid changes for each of the CDRs: CDRL1: SEQ ID NO: 25; CDRL2: SEQ ID NO: 26; CDRL3: SEQ ID NO: 27; CDRH1: SEQ ID NO: 28; CDRH2: SEQ ID NO: 29; and CDRH3: SEQ ID NO: 30.

In one embodiment, the antibody or antigen binding fragment thereof comprises at least three CDRs selected from the following, optionally comprising up to 3 amino acid changes, for example 1, 2, or 3 amino acid changes for each of the CDRs: CDRL1: SEQ ID NO: 33; CDRL2: SEQ ID NO: 34; CDRL3: SEQ ID NO: 35; CDRH1: SEQ ID NO: 36; CDRH2: SEQ ID NO: 37; and CDRH3: SEQ ID NO: 38.

In one embodiment, the antibody or antigen binding fragment thereof comprises at least three CDRs selected from the following, optionally comprising up to 3 amino acid changes, for example 1, 2, or 3 amino acid changes for each of the CDRs: CDRL1: SEQ ID NO: 41; CDRL2: SEQ ID NO: 42; CDRL3: SEQ ID NO: 43; CDRH1: SEQ ID NO: 44; CDRH2: SEQ ID NO: 45; and CDRH3: SEQ ID NO: 46.

In some embodiments, the antibody or antigen binding fragment thereof comprises the light chain CDRL1, CDRL2, and CDRL3 sequences as set forth in SEQ ID NOs: 1, 2, and 3, respectively. In some embodiments, the antibody or antigen binding fragment thereof comprises the heavy chain CDRH1, CDRH2, and CDRH3 sequences as set forth in SEQ ID NOs: 4, 5, and 6, respectively. In a particular embodiment, the antibody or antigen binding fragment thereof comprises the light chain CDRL1, CDRL2, and CDRL3 sequences as set forth in SEQ ID NOs: 1, 2, and 3, respectively, and heavy chain CDRH1, CDRH2, and CDRH3 sequences as set forth in SEQ ID NOs: 4, 5, and 6, respectively.

In some embodiments, the antibody or antigen binding fragment thereof comprises the light chain CDRL1, CDRL2, and CDRL3 sequences as set forth in SEQ ID NOs: 9, 10, and 11, respectively. In some embodiments, the antibody or antigen binding fragment thereof comprises the heavy chain CDRH1, CDRH2, and CDRH3 sequences as set forth in SEQ ID NOs: 12, 13, and 14, respectively. In a particular embodiment, the antibody or antigen binding fragment thereof comprises the light chain CDRL1, CDRL2, and CDRL3 sequences as set forth in SEQ ID NOs: 9, 10, and 11, respectively, and heavy chain CDRH1, CDRH2, and CDRH3 sequences as set forth in SEQ ID NOs: 12, 13, and 14, respectively.

In some embodiments, the antibody or antigen binding fragment thereof comprises the light chain CDRL1, CDRL2, and CDRL3 sequences as set forth in SEQ ID NOs: 17, 18, and 19, respectively. In some embodiments, the antibody or antigen binding fragment thereof comprises the heavy chain CDRH1, CDRH2, and CDRH3 sequences as set forth in SEQ ID NOs: 20, 21, and 22, respectively. In a particular embodiment, the antibody or antigen binding fragment thereof comprises the light chain CDRL1, CDRL2, and CDRL3 sequences as set forth in SEQ ID NOs: 17, 18, and 19, respectively, and heavy chain CDRH1, CDRH2, and CDRH3 sequences as set forth in SEQ ID NOs: 20, 21, and 22, respectively.

In some embodiments, the antibody or antigen binding fragment thereof comprises the light chain CDRL1, CDRL2, and CDRL3 sequences as set forth in SEQ ID NOs: 25, 26, and 27, respectively. In some embodiments, the antibody or antigen binding fragment thereof comprises the heavy chain CDRH1, CDRH2, and CDRH3 sequences as set forth in SEQ ID NOs: 28, 29, and 30, respectively. In a particular embodiment, the antibody or antigen binding fragment thereof comprises the light chain CDRL1, CDRL2, and CDRL3 sequences as set forth in SEQ ID NOs: 25, 26, and 27, respectively, and heavy chain CDRH1, CDRH2, and CDRH3 sequences as set forth in SEQ ID NOs: 28, 29, and 30, respectively.

In some embodiments, the antibody or antigen binding fragment thereof comprises the light chain CDRL1, CDRL2, and CDRL3 sequences as set forth in SEQ ID NOs: 33, 34, and 35, respectively. In some embodiments, the antibody or antigen binding fragment thereof comprises the heavy chain CDRH1, CDRH2, and CDRH3 sequences as set forth in SEQ ID NOs: 36, 37, and 38, respectively. In a particular embodiment, the antibody or antigen binding fragment thereof comprises the light chain CDRL1, CDRL2, and CDRL3 sequences as set forth in SEQ ID NOs: 33, 34, and 35, respectively, and heavy chain CDRH1, CDRH2, and CDRH3 sequences as set forth in SEQ ID NOs: 36, 37, and 38, respectively.

In some embodiments, the antibody or antigen binding fragment thereof comprises the light chain CDRL1, CDRL2, and CDRL3 sequences as set forth in SEQ ID NOs: 41, 42, and –43, respectively. In some embodiments, the antibody or antigen binding fragment thereof comprises the heavy chain CDRH1, CDRH2, and CDRH3 sequences as set forth in SEQ ID NOs: 44, 45, and 46, respectively. In a particular embodiment, the antibody or antigen binding fragment thereof comprises the light chain CDRL1, CDRL2, and CDRL3 sequences as set forth in SEQ ID NOs: 41, 42, and 43, respectively, and heavy chain CDRH1, CDRH2, and CDRH3 sequences as set forth in SEQ ID NOs: 44, 45, and 46, respectively.

Aspects of the invention relate to antibodies or antigen binding fragments thereof that selectively binds to human BCMA comprising a heavy chain variable region sequence and a light chain variable region sequence.

In various embodiments, the antibody or antigen binding fragment thereof comprises a light chain variable region having an amino acid sequence that is at least 85%, 86%, 87%, 88%, 89%, 90%, 91%, 92%, 93%, 94%, 95%, 96%, 97%, 98% or 99% identical to SEQ ID NO: 7, 15, 23, 31, 39, or 47. In one embodiment, the antibody, or antigen-binding fragment thereof, comprises a heavy chain variable region having an amino acid sequence that is at least 85%, 86%, 87%, 88%, 89%, 90%, 91%, 92%, 93%, 94%, 95%, 96%, 97%, 98% or 99% identical to SEQ ID NO: 8, 16, 24, 32, 40, or 48.

In one embodiment, the antibody or antigen binding fragment thereof comprises a light chain variable region having an amino acid sequence that is at least 85%, 86%, 87%, 88%, 89%, 90%, 91%, 92%, 93%, 94%, 95%, 96%, 97%, 98% or 99% identical to SEQ ID NO: 7 and/or a heavy chain variable region having an amino acid sequence that is at least 85%, 86%, 87%, 88%, 89%, 90%, 91%, 92%, 93%, 94%, 95%, 96%, 97%, 98% or 99% identical to SEQ ID NO: 8.

In one embodiment, the antibody or antigen binding fragment thereof comprises a light chain variable region having an amino acid sequence that is at least 85%, 86%, 87%, 88%, 89%, 90%, 91%, 92%, 93%, 94%, 95%, 96%, 97%, 98% or 99% identical to SEQ ID NO: 15 and/or a heavy chain variable region having an amino acid sequence that is at least 85%, 86%, 87%, 88%, 89%, 90%, 91%, 92%, 93%, 94%, 95%, 96%, 97%, 98% or 99% identical to SEQ ID NO: 16.

In one embodiment, the antibody or antigen binding fragment thereof comprises a light chain variable region having an amino acid sequence that is at least 85%, 86%, 87%, 88%, 89%, 90%, 91%, 92%, 93%, 94%, 95%, 96%, 97%, 98% or 99% identical to SEQ ID NO: 23 and/or a heavy chain variable region having an amino acid sequence that is at least 85%, 86%, 87%, 88%, 89%, 90%, 91%, 92%, 93%, 94%, 95%, 96%, 97%, 98% or 99% identical to SEQ ID NO: 24.

In one embodiment, the antibody or antigen binding fragment thereof comprises a light chain variable region having an amino acid sequence that is at least 85%, 86%, 87%, 88%, 89%, 90%, 91%, 92%, 93%, 94%, 95%, 96%, 97%, 98% or 99% identical to SEQ ID NO: 31 and/or a heavy chain variable region having an amino acid sequence that is at least 85%, 86%, 87%, 88%, 89%, 90%, 91%, 92%, 93%, 94%, 95%, 96%, 97%, 98% or 99% identical to SEQ ID NO: 32.

In one embodiment, the antibody or antigen binding fragment thereof comprises a light chain variable region having an amino acid sequence that is at least 85%, 86%, 87%, 88%, 89%, 90%, 91%, 92%, 93%, 94%, 95%, 96%, 97%, 98% or 99% identical to SEQ ID NO: 39 and/or a heavy chain variable region having an amino acid sequence that is at least 85%, 86%, 87%, 88%, 89%, 90%, 91%, 92%, 93%, 94%, 95%, 96%, 97%, 98% or 99% identical to SEQ ID NO: 40.

In one embodiment, the antibody or antigen binding fragment thereof comprises a light chain variable region having an amino acid sequence that is at least 85%, 86%, 87%, 88%, 89%, 90%, 91%, 92%, 93%, 94%, 95%, 96%, 97%, 98% or 99% identical to SEQ ID NO: 47 and/or a heavy chain variable region having an amino acid sequence that is at least 85%, 86%, 87%, 88%, 89%, 90%, 91%, 92%, 93%, 94%, 95%, 96%, 97%, 98% or 99% identical to SEQ ID NO: 48.

In some embodiments, the light chain variable region and/or the heavy chain variable region sequences do not vary within any of the CDR sequences provided herein. For example, in some embodiments, the degree of sequence variation (e.g., 85%, 86%, 87%, 88%, 89%, 90%, 91%, 92%, 93%, 94%, 95%, 96%, 97%, 98%, or 99%) may occur within a heavy chain variable and/or a light chain variable amino acid sequence excluding any of the CDR sequences provided herein.

In some embodiments, the "percent identity" of two amino acid sequences is determined using the algorithm of Karlin and Altschul *Proc. Natl. Acad. Sci. USA* 87:2264-68, 1990, modified as in Karlin and Altschul *Proc. Natl. Acad. Sci. USA* 90:5873-77, 1993. Such an algorithm is incorporated into the NBLAST and XBLAST programs (version 2.0) of Altschul, et al., *J. Mol. Biol.* 215:403-10, 1990. BLAST protein searches can be performed with the XBLAST program, score=50, word length=3 to obtain amino acid sequences homologous to the protein molecules of interest. Where gaps exist between two sequences, Gapped BLAST can be utilized as described in Altschul et al., *Nucleic Acids Res.* 25 (17): 3389-3402, 1997. When utilizing BLAST and Gapped BLAST programs, the default parameters of the respective programs (e.g., XBLAST and NBLAST) can be used.

In various embodiments, the antibody or antigen binding fragment thereof comprises a light chain variable domain comprising an amino acid sequence set forth in SEQ ID NO: 7 and/or a heavy chain variable domain comprising an amino acid sequence set forth in SEQ ID NO: 8.

In various embodiments, the antibody or antigen binding fragment thereof comprises a light chain variable domain comprising an amino acid sequence set forth in SEQ ID NO: 15 and/or a heavy chain variable domain comprising an amino acid sequence set forth in SEQ ID NO: 16.

In various embodiments, the antibody or antigen binding fragment thereof comprises a light chain variable domain comprising an amino acid sequence set forth in SEQ ID NO: 23 and/or a heavy chain variable domain comprising an amino acid sequence set forth in SEQ ID NO: 24.

In various embodiments, the antibody or antigen binding fragment thereof comprises a light chain variable domain comprising an amino acid sequence set forth in SEQ ID NO: 31 and/or a heavy chain variable domain comprising an amino acid sequence set forth in SEQ ID NO: 32.

In various embodiments, the antibody or antigen binding fragment thereof comprises a light chain variable domain comprising an amino acid sequence set forth in SEQ ID NO: 39 and/or a heavy chain variable domain comprising an amino acid sequence set forth in SEQ ID NO: 40.

In various embodiments, the antibody or antigen binding fragment thereof comprises a light chain variable domain comprising an amino acid sequence set forth in SEQ ID NO: 47 and/or a heavy chain variable domain comprising an amino acid sequence set forth in SEQ ID NO: 48.

In any of the antibody or antigen binding fragment thereof contemplated herein, one or more conservative mutations can be introduced into the CDRs or framework sequences at positions where the residues are not likely to be involved in an antibody-antigen interaction. In some embodiments, such conservative mutation(s) can be introduced into the CDRs or framework sequences at position(s) where the residues are not likely to be involved in interacting with a BCMA, as determined based on the crystal structure. In some embodiments, the likely interface (e.g., residues involved in an antigen-antibody interaction) may be deduced from known structural information on other antigens sharing structural similarities.

In various embodiments, the disclosure provides an antibody, or antigen-binding fragment thereof, that competes for binding with an antibody, or antigen-binding fragment thereof, contemplated herein. In one embodiment, the disclosure provides an antibody, or antigen-binding fragment thereof, that binds to the same epitope as an antibody, or antigen-binding fragment thereof, contemplated herein.

Aspects of the disclosure relate to antibodies that compete or cross-compete with any of the specific antibodies, or antigen-binding fragments thereof, as provided herein, e.g., an antibody having one or more CDR sequences (1, 2, 3, 4, 5, or 6 CDR sequences) as described above. In one embodiment, the disclosure provides antibodies, and antigen-binding fragments thereof, that compete or cross-compete with an antibody having light chain CDR sequences as set forth in SEQ ID NOs: 1-3, 9-11, 17-19, 25-27, 33-35, or 41-43 and/or heavy chain CDR sequences as set forth in SEQ ID NOs: 4-6, 12-14, 20-22, 28-30, 36-38, or 44-46. In one embodiment, the disclosure provides antibodies that compete or cross-compete with an antibody, or antigen binding fragment thereof, having a light chain variable region sequence comprising SEQ ID NO: 7, 15, 23, 31, 39, or 47 and/or a heavy chain variable region sequence comprising SEQ ID NO: 8, 16, 24, 32, 40, or 48.

In one embodiment, the disclosure provides antibodies, and antigen-binding fragments thereof, that compete or cross-compete with an antibody having light chain CDR sequences as set forth in SEQ ID NOs: 1-3, and/or heavy chain CDR sequences as set forth in SEQ ID NOs: 4-6. In one embodiment, the disclosure provides antibodies that compete or cross-compete with an antibody, or antigen-binding fragment thereof, having a light chain variable region sequence comprising SEQ ID NO: 7, and/or a heavy chain variable region sequence comprising SEQ ID NO: 8.

In one embodiment, the disclosure provides antibodies, and antigen-binding fragments thereof, that compete or cross-compete with an antibody having light chain CDR sequences as set forth in SEQ ID NOs: 9-11, and/or heavy chain CDR sequences as set forth in SEQ ID NOs: 12-14. In one embodiment, the disclosure provides antibodies that compete or cross-compete with an antibody, or antigen-binding fragment thereof, having a light chain variable region sequence comprising SEQ ID NO: 15, and/or a heavy chain variable region sequence comprising SEQ ID NO: 16.

In one embodiment, the disclosure provides antibodies, and antigen-binding fragments thereof, that compete or cross-compete with an antibody having light chain CDR sequences as set forth in SEQ ID NOs: 17-19, and/or heavy chain CDR sequences as set forth in SEQ ID NOs: 20-22. In one embodiment, the disclosure provides antibodies that compete or cross-compete with an antibody, or antigen-binding fragment thereof, having a light chain variable region sequence comprising SEQ ID NO: 23, and/or a heavy chain variable region sequence comprising SEQ ID NO: 24.

In one embodiment, the disclosure provides antibodies, and antigen-binding fragments thereof, that compete or cross-compete with an antibody having light chain CDR sequences as set forth in SEQ ID NOs: 25-27, and/or heavy chain CDR sequences as set forth in SEQ ID NOs: 28-30. In one embodiment, the disclosure provides antibodies that compete or cross-compete with an antibody, or antigen-binding fragment thereof, having a light chain variable region sequence comprising SEQ ID NO: 31, and/or a heavy chain variable region sequence comprising SEQ ID NO: 32.

In one embodiment, the disclosure provides antibodies, and antigen-binding fragments thereof, that compete or cross-compete with an antibody having light chain CDR sequences as set forth in SEQ ID NOs: 33-35, and/or heavy chain CDR sequences as set forth in SEQ ID NOs: 36-38. In one embodiment, the disclosure provides antibodies that compete or cross-compete with an antibody, or antigen-binding fragment thereof, having a light chain variable region sequence comprising SEQ ID NO: 39, and/or a heavy chain variable region sequence comprising SEQ ID NO: 40.

In one embodiment, the disclosure provides antibodies, and antigen-binding fragments thereof, that compete or cross-compete with an antibody having light chain CDR sequences as set forth in SEQ ID NOs: 41-43, and/or heavy chain CDR sequences as set forth in SEQ ID NOs: 44-46. In one embodiment, the disclosure provides antibodies that compete or cross-compete with an antibody, or antigen-binding fragment thereof, having a light chain variable region sequence comprising SEQ ID NO: 47, and/or a heavy chain variable region sequence comprising SEQ ID NO: 48.

In some embodiments, an antibody or antigen-binding fragment thereof, binds at or near the same epitope as any of the antibodies provided herein. In some embodiments, an antibody, or antigen-binding fragment thereof, binds near an epitope if it binds within 15 or fewer amino acid residues of the epitope. In some embodiments, any of the antibody, or antigen-binding fragment thereof, as provided herein, binds within 1, 2, 3, 4, 5, 6, 7, 8, 9, 10, 11, 12, 13, 14 or 15 amino acid residues of an epitope that is bound by any of the antibodies provided herein.

In another embodiment, provided herein is an antibody or antigen-binding fragment thereof that competes or cross-competes for binding to any of the antigens provided herein (e.g., a human BCMA) with an equilibrium dissociation constant, $K_D$, between the antibody and the protein of less than $10^{-8}$ M. In other embodiments, an antibody competes or cross-competes for binding to BCMA with a $K_D$ in a range from $10^{-11}$ M to $10^{-8}$ M. In some embodiments, provided herein is an BCMA-specific antibody, or antigen-binding fragment thereof, that competes for binding with an antibody, or antigen-binding fragment thereof, contemplated herein. In some embodiments, provided herein is an BCMA-specific antibody, or antigen-binding fragment thereof, that binds to the same epitope as an antibody, or antigen-binding fragment thereof, contemplated herein.

The antibodies provided herein can be characterized using any suitable methods. For example, one method is to identify the epitope to which the antigen binds, or "epitope mapping." There are many suitable methods for mapping and characterizing the location of epitopes on proteins, including solving the crystal structure of an antibody-antigen complex, competition assays, gene fragment expression assays, and synthetic peptide-based assays, as described, for example, in Chapter 11 of Harlow and Lane, Using Antibodies, a Laboratory Manual, Cold Spring Harbor Laboratory Press, Cold Spring Harbor, N.Y., 1999. In an additional example, epitope mapping can be used to determine the sequence to which an antibody binds. The epitope can be a linear epitope, i.e., contained in a single stretch of amino acids, or a conformational epitope formed by a three-dimensional interaction of amino acids that may not necessarily be contained in a single stretch (primary structure linear sequence).

Peptides of varying lengths (e.g., at least 4-19 amino acids long) can be isolated or synthesized (e.g., recombinantly) and used for binding assays with an antibody. In another example, the epitope to which the antibody binds can be determined in a systematic screen by using overlapping peptides derived from the target antigen sequence and determining binding by the antibody. According to the gene fragment expression assays, the open reading frame encoding the target antigen is fragmented either randomly or by specific genetic constructions and the reactivity of the expressed fragments of the antigen with the antibody to be tested is determined. The gene fragments may, for example, be produced by PCR and then transcribed and translated into protein in vitro, in the presence of radioactive amino acids. The binding of the antibody to the radioactively labeled antigen fragments is then determined by immunoprecipitation and gel electrophoresis. Certain epitopes can also be identified by using large libraries of random peptide sequences displayed on the surface of phage particles (phage libraries). Alternatively, a defined library of overlapping peptide fragments can be tested for binding to the test antibody in simple binding assays. In an additional example, mutagenesis of an antigen-binding domain, domain swapping experiments and alanine scanning mutagenesis can be performed to identify residues required, sufficient, and/or necessary for epitope binding. For example, domain swapping experiments can be performed using a mutant of a target antigen in which various fragments of BCMA have been replaced (swapped) with sequences from a closely related, but antigenically distinct protein, such as another member of the BCMA protein family. By assessing binding of the antibody to the mutant BCMA, the importance of the particular antigen fragment to antibody binding can be assessed.

Alternatively, competition assays can be performed using other antibodies known to bind to the same antigen to determine whether an antibody binds to the same epitope as the other antibodies. Competition assays are well known to those of skill in the art.

Further, the interaction of the any of the antibodies provided herein with one or more residues in BCMA can be determined by routine technology. For example, a crystal structure can be determined, and the distances between the residues in BCMA, and one or more residues in the antibody (or antigen-binding fragment), can be determined accordingly. Based on such distance, whether a specific residue in BCMA interacts with one or more residues in the antibody can be determined. Further, suitable methods, such as competition assays and target mutagenesis assays, can be applied to determine the preferential binding of a candidate antibody.

In some embodiments, the antibodies, or antigen-binding fragments thereof, of the present disclosure that selectively bind to BCMA include one or more of complementary determining regions (CDRs) as contemplated herein. In some embodiments, the disclosure provides a nucleic acid molecule that encodes an antibody, or antigen-binding fragment thereof, that selectively binds to a BCMA, as contemplated herein. In one embodiment, the nucleic acid molecules encode one or more of the CDR sequences as contemplated herein.

D. Chimeric Antigen Receptors

In various embodiments, improved genetically engineered receptors that redirect cytotoxicity of immune effector cells toward BCMA-expressing cells (e.g., B cells) are provided. These genetically engineered receptors referred to herein as chimeric antigen receptors (CARs). CARs are molecules that combine antibody-based specificity for a desired antigen (e.g., BCMA) with a T cell receptor-activating intracellular domain to generate a chimeric protein that exhibits a specific anti-BCMA cellular immune activity. As used herein, the term, "chimeric," describes being composed of parts of different proteins or DNAs from different origins.

CARs contemplated herein, comprise an extracellular domain (also referred to as a binding domain or antigen-specific binding domain) that binds to BCMA, a transmembrane domain, and an intracellular signaling domain. Engagement of the anti-BCMA antigen binding domain of the CAR with BCMA on the surface of a target cell results in clustering of the CAR and delivers an activation stimulus to the CAR-containing cell. The main characteristic of CARs is their ability to redirect immune effector cell specificity, thereby triggering proliferation, cytokine production, phagocytosis or production of molecules that can mediate cell death of the target antigen expressing cell in a major histocompatibility (MHC) independent manner, exploiting the cell specific targeting abilities of monoclonal antibodies, soluble ligands or cell specific co-receptors.

In various embodiments, a CAR comprises an extracellular binding domain that comprises an anti-BCMA-specific binding domain; a transmembrane domain; one or more intracellular co-stimulatory signaling domains; and a primary signaling domain.

In particular embodiments, a CAR comprises an extracellular binding domain that comprises an anti-BCMA antibody or antigen binding fragment thereof; one or more hinge domains or spacer domains; a transmembrane domain including; one or more intracellular co-stimulatory signaling domains; and a primary signaling domain.

1. Binding Domain

In particular embodiments, CARs contemplated herein comprise an extracellular binding domain that comprises an anti-BCMA antibody or antigen binding fragment thereof that specifically binds to a human BCMA polypeptide expressed on a B cell. In some embodiments, the antibody or antigen binding fragment thereof specifically binds one or more epitopes of a human BCMA polypeptide. In particular embodiments, the anti-BCMA antibody or antigen binding fragment is a human antibody or antigen binding fragment. In various embodiments, the CARs comprise an anti-BCMA antibody or antigen binding fragment as contemplated herein.

As used herein, the terms, "binding domain," "extracellular domain," "extracellular binding domain," "antigen-specific binding domain," and "extracellular antigen specific binding domain," are used interchangeably and provide a CAR with the ability to specifically bind to the target antigen of interest, e.g., BCMA. The binding domain may be derived either from a natural, synthetic, semi-synthetic, or recombinant source.

In particular embodiments, a CAR contemplated herein comprises antigen-specific binding domain that is a scFv. In various embodiments, the scFv domains are present in a single polypeptide chain and in either orientation (e.g., VL-VH or VH-VL). For example, in some embodiments, the scFv variable light chain is positioned c-terminal to that of the variable heavy chain. In other embodiments, the scFv variable heavy chain is positioned c-terminal to that of the variable light chain. See, e.g., FIG. 1. Generally, the scFv polypeptide further comprises a polypeptide linker between the VH and VL domains which enables the scFv to form the desired structure for antigen binding.

Illustrative examples of variable heavy (VH) chains that are suitable for constructing BCMA CARs contemplated herein include, but are not limited to the amino acid sequences set forth in SEQ ID NO: 8, 16, 24, 32, 40, and 48. Illustrative examples of variable light (VL) chains that are suitable for constructing BCMA CARs contemplated herein include, but are not limited to the amino acid sequences set forth in SEQ ID NO: 7, 15, 23, 31, 39, and 47.

BCMA-specific binding domains provided herein also comprise one, two, three, four, five, or six CDRs. Such CDRs may be nonhuman CDRs or altered nonhuman CDRs selected from CDRL1, CDRL2 and CDRL3 of the light chain and CDRH1, CDRH2 and CDRH3 of the heavy chain. In certain embodiments, a BCMA-specific binding domain comprises (a) a light chain variable region that comprises a light chain CDRL1, a light chain CDRL2, and a light chain CDRL3, and (b) a heavy chain variable region that comprises a heavy chain CDRH1, a heavy chain CDRH2, and a heavy chain CDRH3.

Accordingly, in certain embodiments, the instant disclosure provides a CAR extracellular binding domain, that specifically binds to human BCMA protein and comprises a heavy chain variable region comprising the CDRL1, CDRL2, and CDRL3 region amino acid sequences set forth within variable light chain SEQ ID NOs: 7, 15, 23, 31, 39, or 47 and/or the CDRH1, CDRH2, and CDRH3 region amino acid sequences set forth within variable heavy chain SEQ ID NO: 8, 16, 24, 32, 40, or 48. In particular embodiments, each CDR is defined in accordance with the Kabat definition, Chothia definition, the combination of the Kabat definition and the Chothia definition, the IMGT definition, the AbM definition, or the contact definition of a CDR. In some embodiments, the CDRs are defined in accordance with the Kabat definition. In some embodiments, the CDRs are defined in accordance with the Chothia definition. In some embodiments, the CDRs are defined in accordance with the AbM definition. In some embodiments, the CDRs are defined in accordance with the IMGT definition. In some embodiments, the CDRs are defined in accordance with the contact definition. In some embodiments, the CDRs are defined by a combination of any one of the above-mentioned CDR definitions.

Illustrative examples of light chain CDRs that are suitable for constructing humanized BCMA CARs contemplated herein include, but are not limited to the CDR sequences set forth in SEQ ID NOs: 1-3, 9-11, 17-19, 25-27, 33-35, or 41-43. Illustrative examples of heavy chain CDRs that are suitable for constructing humanized BCMA CARs contemplated herein include, but are not limited to the CDR sequences set forth in SEQ ID NOs: 4-6, 12-14, 20-22, 28-30, 36-38, or 44-46.

In various embodiment, the BCMA-specific binding domain comprises one or more CDR sequences substantially similar to CDRH1, CDRH2, CDRH3, CDRL1, CDRL2, and/or CDRL3 as compared to a corresponding CDR region. For example, the BCMA-specific binding domain may include one or more CDR sequences (e.g., SEQ ID NOs: 1-6, 9-14, 17-22, 25-30, 33-38, or 41-46) each containing up to 1, 2, 3, 4, or, 5 amino acid residue variations as compared to the corresponding CDR region in any one of SEQ ID NOs: 1-6, 9-14, 17-22, 25-30, 33-38, or 41-46.

As used herein, the phrase "amino acid variations" or "amino acid changes" or "changes in amino acid residues" includes amino acid substitutions and/or deletions.

In one embodiment, the BCMA-specific binding domain comprises at least three CDRs selected from the following, optionally comprising up to 3 amino acid changes, for example 1, 2, or 3 amino acid changes for each of the CDRs: CDRL1: SEQ ID NO: 1; CDRL2: SEQ ID NO: 2; CDRL3: SEQ ID NO: 3; CDRH1: SEQ ID NO: 4; CDRH2: SEQ ID NO: 5; and CDRH3: SEQ ID NO: 6.

In one embodiment, the BCMA-specific binding domain comprises at least three CDRs selected from the following, optionally comprising up to 3 amino acid changes, for example 1, 2, or 3 amino acid changes for each of the CDRs: CDRL1: SEQ ID NO: 9; CDRL2: SEQ ID NO: 10; CDRL3: SEQ ID NO: 11; CDRH1: SEQ ID NO: 12; CDRH2: SEQ ID NO: 13; and CDRH3: SEQ ID NO: 14.

In one embodiment, the BCMA-specific binding domain comprises at least three CDRs selected from the following, optionally comprising up to 3 amino acid changes, for example 1, 2, or 3 amino acid changes for each of the CDRs: CDRL1: SEQ ID NO: 17; CDRL2: SEQ ID NO: 18; CDRL3: SEQ ID NO: 19; CDRH1: SEQ ID NO: 20; CDRH2: SEQ ID NO: 21; and CDRH3: SEQ ID NO: 22.

In one embodiment, the BCMA-specific binding domain comprises at least three CDRs selected from the following, optionally comprising up to 3 amino acid changes, for example 1, 2, or 3 amino acid changes for each of the CDRs: CDRL1: SEQ ID NO: 25; CDRL2: SEQ ID NO: 26; CDRL3: SEQ ID NO: 27; CDRH1: SEQ ID NO: 28; CDRH2: SEQ ID NO: 29; and CDRH3: SEQ ID NO: 30.

In one embodiment, the BCMA-specific binding domain comprises at least three CDRs selected from the following, optionally comprising up to 3 amino acid changes, for example 1, 2, or 3 amino acid changes for each of the CDRs: CDRL1: SEQ ID NO: 33; CDRL2: SEQ ID NO: 34; CDRL3: SEQ ID NO: 35; CDRH1: SEQ ID NO: 36; CDRH2: SEQ ID NO: 37; and CDRH3: SEQ ID NO: 38.

In one embodiment, the BCMA-specific binding domain comprises at least three CDRs selected from the following, optionally comprising up to 3 amino acid changes, for example 1, 2, or 3 amino acid changes for each of the CDRs: CDRL1: SEQ ID NO: 41; CDRL2: SEQ ID NO: 42; CDRL3: SEQ ID NO: 43; CDRH1: SEQ ID NO: 44; CDRH2: SEQ ID NO: 45; and CDRH3: SEQ ID NO: 46.

In some embodiments, the BCMA-specific binding domain comprises the light chain CDRL1, CDRL2, and CDRL3 sequences as set forth in SEQ ID NOs: 1, 2, and 3, respectively. In some embodiments, the BCMA-specific binding domain comprises the heavy chain CDRH1, CDRH2, and CDRH3 sequences as set forth in SEQ ID NOs: 4, 5, and 6, respectively. In a particular embodiment, the BCMA-specific binding domain comprises the light chain CDRL1, CDRL2, and CDRL3 sequences as set forth in SEQ ID NOs: 1, 2, and 3, respectively, and heavy chain CDRH1, CDRH2, and CDRH3 sequences as set forth in SEQ ID NOs: 4, 5, and 6, respectively.

In some embodiments, the BCMA-specific binding domain comprises the light chain CDRL1, CDRL2, and CDRL3 sequences as set forth in SEQ ID NOs: 9, 10, and 11, respectively. In some embodiments, the BCMA-specific binding domain comprises the heavy chain CDRH1, CDRH2, and CDRH3 sequences as set forth in SEQ ID NOs: 12, 13, and 14, respectively. In a particular embodiment, the BCMA-specific binding domain comprises the light chain CDRL1, CDRL2, and CDRL3 sequences as set forth in SEQ ID NOs: 9, 10, and 11, respectively, and heavy chain CDRH1, CDRH2, and CDRH3 sequences as set forth in SEQ ID NOs: 12, 13, and 14, respectively.

In some embodiments, the BCMA-specific binding domain comprises the light chain CDRL1, CDRL2, and CDRL3 sequences as set forth in SEQ ID NOs: 17, 18, and 19, respectively. In some embodiments, the BCMA-specific binding domain comprises the heavy chain CDRH1, CDRH2, and CDRH3 sequences as set forth in SEQ ID NOs: 20, 21, and 22, respectively. In a particular embodiment, the BCMA-specific binding domain comprises the light chain CDRL1, CDRL2, and CDRL3 sequences as set forth in SEQ ID NOs: 17, 18, and 19, respectively, and heavy chain CDRH1, CDRH2, and CDRH3 sequences as set forth in SEQ ID NOs: 20, 21, and 22, respectively.

In some embodiments, the BCMA-specific binding domain comprises the light chain CDRL1, CDRL2, and CDRL3 sequences as set forth in SEQ ID NOs: 25, 26, and 27, respectively. In some embodiments, the BCMA-specific binding domain comprises the heavy chain CDRH1, CDRH2, and CDRH3 sequences as set forth in SEQ ID NOs: 28, 29, and 30, respectively. In a particular embodiment, the BCMA-specific binding domain comprises the light chain CDRL1, CDRL2, and CDRL3 sequences as set forth in SEQ ID NOs: 25, 26, and 27, respectively, and heavy chain CDRH1, CDRH2, and CDRH3 sequences as set forth in SEQ ID NOs: 28, 29, and 30, respectively.

In some embodiments, the BCMA-specific binding domain comprises the light chain CDRL1, CDRL2, and CDRL3 sequences as set forth in SEQ ID NOs: 33, 34, and 35, respectively. In some embodiments, the BCMA-specific binding domain comprises the heavy chain CDRH1, CDRH2, and CDRH3 sequences as set forth in SEQ ID NOs: 36, 37, and 38, respectively. In a particular embodiment, the BCMA-specific binding domain comprises the light chain CDRL1, CDRL2, and CDRL3 sequences as set forth in SEQ ID NOs: 33, 34, and 35, respectively, and heavy chain CDRH1, CDRH2, and CDRH3 sequences as set forth in SEQ ID NOs: 36, 37, and 38, respectively.

In some embodiments, the BCMA-specific binding domain comprises the light chain CDRL1, CDRL2, and CDRL3 sequences as set forth in SEQ ID NOs: 41, 42, and 43, respectively. In some embodiments, the BCMA-specific binding domain comprises the heavy chain CDRH1, CDRH2, and CDRH3 sequences as set forth in SEQ ID NOs: 44, 45, and 46, respectively. In a particular embodiment, the BCMA-specific binding domain comprises the light chain CDRL1, CDRL2, and CDRL3 sequences as set forth in SEQ ID NOs: 41, 42, and 43, respectively, and heavy chain CDRH1, CDRH2, and CDRH3 sequences as set forth in SEQ ID NOs: 44, 45, and 46, respectively.

Aspects of the disclosure relate to CARs that comprise an extracellular binding domain that selectively binds to human BCMA (a BCMA-specific binding domain) comprising a heavy chain variable region sequence and a light chain variable region sequence.

In various embodiments, the BCMA-specific binding domain comprises a light chain variable region having an amino acid sequence that is at least 85%, 86%, 87%, 88%, 89%, 90%, 91%, 92%, 93%, 94%, 95%, 96%, 97%, 98% or 99% identical to SEQ ID NO: 7, 15, 23, 31, 39, or 47. In one embodiment, the antibody, or antigen-binding fragment thereof, comprises a heavy chain variable region having an amino acid sequence that is at least 85%, 86%, 87%, 88%, 89%, 90%, 91%, 92%, 93%, 94%, 95%, 96%, 97%, 98% or 99% identical to SEQ ID NO: 8, 16, 24, 32, 40, or 48.

In one embodiment, the BCMA-specific binding domain comprises a light chain variable region having an amino acid sequence that is at least 85%, 86%, 87%, 88%, 89%, 90%, 91%, 92%, 93%, 94%, 95%, 96%, 97%, 98% or 99% identical to SEQ ID NO: 7 and/or a heavy chain variable region having an amino acid sequence that is at least 85%, 86%, 87%, 88%, 89%, 90%, 91%, 92%, 93%, 94%, 95%, 96%, 97%, 98% or 99% identical to SEQ ID NO: 8.

In one embodiment, the BCMA-specific binding domain, comprises a light chain variable region having an amino acid sequence that is at least 85%, 86%, 87%, 88%, 89%, 90%, 91%, 92%, 93%, 94%, 95%, 96%, 97%, 98% or 99% identical to SEQ ID NO: 15 and/or a heavy chain variable region having an amino acid sequence that is at least 85%, 86%, 87%, 88%, 89%, 90%, 91%, 92%, 93%, 94%, 95%, 96%, 97%, 98% or 99% identical to SEQ ID NO: 16.

In one embodiment, the BCMA-specific binding domain comprises a light chain variable region having an amino acid sequence that is at least 85%, 86%, 87%, 88%, 89%, 90%, 91%, 92%, 93%, 94%, 95%, 96%, 97%, 98% or 99% identical to SEQ ID NO: 23 and/or a heavy chain variable region having an amino acid sequence that is at least 85%, 86%, 87%, 88%, 89%, 90%, 91%, 92%, 93%, 94%, 95%, 96%, 97%, 98% or 99% identical to SEQ ID NO: 24.

In one embodiment, the BCMA-specific binding domain comprises a light chain variable region having an amino acid sequence that is at least 85%, 86%, 87%, 88%, 89%, 90%, 91%, 92%, 93%, 94%, 95%, 96%, 97%, 98% or 99% identical to SEQ ID NO: 31 and/or a heavy chain variable region having an amino acid sequence that is at least 85%, 86%, 87%, 88%, 89%, 90%, 91%, 92%, 93%, 94%, 95%, 96%, 97%, 98% or 99% identical to SEQ ID NO: 32.

In one embodiment, the BCMA-specific binding domain comprises a light chain variable region having an amino acid sequence that is at least 85%, 86%, 87%, 88%, 89%, 90%, 91%, 92%, 93%, 94%, 95%, 96%, 97%, 98% or 99% identical to SEQ ID NO: 39 and/or a heavy chain variable region having an amino acid sequence that is at least 85%, 86%, 87%, 88%, 89%, 90%, 91%, 92%, 93%, 94%, 95%, 96%, 97%, 98% or 99% identical to SEQ ID NO: 40.

In one embodiment, the BCMA-specific binding domain comprises a light chain variable region having an amino acid sequence that is at least 85%, 86%, 87%, 88%, 89%, 90%, 91%, 92%, 93%, 94%, 95%, 96%, 97%, 98% or 99% identical to SEQ ID NO: 47 and/or a heavy chain variable region having an amino acid sequence that is at least 85%, 86%, 87%, 88%, 89%, 90%, 91%, 92%, 93%, 94%, 95%, 96%, 97%, 98% or 99% identical to SEQ ID NO: 48.

In some embodiments, the light chain variable region and/or the heavy chain variable region sequences do not vary within any of the CDR sequences provided herein. For example, in some embodiments, the degree of sequence variation (e.g., 80%, 81%, 82%, 83%, 84%, 85%, 86%, 87%, 88%, 89%, 90%, 91%, 92%, 93%, 94%, 95%, 96%, 97%, 98%, or 99%) may occur within a heavy chain variable and/or a light chain variable amino acid sequence excluding any of the CDR sequences provided herein.

In various embodiments, the BCMA-specific binding domain comprises a light chain variable domain comprising an amino acid sequence set forth in SEQ ID NO: 7 and/or a heavy chain variable domain comprising an amino acid sequence set forth in SEQ ID NO: 8.

In various embodiments, the BCMA-specific binding domain comprises a light chain variable domain comprising an amino acid sequence set forth in SEQ ID NO: 15 and/or a heavy chain variable domain comprising an amino acid sequence set forth in SEQ ID NO: 16.

In various embodiments, the BCMA-specific binding domain comprises a light chain variable domain comprising an amino acid sequence set forth in SEQ ID NO: 23 and/or a heavy chain variable domain comprising an amino acid sequence set forth in SEQ ID NO: 24.

In various embodiments, the BCMA-specific binding domain comprises a light chain variable domain comprising an amino acid sequence set forth in SEQ ID NO: 31 and/or a heavy chain variable domain comprising an amino acid sequence set forth in SEQ ID NO: 32.

In various embodiments, the BCMA-specific binding domain comprises a light chain variable domain comprising an amino acid sequence set forth in SEQ ID NO: 39 and/or a heavy chain variable domain comprising an amino acid sequence set forth in SEQ ID NO: 40.

In various embodiments, the BCMA-specific binding domain comprises a light chain variable domain comprising an amino acid sequence set forth in SEQ ID NO: 47 and/or a heavy chain variable domain comprising an amino acid sequence set forth in SEQ ID NO: 48.

In any of the BCMA-specific binding domains contemplated herein, one or more conservative mutations can be introduced into the CDRs or framework sequences at positions where the residues are not likely to be involved in an antibody-antigen interaction. In some embodiments, such conservative mutation(s) can be introduced into the CDRs or framework sequences at position(s) where the residues are not likely to be involved in interacting with a BCMA, as determined based on the crystal structure. In some embodiments, the likely interface (e.g., residues involved in an antigen-antibody interaction) may be deduced from known structural information on other antigens sharing structural similarities.

2. Linkers

In certain embodiments, the CARs contemplated herein may comprise linker residues between the various domains, e.g., added for appropriate spacing and conformation of the molecule. In particular embodiments the linker is a variable region linking sequence. A "variable region linking sequence," is an amino acid sequence that connects the VH and VL domains and provides a spacer function compatible with interaction of the two sub-binding domains so that the resulting polypeptide retains a specific binding affinity to the same target molecule as an antibody that comprises the same light and heavy chain variable regions. CARs contemplated herein, may comprise one, two, three, four, or five or more linkers. In particular embodiments, the length of a linker is about 1 to about 25 amino acids, about 5 to about 20 amino acids, or about 10 to about 20 amino acids, or any intervening length of amino acids. In some embodiments, the linker is 1, 2, 3, 4, 5, 6, 7, 8, 9, 10, 11, 12, 13, 14, 15, 16, 17, 18, 19, 20, 21, 22, 23, 24, 25, or more amino acids long.

Illustrative examples of linkers include glycine polymers (G) n; glycine-serine polymers $(G_{1-5}S_{1-5})_n$, where n is an integer of at least one, two, three, four, or five; glycine-alanine polymers; alanine-serine polymers; and other flexible linkers known in the art. Glycine and glycine-serine polymers are relatively unstructured, and therefore may be able to serve as a neutral tether between domains of fusion proteins such as the CARs contemplated herein. Glycine accesses significantly more phi-psi space than even alanine, and is much less restricted than residues with longer side chains (see Scheraga, *Rev. Computational Chem.* 11173-142 (1992)). The ordinarily skilled artisan will recognize that design of a CAR in particular embodiments can include linkers that are all or partially flexible, such that the linker can include a flexible linker as well as one or more portions that confer less flexible structure to provide for a desired CAR structure.

Other exemplary linkers include, but are not limited to the following amino acid sequences: GGG; DGGGS (SEQ ID NO: 71); TGEKP (SEQ ID NO: 72) (see, e.g., Liu et al., PNAS 5525-5530 (1997)); GGRR (SEQ ID NO: 73) (Pomerantz et al. 1995, supra); (GGGGS) n wherein=1, 2, 3, 4 or 5 (SEQ ID NO: 74) (Kim et al., PNAS 93, 1156-1160

(1996.); EGKSSGSGSESKVD (SEQ ID NO: 75) (Chaudhary et al., 1990, Proc. Natl. Acad. Sci. U.S.A. 87:1066-1070); KESGSVSSEQLAQFRSLD (SEQ ID NO: 76) (Bird et al., 1988, Science 242:423-426), GGRRGGGS (SEQ ID NO: 77); LRQRDGERP (SEQ ID NO: 78); LRQKDGGGSERP (SEQ ID NO: 79); LRQKd (GGGS) 2 ERP (SEQ ID NO: 80). Alternatively, flexible linkers can be rationally designed using a computer program capable of modeling both DNA-binding sites and the peptides themselves (Desjarlais & Berg, *PNAS* 90:2256-2260 (1993), *PNAS* 91:11099-11103 (1994) or by phage display methods. In one embodiment, the linker comprises the following amino acid sequence: GSTSGSGKPGSGEGSTKG (SEQ ID NO: 81) (Cooper et al., *Blood,* 101 (4): 1637-1644 (2003)).

3. Spacer Domain

In particular embodiments, the binding domain of the CAR is followed by one or more "spacer domains," which refers to the region that moves the antigen binding domain away from the effector cell surface to enable proper cell/cell contact, antigen binding and activation (Patel et al., *Gene Therapy,* 1999; 6:412-419). The spacer domain may be derived either from a natural, synthetic, semi-synthetic, or recombinant source. In certain embodiments, a spacer domain is a portion of an immunoglobulin, including, but not limited to, one or more heavy chain constant regions, e.g., CH2 and CH3. The spacer domain can include the amino acid sequence of a naturally occurring immunoglobulin hinge region or an altered immunoglobulin hinge region.

In one embodiment, the spacer domain comprises the CH2 and CH3 domains of IgG1, IgG2, or IgG4 or suitable combinations thereof.

4. Hinge Domain

The binding domain of the CAR is generally followed by one or more "hinge domains," which plays a role in positioning the antigen binding domain away from the effector cell surface to enable proper cell/cell contact, antigen binding and activation. A CAR generally comprises one or more hinge domains between the binding domain and the transmembrane domain (TM). The hinge domain may be derived either from a natural, synthetic, semi-synthetic, or recombinant source. The hinge domain can include the amino acid sequence of a naturally occurring immunoglobulin hinge region or an altered immunoglobulin hinge region.

Illustrative hinge domains suitable for use in the CARs contemplated herein include the hinge region derived from the extracellular regions of type 1 membrane proteins including, but not limited to, CD8α, CD4, CD28 and CD7, which may be wild-type hinge regions from these molecules or may be altered. In one embodiment, the hinge is a PD-1 hinge or CD152 hinge. In another embodiment, the hinge domain comprises a naturally occurring immunoglobin hinge region, e.g., an IgG1, IgG2, IgG3, or IgG4 hinge or suitable combinations thereof. In another embodiment the hinge domain comprises an IgG1 hinge/CH2/CH3, an IgG1 hinge/CH3/hinge/M1, an IgG4 hinge/CH2/CH3, or an IgG4 hinge/CH2.

In various embodiments, the CARs contemplated herein comprise a modified hinge, region. As used herein, the terms "altered hinge region", "modified hinge region", and "modified hinge domain" are used interchangeably and refers to (a) a naturally occurring hinge region with up to 30% amino acid changes (e.g., up to 25%, 20%, 15%, 10%, or 5% amino acid substitutions or deletions), (b) a portion of a naturally occurring hinge region that is at least 10 amino acids (e.g., at least 12, 13, 14 or 15 amino acids) in length with up to 30% amino acid changes (e.g., up to 25%, 20%, 15%, 10%, or 5% amino acid substitutions or deletions), or (c) a portion of a naturally occurring hinge region that comprises the core hinge region (which may be 4, 5, 6, 7, 8, 9, 10, 11, 12, 13, 14, or 15, or at least 4, 5, 6, 7, 8, 9, 10, 11, 12, 13, 14, or 15 amino acids in length).

In various embodiments, the modified hinge region comprises an amino acid sequence having at least 85%, 86%, 87%, 88%, 89%, 90%, 91%, 92%, 93%, 94%, 95%, 96%, 97%, 98%, or 99% amino acid identity to a suitable hinge domain/region as contemplated herein and/or known in the art. In some embodiments, the modified hinge region comprising a hinge sequence as contemplated herein having 4 or fewer, 3 or fewer, or 2 or fewer amino acid substitutions and/or deletions.

In certain embodiments, one or more cysteine residues in a naturally occurring hinge region/domain may be substituted by one or more other amino acid residues to produce a modified hinge domain. In some embodiments, the modified hinge domain comprises one or more cysteine residues substituted with serine(s) or alanine(s). In another embodiment, the modified hinge domain comprises one or more cysteine residues substituted with serine(s). In another embodiment, the modified hinge domain comprises one or more cysteine residues substituted with alanine(s).

In particular embodiments, an altered hinge region comprises substitution of a proline residue by another amino acid residue (e.g., a serine residue).

5. Transmembrane (TM) Domain

The "transmembrane domain" is the portion of a CAR that fuses the extracellular binding portion and intracellular signaling domain and anchors the CAR to the plasma membrane of the immune effector cell. The TM domain may be derived either from a natural, synthetic, semi-synthetic, or recombinant source. The TM domain may be derived from (i.e., comprises at least the transmembrane region(s) of) the alpha or beta chain of the T-cell receptor, CD3δ, CD3ε, CD3γ, CD3ζ, CD4, CD5, CD8α, CD9, CD16, CD22, CD27, CD28, CD33, CD37, CD45, CD64, CD80, CD86, CD134, CD137, CD152, CD154, and PD1. In a particular embodiment, the TM domain is synthetic and predominantly comprises hydrophobic residues such as leucine and valine.

In one embodiment, the CARs comprise a TM domain derived from, PD1, CD152, CD28, or CD8α. In another embodiment, a CAR comprises a TM domain derived from, PD1, CD152, CD28, or CD8α and a short oligo- or polypeptide linker, preferably between 1, 2, 3, 4, 5, 6, 7, 8, 9, or 10 amino acids in length that links the TM domain and the intracellular signaling or co stimulatory domains of the CAR as the case may be. A glycine-serine based linker provides a particularly suitable linker.

6. Intracellular Signaling Domain

In particular embodiments, CARs contemplated herein comprise an intracellular signaling domain. An "intracellular signaling domain," refers to the part of a CAR that participates in transducing the message of effective BCMA CAR binding to a human BCMA polypeptide into the interior of the immune effector cell to elicit effector cell function, e.g., activation, cytokine production, proliferation and cytotoxic activity, including the release of cytotoxic factors to the CAR-bound target cell, or other cellular responses elicited with antigen binding to the extracellular CAR domain.

The term "effector function" refers to a specialized function of an immune effector cell. Effector function of the T cell, for example, may be cytolytic activity or help or activity including the secretion of a cytokine. Thus, the term "intracellular signaling domain" refers to the portion of a protein which transduces the effector function signal and that directs the cell to perform a specialized function. While usually the entire intracellular signaling domain can be employed, in many cases it is not necessary to use the entire domain. To the extent that a truncated portion of an intracellular signaling domain is used, such truncated portion may be used in place of the entire domain as long as it transduces the effector function signal. The term intracellular signaling domain is meant to include any truncated portion of the intracellular signaling domain sufficient to transducing effector function signal.

It is known that signals generated through the TCR alone are insufficient for full activation of the T cell and that a secondary or co-stimulatory signal is also required. Thus, T cell activation can be said to be mediated by two distinct classes of intracellular signaling domains: primary signaling domains that initiate antigen-dependent primary activation through the TCR (e.g., a TCR/CD3 complex) and co-stimulatory signaling domains that act in an antigen-independent manner to provide a secondary or co-stimulatory signal. In preferred embodiments, a CAR contemplated herein comprises an intracellular signaling domain that comprises one or more "co-stimulatory signaling domain" and a "primary signaling domain."

Primary signaling domains regulate primary activation of the TCR complex either in a stimulatory way, or in an inhibitory way. Primary signaling domains that act in a stimulatory manner may contain signaling motifs which are known as immunoreceptor tyrosine-based activation motifs or ITAMs.

Illustrative examples of ITAM containing primary signaling domains that are of particular use in the invention include those derived from TCRζ, FcRγ, FcRβ, CD3γ, CD3δ, CD3ε, CD3ζ, CD22, CD79a, CD79b, and CD66d. In particular preferred embodiments, a CAR comprises a CD3ζ primary signaling domain and one or more co-stimulatory signaling domains. The intracellular primary signaling and co-stimulatory signaling domains may be linked in any order in tandem to the carboxyl terminus of the transmembrane domain.

CARs contemplated herein comprise one or more co-stimulatory signaling domains to enhance the efficacy and expansion of T cells expressing CAR receptors. As used herein, the term, "co-stimulatory signaling domain," or "co-stimulatory domain", refers to an intracellular signaling domain of a co-stimulatory molecule. Co-stimulatory molecules are cell surface molecules other than antigen receptors or Fc receptors that provide a second signal required for efficient activation and function of T lymphocytes upon binding to antigen. Illustrative examples of such co-stimulatory molecules include CARD11, CD2, CD7, CD27, CD28, CD30, CD40, CD54 (ICAM), CD83, CD134 (OX40), CD137 (4-1BB), CD150 (SLAMF1), CD152 (CTLA4), CD223 (LAG3), CD270 (HVEM), CD273 (PD-L2), CD274 (PD-L1), CD278 (ICOS), DAP10, LAT, NKD2C SLP76, TRIM, and ZAP70.

In one embodiment, a CAR comprises one or more co-stimulatory signaling domains selected from the group consisting of CD28, CD137, and CD134, and a CD3ζ primary signaling domain.

In another embodiment, a CAR comprises CD28 and CD137 co-stimulatory signaling domains and a CD3ζ primary signaling domain.

In yet another embodiment, a CAR comprises CD28 and CD134 co-stimulatory signaling domains and a CD3ζ primary signaling domain.

In one embodiment, a CAR comprises CD137 and CD134 co-stimulatory signaling domains and a CD3ζ primary signaling domain.

E. Illustrative Embodiments of Cars

In one embodiment, a CAR comprises an antibody or antigen-specific binding fragment thereof that binds an antigen; a hinge region; a transmembrane domain; one or more intracellular co-stimulatory signaling domains from a co-stimulatory molecule; and a primary signaling domain. In particular embodiments, CARs contemplated herein comprise an anti-BCMA antibody or antigen binding fragment thereof that specifically binds to a BCMA polypeptide expressed on B cells.

In one embodiment, a CAR comprises an anti-BCMA scFv that binds a BCMA polypeptide; a spacer or hinge domain; a transmembrane domain derived from a polypeptide selected from the group consisting of: alpha, beta or zeta chain of the T-cell receptor, CD3δ, CD3ε, CD3γ, CD3ζ, CD4, CD5, CD8α, CD9, CD16, CD22, CD27, CD28, CD33, CD37, CD45, CD64, CD80, CD86, CD134, CD137, CD152, CD154, and PD1; and one or more intracellular co-stimulatory signaling domains from a co-stimulatory molecule selected from the group consisting of: TLR1, TLR2, TLR3, TLR4, TLR5, TLR6, TLR7, TLR8, TLR9, TLR10, CARD11, CD2, CD7, CD27, CD28, CD30, CD40, CD54 (ICAM), CD83, CD134 (OX40), CD137 (4-1BB), CD150 (SLAMF1), CD152 (CTLA4), CD223 (LAG3), CD270 (HVEM), CD273 (PD-L2), CD274 (PD-L1), CD278 (ICOS), DAP10, LAT, NKD2C, SLP76, TRIM, TNFR2, and ZAP70; and a primary signaling domain from TCRζ, FcRγ, FcRβ, CD3γ, CD3δ, CD3ε, CD3ζ, CD22, CD79a, CD79b, and CD66d.

In one embodiment, a CAR comprises an anti-BCMA scFv that binds a BCMA polypeptide; a spacer domain or a hinge domain selected from the group consisting of: a CD8α hinge, a CD4 hinge, a CD28 hinge, a CD7 hinge, a PD-1 hinge, a CD152 hinge, an IgG1 hinge, an IgG2 hinge, an IgG3 hinge, an IgG4 hinge, an IgG1 hinge/CH2/CH3, an IgG1 hinge/CH3/hinge/M1, an IgG4 hinge/CH2/CH3, or an IgG4 hinge/CH2; a transmembrane domain derived from a polypeptide selected from the group consisting of: alpha, beta or zeta chain of the T-cell receptor, CD3δ, CD3ε, CD3γ, CD3ζ, CD4, CD5, CD8α, CD9, CD16, CD22, CD27, CD28, CD33, CD37, CD45, CD64, CD80, CD86, CD134, CD137, CD152, CD154, and PD1; and one or more intracellular co-stimulatory signaling domains from a co-stimulatory molecule selected from the group consisting of: TLR1, TLR2, TLR3, TLR4, TLR5, TLR6, TLR7, TLR8, TLR9, TLR10, CARD11, CD2, CD7, CD27, CD28, CD30, CD40, CD54 (ICAM), CD83, CD134 (OX40), CD137 (4-1BB), CD150 (SLAMF1), CD152 (CTLA4), CD223 (LAG3), CD270 (HVEM), CD273 (PD-L2), CD274 (PD-L1), CD278 (ICOS), DAP10, LAT, NKD2C, SLP76, TRIM, TNFR2, and ZAP70; and a primary signaling domain from TCRζ, FcRγ, FcRβ, CD3γ, CD3δ, CD3ε, CD3ζ, CD22, CD79a, CD79b, and CD66d.

In one embodiment, a CAR comprises an anti-BCMA scFv that binds a BCMA polypeptide; a hinge domain selected from the group consisting of: a CD8α hinge, a CD4 hinge, a CD28 hinge, a CD7 hinge, a PD-1 hinge, a CD152 hinge, an IgG1 hinge, an IgG2 hinge, an IgG3 hinge, an IgG4 hinge, an IgG1 hinge/CH2/CH3, an IgG1 hinge/CH3/hinge/M1, an IgG4 hinge/CH2/CH3, or an IgG4 hinge/CH2; a transmembrane domain derived from a polypeptide selected from the group consisting of: alpha, beta or zeta chain of the T-cell receptor, CD3δ, CD3ε, CD3γ, CD3ζ, CD4, CD5, CD8α, CD9, CD16, CD22, CD27, CD28, CD33, CD37, CD45, CD64, CD80, CD86, CD134, CD137, CD152, CD154, and PD1; a short oligo- or polypeptide linker, preferably between 1, 2, 3, 4, 5, 6, 7, 8, 9, or 10 amino acids in length that links the TM domain to the intracellular signaling domain of the CAR; and one or more intracellular co-stimulatory signaling domains from a co-stimulatory molecule selected from the group consisting of: TLR1, TLR2, TLR3, TLR4, TLR5, TLR6, TLR7, TLR8, TLR9, TLR10, CARD11, CD2, CD7, CD27, CD28, CD30, CD40, CD54 (ICAM), CD83, CD134 (OX40), CD137 (4-1BB), CD150 (SLAMF1), CD152 (CTLA4), CD223 (LAG3), CD270 (HVEM), CD273 (PD-L2), CD274 (PD-L1), CD278 (ICOS), DAP10, LAT, NKD2C, SLP76, TRIM, TNFR2, and ZAP70; and a primary signaling domain from TCRζ, FcRγ, FcRβ, CD3γ, CD3δ, CD3ε, CD3ζ, CD22, CD79a, CD,79b, and CD66d.

In a particular embodiment, a CAR comprises an anti-BCMA scFv that binds a BCMA polypeptide; a spacer domain comprising one or more fragments of an IgG2 and/or IgG4 hinge/CH2/CH3 polypeptide; a CD28 transmembrane domain; a CD137 intracellular co-stimulatory signaling domain; and a CD3ζ primary signaling domain.

In a particular embodiment, a CAR comprises an anti-BCMA scFv that binds a BCMA polypeptide; a hinge domain comprising an IgG1 hinge/CH2/CH3 polypeptide and a CD8α polypeptide; a CD8α transmembrane domain comprising a polypeptide linker of about 3 to about 10 amino acids; a CD137 intracellular co-stimulatory signaling domain; and a CD3ζ primary signaling domain.

In a particular embodiment, a CAR comprises an anti-BCMA scFv that binds a BCMA polypeptide; a hinge domain comprising a CD8α polypeptide; a CD8α transmembrane domain comprising a polypeptide linker of about 3 to about 10 amino acids; a CD134 intracellular co-stimulatory signaling domain; and a CD3ζ primary signaling domain.

In a particular embodiment, a CAR comprises an anti-BCMA scFv that binds a BCMA polypeptide; a hinge domain comprising a CD8α polypeptide; a CD8α transmembrane domain comprising a polypeptide linker of about 3 to about 10 amino acids; a CD28 intracellular co-stimulatory signaling domain; and a CD3ζ primary signaling domain.

Moreover, the design of the CARs contemplated herein enable improved expansion, long-term persistence, and tolerable cytotoxic properties in T cells expressing the CARs compared to non-modified T cells or T cells modified to express other CARs.

In various embodiments, the improved compositions and methods of adoptive cell therapy disclosed herein, provide genetically modified immune effector cells (e.g., CAR T cells) that target cells expressing BCMA and have human derived antigen binding domains, display improved cytokine release, and low antigen independent signaling.

In particular embodiments, the improved CAR T cells display high IFNγ release in co-culture with BCMA expressing cells. In some embodiments, the improved CAR T cells display similar or higher IFNγ release in co-culture with BCMA expressing cells compared to the same CAR T cell except that the CAR comprises an extracellular domain comprising a murine derived anti-BCMA scFv. In some embodiments, the co-cultured BCMA expressing cells are Daudi cells and/or HT1080.BCMA cells.

In particular embodiments, the improved CAR T cells display high IFNγ release in co-culture with low antigen density (low BCMA expressing) cells. A cell or cell line is characterized as having low BCMA expression if it has at least 5-fold (e.g., at least 5-fold, at least 10-fold, at least 15-fold, or at least 20-fold) less surface BCMA expression than Daudi, HT1080.BCMA, and/or RPMI-8226 cells. In some embodiments, the cells are cultured under the same or similar culture conditions. In some embodiments, the low BCMA expressing cells have at least 5-fold less surface BCMA expression compared to Daudi, HT1080.BCMA, and/or RPMI-8226 cells. In some embodiments, the low BCMA expressing cells have at least 10-fold less surface BCMA expression compared to HT1080.BCMA cells. In some embodiments, the low BCMA expressing cells have at least 10-fold less surface BCMA expression compared to RPMI-8226 cells. Assays for measuring protein surface expression are known to those of skill in the art (e.g., FACS analysis).

In some embodiments, the improved CAR T cells display higher IFNγ release in co-culture with low antigen density (low BCMA expressing) cells compared to the same CAR T cell except that the CAR comprises an extracellular domain comprising a murine derived anti-BCMA scFv. In some embodiments, the low BCMA expressing cells are RL cells and/or Toledo cells.

In some embodiments, the improved CAR T cells display lower antigen independent signaling compared to the same CAR T cell except that the CAR comprises an extracellular domain comprising a murine derived anti-BCMA scFv.

In some embodiments, the improved CAR T cells display lower antigen independent signaling compared to the same CAR T cell except that the CAR comprises an extracellular domain comprising a murine derived anti-BCMA scFv.

F. Polypeptides

The present disclosure contemplates, in part, CAR polypeptides and fragments thereof, cells and compositions comprising the same, and vectors that express polypeptides. In preferred embodiments, a polypeptide comprising one or more CARs as set forth in SEQ ID NOs: 50, 52, 54, 56, 58, 60, 62, 64, 66, and 68 is provided.

"Polypeptide," "polypeptide fragment," "peptide" and "protein" are used interchangeably, unless specified to the contrary, and according to conventional meaning, i.e., as a sequence of amino acids. Polypeptides are not limited to a specific length, e.g., they may comprise a full-length protein sequence or a fragment of a full length protein, and may include post-translational modifications of the polypeptide, for example, glycosylations, acetylations, phosphorylations and the like, as well as other modifications known in the art, both naturally occurring and non-naturally occurring. In various embodiments, the CAR polypeptides contemplated herein comprise a signal (or leader) sequence at the N-terminal end of the protein, which co-translationally or post-translationally directs transfer of the protein. Illustrative examples of suitable signal sequences useful in CARs disclosed herein include, but are not limited to the IgG1 heavy chain signal sequence and the CD8α signal sequence. Polypeptides can be prepared using any of a variety of well-known recombinant and/or synthetic techniques. Polypeptides contemplated herein specifically encompass the CARs of the present disclosure, or sequences that have deletions from, additions to, and/or substitutions of one or more amino acid of a CAR as disclosed herein.

An "isolated peptide" or an "isolated polypeptide" and the like, as used herein, refer to in vitro isolation and/or purification of a peptide or polypeptide molecule from a cellular environment, and from association with other components of the cell, i.e., it is not significantly associated with in vivo substances. Similarly, an "isolated cell" refers to a cell that has been obtained from an in vivo tissue or organ and is substantially free of extracellular matrix.

Polypeptides include "polypeptide variants." Polypeptide variants may differ from a naturally occurring polypeptide in one or more substitutions, deletions, additions and/or insertions. Such variants may be naturally occurring or may be synthetically generated, for example, by modifying one or more of the above polypeptide sequences. For example, in particular embodiments, it may be desirable to improve the binding affinity and/or other biological properties of the CARs by introducing one or more substitutions, deletions, additions and/or insertions into a binding domain, hinge, TM domain, co-stimulatory signaling domain or primary signaling domain of a CAR polypeptide. Preferably, polypeptides contemplated herein include polypeptides having at least about 65%, 70%, 75%, 85%, 90%, 95%, 98%, or 99% amino acid identity thereto.

Polypeptides include "polypeptide fragments." Polypeptide fragments refer to a polypeptide, which can be monomeric or multimeric, that has an amino-terminal deletion, a carboxyl-terminal deletion, and/or an internal deletion or substitution of a naturally-occurring or recombinantly-produced polypeptide. In certain embodiments, a polypeptide fragment can comprise an amino acid chain at least 5 to about 500 amino acids long. It will be appreciated that in certain embodiments, fragments are at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 150, 200, 250, 300, 350, 400, or 450 amino acids long. Particularly useful polypeptide fragments include functional domains, including antigen-binding domains or fragments of antibodies. In the case of a murine anti-BCMA antibody, useful fragments include, but are not limited to: a CDR region, a CDR3 region of the heavy or light chain; a variable region of a heavy or light chain; a portion of an antibody chain or variable region including two CDRs; and the like.

The polypeptide may also be fused in-frame or conjugated to a linker or other sequence for ease of synthesis, purification or identification of the polypeptide (e.g., poly-His), or to enhance binding of the polypeptide to a solid support.

As noted above, polypeptides may be altered in various ways including amino acid substitutions, deletions, truncations, and insertions. Methods for such manipulations are generally known in the art. For example, amino acid sequence variants of a reference polypeptide can be prepared by mutations in the DNA. Methods for mutagenesis and nucleotide sequence alterations are well known in the art. See, for example, Kunkel (1985*, Proc. Natl. Acad. Sci. USA.* 82:488-492), Kunkel et al., (1987*, Methods in Enzymol,* 154:367-382), U.S. Pat. No. 4,873,192, Watson, J. D. et al., (*Molecular Biology of the Gene*, Fourth Edition, Benjamin/Cummings, Menlo Park, Calif., 1987) and the references cited therein. Guidance as to appropriate amino acid substitutions that do not affect biological activity of the protein of interest may be found in the model of Dayhoff et al., (1978) *Atlas of Protein Sequence and Structure* (Natl. *Biomed. Res.* Found., Washington, D.C.).

In certain embodiments, a variant will contain conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. Modifications may be made in the structure of the polynucleotides and polypeptides of the present disclosure and still obtain a functional molecule that encodes a variant or derivative polypeptide with desirable characteristics. When it is desired to alter the amino acid sequence of a polypeptide to create an equivalent, or even an improved, variant polypeptide as contemplated herein, one skilled in the art, for example, can change one or more of the codons of the encoding DNA sequence, e.g., according to Table 1.

TABLE 1

| Amino Acid Codons | | | |
|---|---|---|---|
| Amino Acids | One letter code | Three letter code | Codons |
| Alanine | A | Ala | GCA GCC GCG GCU |
| Cysteine | C | Cys | UGC UGU |
| Aspartic acid | D | Asp | GAC GAU |
| Glutamic acid | E | Glu | GAA GAG |
| Phenylalanine | F | Phe | UUC UUU |
| Glycine | G | Gly | GGA GGC GGG GGU |
| Histidine | H | His | CAC CAU |
| Isoleucine | I | Iso | AUA AUC AUU |
| Lysine | K | Lys | AAA AAG |
| Leucine | L | Leu | UUA UUG CUA CUC CUG CUU |
| Methionine | M | Met | AUG |
| Asparagine | N | Asn | AAC AAU |
| Proline | P | Pro | CCA CCC CCG CCU |
| Glutamine | Q | Gln | CAA CAG |
| Arginine | R | Arg | AGA AGG CGA CGC CGG CGU |
| Serine | S | Ser | AGC AGU UCA UCC UCG UCU |
| Threonine | T | Thr | ACA ACC ACG ACU |
| Valine | V | Val | GUA GUC GUG GUU |
| Tryptophan | W | Trp | UGG |
| Tyrosine | Y | Tyr | UAC UAU |

Guidance in determining which amino acid residues can be substituted, inserted, or deleted without abolishing biological activity can be found using computer programs well known in the art, such as DNASTAR™ software. Preferably, amino acid changes in the protein variants disclosed herein are conservative amino acid changes, i.e., substitutions of similarly charged or uncharged amino acids. A conservative amino acid change involves substitution of one of a family of amino acids which are related in their side chains. Naturally occurring amino acids are generally divided into four families: acidic (aspartate, glutamate), basic (lysine, arginine, histidine), non-polar (alanine, valine, leucine, isoleucine, proline, phenylalanine, methionine, tryptophan), and uncharged polar (glycine, asparagine, glutamine, cysteine, serine, threonine, tyrosine) amino acids. Phenylalanine, tryptophan, and tyrosine are sometimes classified jointly as aromatic amino acids. In a peptide or protein, suitable conservative substitutions of amino acids are known to those of skill in this art and generally can be made without altering a biological activity of a resulting molecule. Those of skill in this art recognize that, in general, single amino acid substitutions in non-essential regions of a polypeptide do not substantially alter biological activity (see, e.g., Watson et al. *Molecular Biology of the Gene,* 4th Edition, 1987, The Benjamin/Cummings Pub. Co., p.224). Exemplary conservative substitutions are described in U.S. Provisional Patent Application No. 61/241,647, the disclosure of which is herein incorporated by reference.

In making such changes, the hydropathic index of amino acids may be considered. The importance of the hydropathic amino acid index in conferring interactive biologic function on a protein is generally understood in the art (Kyte and Doolittle, 1982, incorporated herein by reference). Each amino acid has been assigned a hydropathic index on the basis of its hydrophobicity and charge characteristics (Kyte and Doolittle, 1982). These values are: isoleucine (±4.5); valine (±4.2); leucine (±3.8); phenylalanine (±2.8); cysteine/cysteine (±2.5); methionine (±1.9); alanine (±1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those within ±1 are particularly preferred, and those within ±0.5 are even more particularly preferred. It is also understood in the art that the substitution of like amino acids can be made effectively on the basis of hydrophilicity.

As detailed in U.S. Pat. No. 4,554,101, the following hydrophilicity values have been assigned to amino acid residues: arginine (±3.0); lysine (±3.0); aspartate (±3.0±1); glutamate (±3.0±1); serine (±0.3); asparagine (±0.2); glutamine (±0.2); glycine (0); threonine (−0.4); proline (−0.5+1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those within ±1 are particularly preferred, and those within ±0.5 are even more particularly preferred.

As outlined above, amino acid substitutions may be based on the relative similarity of the amino acid side-chain substituents, for example, their hydrophobicity, hydrophilicity, charge, size, and the like:

Polypeptide variants further include glycosylated forms, aggregative conjugates with other molecules, and covalent conjugates with unrelated chemical moieties (e.g., pegylated molecules). Covalent variants can be prepared by linking functionalities to groups which are found in the amino acid chain or at the N- or C-terminal residue, as is known in the art. Variants also include allelic variants, species variants, and muteins. Truncations or deletions of regions which do not affect functional activity of the proteins are also variants.

In one embodiment, where expression of two or more polypeptides is desired, the polynucleotide sequences encoding them can be separated by and IRES sequence as discussed elsewhere herein. In another embodiment, two or more polypeptides can be expressed as a fusion protein that comprises one or more self-cleaving polypeptide sequences.

Polypeptides of the present disclosure include fusion polypeptides. In preferred embodiments, fusion polypeptides and polynucleotides encoding fusion polypeptides are provided, e.g., CARs. Fusion polypeptides and fusion proteins refer to a polypeptide having at least two, three, four, five, six, seven, eight, nine, or ten or more polypeptide segments. Fusion polypeptides are typically linked C-terminus to N-terminus, although they can also be linked C-terminus to C-terminus, N-terminus to N-terminus, or N-terminus to C-terminus. The polypeptides of the fusion protein can be in any order or a specified order. Fusion polypeptides or fusion proteins can also include conservatively modified variants, polymorphic variants, alleles, mutants, subsequences, and interspecies homologs, so long as the desired transcriptional activity of the fusion polypeptide is preserved. Fusion polypeptides may be produced by chemical synthetic methods or by chemical linkage between the two moieties or may generally be prepared using other standard techniques. Ligated DNA sequences comprising the fusion polypeptide are operably linked to suitable transcriptional or translational control elements as discussed elsewhere herein.

In one embodiment, a fusion partner comprises a sequence that assists in expressing the protein (an expression enhancer) at higher yields than the native recombinant protein. Other fusion partners may be selected so as to increase the solubility of the protein or to enable the protein to be targeted to desired intracellular compartments or to facilitate transport of the fusion protein through the cell membrane.

Fusion polypeptides may further comprise a polypeptide cleavage signal between each of the polypeptide domains contemplated herein. In addition, polypeptide site can be put into any linker peptide sequence. Exemplary polypeptide cleavage signals include polypeptide cleavage recognition sites such as protease cleavage sites, nuclease cleavage sites (e.g., rare restriction enzyme recognition sites, self-cleaving ribozyme recognition sites), and self-cleaving viral oligopeptides (see deFelipe and Ryan, 2004. *Traffic,* 5 (8); 616-26).

Suitable protease cleavages sites and self-cleaving peptides are known to the skilled person (see, e.g., in Ryan et al., 1997. *J. Gener. Virol.* 78, 699-722; Scymczak et al. (2004) *Nature Biotech.* 5, 589-594). Exemplary protease cleavage sites include, but are not limited to the cleavage sites of potyvirus NIa proteases (e.g., tobacco etch virus protease), potyvirus HC proteases, potyvirus P1 (P35) proteases, byovirus NIa proteases, byovirus RNA-2-encoded proteases, aphthovirus L proteases, enterovirus 2A proteases, rhinovirus 2A proteases, picorna 3C proteases, comovirus 24K proteases, nepovirus 24K proteases, RTSV (rice tungro spherical virus) 3C-like protease, PYVF (parsnip yellow fleck virus) 3C-like protease, heparin, thrombin, factor Xa and enterokinase. Due to its high cleavage stringency, TEV (tobacco etch virus) protease cleavage sites are preferred in one embodiment, e.g., EXXYXQ (G/S) (SEQ ID NO: 82), for example, ENLYFQG (SEQ ID NO: 83) and ENLYFQS (SEQ ID NO: 84), wherein X represents any amino acid (cleavage by TEV occurs between Q and G or Q and S).

In particular embodiments, the polypeptide cleavage signal is a viral self-cleaving peptide or ribosomal skipping sequence.

Illustrative examples of ribosomal skipping sequences include, but are not limited to: a 2A or 2A-like site, sequence or domain (Donnelly et al., 2001. *J. Gen. Virol.* 82:1027-1041). In a particular embodiment, the viral 2A peptide is an aphthovirus 2A peptide, a potyvirus 2A peptide, or a cardiovirus 2A peptide.

In one embodiment, the viral 2A peptide is selected from the group consisting of: a foot-and-mouth disease virus (FMDV) 2A peptide, an equine rhinitis A virus (ERAV) 2A peptide, a Thosea asigna virus (TaV) 2A peptide, a porcine teschovirus-1 (PTV-1) 2A peptide, a Theilovirus 2A peptide, and an encephalomyocarditis virus 2A peptide.

Illustrative examples of 2A sites are provided in Table 2.

TABLE 2

| | |
|---|---|
| SEQ ID NO: 85 | GSGATNFSLLKQAGDVEENPGP |
| SEQ ID NO: 86 | ATNFSLLKQAGDVEENPGP |
| SEQ ID NO: 87 | LLKQAGDVEENPGP |
| SEQ ID NO: 88 | GSGEGRGSLLTCGDVEENPGP |
| SEQ ID NO: 89 | EGRGSLLTCGDVEENPGP |
| SEQ ID NO: 90 | LLTCGDVEENPGP |
| SEQ ID NO: 91 | GSGQCTNYALLKLAGDVESNPGP |
| SEQ ID NO: 92 | QCTNYALLKLAGDVESNPGP |
| SEQ ID NO: 93 | LLKLAGDVESNPGP |
| SEQ ID NO: 94 | GSGVKQTLNFDLLKLAGDVESNPGP |
| SEQ ID NO: 95 | VKQTLNFDLLKLAGDVESNPGP |
| SEQ ID NO: 96 | LLKLAGDVESNPGP |
| SEQ ID NO: 97 | LLNFDLLKLAGDVESNPGP |
| SEQ ID NO: 98 | TLNFDLLKLAGDVESNPGP |
| SEQ ID NO: 99 | LLKLAGDVESNPGP |
| SEQ ID NO: 100 | NFDLLKLAGDVESNPGP |
| SEQ ID NO: 101 | QLLNFDLLKLAGDVESNPGP |
| SEQ ID NO: 102 | APVKQTLNFDLLKLAGDVESNPGP |
| SEQ ID NO: 103 | VTELLYRMKRAETYCPRPLLAIHPT EARHKQKIVAPVKQT |
| SEQ ID NO: 104 | LNFDLLKLAGDVESNPGP |
| SEQ ID NO: 105 | LLAIHPTEARHKQKIVAPVKQTLNF DLLKLAGDVESNPGP |
| SEQ ID NO: 106 | EARHKQKIVAPVKQTLNFDLLKLAG DVESNPGP |

In preferred embodiments, a polypeptide contemplated herein comprises a CAR polypeptide.

G. Polynucleotides

In preferred embodiments, a polynucleotide encoding one or more CAR polypeptides is provided, e.g., SEQ ID NOs: 49, 51, 53, 55, 57, 59, 61, 63, 65, and 67. In some embodiments, the polynucleotide encodes an amino acid sequence as set forth in any one of SEQ ID NOs: 50, 52, 54, 56, 58, 60, 62, 64, 66, and 68.

In other embodiments, a polynucleotide encoding an anti-BMCA CAR, antibody, or fragment thereof is provided. In some embodiments, the polynucleotide encodes an anti-BMCA CAR, antibody, or fragment thereof, comprising variable light chain CDRL1, CDRL2, and CDRL3 sequences set forth in SEQ ID NOs: 1-3, 9-11, 17-19, 25-27, 33-35, or 41-43 and/or variable heavy chain CDRH1, CDRH2, and CDRH3 sequences set forth in SEQ ID NOs: 4-6, 12-14, 20-22, 28-30, 36-38, or 44-46.

In some embodiments, the polynucleotide encodes an anti-BMCA CAR, antibody, or fragment thereof, comprising a variable light chain comprising an amino acid sequence set forth in any one of SEQ ID NOs: 7, 15, 23, 31, 39, or 47. In some embodiments, the polynucleotide encodes an anti-BMCA CAR, antibody, or fragment thereof, comprising a variable light chain comprising an amino acid sequence set forth in any one of SEQ ID NOs: 8, 16, 24, 32, 40, or 48. In some embodiments, the polynucleotide encodes an anti-BMCA CAR, antibody, or fragment thereof, comprising a variable light chain comprising an amino acid sequence set forth in any one of SEQ ID NOs: 7, 15, 23, 31, 39, or 47, and a variable heavy chain comprising an amino acid sequence set forth in any one of SEQ ID NOs: 8, 16, 24, 32, 40, or 48.

As used herein, the terms "polynucleotide" or "nucleic acid" refer to deoxyribonucleic acid (DNA), ribonucleic acid (RNA) and DNA/RNA hybrids. Polynucleotides may be single-stranded or double-stranded and either recombinant, synthetic, or isolated. Polynucleotides include, but are not limited to: pre-messenger RNA (pre-mRNA), messenger RNA (mRNA), RNA, genomic DNA (gDNA), PCR amplified DNA, complementary DNA (cDNA), synthetic DNA, or recombinant DNA. Polynucleotides refer to a polymeric form of nucleotides of at least 5, at least 10, at least 15, at least 20, at least 25, at least 30, at least 40, at least 50, at least 100, at least 200, at least 300, at least 400, at least 500, at least 1000, at least 5000, at least 10000, or at least 15000 or more nucleotides in length, either ribonucleotides or deoxyribonucleotides or a modified form of either type of nucleotide, as well as all intermediate lengths. It will be readily understood that "intermediate lengths," in this context, means any length between the quoted values, such as 6, 7, 8, 9, etc., 101, 102, 103, etc.; 151, 152, 153, etc.; 201, 202, 203, etc. In particular embodiments, polynucleotides or variants have at least or about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to a reference sequence.

As used herein, "isolated polynucleotide" refers to a polynucleotide that has been purified from the sequences which flank it in a naturally occurring state, e.g., a DNA fragment that has been removed from the sequences that are normally adjacent to the fragment. In particular embodiments, an "isolated polynucleotide" also refers to a complementary DNA (cDNA), a recombinant DNA, or other polynucleotide that does not exist in nature and that has been made by the hand of man. In particular embodiments, an isolated polynucleotide is a synthetic polynucleotide, a semi-synthetic polynucleotide, or a polynucleotide obtained or derived from a recombinant source.

In various embodiments, a polynucleotide comprises an mRNA encoding a polypeptide contemplated herein. In certain embodiments, the mRNA comprises a cap, one or more nucleotides, and a poly(A) tail.

In particular embodiments, polynucleotides may be codon-optimized. As used herein, the term "codon-optimized" refers to substituting codons in a polynucleotide encoding a polypeptide in order to increase the expression, stability and/or activity of the polypeptide. Factors that influence codon optimization include, but are not limited to one or more of: (i) variation of codon biases between two or more organisms or genes or synthetically constructed bias tables, (ii) variation in the degree of codon bias within an organism, gene, or set of genes, (iii) systematic variation of codons including context, (iv) variation of codons according to their decoding tRNAs, (v) variation of codons according to GC %, either overall or in one position of the triplet, (vi) variation in degree of similarity to a reference sequence for example a naturally occurring sequence, (vii) variation in the codon frequency cutoff, (viii) structural properties of mRNAs transcribed from the DNA sequence, (ix) prior knowledge about the function of the DNA sequences upon which design of the codon substitution set is to be based, (x) systematic variation of codon sets for each amino acid, and/or (xi) isolated removal of spurious translation initiation sites.

As used herein, the terms "polynucleotide variant" and "variant" and the like refer to polynucleotides displaying substantial sequence identity with a reference polynucleotide sequence or polynucleotides that hybridize with a reference sequence under stringent conditions that are defined hereinafter. These terms include polynucleotides in which one or more nucleotides have been added or deleted, or replaced with different nucleotides compared to a reference polynucleotide. In this regard, it is well understood in the art that certain alterations inclusive of mutations, additions, deletions and substitutions can be made to a reference polynucleotide whereby the altered polynucleotide retains the biological function or activity of the reference polynucleotide.

Polynucleotide variants include polynucleotide fragments that encode biologically active polypeptide fragments or variants. As used herein, the term "polynucleotide fragment" refers to a polynucleotide fragment at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 150, 200, 250, 300, 350, 400, 450, 500, 550, 600, 650, 700, 750, 800, 850, 900, 950, 1000, 1100, 1200, 1300, 1400, 1500, 1600, 1700 or more nucleotides in length that encodes a polypeptide variant that retains at least 100%, at least 90%, at least 80%, at least 70%, at least 60%, at least 50%, at least 40%, at least 30%, at least 20%, at least 10%, or at least 5% of the naturally occurring polypeptide activity. Polynucleotide fragments refer to a polynucleotide that encodes a polypeptide that has an amino-terminal deletion, a carboxyl-terminal deletion, and/or an internal deletion or substitution of one or more amino acids of a naturally occurring or recombinantly-produced polypeptide.

The recitations "sequence identity" or, for example, comprising a "sequence 50% identical to," as used herein, refer to the extent that sequences are identical on a nucleotide-by-nucleotide basis or an amino acid-by-amino acid basis over a window of comparison. Thus, a "percentage of sequence identity" may be calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. Included are nucleotides and polypeptides having at least about 50%, 55%, 60%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 86%, 97%, 98%, or 99% sequence identity to any of the reference sequences contemplated herein, typically where the polypeptide variant maintains at least one biological activity of the reference polypeptide.

Terms used to describe sequence relationships between two or more polynucleotides or polypeptides include "reference sequence," "comparison window," "sequence identity," "percentage of sequence identity," and "substantial identity". A "reference sequence" is at least 12 but frequently 15 to 18 and often at least 25 monomer units, inclusive of nucleotides and amino acid residues, in length. Because two polynucleotides may each comprise (1) a sequence (i.e., only a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window" refers to a conceptual segment of at least 6 contiguous positions, usually about 50 to about 100, more usually about 100 to about 150 in which a sequence is compared to a reference sequence of the same number of contiguous positions after the two sequences are optimally aligned. The comparison window may comprise additions or deletions (i.e., gaps) of about 20% or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, WI, USA) or by inspection and the best alignment (i.e., resulting in the highest percentage homology over the comparison window) generated by any of the various methods selected. Reference also may be made to the BLAST family of programs as for example disclosed by Altschul et al., 1997, Nucl. Acids Res. 25:3389. A detailed discussion of sequence analysis can be found in Unit 19.3 of Ausubel et al., Current Protocols in Molecular Biology, John Wiley & Sons Inc, 1994-1998, Chapter 15.

Terms that describe the orientation of polynucleotides include: 5' (normally the end of the polynucleotide having a free phosphate group) and 3' (normally the end of the polynucleotide having a free hydroxyl (OH) group). Polynucleotide sequences can be annotated in the 5' to 3' orientation or the 3' to 5' orientation. For DNA and mRNA, the 5' to 3' strand is designated the "sense," "plus," or "coding" strand because its sequence is identical to the sequence of the premessenger (premRNA) [except for uracil (U) in RNA, instead of thymine (T) in DNA]. For DNA and mRNA, the complementary 3' to 5' strand which is the strand transcribed by the RNA polymerase is designated as "template," "antisense," "minus," or "non-coding" strand. As used herein, the term "reverse orientation" refers to a 5' to 3' sequence written in the 3' to 5' orientation, or a 3' to 5' sequence written in the 5' to 3' orientation.

The terms "complementary" and "complementarity" refer to polynucleotides (i.e., a sequence of nucleotides) related by the base-pairing rules. For example, the complementary strand of the DNA sequence 5' A GTC ATG 3' is 3'TCAGTAC5'. The latter sequence is often written as the reverse complement with the 5' end on the left and the 3' end on the right, 5' C ATGACT 3'. A sequence that is equal to its reverse complement is said to be a palindromic sequence. Complementarity can be "partial," in which only some of the nucleic acids' bases are matched according to the base pairing rules. Or, there can be "complete" or "total" complementarity between the nucleic acids.

Moreover, it will be appreciated by those of ordinary skill in the art that, as a result of the degeneracy of the genetic code, there are many nucleotide sequences that encode a polypeptide, or fragment of variant thereof, as contemplated herein. Some of these polynucleotides bear minimal homology to the nucleotide sequence of any native gene. Nonetheless, polynucleotides that vary due to differences in codon usage are specifically contemplated in particular embodiments, for example polynucleotides that are optimized for human and/or primate codon selection. Further, alleles of the genes comprising the polynucleotide sequences provided herein may also be used. Alleles are endogenous genes that are altered as a result of one or more mutations, such as deletions, additions and/or substitutions of nucleotides.

The term "nucleic acid cassette" or "expression cassette" as used herein refers to genetic sequences within the vector which can express an RNA, and subsequently a polypeptide. In one embodiment, the nucleic acid cassette contains a gene(s)-of-interest, e.g., a polynucleotide(s)-of-interest. In another embodiment, the nucleic acid cassette contains one or more expression control sequences, e.g., a promoter, enhancer, poly (A) sequence, and a gene(s)-of-interest, e.g., a polynucleotide(s)-of-interest. Vectors may comprise 1, 2, 3, 4, 5, 6, 7, 8, 9 or 10 or more nucleic acid cassettes. The nucleic acid cassette is positionally and sequentially oriented within the vector such that the nucleic acid in the cassette can be transcribed into RNA, and when necessary, translated into a protein or a polypeptide, undergo appropriate post-translational modifications required for activity in the transformed cell, and be translocated to the appropriate compartment for biological activity by targeting to appropriate intracellular compartments or secretion into extracellular compartments. Preferably, the cassette has its 3' and 5' ends adapted for ready insertion into a vector, e.g., it has restriction endonuclease sites at each end. In a preferred embodiment, the nucleic acid cassette encodes a CAR. The cassette can be removed and inserted into a plasmid or viral vector as a single unit.

Polynucleotides include polynucleotide(s)-of-interest. As used herein, the term "polynucleotide-of-interest" refers to a polynucleotide encoding a polypeptide, polypeptide variant, or fusion polypeptide. A vector may comprise 1, 2, 3, 4, 5, 6, 7, 8, 9, or 10 polynucleotides-of-interest. In certain embodiments, the polynucleotide-of-interest encodes a polypeptide that provides a therapeutic effect in the treatment or prevention of a disease or disorder. Polynucleotides-of-interest, and polypeptides encoded therefrom, include both polynucleotides that encode wild-type polypeptides, as well as functional variants and fragments thereof. In particular embodiments, a functional variant has at least 80%, at least 90%, at least 95%, or at least 99% identity to a corresponding wild-type reference polynucleotide or polypeptide sequence. In certain embodiments, a functional variant or fragment has at least 50%, at least 60%, at least 70%, at least 80%, or at least 90% of a biological activity of a corresponding wild-type polypeptide.

The polynucleotides contemplated herein, regardless of the length of the coding sequence itself, may be combined with other DNA sequences, such as promoters and/or enhancers, untranslated regions (UTRs), signal sequences, Kozak sequences, polyadenylation signals, additional restriction enzyme sites, multiple cloning sites, internal ribosomal entry sites (IRES), recombinase recognition sites (e.g., LoxP, FRT, and Att sites), termination codons, transcriptional termination signals, and polynucleotides encoding self-cleaving polypeptides, epitope tags, as disclosed elsewhere herein or as known in the art, such that their overall length may vary considerably. It is therefore contemplated that a polynucleotide fragment of almost any length may be employed in particular embodiments, with the total length preferably being limited by the ease of preparation and use in the intended recombinant DNA protocol.

Polynucleotides can be prepared, manipulated and/or expressed using any of a variety of well-established techniques known and available in the art. In order to express a desired polypeptide, a nucleotide sequence encoding the polypeptide, can be inserted into appropriate vector.

Illustrative examples of vectors include, but are not limited to plasmid, autonomously replicating sequences, and transposable elements, e.g., piggyBac, Sleeping Beauty, Mos1, Tc1/mariner, Tol2, mini-Tol2, Tc3, MuA, Himar I, Frog Prince, and derivatives thereof.

Additional Illustrative examples of vectors include, without limitation, plasmids, phagemids, cosmids, artificial chromosomes such as yeast artificial chromosome (YAC), bacterial artificial chromosome (BAC), or P1-derived artificial chromosome (PAC), bacteriophages such as lambda phage or M13 phage, and animal viruses.

Illustrative examples of viruses useful as vectors include, without limitation, retrovirus (including lentivirus), adenovirus, adeno-associated virus, herpesvirus (e.g., herpes simplex virus), poxvirus, baculovirus, papillomavirus, and papovavirus (e.g., SV40).

Illustrative examples of expression vectors include, but are not limited to, pClneo vectors (Promega) for expression in mammalian cells; pLenti4/V5-DEST™, pLenti6/V5-DEST™, and pLenti6.2/V5-GW/lacZ (Invitrogen) for lentivirus-mediated gene transfer and expression in mammalian cells. In particular embodiments, coding sequences of polypeptides disclosed herein can be ligated into such expression vectors for the expression of the polypeptides in mammalian cells.

In one embodiment, a vector encoding a CAR contemplated herein comprises the polynucleotide sequence set forth in SEQ ID NO: 49, 51, 53, 55, 57, 59, 61, 63, 65, and 67.

In particular embodiments, the vector is an episomal vector or a vector that is maintained extrachromosomally. As used herein, the term "episomal" refers to a vector that is able to replicate without integration into host's chromosomal DNA and without gradual loss from a dividing host cell also meaning that said vector replicates extrachromosomally or episomally.

The "control elements" or "regulatory sequences" present in an expression vector are those non-translated regions of the vector-origin of replication, selection cassettes, promoters, enhancers, translation initiation signals (Shine Dalgarno sequence or Kozak sequence) introns, a polyadenylation sequence, 5' and 3' untranslated regions-which interact with host cellular proteins to carry out transcription and translation. Such elements may vary in their strength and specificity. Depending on the vector system and host utilized, any number of suitable transcription and translation elements, including ubiquitous promoters and inducible promoters may be used.

In particular embodiments, vectors include, but are not limited to expression vectors and viral vectors, will include exogenous, endogenous, or heterologous control sequences such as promoters and/or enhancers. An "endogenous" control sequence is one which is naturally linked with a given gene in the genome. An "exogenous" control sequence is one which is placed in juxtaposition to a gene by means of genetic manipulation (i.e., molecular biological techniques) such that transcription of that gene is directed by the linked enhancer/promoter. A "heterologous" control sequence is an exogenous sequence that is from a different species than the cell being genetically manipulated.

The term "promoter" as used herein refers to a recognition site of a polynucleotide (DNA or RNA) to which an RNA polymerase binds. An RNA polymerase initiates and transcribes polynucleotides operably linked to the promoter. In particular embodiments, promoters operative in mammalian cells comprise an AT-rich region located approximately 25 to 30 bases upstream from the site where transcription is initiated and/or another sequence found 70 to 80 bases upstream from the start of transcription, a CNCAAT region where N may be any nucleotide.

The term "enhancer" refers to a segment of DNA which contains sequences capable of providing enhanced transcription and in some instances can function independent of their orientation relative to another control sequence. An enhancer can function cooperatively or additively with promoters and/or other enhancer elements. The term "promoter/enhancer" refers to a segment of DNA which contains sequences capable of providing both promoter and enhancer functions.

The term "operably linked", refers to a juxtaposition wherein the components described are in a relationship permitting them to function in their intended manner. In one embodiment, the term refers to a functional linkage between a nucleic acid expression control sequence (such as a promoter, and/or enhancer) and a second polynucleotide sequence, e.g., a polynucleotide-of-interest, wherein the expression control sequence directs transcription of the nucleic acid corresponding to the second sequence.

As used herein, the term "constitutive expression control sequence" refers to a promoter, enhancer, or promoter/enhancer that continually or continuously allows for transcription of an operably linked sequence. A constitutive expression control sequence may be a "ubiquitous" promoter, enhancer, or promoter/enhancer that allows expression in a wide variety of cell and tissue types or a "cell specific," "cell type specific," "cell lineage specific," or "tissue specific" promoter, enhancer, or promoter/enhancer that allows expression in a restricted variety of cell and tissue types, respectively.

Illustrative ubiquitous expression control sequences suitable for use in particular embodiments include, but are not limited to, a cytomegalovirus (CMV) immediate early promoter, a viral simian virus 40 (SV40) (e.g., early or late), a Moloney murine leukemia virus (MoMLV) LTR promoter, a Rous sarcoma virus (RSV) LTR, a herpes simplex virus (HSV) (thymidine kinase) promoter, H5, P7.5, and P11 promoters from vaccinia virus, an elongation factor 1-alpha (EF1a) promoter, early growth response 1 (EGR1), ferritin H (FerH), ferritin L (FerL), Glyceraldehyde 3-phosphate dehydrogenase (GAPDH), eukaryotic translation initiation factor 4A1 (EIF4A1), heat shock 70 kDa protein 5 (HSPA5), heat shock protein 90 kDa beta, member 1 (HSP90B1), heat shock protein 70 kDa (HSP70), β-kinesin (β-KIN), the human ROSA 26 locus (Irions et al., *Nature Biotechnology* 25, 1477-1482 (2007)), a Ubiquitin C promoter (UBC), a phosphoglycerate kinase-1 (PGK) promoter, a cytomegalovirus enhancer/chicken β-actin (CAG) promoter, a β-actin promoter and a myeloproliferative sarcoma virus enhancer, negative control region deleted, d1587rev primer-binding site substituted (MND) U3 promoter (Haas et al. *Journal of Virology.* 2003; 77 (17): 9439-9450).

In one embodiment, a vector comprises an MNDU3 promoter.

In one embodiment, a vector comprises an EF1a promoter comprising the first intron of the human EF1a gene.

In one embodiment, a vector comprises an EF1a promoter that lacks the first intron of the human EF1a gene.

In a particular embodiment, it may be desirable to express a polynucleotide comprising a CAR from a T cell specific promoter.

As used herein, "conditional expression" may refer to any type of conditional expression including, but not limited to, inducible expression; repressible expression; expression in cells or tissues having a particular physiological, biological, or disease state, etc. This definition is not intended to exclude cell type or tissue specific expression. Certain embodiments provide conditional expression of a polynucleotide-of-interest, e.g., expression is controlled by subjecting a cell, tissue, organism, etc., to a treatment or condition that causes the polynucleotide to be expressed or that causes an increase or decrease in expression of the polynucleotide encoded by the polynucleotide-of-interest.

Illustrative examples of inducible promoters/systems include, but are not limited to, steroid-inducible promoters such as promoters for genes encoding glucocorticoid or estrogen receptors (inducible by treatment with the corresponding hormone), metallothionine promoter (inducible by treatment with various heavy metals), MX-1 promoter (inducible by interferon), the "GeneSwitch" mifepristone-regulatable system (Sirin et al., 2003, *Gene,* 323:67), the cumate inducible gene switch (WO 2002/088346), tetracycline-dependent regulatory systems, etc.

Conditional expression can also be achieved by using a site-specific DNA recombinase. According to certain embodiments the vector comprises at least one (typically two) site(s) for recombination mediated by a site-specific recombinase. As used herein, the terms "recombinase" or "site specific recombinase" include excisive or integrative proteins, enzymes, co-factors or associated proteins that are involved in recombination reactions involving one or more recombination sites (e.g., two, three, four, five, seven, ten, twelve, fifteen, twenty, thirty, fifty, etc.), which may be wild-type proteins (see Landy, *Current Opinion in Biotechnology* 3:699-707 (1993)), or mutants, derivatives (e.g., fusion proteins containing the recombination protein sequences or fragments thereof), fragments, and variants thereof. Illustrative examples of recombinases suitable for use in particular embodiments include, but are not limited to: Cre, Int, IHF, Xis, Flp, Fis, Hin, Gin, @C31, Cin, Tn3 resolvase, TndX, XerC, XerD, TnpX, Hjc, Gin, SpCCE1, and ParA.

The vectors may comprise one or more recombination sites for any of a wide variety of site-specific recombinases. It is to be understood that the target site for a site-specific recombinase is in addition to any site(s) required for integration of a vector, e.g., a retroviral" vector or lentiviral vector. As used herein, the terms "recombination sequence,"

"recombination site," or "site specific recombination site" refer to a particular nucleic acid sequence to which a recombinase recognizes and binds.

For example, one recombination site for Cre recombinase is loxP which is a 34 base pair sequence comprising two 13 base pair inverted repeats (serving as the recombinase binding sites) flanking an 8 base pair core sequence (see FIG. 1 of Sauer, B., *Current Opinion in Biotechnology* 5:521-527 (1994)). Other exemplary loxP sites include, but are not limited to: lox511 (Hoess et al., 1996; Bethke and Sauer, 1997), lox5171 (Lee and Saito, 1998), lox2272 (Lee and Saito, 1998), m2 (Langer et al., 2002), lox71 (Albert et al., 1995), and lox66 (Albert et al., 1995).

Suitable recognition sites for the FLP recombinase include, but are not limited to: FRT (McLeod, et al., 1996), $F_1$, $F_2$, $F_3$ (Schlake and Bode, 1994), $F_4$, $F_5$ (Schlake and Bode, 1994), FRT (LE) (Senecoff et al., 1988), FRT(RE) (Senecoff et al., 1988).

Other examples of recognition sequences are the attB, attP, attL, and attR sequences, which are recognized by the recombinase enzyme λ Integrase, e.g., phi-c31. The φC31 SSR mediates recombination only between the heterotypic sites attB (34 bp in length) and attP (39 bp in length) (Groth et al., 2000). attB and attP, named for the attachment sites for the phage integrase on the bacterial and phage genomes, respectively, both contain imperfect inverted repeats that are likely bound by φC31 homodimers (Groth et al., 2000). The product sites, attL and attR, are effectively inert to further φC31-mediated recombination (Belteki et al., 2003), making the reaction irreversible. For catalyzing insertions, it has been found that attB-bearing DNA inserts into a genomic attP site more readily than an attP site into a genomic attB site (Thyagarajan et al., 2001; Belteki et al., 2003). Thus, typical strategies position by homologous recombination an attP-bearing "docking site" into a defined locus, which is then partnered with an attB-bearing incoming sequence for insertion.

As used herein, an "internal ribosome entry site" or "IRES" refers to an element that promotes direct internal ribosome entry to the initiation codon, such as ATG, of a cistron (a protein encoding region), thereby leading to the cap-independent translation of the gene. See, e.g., Jackson et al., 1990. *Trends Biochem Sci* 15 (12): 477-83) and Jackson and Kaminski. 1995. *RNA* 1(10):985-1000. In particular embodiments, vectors include one or more polynucleotides-of-interest that encode one or more polypeptides. In particular embodiments, to achieve efficient translation of each of the plurality of polypeptides, the polynucleotide sequences can be separated by one or more IRES sequences or polynucleotide sequences encoding self-cleaving polypeptides. In one embodiment, the IRES used in polynucleotides contemplated herein is an EMCV IRES.

As used herein, the term "Kozak sequence" refers to a short nucleotide sequence that greatly facilitates the initial binding of mRNA to the small subunit of the ribosome and increases translation. The consensus Kozak sequence is (GCC) RCCATGG (SEQ ID NO: 107), where R is a purine (A or G) (Kozak, 1986. *Cell.* 44 (2):283-92, and Kozak, 1987. *Nucleic Acids Res.* 15(20):8125-48). In particular embodiments, the vectors comprise polynucleotides that have a consensus Kozak sequence and that encode a desired polypeptide, e.g., a CAR.

Elements directing the efficient termination and polyadenylation of the heterologous nucleic acid transcripts increases heterologous gene expression. Transcription termination signals are generally found downstream of the polyadenylation signal. In particular embodiments, vectors comprise a polyadenylation sequence 3' of a polynucleotide encoding a polypeptide to be expressed. The term "polyA site" or "polyA sequence" as used herein denotes a DNA sequence which directs both the termination and polyadenylation of the nascent RNA transcript by RNA polymerase II. Polyadenylation sequences can promote mRNA stability by addition of a polyA tail to the 3' end of the coding sequence and thus, contribute to increased translational efficiency. Cleavage and polyadenylation is directed by a poly (A) sequence in the RNA. The core poly (A) sequence for mammalian pre-mRNAs has two recognition elements flanking a cleavage-polyadenylation site. Typically, an almost invariant AAUAAA hexamer lies 20-50 nucleotides upstream of a more variable element rich in U or GU residues. Cleavage of the nascent transcript occurs between these two elements and is coupled to the addition of up to 250 adenosines to the 5' cleavage product. In particular embodiments, the core poly (A) sequence is an ideal polyA sequence (e.g., AATAAA, ATTAAA, AGTAAA). In particular embodiments, the poly (A) sequence is an SV40 polyA sequence, a bovine growth hormone polyA sequence (BGHpA), a rabbit β-globin polyA sequence (rβgpA), variants thereof, or another suitable heterologous or endogenous polyA sequence known in the art.

In some embodiments, a polynucleotide or cell harboring the polynucleotide utilizes a suicide gene, including an inducible suicide gene to reduce the risk of direct toxicity and/or uncontrolled proliferation. In specific aspects, the suicide gene is not immunogenic to the host harboring the polynucleotide or cell. A certain example of a suicide gene that may be used is caspase-9 or caspase-8 or cytosine deaminase. Caspase-9 can be activated using a specific chemical inducer of dimerization (CID).

H. Vectors

In particular embodiments, one or more polynucleotides encoding a CAR are introduced into a cell (e.g., an immune effector cell) by non-viral or viral vectors. In some embodiments, a polycistronic polynucleotide encoding a CAR is introduced into a cell by a non-viral or viral vector.

The term "vector" is used herein to refer to a nucleic acid molecule capable transferring or transporting another nucleic acid molecule. The transferred nucleic acid is generally linked to, e.g., inserted into, the vector nucleic acid molecule. A vector may include sequences that direct autonomous replication in a cell, or may include sequences sufficient to allow integration into host cell DNA. In particular embodiments, non-viral vectors are used to deliver one or more polynucleotides contemplated herein to a T cell.

Illustrative examples of non-viral vectors include, but are not limited to mRNA, plasmids (e.g., DNA plasmids or RNA plasmids), transposons, cosmids, and bacterial artificial chromosomes.

Illustrative methods of non-viral delivery of polynucleotides or vectors contemplated in particular embodiments include, but are not limited to: electroporation, sonoporation, lipofection, microinjection, biolistics, virosomes, liposomes, immunoliposomes, nanoparticles, polycation or lipid: nucleic acid conjugates, naked DNA, artificial virions, DEAE-dextran-mediated transfer, gene gun, and heat-shock.

Illustrative examples of polynucleotide delivery systems suitable for use in particular embodiments contemplated in particular embodiments include, but are not limited to those provided by Amaxa Biosystems, Maxcyte, Inc., BTX Molecular Delivery Systems, and Copernicus Therapeutics Inc. Lipofection reagents are sold commercially (e.g., Transfectam™ and Lipofectin™). Cationic and neutral lipids that are suitable for efficient receptor-recognition lipofection of polynucleotides have been described in the literature. See e.g., Liu et al. (2003) *Gene Therapy.* 10:180-187; and Balazs et al. (2011) *Journal of Drug Delivery.* 2011:1-12. Antibody-targeted, bacterially derived, non-living nanocell-based delivery is also contemplated in particular embodiments.

In various embodiments, the polynucleotide is an mRNA that is introduced into a cell in order to transiently express a desired polypeptide.

As used herein, "transient" refers to expression of a non-integrated transgene for a period of hours, days or weeks, wherein the period of time of expression is less than the period of time for expression of the polynucleotide if integrated into the genome or contained within a stable plasmid replicon in the cell.

In particular embodiments, the mRNA encoding a polypeptide is an in vitro transcribed mRNA. As used herein, "in vitro transcribed RNA" refers to RNA, preferably mRNA that has been synthesized in vitro. Generally, the in vitro transcribed RNA is generated from an in vitro transcription vector. The in vitro transcription vector comprises a template that is used to generate the in vitro transcribed RNA.

In particular embodiments, mRNAs may further comprise a comprise a 5' cap or modified 5' cap and/or a poly (A) sequence. As used herein, a 5' cap (also termed an RNA cap, an RNA 7-methylguanosine cap or an RNA m7G cap) is a modified guanine nucleotide that has been added to the "front" or 5' end of a eukaryotic messenger RNA shortly after the start of transcription. The .5' cap comprises a terminal group which is linked to the first transcribed nucleotide and recognized by the ribosome and protected from RNases. The capping moiety can be modified to modulate functionality of mRNA such as its stability or efficiency of translation. In a particular embodiment, the mRNA comprises a poly (A) sequence of between about 50 and about 5000 adenines. In one embodiment, the mRNA comprises a poly (A) sequence of between about 100 and about 1000 bases, between about 200 and about 500 bases, or between about 300 and about 400 bases. In one embodiment, the mRNA comprises a poly (A) sequence of about 65 bases, about 100 bases, about 200 bases, about 300 bases, about 400 bases, about 500 bases, about 600 bases, about 700 bases, about 800 bases, about 900 bases, or about 1000 or more bases. poly (A) sequences can be modified chemically or enzymatically to modulate mRNA functionality such as localization, stability or efficiency of translation.

Viral vectors comprising polynucleotides contemplated in particular embodiments can be delivered in vivo by administration to an individual patient, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient (e.g., mobilized peripheral blood, lymphocytes, bone marrow aspirates, tissue biopsy, etc.) or universal donor hematopoietic stem cells, followed by reimplantation of the cells into a patient.

In one embodiment, a viral vector comprising a polynucleotide encoding a CAR is administered directly to an organism for transduction of cells in vivo. Alternatively, naked DNA can be administered. Administration is by any of the routes normally used for introducing a molecule into ultimate contact with blood or tissue cells including, but not limited to, injection, infusion, topical application and electroporation. Suitable methods of administering such nucleic acids are available and well known to those of skill in the art, and, although more than one route can be used to administer a particular composition, a particular route can often provide a more immediate and more effective reaction than another route.

Illustrative examples of viral vector systems suitable for use in particular embodiments contemplated herein include but are not limited to adeno-associated virus (AAV), retrovirus, herpes simplex virus, adenovirus, and vaccinia virus vectors.

In various embodiments, one or more polynucleotides encoding a CAR are introduced into an immune effector cell, e.g., a T cell, by transducing the cell with a recombinant adeno-associated virus (rAAV), comprising the one or more polynucleotides.

AAV is a small (~26 nm) replication-defective, primarily episomal, non-enveloped virus. AAV can infect both dividing and non-dividing cells and may incorporate its genome into that of the host cell. Recombinant AAV (rAAV) are typically composed of, at a minimum, a transgene and its regulatory sequences, and 5' and 3' AAV inverted terminal repeats (ITRs). The ITR sequences are about 145 bp in length. In particular embodiments, the rAAV comprises ITRs and capsid sequences isolated from AAV1, AAV2, AAV3, AAV4, AAV5, AAV6, AAV7, AAV8, AAV9, or AAV10.

In some embodiments, a chimeric rAAV is used the ITR sequences are isolated from one AAV serotype and the capsid sequences are isolated from a different AAV serotype. For example, a rAAV with ITR sequences derived from AAV2 and capsid sequences derived from AAV6 is referred to as AAV2/AAV6. In particular embodiments, the rAAV vector may comprise ITRs from AAV2, and capsid proteins from any one of AAV1, AAV2, AAV3, AAV4, AAV5, AAV6, AAV7, AAV8, AAV9, or AAV10. In a preferred embodiment, the rAAV comprises ITR sequences derived from AAV2 and capsid sequences derived from AAV6. In a preferred embodiment, the rAAV comprises ITR sequences derived from AAV2 and capsid sequences derived from AAV2.

In some embodiments, engineering and selection methods can be applied to AAV capsids to make them more likely to transduce cells of interest.

Construction of rAAV vectors, production, and purification thereof have been disclosed, e.g., in U.S. Pat. Nos. 9,169,494; 9,169,492; 9,012,224; 8,889,641; 8,809,058; and 8,784,799, each of which is incorporated by reference herein, in its entirety.

In various embodiments, one or more polynucleotides encoding a CAR are introduced into an immune effector cell, by transducing the cell with a retrovirus, e.g., lentivirus, comprising the one or more polynucleotides.

As used herein, the term "retrovirus" refers to an RNA virus that reverse transcribes its genomic RNA into a linear double-stranded DNA copy and subsequently covalently integrates its genomic DNA into a host genome. Illustrative retroviruses suitable for use in particular embodiments, include, but are not limited to: Moloney murine leukemia virus (M-MuLV), Moloney murine sarcoma virus (MoMSV), Harvey murine sarcoma virus (HaMuSV), murine mammary tumor virus (MuMTV), gibbon ape leukemia virus (GaLV), feline leukemia virus (FLV), spumavirus, Friend murine leukemia virus, Murine Stem Cell Virus (MSCV) and Rous Sarcoma Virus (RSV)) and lentivirus.

As used herein, the term "lentivirus" refers to a group (or genus) of complex retroviruses. Illustrative lentiviruses include, but are not limited to: HIV (human immunodeficiency virus; including HIV type 1, and HIV 2); visna-maedi virus (VMV) virus; the caprine arthritis-encephalitis virus (CAEV); equine infectious anemia virus (EIAV); feline immunodeficiency virus (FIV); bovine immune deficiency virus (BIV); and simian immunodeficiency virus (SIV). In one embodiment, HIV based vector backbones (i.e., HIV cis-acting sequence elements) are preferred.

In various embodiments, a lentiviral vector contemplated herein comprises one or more LTRs, and one or more, or all, of the following accessory elements: a cPPT/FLAP, a Psi(Ψ) packaging signal, an export element, poly (A) sequences, and may optionally comprise a WPRE or HPRE, an insulator element, a selectable marker, and a cell suicide gene, as discussed elsewhere herein.

In particular embodiments, lentiviral vectors contemplated herein may be integrative or non-integrating or integration defective lentivirus. As used herein, the term "integration defective lentivirus" or "IDLV" refers to a lentivirus having an integrase that lacks the capacity to integrate the viral genome into the genome of the host cells. Integration-incompetent viral vectors have been described in patent application WO 2006/010834, which is herein incorporated by reference in its entirety.

Illustrative mutations in the HIV-1 pol gene suitable to reduce integrase activity include, but are not limited to: H12N, H12C, H16C, H16V, S81 R, D41A, K42A, H51A, Q53C, D55V, D64E, D64V, E69A, K71A, E85A, E87A, D116N, D1161, D116A, N120G, N1201, N120E, E152G, E152A, D35E, K156E, K156A, E157A, K159E, K159A, K160A, R166A, D167A, E170A, H171A, K173A, K186Q, K186T, K188T, E198A, R199c, R199T, R199A, D202A, K211A, Q214L, Q216L, Q221 L, W235F, W235E, K236S, K236A, K246A, G247W, D253A, R262A, R263A and K264H.

In one embodiment, the HIV-1 integrase deficient pol gene comprises a D64V, D116I, D116A, E152G, or E152A mutation; D64V, D116I, and E152G mutations; or D64V, D116A, and E152A mutations.

In one embodiment, the HIV-1 integrase deficient pol gene comprises a D64V mutation.

The term "long terminal repeat (LTR)" refers to domains of base pairs located at the ends of retroviral DNAs which, in their natural sequence context, are direct repeats and contain U3, R and U5 regions.

As used herein, the term "FLAP element" or "cPPT/FLAP" refers to a nucleic acid whose sequence includes the central polypurine tract and central termination sequences (cPPT and CTS) of a retrovirus, e.g., HIV-1 or HIV-2. Suitable FLAP elements are described in U.S. Pat. No. 6,682,907 and in Zennou, et al., 2000, *Cell*, 101:173. In another embodiment, a lentiviral vector contains a FLAP element with one or more mutations in the cPPT and/or CTS elements. In yet another embodiment, a lentiviral vector comprises either a cPPT or CTS element. In yet another embodiment, a lentiviral vector does not comprise a cPPT or CTS element.

As used herein, the term "packaging signal" or "packaging sequence" refers to psi [Ψ] sequences located within the retroviral genome which are required for insertion of the viral RNA into the viral capsid or particle, see e.g., Clever et al., 1995. *J. of Virology*, Vol. 69, No. 4; pp. 2101-2109.

The term "export element" refers to a cis-acting post-transcriptional regulatory element which regulates the transport of an RNA transcript from the nucleus to the cytoplasm of a cell. Examples of RNA export elements include, but are not limited to, the human immunodeficiency virus (HIV) rev response element (RRE) (see e.g., Cullen et al., 1991. *J. Virol.* 65:1053; and Cullen et al., 1991. *Cell* 58:423), and the hepatitis B virus post-transcriptional regulatory element (HPRE).

In particular embodiments, expression of heterologous sequences in viral vectors is increased by incorporating posttranscriptional regulatory elements, efficient polyadenylation sites, and optionally, transcription termination signals into the vectors. A variety of posttranscriptional regulatory elements can increase expression of a heterologous nucleic acid at the protein, e.g., woodchuck hepatitis virus posttranscriptional regulatory element (WPRE; Zufferey et al., 1999, *J. Virol.*, 73:2886); the posttranscriptional regulatory element present in hepatitis B virus (HPRE) (Huang et al., *Mol. Cell. Biol.*, 5:3864); and the like (Liu et al., 1995, *Genes Dev.*, 9:1766).

Lentiviral vectors preferably contain several safety enhancements as a result of modifying the LTRs. "Self-inactivating" (SIN) vectors refers to replication-defective vectors, e.g., in which the right (3') LTR enhancer-promoter region, known as the U3 region, has been modified (e.g., by deletion or substitution) to prevent viral transcription beyond the first round of viral replication. An additional safety enhancement is provided by replacing the U3 region of the 5' LTR with a heterologous promoter to drive transcription of the viral genome during production of viral particles. Examples of heterologous promoters which can be used include, for example, viral simian virus 40 (SV40) (e.g., early or late), cytomegalovirus (CMV) (e.g., immediate early), Moloney murine leukemia virus (MoMLV), Rous sarcoma virus (RSV), and herpes simplex virus (HSV) (thymidine kinase) promoters.

The terms "pseudotype" or "pseudotyping" as used herein, refer to a virus that has viral envelope proteins that have been substituted with those of another virus possessing preferable characteristics. For example, HIV can be pseudotyped with vesicular stomatitis virus G-protein (VSV-G) envelope proteins, which allows HIV to infect a wider range of cells because HIV envelope proteins (encoded by the env gene) normally target the virus to $CD4^+$ presenting cells.

In certain embodiments, lentiviral vectors are produced according to known methods. See e.g., Kutner et al., *BMC Biotechnol.* 2009; 9:10. doi: 10.1186/1472-6750-9-10; Kutner et al. *Nat. Protoc.* 2009; 4 (4): 495-505. doi: 10.1038/nprot.2009.22.

According to certain specific embodiments contemplated herein, most or all of the viral vector backbone sequences are derived from a lentivirus, e.g., HIV-1. However, it is to be understood that many different sources of retroviral and/or lentiviral sequences can be used, or combined and numerous substitutions and alterations in certain of the lentiviral sequences may be accommodated without impairing the ability of a transfer vector to perform the functions described herein. Moreover, a variety of lentiviral vectors are known in the art, see Naldini et al., (1996a, 1996b, and 1998); Zufferey et al., (1997); Dull et al., 1998, U.S. Pat. Nos. 6,013,516; and 5,994,136, many of which may be adapted to produce a viral vector or transfer plasmid contemplated herein.

In various embodiments, one or more polynucleotides encoding a CAR are introduced into an immune effector cell by transducing the cell with an adenovirus comprising the one or more polynucleotides.

Adenoviral based vectors are capable of very high transduction efficiency in many cell types and do not require cell division. With such vectors, high titer and high levels of expression have been obtained. This vector can be produced in large quantities in a relatively simple system. Most adenovirus vectors are engineered such that a transgene replaces the Ad Ela, E1b, and/or E3 genes; subsequently the replication defective vector is propagated in human 293 cells that supply deleted gene function in trans. Ad vectors can transduce multiple types of tissues in vivo, including non-dividing, differentiated cells such as those found in liver, kidney and muscle. Conventional Ad vectors have a large carrying capacity.

Generation and propagation of the current adenovirus vectors, which are replication deficient, may utilize a unique helper cell line, designated 293, which was transformed from human embryonic kidney cells by Ad5 DNA fragments and constitutively expresses E1 proteins (Graham et al., 1977). Since the E3 region is dispensable from the adenovirus genome (Jones & Shenk, 1978), the current adenovirus vectors, with the help of 293 cells, carry foreign DNA in either the E1, the D3 or both regions (Graham & Prevec, 1991). Adenovirus vectors have been used in eukaryotic gene expression (Levrero et al., 1991; Gomez-Foix et al., 1992) and vaccine development (Grunhaus & Horwitz, 1992; Graham & Prevec, 1992). Studies in administering recombinant adenovirus to different tissues include trachea instillation (Rosenfeld et al., 1991; Rosenfeld et al., 1992), muscle injection (Ragot et al., 1993), peripheral intravenous injections (Herz & Gerard, 1993) and stereotactic inoculation into the brain (Le Gal La Salle et al., 1993). An example of the use of an Ad vector in a clinical trial involved polynucleotide therapy for antitumor immunization with intramuscular injection (Sterman et al., *Hum. Gene Ther.* 7:1083-9 (1998)).

In various embodiments, one or more polynucleotides encoding a CAR are introduced into an immune effector cell by transducing the cell with a herpes simplex virus, e.g., HSV-1, HSV-2, comprising the one or more polynucleotides. In some embodiments, one or more polynucleotides encoding a polycistronic message encoding a CAR are introduced into an immune effector cell by transducing the cell with a herpes simplex virus, e.g., HSV-1, HSV-2, comprising the one or more polynucleotides.

The mature HSV virion consists of an enveloped icosahedral capsid with a viral genome consisting of a linear double-stranded DNA molecule that is 152 kb. In one embodiment, the HSV based viral vector is deficient in one or more essential or non-essential HSV genes. In one embodiment, the HSV based viral vector is replication deficient. Most replication deficient HSV vectors contain a deletion to remove one or more intermediate-early, early, or late HSV genes to prevent replication. For example, the HSV vector may be deficient in an immediate early gene selected from the group consisting of: ICP4, ICP22, ICP27, ICP47, and a combination thereof. Advantages of the HSV vector are its ability to enter a latent stage that can result in long-term DNA expression and its large viral DNA genome that can accommodate exogenous DNA inserts of up to 25 kb. HSV-based vectors are described in, for example, U.S. Pat. Nos. 5,837,532, 5,846,782, and 5,804,413, and International Patent Applications WO 91/02788, WO 96/04394, WO 98/15637, and WO 99/06583, each of which are incorporated by reference herein in its entirety.

I. Genetically Modified Cells

In various embodiments, cells genetically modified to express the CARs contemplated herein, for use in the treatment of B cell related conditions. As used herein, the term "genetically engineered" or "genetically modified" refers to the addition of extra genetic material in the form of DNA or RNA into the total genetic material in a cell. The terms, "genetically modified cells," "modified cells," and, "redirected cells," are used interchangeably. As used herein, the term "gene therapy" refers to the introduction of extra genetic material in the form of DNA or RNA into the total genetic material in a cell that restores, corrects, or modifies expression of a gene, or for the purpose of expressing a therapeutic polypeptide, e.g., a CAR.

In particular embodiments, the CARs contemplated herein are introduced and expressed in immune effector cells so as to redirect their specificity to a target antigen of interest, e.g., a BCMA polypeptide. An "immune effector cell," is any cell of the immune system that has one or more effector functions (e.g., cytotoxic cell killing activity, secretion of cytokines, induction of ADCC and/or CDC). Illustrative immune effector cells contemplated herein are T lymphocytes, including but not limited to cytotoxic T cells (CTLs; CD8+ T cells), TILs, and helper T cells (HTLs; CD4+ T cells). In a particular embodiment, the cells comprise αβ T cells. In a particular embodiment, the cells comprise γδ T cells. In one embodiment, immune effector cells include natural killer (NK) cells. In one embodiment, immune effector cells include natural killer T (NKT) cells.

Immune effector cells can be autologous/autogeneic ("self") or non-autologous ("non-self," e.g., allogeneic, syngeneic or xenogeneic). "Autologous," as used herein, refers to cells from the same subject. "Allogeneic," as used herein, refers to cells of the same species that differ genetically to the cell in comparison. "Syngeneic," as used herein, refers to cells of a different subject that are genetically identical to the cell in comparison. "Xenogeneic," as used herein, refers to cells of a different species to the cell in comparison. In preferred embodiments, the cells are autologous.

Illustrative immune effector cells used with the CARs contemplated in particular embodiments include T lymphocytes. The terms "T cell" or "T lymphocyte" are art-recognized and are intended to include thymocytes, immature T lymphocytes, mature T lymphocytes, resting T lymphocytes, or activated T lymphocytes. A T cell can be a T helper (Th) cell, for example a T helper 1 (Th1) or a T helper 2 (Th2) cell. The T cell can be a helper T cell (HTL; CD4+ T cell) CD4+ T cell, a cytotoxic T cell (CTL; CD8+ T cell), CD4+CD8+ T cell, CD4-CD8-T cell, or any other subset of T cells. Other illustrative populations of T cells suitable for use in particular embodiments include naïve T cells (TN), T memory stem cells (TSCM), central memory T cells (TCM), effector memory T cells (TEM), and effector T cells (TEFF).

As would be understood by the skilled person, other cells may also be used as immune effector cells with the CARs herein. In particular, immune effector cells also include NK cells, NKT cells, neutrophils, and macrophages. Immune effector cells also include progenitors of effector cells wherein such progenitor cells can be induced to differentiate into an immune effector cells in vivo or in vitro. Thus, in particular embodiments, immune effector cell includes progenitors of immune effectors cells such as hematopoietic stem cells (HSCs) contained within the CD34+ population of cells derived from cord blood; bone marrow or mobilized peripheral blood which upon administration in a subject differentiate into mature immune effector cells, or which can be induced in vitro to differentiate into mature immune effector cells.

The term, "CD34+ cell," as used herein refers to a cell expressing the CD34 protein on its cell surface. "CD34," as used herein refers to a cell surface glycoprotein (e.g., sialomucin protein) that often acts as a cell-cell adhesion factor and is involved in T cell entrance into lymph nodes. The CD34+ cell population contains hematopoietic stem cells (HSC), which upon administration to a patient differentiate and contribute to all hematopoietic lineages, including T cells, NK cells, NKT cells, neutrophils and cells of the monocyte/macrophage lineage.

Methods for making the immune effector cells that express a CAR contemplated herein are provided in particular embodiments. In one embodiment, the method comprises transfecting or transducing immune effector cells isolated from an individual such that the immune effector cells express one or more CARs contemplated herein. In certain embodiments, the immune effector cells are isolated from an individual and genetically modified without further manipulation in vitro. Such cells can then be directly re-administered into the individual. In further embodiments, the immune effector cells are first activated and stimulated to proliferate in vitro prior to being genetically modified to express a CAR. In this regard, the immune effector cells may be cultured before and/or after being genetically modified (i.e., transduced or transfected to express a CAR contemplated herein).

In particular embodiments, prior to in vitro manipulation or genetic modification of the immune effector cells contemplated herein, the source of cells is obtained from a subject. In particular embodiments, modified immune effector cells comprise T cells.

In particular embodiments, PBMCs may be directly genetically modified to express a CAR using methods contemplated herein. In certain embodiments, after isolation of PBMC, T lymphocytes are further isolated and in certain embodiments, both cytotoxic and helper T lymphocytes can be sorted into naïve, memory, and effector T cell subpopulations either before or after genetic modification and/or expansion.

The immune effector cells, such as T cells, can be genetically modified following isolation using known methods, or the immune effector cells can be activated and expanded (or differentiated in the case of progenitors) in vitro prior to being genetically modified. In a particular embodiment, the immune effector cells, such as T cells, are genetically modified with the chimeric antigen receptors contemplated herein (e.g., transduced with a viral vector comprising a nucleic acid encoding a CAR or a polycistronic message encoding a CAR) and then are activated and expanded in vitro. In various embodiments, T cells can be activated and expanded before or after genetic modification to express a CAR, using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005.

In one embodiment, CD34+ cells are transduced with a nucleic acid construct contemplated herein. In certain embodiments, the transduced CD34+ cells differentiate into mature immune effector cells in vivo following administration into a subject, generally the subject from whom the cells were originally isolated. In another embodiment, CD34+ cells may be stimulated in vitro prior to exposure to or after being genetically modified with a CAR as contemplated herein, with one or more of the following cytokines: Flt-3 ligand (FLT3), stem cell factor (SCF), megakaryocyte growth and differentiation factor (TPO), IL-3 and IL-6 according to the methods described previously (Asheuer et al., 2004; Imren, et al., 2004).

In particular embodiments, a population of modified immune effector cells for the treatment of cancer comprises a CAR contemplated herein. For example, a population of modified immune effector cells are prepared from peripheral blood mononuclear cells (PBMCs) obtained from a patient diagnosed with B cell malignancy described herein (autologous donors). The PBMCs form a heterogeneous population of T lymphocytes that can be CD4+, CD8+, or CD4+ and CD8+.

The PBMCs also can include other cytotoxic lymphocytes such as NK cells or NKT cells. An expression vector carrying the coding sequence of a CAR contemplated in particular embodiments is introduced into a population of human donor T cells, NK cells or NKT cells. In particular embodiments, successfully transduced T cells that carry the expression vector can be sorted using flow cytometry to isolate CD3 positive T cells and then further propagated to increase the number of these CAR protein expressing T cells in addition to cell activation using anti-CD3 antibodies and or anti-CD28 antibodies and IL-2 or any other methods known in the art as described elsewhere herein. Standard procedures are used for cryopreservation of T cells expressing the CAR protein T cells for storage and/or preparation for use in a human subject. In one embodiment, the in vitro transduction, culture and/or expansion of T cells are performed in the absence of non-human animal derived products such as fetal calf serum and fetal bovine serum. Since a heterogeneous population of PBMCs is genetically modified, the resultant transduced cells are a heterogeneous population of modified cells comprising a BCMA targeting CAR as contemplated herein.

In a further embodiment, a mixture of, e.g., one, two, three, four, five or more, different expression vectors can be used in genetically modifying a donor population of immune effector cells wherein each vector encodes a different chimeric antigen receptor protein as contemplated herein. The resulting modified immune effector cells forms a mixed population of modified cells.

Genetically engineered cells, including T cells, can be manufactured using various methods known in the art, see, e.g., WO 2016/094304 which is incorporated herein by reference in its entirety.

J. Compositions and Formulations

In particular embodiments, formulation of pharmaceutically-acceptable carrier solutions is well-known to those of skill in the art, as is the development of suitable dosing and treatment regimens for using the particular compositions contemplated herein in a variety of treatment regimens, including e.g., enteral and parenteral, e.g., intravascular, intravenous, intrarterial, intraosseously, intraventricular, intracerebral, intracranial, intraspinal, intrathecal, and intramedullary administration and formulation. It would be understood by the skilled artisan that particular embodiments contemplated herein may comprise other formulations, such as those that are well known in the pharmaceutical art, and are described, for example, in *Remington: The Science and Practice of Pharmacy*, volume I and volume II. 22nd Edition. Edited by Loyd V. Allen Jr. Philadelphia, PA: Pharmaceutical Press; 2012, which is incorporated by reference herein, in its entirety.

The compositions contemplated herein may comprise one or more anti-BCMA antibodies or fragments thereof, CAR polypeptides, polynucleotides, vectors comprising same, or genetically modified immune effector cells, etc., as contemplated herein. Compositions include, but are not limited to pharmaceutical compositions. In preferred embodiments, a composition comprises one or more cells modified to express a CAR.

A "pharmaceutical composition" refers to a composition formulated in pharmaceutically-acceptable or physiologically-acceptable solutions for administration to a cell or an animal, either alone, or in combination with one or more other modalities of therapy. It will also be understood that, if desired, the compositions may be administered in combination with other agents as well, such as, e.g., cytokines, growth factors, hormones, small molecules, chemotherapeutics, pro-drugs, drugs, antibodies, or other various pharmaceutically-active agents. There is virtually no limit to other components that may also be included in the compositions, provided that the additional agents do not adversely affect the ability of the composition to deliver the intended therapy. In preferred embodiments, a pharmaceutical composition comprises a pharmaceutically acceptable carrier, diluent or excipient and one or more cells modified to express a CAR as contemplated herein. In some embodiments, a pharmaceutical composition comprises a pharmaceutically acceptable carrier, diluent or excipient and an anti-BCMA antibody or fragment thereof as contemplated herein.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein "pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, surfactant, or emulsifier which has been approved by the United States Food and Drug Administration as being acceptable for use in humans or domestic animals. Exemplary pharmaceutically acceptable carriers include, but are not limited to, to sugars, such as lactose, glucose and sucrose; starches, such as corn starch and potato starch; cellulose, and its derivatives, such as sodium carboxymethyl cellulose, ethyl cellulose and cellulose acetate; tragacanth; malt; gelatin; talc; cocoa butter, waxes, animal and vegetable fats, paraffins, silicones, bentonites, silicic acid, zinc oxide; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and any other compatible substances employed in pharmaceutical formulations.

In particular embodiments, compositions comprise an amount of CAR-expressing immune effector cells contemplated herein. In other embodiments, compositions comprise an amount of an anti-BCMA antibody or fragment thereof contemplated herein. As used herein, the term "amount" refers to "an amount effective" or "an effective amount" of a genetically modified therapeutic cell, e.g., T cell, to achieve a beneficial or desired prophylactic or therapeutic result, including clinical results.

A "prophylactically effective amount" refers to an amount of a genetically modified therapeutic cells effective to achieve the desired prophylactic result. Typically, but not necessarily, since a prophylactic dose is used in subjects prior to or at an earlier stage of disease, the prophylactically effective amount is less than the therapeutically effective amount.

A "therapeutically effective amount" of a genetically modified therapeutic cell may vary according to factors such as the disease state, age, sex, and weight of the individual, and the ability of the stem and progenitor cells to elicit a desired response in the individual. A therapeutically effective amount is also one in which any toxic or detrimental effects of the virus or transduced therapeutic cells are outweighed by the therapeutically beneficial effects. The term "therapeutically effective amount" includes an amount that is effective to "treat" a subject (e.g., a patient). When a therapeutic amount is indicated, the precise amount of the compositions to be administered can be determined by a physician with consideration of individual differences in age, weight, tumor size, extent of infection or metastasis, and condition of the patient (subject).

It can generally be stated that a pharmaceutical composition comprising the T cells contemplated herein may be administered at a dosage of 102 to $10^{10}$ cells/kg body weight, preferably.105 to $10^6$ cells/kg body weight, including all integer values within those ranges. The number of cells will depend upon the ultimate use for which the composition is intended as will the type of cells included therein. For uses provided herein, the cells are generally in a volume of a liter or less, can be 500 mLs or less, even 250 mLs or 100 mLs or less. Hence the density of the desired cells is typically greater than $10^6$ cells/ml and generally is greater than $10^7$ cells/ml, generally $10^8$ cells/ml or greater. The clinically relevant number of immune cells can be apportioned into multiple infusions that cumulatively equal or exceed $10^5$, $10^6$, $10^7$, $10^8$, $10^9$, $10^{10}$, $10^{11}$, or $10^{12}$ cells. In some aspects, particularly since all the infused cells will be redirected to a particular target antigen, lower numbers of cells, in the range of $10^6$/kilogram ($10^6$-$10^{11}$ per patient) may be administered. Compositions may be administered multiple times at dosages within these ranges. The cells may be allogeneic, syngeneic, xenogeneic, or autologous to the patient undergoing therapy. If desired, the treatment may also include administration of mitogens (e.g., PHA) or lymphokines, cytokines, and/or chemokines (e.g., IFN-γ, IL-2, IL-12, TNF-alpha, IL-18, and TNF-beta, GM-CSF, IL-4, IL-13, Flt3-L, RANTES, MIP1α, etc.) as contemplated herein to enhance induction of the immune response.

Generally, compositions comprising the cells activated and expanded as contemplated herein may be utilized in the treatment and prevention of diseases that arise in individuals who are immunocompromised. In particular embodiments, compositions comprising immune effector cells modified to express a CAR contemplated herein are used in the treatment of cancer (e.g., B cell malignancies). The modified immune effector cells may be administered either alone, or as a pharmaceutical composition in combination with carriers, diluents, excipients, and/or with other components such as IL-2 or other cytokines or cell populations. In particular embodiments, pharmaceutical compositions comprise an amount of genetically modified T cells, in combination with one or more pharmaceutically or physiologically acceptable carriers, diluents or excipients.

Pharmaceutical compositions comprising an immune effector cell population modified to express a CAR (e.g., T cells) or an antibody, or fragment thereof, may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions are preferably formulated for parenteral administration, e.g., intravascular (intravenous or intraarterial), intraperitoneal or intramuscular administration.

The liquid pharmaceutical compositions, whether they be solutions, suspensions or other like form, may include one or more of the following: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. An injectable pharmaceutical composition is preferably sterile.

In one embodiment, the immune effector cell (e.g., T cell) compositions contemplated herein are formulated in a pharmaceutically acceptable cell culture medium. Such compositions are suitable for administration to human subjects. In particular embodiments, the pharmaceutically acceptable cell culture medium is a serum free medium.

Serum-free medium has several advantages over serum containing medium, including a simplified and better-defined composition, a reduced degree of contaminants, elimination of a potential source of infectious agents, and lower cost. In various embodiments, the serum-free medium is animal-free, and may optionally be protein-free. Optionally, the medium may contain biopharmaceutically acceptable recombinant proteins. "Animal-free" medium refers to medium wherein the components are derived from non-animal sources. Recombinant proteins replace native animal proteins in animal-free medium and the nutrients are obtained from synthetic, plant or microbial sources. "Protein-free" medium, in contrast, is defined as substantially free of protein.

Illustrative examples of serum-free media used in particular compositions includes, but is not limited to QBSF-60 (Quality Biological, Inc.), StemPro-34 (Life Technologies), and X-VIVO 10.

In one preferred embodiment, compositions comprising immune effector cells contemplated herein are formulated in a solution comprising PlasmaLyte A.

In another preferred embodiment, compositions comprising immune effector cells contemplated herein are formulated in a solution comprising a cryopreservation medium. For example, cryopreservation media with cryopreservation agents may be used to maintain a high cell viability outcome post-thaw. Illustrative examples of cryopreservation media used in particular compositions includes, but is not limited to, CryoStor CS10, CryoStor CS5, and CryoStor CS2.

In a more preferred embodiment, compositions comprising immune effector cells contemplated herein are formulated in a solution comprising 50:50 PlasmaLyte A to CryoStor CS10.

In a particular embodiment, compositions comprise an effective amount of immune effector cells modified to express a CAR, alone or in combination with one or more therapeutic agents. Thus, the CAR-expressing immune effector cell compositions may be administered alone or in combination with other known cancer treatments, such as radiation therapy, chemotherapy, transplantation, immunotherapy, hormone therapy, photodynamic therapy, etc. The compositions may also be administered in combination with antibiotics. Such therapeutic agents may be accepted in the art as a standard treatment for a particular disease state as contemplated herein, such as a particular cancer. Exemplary therapeutic agents contemplated in particular embodiments include cytokines, growth factors, steroids, NSAIDs, DMARDs, anti-inflammatories, chemotherapeutics, radiotherapeutics, therapeutic antibodies, or other active and ancillary agents.

In certain embodiments, compositions comprising immune effector cells modified to express a CAR may be administered in conjunction with any number of chemotherapeutic agents.

A variety of other therapeutic agents may be used in conjunction with the compositions contemplated herein. In one embodiment, the composition comprising immune effector cells a CAR is administered with an anti-inflammatory agent.

In one embodiment, the composition comprising immune effector cells a CAR is administered with a therapeutic antibody. Illustrative examples of therapeutic antibodies suitable for combination with the CAR modified T cells contemplated in particular embodiments, include but are not limited to, atezolizumab, avelumab, bavituximab, bevacizumab (avastin), bivatuzumab, blinatumomab, cemiplimab, conatumumab, crizotinib, daratumumab, duligotumab, dacetuzumab, dalotuzumab, durvalumab, elotuzumab (HuLuc63), gemtuzumab, ibritumomab, indatuximab, inotuzumab, ipilimumab, lorvotuzumab, lucatumumab, milatuzumab, moxetumomab, nivolumab, ocaratuzumab, ofatumumab, pembrolizumab, rituximab, siltuximab, teprotumumab, and ublituximab.

K. Therapeutic Methods

The genetically modified immune effector cells expressing a CAR contemplated herein provide improved methods of adoptive immunotherapy for use in the prevention, treatment, and amelioration of B cell related conditions that include, but are not limited to immunoregulatory conditions and hematological malignancies.

In various embodiments, the genetically modified immune effector cells contemplated herein provide improved methods of adoptive immunotherapy for use in increasing the cytotoxicity in cancer cells in a subject or for use in decreasing the number of cancer cells in a subject.

In particular embodiments, the specificity of a primary immune effector cell is redirected to cells expressing a particular antigen, e.g., cancer cells, by genetically modifying the primary immune effector cell with a CAR as contemplated herein. In various embodiments, a viral vector is used to genetically modify an immune effector cell with a particular polynucleotide encoding a CAR. In particular embodiments, the CAR comprises an anti-BCMA antigen binding domain that binds a BCMA polypeptide; a hinge domain; a transmembrane (TM) domain, a short oligo- or polypeptide linker, that links the TM domain to the intracellular signaling domain of the CAR; and one or more intracellular co-stimulatory signaling domains; and a primary signaling domain.

In one embodiment, a type of cellular therapy where T cells are genetically modified to express a CAR that targets BCMA expressing cancer cells, and the T cells are infused to a recipient in need thereof is provided. The infused cell is able to kill disease causing cells in the recipient. Unlike antibody therapies, T cell therapies are able to replicate in vivo resulting in long-term persistence that can lead to sustained cancer therapy.

In one embodiment, T cells that express a CAR can undergo robust in vivo T cell expansion and can persist for an extended amount of time. In another embodiment, T cells that express a CAR evolve into specific memory T cells or stem cell memory T cells that can be reactivated to inhibit any additional tumor formation or growth.

In particular embodiments, compositions comprising immune effector cells that express a CAR contemplated herein are used in the treatment of conditions associated particular antigen-expressing cancer cells or cancer stem cells.

Illustrative examples of conditions that can be treated, prevented or ameliorated using the immune effector cells comprising the CARs contemplated herein include, but are not limited to: systemic lupus erythematosus, rheumatoid arthritis, myasthenia gravis, autoimmune hemolytic anemia, idiopathic thrombocytopenia purpura, anti-phospholipid syndrome, Chagas' disease, Grave's disease, Wegener's granulomatosis, poly-arteritis nodosa, Sjogren's syndrome, pemphigus vulgaris, scleroderma, multiple sclerosis, anti-phospholipid syndrome, ANCA associated vasculitis, Goodpasture's disease, Kawasaki disease, and rapidly progressive glomerulonephritis.

The modified immune effector cells may also have application in plasma cell disorders such as heavy-chain disease, primary or immunocyte-associated amyloidosis, and monoclonal gammopathy of undetermined significance (MGUS).

As use herein, "B cell malignancy" refers to a type of cancer that forms in B cells (a type of immune system cell) as discussed infra.

In a particular embodiment, compositions comprising T cells that express a CAR contemplated herein are used in the treatment of osteosarcoma or Ewing's sarcoma.

In a particular embodiment, compositions comprising T cells that express a CAR contemplated herein are used in the treatment of liquid or hematological cancers.

In certain embodiments, the liquid or hematological cancer is selected from the group consisting of: leukemias, lymphomas, and multiple myelomas.

In certain embodiments, the liquid or hematological cancer is selected from the group consisting of: acute lymphocytic leukemia (ALL), acute myeloid leukemia (AML), myeloblastic, promyelocytic, myelomonocytic, monocytic, erythroleukemia, hairy cell leukemia (HCL), chronic lymphocytic leukemia (CLL), and chronic myeloid leukemia (CML), chronic myelomonocytic leukemia (CMML) and polycythemia vera, Hodgkin lymphoma, nodular lymphocyte-predominant Hodgkin lymphoma, Burkitt lymphoma, small lymphocytic lymphoma (SLL), diffuse large B-cell lymphoma (DLBCL), follicular lymphoma, immunoblastic large cell lymphoma, precursor B-lymphoblastic lymphoma, mantle cell lymphoma, marginal zone lymphoma, mycosis fungoides, anaplastic large cell lymphoma, Sézary syndrome, precursor T-lymphoblastic lymphoma, multiple myeloma, overt multiple myeloma, smoldering multiple myeloma, plasma cell leukemia, non-secretory myeloma, IgD myeloma, osteosclerotic myeloma, solitary plasmacytoma of bone, and extramedullary plasmacytoma.

In certain embodiments, the liquid or hematological cancer is selected from the group consisting of: acute lymphocytic leukemia (ALL), chronic lymphocytic leukemia (CLL), hairy cell leukemia (HCL), multiple myeloma (MM), acute myeloid leukemia (AML), or chronic myeloid leukemia (CML).

In preferred embodiments, the liquid or hematological cancer is multiple myeloma (MM).

In preferred embodiments, the liquid or hematological cancer is relapsed/refractory multiple myeloma (MM).

In particular embodiments, methods comprising administering a therapeutically effective amount of immune effector cells that express a CAR contemplated herein or a composition comprising the same, to a patient in need thereof, alone or in combination with one or more therapeutic agents, are provided. In certain embodiments, the cells are used in the treatment of patients at risk for developing a cancer or a condition associated with cancer cells. Thus, in particular embodiments, methods for the treatment or prevention or amelioration of at least one symptom of cancer or condition associated with abnormal B cell activity (e.g., B cell malignancy) comprising administering to a subject in need thereof, a therapeutically effective amount of the modified T cells that express a CAR contemplated herein.

As used herein, the terms "individual" and "subject" are often used interchangeably and refer to any animal that exhibits a symptom of a disease, disorder, or condition that can be treated with the gene therapy vectors, cell-based therapeutics, and methods contemplated elsewhere herein. In preferred embodiments, a subject includes any animal that exhibits symptoms of a disease, disorder, or condition related to cancer that can be treated with the gene therapy vectors, cell-based therapeutics, and methods contemplated elsewhere herein. Suitable subjects (e.g., patients) include laboratory animals (such as mouse, rat, rabbit, or guinea pig), farm animals, and domestic animals or pets (such as a cat or dog). Non-human primates and, preferably, human patients, are included. Typical subjects include human patients that have cancer (e.g., a B cell malignancy), have been diagnosed with a cancer (e.g., a B cell malignancy), or are at risk or having a cancer (e.g., a B cell malignancy).

As used herein, the term "patient" refers to a subject that has been diagnosed with a particular disease, disorder, or condition that can be treated with the gene therapy vectors, cell-based therapeutics, and methods disclosed elsewhere herein.

As used herein "treatment" or "treating," includes any beneficial or desirable effect on the symptoms or pathology of a disease or pathological condition, and may include even minimal reductions in one or more measurable markers of the disease or condition being treated. Treatment can involve optionally either the reduction the disease or condition, or the delaying of the progression of the disease or condition. "Treatment" does not necessarily indicate complete eradication or cure of the disease or condition, or associated symptoms thereof.

As used herein, "prevent," and similar words such as "prevented," "preventing" etc., indicate an approach for preventing, inhibiting, or reducing the likelihood of the occurrence or recurrence of, a disease or condition. It also refers to delaying the onset or recurrence of a disease or condition or delaying the occurrence or recurrence of the symptoms of a disease or condition. As used herein, "prevention" and similar words also includes reducing the intensity, effect, symptoms and/or burden of a disease or condition prior to onset or recurrence of the disease or condition.

As used herein, the phrase "ameliorating at least one symptom of" refers to decreasing one or more symptoms of the disease or condition for which the subject is being treated. In particular embodiments, the disease or condition being treated is a cancer, wherein the one or more symptoms ameliorated include, but are not limited to, weakness, fatigue, shortness of breath, easy bruising and bleeding, frequent infections, enlarged lymph nodes, distended or painful abdomen (due to enlarged abdominal organs), bone or joint pain, fractures, unplanned weight loss, poor appetite, night sweats, persistent mild fever, and decreased urination (due to impaired kidney function).

By "enhance" or "promote," or "increase" or "expand" refers generally to the ability of a composition contemplated herein, e.g., a genetically modified T cells that express a CAR, to produce, elicit, or cause a greater physiological response (i.e., downstream effects) compared to the response caused by either vehicle or a control molecule/composition. A measurable physiological response may include an increase in T cell expansion, activation, persistence, and/or an increase in cancer cell killing ability, among others apparent from the understanding in the art and the description herein. An "increased" or "enhanced" amount is typically a "statistically significant" amount, and may include an increase that is 1.1, 1.2, 1.5, 2, 3, 4, 5, 6, 7, 8, 9, 10, 15, 20, 30 or more times (e.g., 500, 1000 times) (including all integers and decimal points in between and above 1, e.g., 1.5, 1.6, 1.7. 1.8, etc.) the response produced by vehicle or a control composition.

By "decrease" or "lower," or "lessen," or "reduce," or "abate" refers generally to the ability of composition contemplated herein to produce, elicit, or cause a lesser physiological response (i.e., downstream effects) compared to the response caused by either vehicle or a control molecule/composition. A "decrease" or "reduced" amount is typically a "statistically significant" amount, and may include an decrease that is 1.1, 1.2, 1.5, 2, 3, 4, 5, 6, 7, 8, 9, 10, 15, 20, 30 or more times (e.g., 500, 1000 times) (including all integers and decimal points in between and above 1, e.g., 1.5, 1.6, 1.7. 1.8, etc.) the response (reference response) produced by vehicle, a control composition, or the response in a particular cell lineage.

By "maintain," or "preserve," or "maintenance," or "no change," or "no substantial change," or "no substantial decrease" refers generally to the ability of a composition contemplated herein to produce, elicit, or cause a similar physiological response (i.e., downstream effects) in a cell, as compared to the response caused by either vehicle, a control molecule/composition, or the response in a particular cell lineage. A comparable response is one that is not significantly different or measurable different from the reference response.

In one embodiment, a method of treating a B cell related condition or cancer in a subject in need thereof comprises administering an effective amount, e.g., therapeutically effective amount of a composition comprising genetically modified immune effector cells contemplated herein. The quantity and frequency of administration will be determined by such factors as the condition of the patient, and the type and severity of the patient's disease, although appropriate dosages may be determined by clinical trials.

In one embodiment, the amount of immune effector cells, e.g., T cells that express a CAR, in the composition administered to a subject is at least $0.1\times10^5$ cells, at least $0.5\times10^5$ cells, at least $1\times10^5$ cells, at least $5\times10^5$ cells, at least $1\times10^6$ cells, at least $0.5\times10^7$ cells, at least $1\times10^7$ cells, at least $0.5\times10^8$ cells, at least $1\times10^8$ cells, at least $0.5\times10^9$ cells, at least $1\times10^9$ cells, at least $2\times10^{\circ}$ cells, at least $3\times10^9$ cells, at least $4\times10^9$ cells, at least $5\times10^9$ cells, or at least $1\times10^{10}$ cells.

In particular embodiments, about $1\times10^7$ T cells to about $1\times10^9$ T cells, about $2\times10^7$ T cells to about $0.9\times10^9$ T cells, about $3\times10^7$ T cells to about $0.8\times10^9$ T cells, about $4\times10^7$ T cells to about $0.7\times10^9$ T cells, about $5\times10^7$ T cells to about $0.6\times10^9$ T cells, or about $5\times10^7$ T cells to about $0.5\times10^9$ T cells are administered to a subject.

In one embodiment, the amount of immune effector cells, e.g., T cells that express an a CAR, in the composition administered to a subject is at least $0.1\times10^4$ cells/kg of bodyweight, at least $0.5\times10^4$ cells/kg of bodyweight, at least $1\times10^4$ cells/kg of bodyweight, at least $5\times10^4$ cells/kg of bodyweight, at least $1\times10^5$ cells/kg of bodyweight, at least $0.5\times10^6$ cells/kg of bodyweight, at least $1\times10^6$ cells/kg of bodyweight, at least $0.5\times10^7$ cells/kg of bodyweight, at least $1\times10^7$ cells/kg of bodyweight, at least $0.5\times10^8$ cells/kg of bodyweight, at least $1\times10^8$ cells/kg of bodyweight, at least $2\times10^8$ cells/kg of bodyweight, at least $3\times10^8$ cells/kg of bodyweight, at least $4\times10^8$ cells/kg of bodyweight, at least $5\times10^8$ cells/kg of bodyweight, or at least $1\times10^9$ cells/kg of bodyweight.

In particular embodiments, about $1\times10^6$ T cells/kg of bodyweight to about $1\times10^8$ T cells/kg of bodyweight, about $2\times10^6$ T cells/kg of bodyweight to about $0.9\times10^8$ T cells/kg of bodyweight, about $3\times10^6$ T cells/kg of bodyweight to about $0.8\times10^8$ T cells/kg of bodyweight, about $4\times10^6$ T cells/kg of bodyweight to about $0.7\times10^8$ T cells/kg of bodyweight, about $5\times10^6$ T cells/kg of bodyweight to about $0.6\times10^8$ T cells/kg of bodyweight, or about $5\times10^6$ T cells/kg of bodyweight to about $0.5\times10^8$ T cells/kg of bodyweight are administered to a subject.

One of ordinary skill in the art would recognize that multiple administrations of the compositions contemplated herein may be required to affect the desired therapy. For example, a composition may be administered 1, 2, 3, 4, 5, 6, 7, 8, 9, or 10 or more times over a span of 1 week, 2 weeks, 3 weeks, 1 month, 2 months, 3 months, 4 months, 5 months, 6 months, 1 year, 2 years, 5, years, 10 years, or more.

In certain embodiments, it may be desirable to administer activated immune effector cells to a subject and then subsequently redraw blood (or have an apheresis performed), activate immune effector cells therefrom, and reinfuse the patient with these activated and expanded immune effector cells. This process can be carried out multiple times every few weeks. In certain embodiments, immune effector cells can be activated from blood draws of from 10 cc to 400 cc. In certain embodiments, immune effector cells are activated from blood draws of 20 cc, 30 cc, 40 cc, 50 cc, 60 cc, 70 cc, 80 cc, 90 cc, 100 cc, 150 cc, 200 cc, 250 cc, 300 cc, 350 cc, or 400 cc or more. Not to be bound by theory, using this multiple blood draw/multiple reinfusion protocol may serve to select out certain populations of immune effector cells.

The administration of the compositions contemplated herein may be carried out in any convenient manner, including by aerosol inhalation, injection, ingestion, transfusion, implantation or transplantation. In a preferred embodiment, compositions are administered parenterally. The phrases "parenteral administration" and "administered parenterally" as used herein refers to modes of administration other than enteral and topical administration, usually by injection, and includes, without limitation, intravascular, intravenous, intramuscular, intraarterial, intrathecal, intracapsular, intraorbital, intratumoral, intracardiac, intradermal, intraperitoneal, transtracheal, subcutaneous, subcuticular, intraarticular, subcapsular, subarachnoid, intraspinal and intrasternal injection and infusion. In one embodiment, the compositions contemplated herein are administered to a subject by direct injection into a tumor, lymph node, or site of infection.

In one embodiment, a subject in need thereof is administered an effective amount of a composition to increase a cellular immune response to a B cell related condition in the subject. The immune response may include cellular immune responses mediated by cytotoxic T cells capable of killing infected cells, regulatory T cells, and helper T cell responses. Humoral immune responses, mediated primarily by helper T cells capable of activating B cells thus leading to antibody production, may also be induced. A variety of techniques may be used for analyzing the type of immune responses induced by the compositions, which are well described in the art; e.g., *Current Protocols in Immunology*, Edited by: John E. Coligan, Ada M. Kruisbeek, David H. Margulies, Ethan M. Shevach, Warren Strober (2001) John Wiley & Sons, NY, N.Y.

In one embodiment, a method of treating a subject diagnosed with a B cell related condition or cancer is provided comprising removing immune effector cells from the subject diagnosed with a cancer or BCMA-expressing B cell related condition, genetically modifying said immune effector cells with a vector comprising a nucleic acid encoding a CAR contemplated herein, thereby producing a population of modified immune effector cells, and administering the population of modified immune effector cells to the same subject. In a preferred embodiment, the immune effector cells comprise T cells.

In certain embodiments, methods for stimulating an immune effector cell mediated immune modulator response to a target cell population in a subject are provided comprising the steps of administering to the subject an immune effector cell population expressing a nucleic acid construct encoding a CAR molecule.

The methods for administering the cell compositions contemplated in particular embodiments includes any method which is effective to result in reintroduction of ex vivo genetically modified immune effector cells that either directly express a CAR contemplated herein in the subject or on reintroduction of the genetically modified progenitors of immune effector cells that on introduction into a subject differentiate into mature immune effector cells that express the CAR. One method comprises transducing peripheral blood T cells ex vivo with a nucleic acid construct contemplated herein and returning the transduced cells into the subject.

L. SEQUENCE LISTING

| Description | Sequence | SEQ ID NO: |
|---|---|---|
| CAR1 - CDRL1 | GASQSVTSSYLA | 1 |
| CAR1 - CDRL2 | DASGRAT | 2 |
| CAR1 - CDRL3 | QQYGSSPFT | 3 |
| CAR1 - CDRH1 | GGSISSSRYYWD | 4 |
| CAR1 - CDRH2 | SLYYSGNTY | 5 |
| CAR1 - CDRH3 | QGATHALDL | 6 |
| CAR1 - variable light chain | EIVLTQSPAT LSLSPGERAT LSCGASQSVT SSYLAWYQQK PGLAPRLLIY DASGRATGIP DRFSGSGSGT DFSLTISRLE PEDFAVYYCQ QYGSSPFTFG PGTKVDIK | 7 |
| CAR1 - variable heavy chain | QLQLQESGPG LVKPSETLSL TCTVSGGSIS SSRYYWDWIR QPPGKGLEWI GSLYYSGNTY YKPSLKSRVT ISVDTSKNQF SLKLTSVTAA DTAVYYCARQ GATHALDLWG PGTMVTVSS | 8 |
| CAR2/CAR3 - CDRL1 | RASQDISSFLA | 9 |
| CAR2/CAR3 - CDRL2 | AASTLQS | 10 |
| CAR2/CAR3 - CDRL3 | QQFNSYPRT | 11 |
| CAR2/CAR3 - CDRH1 | GYTFSNNGFS | 12 |
| CAR2/CAR3 - CDRH2 | WISGFNGKTY | 13 |
| CAR2/CAR3 - CDRH3 | GLLLSGELWGFDY | 14 |
| CAR2/CAR3 - variable light chain | DIQLTQSPSF LSASVGDRVT ITCRASQDIS SFLAWYQQKP GKAPKLLIFA ASTLQSGVPS RISGSGSGTE FTLTISSLQP EDFATYYCQQ FNSYPRTFGQ GTKVEIK | 15 |
| CAR2/CAR3 - variable heavy chain | QVQLVQSGAE VKKPGASVKV SCKASGYTFS NNGFSWVRQA PGQGLEWMGW ISGFNGKTYY TKTLQGRVTM TIDTSTSTAY MDLRSLRSDD TAVYYCARGL LLSGELWGFD YWGQGTLVTV SS | 16 |
| CAR4/CAR5 - CDRL1 | RASQDIRNYLG | 17 |
| CAR4/CAR5 - CDRL2 | AASSLQS | 18 |

-continued

L. SEQUENCE LISTING

| Description | Sequence | SEQ ID NO: |
|---|---|---|
| CAR4/CAR5 - CDRL3 | LQDYIYPWT | 19 |
| CAR4/CAR5 - CDRH1 | GFTFSSYGMH | 20 |
| CAR4/CAR5 - CDRH2 | VISYDGRNKN | 21 |
| CAR4/CAR5 - CDRH3 | EGEATYYDILTGPFDY | 22 |
| CAR4/CAR5 - variable light chain | DIQMTQSPSS LSASVGDRIT ITCRASQDIR NYLGWYQQKP GKAPKVLIFA ASSLQSGVPS RFSGSGSGTD FTLTISSLQP EDFATYYCLQ DYIYPWTFAQ GTKVEIK | 23 |
| CAR4/CAR5 - variable heavy chain | QVQLVESGGG VVQPGRSLRL SCAASGFTFS SYGMHWVRQA PGKGLEWVAV ISYDGRNKNY ADSVKGRFTI SRDNSKNTLY LQMNSLRAED TAVYYCAREG EATYYDILTG PFDYWGQGTL VTVSS | 24 |
| CAR6 - CDRL1 | RASQGISSYLA | 25 |
| CAR6 - CDRL2 | VASTLQS | 26 |
| CAR6 - CDRL3 | QQLYSYPRA | 27 |
| CAR6 - CDRH1 | GFTFSSYGMH | 28 |
| CAR6 - CDRH2 | VISYDGRNKN | 29 |
| CAR6 - CDRH3 | EGEATYYDILTGPFDY | 30 |
| CAR6 - variable light chain | DIQLTQSPSF LSASVGDRVS ITCRASQGIS SYLAWYQQKP GKAPKVLIYV ASTLQSGVPS RFSGSGSGTE FTLTISSLQP DDFATYYCQQ LYSYPRAFGQ GTKVEIK | 31 |
| CAR6 - variable heavy chain | QVQLVESGGG VVQPGRSLRL SCAASGFTFS SYGMHWVRQA PGKGLEWVAV ISYDGRNKNY ADSVKGRFTI SRDNSKNTLY LQMNSLRAED TAVYYCAREG EATYYDILTG PFDYWGQGTL VTVSS | 32 |
| CAR7/CAR8 - CDRL1 | KSSQSLLYSDGKTFLY | 33 |
| CAR7/CAR8 - CDRL2 | EGSNRFS | 34 |
| CAR7/CAR8 - CDRL3 | MQSIQLPNT | 35 |
| CAR7/CAR8 - CDRH1 | GYTFSTYGIG | 36 |
| CAR7/CAR8 - CDRH2 | WISAYSGKTN | 37 |
| CAR7/CAR8 - CDRH3 | DDGAGTDYYYGMDV | 38 |
| CAR7/CAR8 - variable light chain | DIVMTQTPLS LSVTPGQPAS ISCKSSQSLL YSDGKTFLYW YLQKPGQPPQ LLIYEGSNRF SGVPDRFSGS GSGTDFTLKI SRVEAEDVGV FYCMQSIQLP NTFGQGTKLE IK | 39 |
| CAR7/CAR8 - variable heavy chain | QVQLVQSGAE VKKPGASVKV SCKGSGYTFS TYGIGWVRQA PGQGLEWLAW ISAYSGKTNY AQKVQGRVTL TTDTSTNTAY MELRSLRSDD TAVYYCARDD GAGTDYYYGM DVWGQGTTVT VS | 40 |
| CAR9/CAR10 - CDRL1 | RASQDISSFLA | 41 |
| CAR9/CAR10 - CDRL2 | AASTLQS | 42 |

-continued

L. SEQUENCE LISTING

| Description | Sequence | SEQ ID NO: |
|---|---|---|
| CAR9/CAR10 - CDRL3 | QQFNSYPRT | 43 |
| CAR9/CAR10 - CDRH1 | GYTFSNNGFS | 44 |
| CAR9/CAR10 - CDRH2 | WISGFNGKTY | 45 |
| CAR9/CAR10 - CDRH3 | GLLLSGELWGFDY | 46 |
| CAR9/CAR10 - variable light chain | DIQLAQSPSF LSASVGDRVT ITCRASQDIS SFLAWYQQKP GKAPKLLIFA ASTLQSGVPS RISGSGSGTE FTLTISSLQP EDFATYYCQQ FNSYPRTFGQ GTKVEIK | 47 |
| CAR9/CAR10 - variable heavy chain | QVQLVQSGAE VKKPGASVKV SCKASGYTFS NNGFSWVRQA PGQGLEWMGW ISGFNGKTYY TKTLQGRVTM TIDTSTSTAY MDLRSLRSDD TAVYYCARGL LLSGELWGFD YWGQGTLVTV SS | 48 |
| Polynucleotide of anti-BCMA CAR1 | ATGGCCCTGCCTGTGACCGCCCTTCTCCTGCCCCTTGCTCTGCTCC TCCATGCCGCCAGGCCTCAACTGCAGCTGCAGGAGAGTGGCCCCGG CTTGGTGAAGCCTAGTGAAACACTCAGCCTTACGTGCACTGTTTCT GGGGGCAGTATATCCTCCAGCCGCTATTACTGGGATTGGATCCGGC AGCCGCCCGGGAAGGGACTTGAATGGATTGGAAGCCTCTACTACTC CGGAAATACTTACTATAAACCATCCCTGAAGAGTAGAGTTACAATT AGCGTAGACACCAGCAAGAATCAATTTTCTCTTAAACTGACATCAG TGACTGCCGCAGATACTGCTGTGTACTACTGTGCACGGCAGGGAGC TACTCACGCCCTGGACCTCTGGGGACCTGGTACTATGGTCACGGTC TCTTCTGGAGGAGGAGGGTCAGGCGGAGGAGGTTCCGGGGGCGGAG GGTCCGAAATTGTTCTTACGCAGTCACCCGCCACACTTTCTCTGTC CCCGGGGGAACGGGCTACTCTGTCCTGTGGGGCTTCCCAATCCGTG ACCAGCTCCTACCTTGCCTGGTATCAACAGAAACCTGGTCTCGCCC CACGGCTGCTTATCTACGATGCATCTGGCAGAGCTACCGGTATACC AGACAGGTTTTCTGGTTCCGGTAGCGGAACCGATTTTAGTCTGACT ATCTCACGGCTGGAGCCCGAGGATTTCGCGGTGTATTACTGTCAGC AGTACGGGAGCAGTCCATTTACCTTTGGACCTGGCACGAAGGTGGA TATAAAGACCACAACACCTGCTCCAAGGCCCCCCACACCCGCTCCA ACTATAGCCAGCCAACCATTGAGCCTCAGACCTGAAGCTTGCAGGC CCGCAGCAGGAGGCGCCGTCCATACGCGAGGCCTGGACTTCGCGTG TGATATTTATATTTGGGCCCCTTTGGCCGGAACATGTGGGGTGTTG CTTCTCTCCCTTGTGATCACTCTGTATTGTAAGCGCGGGAGAAAGA AGCTCCTGTACATCTTCAAGCAGCCTTTTATGCGACCTGTGCAAAC CACTCAGGAAGAAGATGGGTGTTCATGCCGCTTCCCCGAGGAGGAA GAAGGAGGGTGTGAACTGAGGGTGAAATTTTCTAGAAGCGCCGATG CTCCCGCATATCAGCAGGGTCAGAATCAGCTCTACAATGAATTGAA TCTCGGCAGGCGAGAAGAGTACGATGTTCTGGACAAGAGACGGGGC AGGGATCCCGAGATGGGGGGAAAGCCCCGGAGAAAAAATCCTCAGG AGGGGTTGTACAATGAGCTGCAGAAGGACAAGATGGCTGAAGCCTA TAGCGAGATCGGAATGAAAGGCGAAAGACGCAGAGGCAAGGGGCAT GACGGTCTGTACCAGGGTCTCTCTACAGCCACCAAGGACACTTATG ATGCGTTGCATATGCAAGCCTTGCCACCCCGCTAA | 49 |
| Polypeptide of anti-BCMA CAR1 | MALPVTALLL PLALLLHAAR PQLQLQESGP GLVKPSETLS LTCTVSGGSI SSSRYYWDWI RQPPGKGLEW IGSLYYSGNT YYKPSLKSRV TISVDTSKNQ FSLKLTSVTA ADTAVYYCAR QGATHALDLW GPGTMVTVSS GGGGSGGGGS GGGGSEIVLT QSPATLSLSP GERATLSCGA SQSVTSSYLA WYQQKPGLAP RLLIYDASGR ATGIPDRFSG SGSGTDFSLT ISRLEPEDFA VYYCQQYGSS PETFGPGTKV DIKTTTPAPR PPTPAPTIAS QPLSLRPEAC RPAAGGAVHT RGLDFACDIY IWAPLAGTCG VLLLSLVITL YCKRGRKKLL YIFKQPFMRP VQTTQEEDGC SCRFPEEEEG GCELRVKFSR SADAPAYQQG QNQLYNELNL GRREEYDVLD KRRGRDPEMG GKPRRKNPQE GLYNELQKDK MAEAYSEIGM KGERRRGKGH DGLYQGLSTA TKDTYDALHM QALPPR | 50 |
| Polynucleotide of anti-BCMA CAR2 | ATGGCGCTTCCCGTTACCGCTCTCCTCCTGCCCCTGGCCCTGCTGC TGCACGCAGCCCGCCCACAGGTCCAGCTCGTTCAGTCTGGAGCCGA AGTAAAGAAGCCCGGGGCATCAGTAAAGGTCTCTTGTAAGGCTAGC GGGTACACATTTAGTAACAATGGCTTCTCTTGGGTGAGGCAGGCTC CCGGACAGGGCCTGGAGTGGATGGGGTGGATCAGCGGGTTCAACGG | 51 |

-continued

L. SEQUENCE LISTING

| Description | Sequence | SEQ ID NO: |
|---|---|---|
| | GAAAACATATTACACCAAAACACTGCAGGGACGGGTCACTATGACA<br>ATCGACACATCCACCAGCACAGCCTACATGGACCTTAGATCCTTGA<br>GATCAGATGATACCGCCGTGTACTACTGCGCAAGAGGACTCCTCTT<br>GAGTGGAGAACTTTGGGGATTCGATTATTGGGGACAGGGCACCCTC<br>GTGACTGTTTCAAGCGGTGGAGGCGGCAGCGGCGGGGGCGGATCTG<br>GAGGAGGAGGAAGTGACATTCAGCTCACACAGTCCCCTAGCTTCCT<br>CTCTGCATCAGTGGGCGACCGCGTTACTATTACCTGCAGGGCCAGC<br>CAGGATATTTCTAGCTTCCTTGCCTGGTATCAACAGAAGCCAGGGA<br>AAGCACCTAAACTTCTGATTTTCGCTGCATCCACCCTGCAATCAGG<br>AGTCCCATCTCGAATAAGCGGCTCCGGATCAGGAACAGAGTTTACG<br>CTCACAATAAGTAGTCTGCAGCCCGAGGACTTCGCTACCTATTACT<br>GCCAGCAGTTCAATAGCTATCCCCGCACCTTCGGGCAGGGTACGAA<br>GGTCGAGATTAAGACCACAACACCTGCTCCAAGGCCCCCCACACCC<br>GCTCCAACTATAGCCAGCCAACCATTGAGCCTCAGACCTGAAGCTT<br>GCAGGCCCGCAGCAGGAGGCGCCGTCCATACGCGAGGCCTGGACTT<br>CGCGTGTGATATTTATATTTGGGCCCCTTTGGCCGGAACATGTGGG<br>GTGTTGCTTCTCTCCCTTGTGATCACTCTGTATTGTAAGCGCGGGA<br>GAAAGAAGCTCCTGTACATCTTCAAGCAGCCTTTTATGCGACCTGT<br>GCAAACCACTCAGGAAGAAGATGGGTGTTCATGCCGCTTCCCCGAG<br>GAGGAAGAAGGAGGGTGTGAACTGAGGGTGAAATTTTCTAGAAGCG<br>CCGATGCTCCCGCATATCAGCAGGGTCAGAATCAGCTCTACAATGA<br>ATTGAATCTCGGCAGGCGAGAAGAGTACGATGTTCTGGACAAGAGA<br>CGGGGCAGGGATCCCGAGATGGGGGGAAAGCCCCGGAGAAAAAATC<br>CTCAGGAGGGGTTGTACAATGAGCTGCAGAAGGACAAGATGGCTGA<br>AGCCTATAGCGAGATCGGAATGAAAGGCGAAAGACGCAGAGGCAAG<br>GGGCATGACGGTCTGTACCAGGGTCTCTCTACAGCCACCAAGGACA<br>CTTATGATGCGTTGCATATGCAAGCCTTGCCACCCCGCTAA | |
| Polypeptide of anti-BCMA CAR2 | MALPVTALLL PLALLLHAAR PQVQLVQSGA EVKKPGASVK<br>VSCKASGYTF SNNGFSWVRQ APGQGLEWMG WISGFNGKTY<br>YTKTLQGRVT MTIDTSTSTA YMDLRSLRSD DTAVYYCARG<br>LLLSGELWGF DYWGQGTLVT VSSGGGGSGG GGSGGGGSDI<br>QLTQSPSFLS ASVGDRVTIT CRASQDISSF LAWYQQKPGK<br>APKLLIFAAS TLQSGVPSRI SGSGSGTEFT LTISSLQPED<br>FATYYCQQFN SYPRTFGQGT KVEIKTTTPA PRPPTPAPTI<br>ASQPLSLRPE ACRPAAGGAV HTRGLDFACD IYIWAPLAGT<br>CGVLLLSLVI TLYCKRGRKK LLYIFKQPFM RPVQTTQEED<br>GCSCRFPEEE EGGCELRVKF SRSADAPAYQ QGQNQLYNEL<br>NLGRREEYDV LDKRRGRDPE MGGKPRRKNP QEGLYNELQK<br>DKMAEAYSEI GMKGERRRGK GHDGLYQGLS TATKDTYDAL<br>HMQALPPR | 52 |
| Polynucleotide of anti-BCMA CAR3 | ATGGCCCTGCCCGTTACAGCCTTGCTTCTGCCCCTCGCGCTGCTTT<br>TGCACGCTGCGAGGCCAGACATCCAGTTGACACAATCACCATCCTT<br>TCTTAGTGCCTCTGTGGGAGATAGAGTCACCATCACGTGCCGAGCA<br>TCTCAGGATATCAGTAGCTTCTTGGCATGGTATCAGCAGAAACCTG<br>GCAAGGCCCCTAAACTGCTCATCTTCGCTGCGTCCACTCTGCAGTC<br>CGGAGTCCCAAGCAGAATCAGTGGTTCCGGATCAGGAACTGAGTTT<br>ACCCTCACAATTAGCAGTTTGCAGCCCGAAGATTTCGCCACCTATT<br>ACTGTCAGCAGTTTAACTCATACCCTAGGACTTTCGGACAGGGGAC<br>CAAGGTCGAGATCAAGGGCGGTGGGGGCTCCGGCGGAGGCGGATCA<br>GGTGGTGGAGGTTCTCAGGTACAGCTTGTCCAGTCAGGCGCCGAGG<br>TGAAAAAACCTGGGGCCTCAGTGAAGGTCTCCTGCAAAGCAAGCGG<br>TTATACGTTCTCCAACAACGGGTTCTCATGGGTAAGGCAAGCTCCT<br>GGACAGGGGCTCGAATGGATGGGGTGGATCAGCGGCTTCAATGGCA<br>AGACCTATTACACCAAGACCCTTCAAGGCAGAGTAACGATGACTAT<br>CGATACTAGTACAAGCACCGCCTATATGGACCTTAGGTCCCTCCGC<br>TCTGATGATACCGCCGTCTATTACTGCGCCCGCGGCCTGCTGTTGA<br>GCGGCGAGCTGTGGGGATTCGATTACTGGGGGCAAGGCACCCTGGT<br>CACTGTGTCCTCTACCACAACACCTGCTCCAAGGCCCCCCACACCC<br>GCTCCAACTATAGCCAGCCAACCATTGAGCCTCAGACCTGAAGCTT<br>GCAGGCCCGCAGCAGGAGGCGCCGTCCATACGCGAGGCCTGGACTT<br>CGCGTGTGATATTTATATTTGGGCCCCTTTGGCCGGAACATGTGGG<br>GTGTTGCTTCTCTCCCTTGTGATCACTCTGTATTGTAAGCGCGGGA<br>GAAAGAAGCTCCTGTACATCTTCAAGCAGCCTTTTATGCGACCTGT<br>GCAAACCACTCAGGAAGAAGATGGGTGTTCATGCCGCTTCCCCGAG<br>GAGGAAGAAGGAGGGTGTGAACTGAGGGTGAAATTTTCTAGAAGCG<br>CCGATGCTCCCGCATATCAGCAGGGTCAGAATCAGCTCTACAATGA | 53 |

-continued

L. SEQUENCE LISTING

| Description | Sequence | SEQ ID NO: |
|---|---|---|
| | ATTGAATCTCGGCAGGCGAGAAGAGTACGATGTTCTGGACAAGAGA CGGGGCAGGGATCCCGAGATGGGGGGAAAGCCCCGGAGAAAAAATC CTCAGGAGGGGTTGTACAATGAGCTGCAGAAGGACAAGATGGCTGA AGCCTATAGCGAGATCGGAATGAAAGGCGAAAGACGCAGAGGCAAG GGGCATGACGGTCTGTACCAGGGTCTCTCTACAGCCACCAAGGACA CTTATGATGCGTTGCATATGCAAGCCTTGCCACCCCGCTAA | |
| Polypeptide of anti-BCMA CAR3 | MALPVTALLL PLALLLHAAR PDIQLTQSPS FLSASVGDRV TITCRASQDI SSFLAWYQQK PGKAPKLLIF AASTLQSGVP SRISGSGSGT EFTLTISSLQ PEDFATYYCQ QFNSYPRTFG QGTKVEIKGG GGSGGGGSGG GGSQVQLVQS GAEVKKPGAS VKVSCKASGY TFSNNGFSWV ROAPGQGLEW MGWISGFNGK TYYTKTLQGR VTMTIDTSTS TAYMDLRSLR SDDTAVYYCA RGLLLSGELW GFDYWGQGTL VTVSSTTTPA PRPPTPAPTI ASQPLSLRPE ACRPAAGGAV HTRGLDFACD IYIWAPLAGT CGVLLLSLVI TLYCKRGRKK LLYIFKQPFM RPVQTTQEED GCSCRFPEEE EGGCELRVKF SRSADAPAYQ QGQNQLYNEL NLGRREEYDV LDKRRGRDPE MGGKPRRKNP QEGLYNELQK DKMAEAYSEI GMKGERRRGK GHDGLYQGLS TATKDTYDAL HMQALPPR | 54 |
| Polynucleotide of anti-BCMA CAR4 | ATGGCGCTGCCAGTCACAGCATTGCTGCTGCCTCTGGCACTCCTGT TGCATGCAGCCCGCCCACAGGTGCAGCTGGTGGAAAGCGGTGGGGG GGTGGTGCAGCCCGGCAGAAGTCTGAGACTCAGCTGTGCAGCAAGT GGCTTCACATTCAGTTCTTACGGCATGCACTGGGTGCGACAGGCTC CCGGGAAGGGACTGGAGTGGGTGGCAGTGATATCATACGATGGTAG GAATAAGAATTACGCTGATTCAGTCAAGGGACGATTCACAATCAGT CGCGACAATTCCAAGAACACCCTTTACCTGCAGATGAATAGCCTCA GGGCGGAGGATACTGCAGTCTACTATTGCGCAAGAGAGGGAGAAGC TACCTACTACGACATACTGACTGGGCCATTTGATTATTGGGGCCAA GGAACTCTTGTCACTGTGAGCAGCGGCGGCGGAGGCTCTGGAGGAG GGGGATCAGGCGGGGGAGGATCCGACATCCAGATGACCCAGAGCCC TTCTTCTCTGTCAGCTAGTGTAGGCGATCGAATCACTATCACTTGC AGGGCCTCCCAGGACATCCGCAACTACCTGGGATGGTATCAGCAGA AGCCAGGCAAAGCTCCGAAGGTTCTCATTTTTGCCGCCTCTTCCCT CCAGTCAGGGGTGCCCTCTAGGTTTAGCGGCAGCGGTAGCGGAACA GACTTCACCCTTACCATCTCATCTCTCCAGCCCGAGGACTTCGCTA CCTATTATTGCCTCCAAGATTATATATATCCTTGGACCTTCGCACA AGGCACTAAAGTTGAGATCAAAACCACAACACCTGCTCCAAGGCCC CCCACACCCGCTCCAACTATAGCCAGCCAACCATTGAGCCTCAGAC CTGAAGCTTGCAGGCCCGCAGCAGGAGGCGCCGTCCATACGCGAGG CCTGGACTTCGCGTGTGATATTTATATTTGGGCCCCTTTGGCCGGA ACATGTGGGGTGTTGCTTCTCTCCCTTGTGATCACTCTGTATTGTA AGCGCGGGAGAAAGAAGCTCCTGTACATCTTCAAGCAGCCTTTTAT GCGACCTGTGCAAACCACTCAGGAAGAAGATGGGTGTTCATGCCGC TTCCCCGAGGAGGAAGAAGGAGGGTGTGAACTGAGGGTGAAATTTT CTAGAAGCGCCGATGCTCCCGCATATCAGCAGGGTCAGAATCAGCT CTACAATGAATTGAATCTCGGCAGGCGAGAAGAGTACGATGTTCTG GACAAGAGACGGGGCAGGGATCCCGAGATGGGGGGAAAGCCCCGGA GAAAAAATCCTCAGGAGGGGTTGTACAATGAGCTGCAGAAGGACAA GATGGCTGAAGCCTATAGCGAGATCGGAATGAAAGGCGAAAGACGC AGAGGCAAGGGGCATGACGGTCTGTACCAGGGTCTCTCTACAGCCA CCAAGGACACTTATGATGCGTTGCATATGCAAGCCTTGCCACCCCG CTAA | 55 |
| Polypeptide of anti-BCMA CAR4 | MALPVTALLL PLALLLHAAR PQVQLVESGG GVVQPGRSLR LSCAASGFTF SSYGMHWVRQ APGKGLEWVA VISYDGRNKN YADSVKGRFT ISRDNSKNTL YLQMNSLRAE DTAVYYCARE GEATYYDILT GPFDYWGQGT LVTVSSGGGG SGGGGSGGGG SDIQMTQSPS SLSASVGDRI TITCRASQDI RNYLGWYQQK PGKAPKVLIF AASSLQSGVP SRFSGSGSGT DFTLTISSLQ PEDFATYYCL QDYIYPWTFA QGTKVEIKTT TPAPRPPTPA PTIASQPLSL RPEACRPAAG GAVHTRGLDF ACDIYIWAPL AGTCGVLLLS LVITLYCKRG RKKLLYIFKQ PFMRPVQTTQ EEDGCSCRFP EEEEGGCELR VKFSRSADAP AYQQGQNQLY NELNLGRREE YDVLDKRRGR DPEMGGKPRR KNPQEGLYNE LQKDKMAEAY SEIGMKGERR RGKGHDGLYQ GLSTATKDTY DALHMQALPP R | 56 |
| Polynucleotide of anti-BCMA CAR5 | ATGGCACTCCCCGTGACTGCCCTGCTTCTTCCACTGGCACTGCTGC TCCATGCAGCCAGGCCCGATATTCAAATGACTCAGAGTCCCAGCTC ACTCAGCGCTAGCGTCGGAGATAGGATAACCATCACATGTCGGGCC AGCCAAGACATCCGGAACTATCTTGGATGGTATCAGCAAAAACCCG | 57 |

-continued

L. SEQUENCE LISTING

| Description | Sequence | SEQ ID NO: |
|---|---|---|
| | GGAAGGCTCCTAAAGTGCTGATTTTCGCCGCTAGCTCACTGCAGTC CGGGGTGCCGAGTAGGTTTTCCGGCTCTGGTAGTGGCACCGACTTC ACCCTTACAATATCAAGCCTCCAGCCAGAGGACTTCGCGACTTACT ATTGTCTGCAGGATTACATCTACCCGTGGACCTTCGCCCAGGGAAC TAAGGTCGAGATTAAGGGTGGTGGTGGCAGCGGCGGGGGCGGTTCC GGGGGAGGAGGATCCCAGGTCCAACTCGTGGAGTCCGGTGGTGGCG TGGTGCAGCCTGGAAGATCCCTGCGGCTCTCTTGTGCCGCTAGCGG ATTTACATTCAGTAGCTATGGGATGCATTGGGTTCGCCAGGCTCCG GGCAAAGGATTGGAGTGGGTGGCGGTCATATCATATGACGGCCGGA ACAAAAATTATGCTGATTCTGTGAAGGGGAGGTTCACTATTAGTAG AGACAATAGTAAGAATACGCTGTACTTGCAGATGAACTCTCTTCGA GCAGAAGATACTGCCGTGTACTATTGTGCGCGCGAGGGGGAAGCCA CTTACTACGACATTCTGACAGGGCCTTTCGATTATTGGGGACAGGG TACTCTCGTTACAGTGTCCTCAACCACAACACCTGCTCCAAGGCCC CCCACACCCGCTCCAACTATAGCCAGCCAACCATTGAGCCTCAGAC CTGAAGCTTGCAGGCCCGCAGCAGGAGGCGCCGTCCATACGCGAGG CCTGGACTTCGCGTGTGATATTTATATTTGGGCCCCTTTGGCCGGA ACATGTGGGGTGTTGCTTCTCTCCCTTGTGATCACTCTGTATTGTA AGCGCGGGAGAAAGAAGCTCCTGTACATCTTCAAGCAGCCTTTTAT GCGACCTGTGCAAACCACTCAGGAAGAAGATGGTGTTCATGCCGC TTCCCCGAGGAGGAAGAAGGAGGGTGTGAACTGAGGGTGAAATTTT CTAGAAGCGCCGATGCTCCCGCATATCAGCAGGGTCAGAATCAGCT CTACAATGAATTGAATCTCGGCAGGCGAGAAGAGTACGATGTTCTG GACAAGAGACGGGGCAGGGATCCCGAGATGGGGGGAAAGCCCCGGA GAAAAAATCCTCAGGAGGGGTTGTACAATGAGCTGCAGAAGGACAA GATGGCTGAAGCCTATAGCGAGATCGGAATGAAAGGCGAAAGACGC AGAGGCAAGGGGCATGACGGTCTGTACCAGGGTCTCTCTACAGCCA CCAAGGACACTTATGATGCGTTGCATATGCAAGCCTTGCCACCCCG CTAA | |
| Polypeptide of anti-BCMA CAR5 | MALPVTALLL PLALLLHAAR PDIQMTQSPS SLSASVGDRI TITCRASQDI RNYLGWYQQK PGKAPKVLIF AASSLQSGVP SRFSGSGSGT DFTLTISSLQ PEDFATYYCL QDYIYPWTFA QGTKVEIKGG GGSGGGGSGG GGSQVQLVES GGGVVQPGRS LRLSCAASGF TFSSYGMHWV RQAPGKGLEW VAVISYDGRN KNYADSVKGR FTISRDNSKN TLYLQMNSLR AEDTAVYYCA REGEATYYDI LTGPFDYWGQ GTLVTVSSTT TPAPRPPTPA PTIASQPLSL RPEACRPAAG GAVHTRGLDF ACDIYIWAPL AGTCGVLLLS LVITLYCKRG RKKLLYIFKQ PFMRPVQTTQ EEDGCSCRFP EEEEGGCELR VKFSRSADAP AYQQGQNQLY NELNLGRREE YDVLDKRRGR DPEMGGKPRR KNPQEGLYNE LQKDKMAEAY SEIGMKGERR RGKGHDGLYQ GLSTATKDTY DALHMQALPP R | 58 |
| Polynucleotide of anti-BCMA CAR6 | ATGGCCCTGCCAGTAACAGCCCTCTTGCTCCCCCTGGCACTTCTGC TGCACGCCGCGCGGCCCCAGGTGCAGCTTGTGGAGAGCGGAGGCGG CGTGGTGCAGCCAGGGAGGAGCTTGAGACTCTCTTGTGCTGCCTCA GGATTCACTTTTAGTAGTTACGGTATGCACTGGGTGCGCCAGGCTC CCGGAAAAGGACTGGAGTGGGTGGCAGTGATCAGCTACGATGGGAG GAACAAGAATTATGCTGACAGTGTGAAAGGGAGGTTCACGATATCT CGAGATAATTCAAAGAACACCCTGTACCTGCAGATGAACAGTCTTA GAGCTGAGGATACTGCTGTGTACTACTGCGCTAGAGAAGGGGAAGC CACGTACTACGACATTCTGACAGGCCCTTTTGACTACTGGGGCCAA GGCACACTCGTTACTGTGAGCAGTGGTGGAGGGGGCAGTGGAGGCG GAGGTTCTGGTGGAGGGGGTAGTGATATCCAACTGACGCAGAGCCC AAGCTTCTTGAGTGCGTCTGTGGGGGACCGGGTCTCTATCACCTGT CGGGCTTCTCAGGGGATCAGTTCCTATCTGGCATGGTATCAGCAGA AGCCTGGCAAAGCCCCAAAGGTATTGATCTACGTCGCATCAACGCT GCAGTCCGGGGTGCCTTCTCGGTTCAGCGGGTCTGGTAGTGGAACT GAGTTTACACTGACCATAAGCAGTCTGCAACCCGATGATTTCGCCA CTTATTACTGCCAACAGCTTTACTCTTATCCGCGCGCATTTGGCCA GGGGACTAAAGTAGAGATTAAAACCACAACACCTGCTCCAAGGCCC CCCACACCCGCTCCAACTATAGCCAGCCAACCATTGAGCCTCAGAC CTGAAGCTTGCAGGCCCGCAGCAGGAGGCGCCGTCCATACGCGAGG CCTGGACTTCGCGTGTGATATTTATATTTGGGCCCCTTTGGCCGGA ACATGTGGGGTGTTGCTTCTCTCCCTTGTGATCACTCTGTATTGTA AGCGCGGGAGAAAGAAGCTCCTGTACATCTTCAAGCAGCCTTTTAT GCGACCTGTGCAAACCACTCAGGAAGAAGATGGGTGTTCATGCCGC TTCCCCGAGGAGGAAGAAGGAGGGTGTGAACTGAGGGTGAAATTTT CTAGAAGCGCCGATGCTCCCGCATATCAGCAGGGTCAGAATCAGCT CTACAATGAATTGAATCTCGGCAGGCGAGAAGAGTACGATGTTCTG GACAAGAGACGGGGCAGGGATCCCGAGATGGGGGGAAAGCCCCGGA GAAAAAATCCTCAGGAGGGGTTGTACAATGAGCTGCAGAAGGACAA | 59 |

-continued

L. SEQUENCE LISTING

| Description | Sequence | SEQ ID NO: |
|---|---|---|
| | GATGGCTGAAGCCTATAGCGAGATCGGAATGAAAGGCGAAAGACGC AGAGGCAAGGGGCATGACGGTCTGTACCAGGGTCTCTCTACAGCCA CCAAGGACACTTATGATGCGTTGCATATGCAAGCCTTGCCACCCCG CTAA | |
| Polypeptide of anti-BCMA CAR6 | MALPVTALLL PLALLLHAAR PQVQLVESGG GVVQPGRSLR LSCAASGFTF SSYGMHWVRQ APGKGLEWVA VISYDGRNKN YADSVKGRFT ISRDNSKNTL YLQMNSLRAE DTAVYYCARE GEATYYDILT GPFDYWGQGT LVTVSSGGGG SGGGGSGGGG SDIQLTQSPS FLSASVGDRV SITCRASQGI SSYLAWYQQK PGKAPKVLIY VASTLQSGVP SRFSGSGSGT EFTLTISSLQ PDDFATYYCQ QLYSYPRAFG QGTKVEIKTT TPAPRPPTPA PTIASQPLSL RPEACRPAAG GAVHTRGLDF ACDIYIWAPL AGTCGVLLLS LVITLYCKRG RKKLLYIFKQ PFMRPVQTTQ EEDGCSCRFP EEEEGGCELR VKFSRSADAP AYQQGQNQLY NELNLGRREE YDVLDKRRGR DPEMGGKPRR KNPQEGLYNE LQKDKMAEAY SEIGMKGERR RGKGHDGLYQ GLSTATKDTY DALHMQALPP R | 60 |
| Polynucleotide of anti-BCMA CAR7 | ATGGCCCTGCCCGTAACCGCCCTTCTGCTGCCTCTGGCTCTGCTTC TCCACGCAGCAAGGCCTCAGGTCCAGCTGGTGCAATCTGGAGCCGA GGTCAAGAAACCTGGCGCAAGCGTGAAGGTGTCTTGTAAAGGGAGC GGCTATACGTTTTCCACGTACGGCATTGGCTGGGTTAGACAAGCGC CTGGCCAAGGCCTGGAGTGGCTGGCATGGATTTCCGCTTACAGTGG TAAGACGAACTACGCACAGAAGGTCCAGGGCAGAGTGACCCTCACA ACTGATACTAGCACCAACACCGCGTATATGGAGCTTCGGTCCCTGC GGTCTGATGACACAGCCGTCTATTATTGCGCCAGGGACGACGGTGC GGGCACAGATTATTATTATGGCATGGACGTTTGGGGGCAGGGCACC ACAGTCACTGTCAGCAGCGGGGGGGGAGGATCCGGGGGAGGCGGAT CTGGTGGGGGAGGATCCGACATTGTGATGACCCAGACCCCACTGTC ACTGTCTGTGACCCCGGGTCAGCCAGCTTCTATTAGCTGTAAGTCC TCACAAAGCCTCCTTTATAGCGACGGGAAAACATTTCTTTATTGGT ATCTGCAGAAACCCGGCCAGCCTCCCCAGTTGCTCATTTACGAGGG TTCCAACCGATTCAGCGGAGTTCCTGACAGATTCTCTGGATCTGGC TCAGGAACTGATTTCACTCTGAAGATTTCAAGGGTTGAGGCAGAGG ATGTGGGCGTGTTCTACTGCATGCAATCTATCCAGTTGCCCAATAC ATTCGGGCAGGGGACAAAGCTCGAGATTAAAACCACAACACCTGCT CCAAGGCCCCCCACACCCGCTCCAACTATAGCCAGCCAACCATTGA GCCTCAGACCTGAAGCTTGCAGGCCCGCAGCAGGAGGCGCCGTCCA TACGCGAGGCCTGGACTTCGCGTGTGATATTTATATTTGGGCCCCT TTGGCCGGAACATGTGGGGTGTTGCTTCTCTCCCTTGTGATCACTC TGTATTGTAAGCGCGGGAGAAAGAAGCTCCTGTACATCTTCAAGCA GCCTTTTATGCGACCTGTGCAAACCACTCAGGAAGAAGATGGGTGT TCATGCCGCTTCCCCGAGGAGGAAGAAGGAGGGTGTGAACTGAGGG TGAAATTTTCTAGAAGCGCCGATGCTCCCGCATATCAGCAGGGTCA GAATCAGCTCTACAATGAATTGAATCTCGGCAGGCGAGAAGAGTAC GATGTTCTGGACAAGAGACGGGGCAGGGATCCCGAGATGGGGGGAA AGCCCCGGAGAAAAAATCCTCAGGAGGGGTTGTACAATGAGCTGCA GAAGGACAAGATGGCTGAAGCCTATAGCGAGATCGGAATGAAAGGC GAAAGACGCAGAGGCAAGGGGCATGACGGTCTGTACCAGGGTCTCT CTACAGCCACCAAGGACACTTATGATGCGTTGCATATGCAAGCCTT GCCACCCCGCTAA | 61 |
| Polypeptide of anti-BCMA CAR7 | MALPVTALLL PLALLLHAAR PQVQLVQSGA EVKKPGASVK VSCKGSGYTF STYGIGWVRQ APGQGLEWLA WISAYSGKTN YAQKVQGRVT LTTDTSTNTA YMELRSLRSD DTAVYYCARD DGAGTDYYYG MDVWGQGTTV TVSSGGGGSG GGGSGGGGSD IVMTQTPLSL SVTPGQPASI SCKSSQSLLY SDGKTFLYWY LQKPGQPPQL LIYEGSNRFS GVPDRFSGSG SGTDFTLKIS RVEAEDVGVF YCMQSIQLPN TFGQGTKLEI KTTTPAPRPP TPAPTIASQP LSLRPEACRP AAGGAVHTRG LDFACDIYIW APLAGTCGVL LLSLVITLYC KRGRKKLLYI FKQPFMRPVQ TTQEEDGCSC RFPEEEEGGC ELRVKFSRSA DAPAYQQGQN QLYNELNLGR REEYDVLDKR RGRDPEMGGK PRRKNPQEGL YNELQKDKMA EAYSEIGMKG ERRRGKGHDG LYQGLSTATK DTYDALHMQA LPPR | 62 |
| Polynucleotide of anti-BCMA CAR8 | ATGGCTCTCCCTGTCACTGCTCTGCTCCTTCCTCTGGCGCTTCTGC TGCATGCTGCCCGACCCGATATTGTGATGACGCAGACCCCCCTGTC TCTGTCCGTCACCCCAGGGCAGCCGGCGTCCATCTCCTGTAAGAGC AGCCAGTCTCTTCTGTACTCTGATGGAAAGACATTTTTGTACTGGT ACTTGCAGAAGCCTGGGCAACCTCCGCAGCTCTTGATTTACGAAGG ATCCAATAGATTCAGCGGAGTGCCCGATAGATTTAGCGGTTCTGGA | 63 |

-continued

L. SEQUENCE LISTING

| Description | Sequence | SEQ ID NO: |
|---|---|---|
| | TCTGGTACGGACTTCACACTGAAAATCTCACGGGTTGAGGCTGAAG ATGTGGGCGTGTTTTACTGCATGCAAAGCATACAACTGCCGAACAC CTTCGGCCAAGGAACTAAGCTGGAGATTAAGGGAGGAGGAGGGAGC GGTGGCGGCGGTTCTGGTGGCGGCGGATCCCAGGTCCAGTTGGTAC AATCTGGGGCCGAAGTTAAGAAACCGGGGGCTAGCGTGAAGGTATC TTGCAAAGGCAGTGGCTACACATTCTCTACTTACGGAATCGGATGG GTGAGACAGGCTCCTGGTCAGGGTCTGGAATGGCTCGCGTGGATCA GTGCGTATTCAGGAAAAACCAATTACGCTCAGAAGGTGCAAGGCCG CGTGACACTGACCACTGACACCTCCACCAACACAGCTTACATGGAG CTGCGATCTCTCAGATCTGACGATACTGCAGTGTATTACTGTGCCC GCGATGACGGGGCTGGCACGGACTACTATTATGGGATGGATGTGTG GGGACAAGGCACCACAGTAACTGTGAGCAGTACCACAACACCTGCT CCAAGGCCCCCCACACCCGCTCCAACTATAGCCAGCCAACCATTGA GCCTCAGACCTGAAGCTTGCAGGCCCGCAGCAGGAGGCGCCGTCCA TACGCGAGGCCTGGACTTCGCGTGTGATATTTATATTTGGGCCCCT TTGGCCGGAACATGTGGGGTGTTGCTTCTCTCCCTTGTGATCACTC TGTATTGTAAGCGCGGGAGAAAGAAGCTCCTGTACATCTTCAAGCA GCCTTTTATGCGACCTGTGCAAACCACTCAGGAAGAAGATGGGTGT TCATGCCGCTTCCCCGAGGAGGAAGAAGGAGGGTGTGAACTGAGGG TGAAATTTTCTAGAAGCGCCGATGCTCCCGCATATCAGCAGGGTCA GAATCAGCTCTACAATGAATTGAATCTCGGCAGGCGAGAAGAGTAC GATGTTCTGGACAAGAGACGGGGCAGGGATCCCGAGATGGGGGGAA AGCCCCGGAGAAAAAATCCTCAGGAGGGGTTGTACAATGAGCTGCA GAAGGACAAGATGGCTGAAGCCTATAGCGAGATCGGAATGAAAGGC GAAAGACGCAGAGGCAAGGGGCATGACGGTCTGTACCAGGGTCTCT CTACAGCCACCAAGGACACTTATGATGCGTTGCATATGCAAGCCTT GCCACCCCGCTAA | |
| Polypeptide of anti-BCMA CAR8 | MALPVTALLL PLALLLHAAR PDIVMTQTPL SLSVTPGQPA SISCKSSQSL LYSDGKTFLY WYLQKPGQPP QLLIYEGSNR FSGVPDRFSG SGSGTDFTLK ISRVEAEDVG VFYCMQSIQL PNTFGQGTKL EIKGGGGSGG GGSGGGGSQV QLVQSGAEVK KPGASVKVSC KGSGYTFSTY GIGWVROAPG QGLEWLAWIS AYSGKTNYAQ KVQGRVTLTT DTSTNTAYME LRSLRSDDTA VYYCARDDGA GTDYYYGMDV WGQGTTVTVS STTTPAPRPP TPAPTIASQP LSLRPEACRP AAGGAVHTRG LDFACDIYIW APLAGTCGVL LLSLVITLYC KRGRKKLLYI FKQPFMRPVQ TTQEEDGCSC RFPEEEEGGC ELRVKFSRSA DAPAYQQGQN QLYNELNLGR REEYDVLDKR RGRDPEMGGK PRRKNPQEGL YNELQKDKMA EAYSEIGMKG ERRRGKGHDG LYQGLSTATK DTYDALHMQA LPPR | 64 |
| Polynucleotide of anti-BCMA CAR9 | ATGGCTCTGCCCGTGACTGCCCTGCTGCTGCCGTTGGCACTGCTTT TGCACGCTGCACGGCCGCAGGTGCAATTGGTCCAGTCCGGCGCCGA GGTCAAAAAGCCTGGAGCCTCTGTGAAGGTGTCCTGTAAAGCTTCT GGATACACATTCTCCAACAACGGCTTCTCCTGGGTGCGGCAAGCTC CAGGGCAAGGACTGGAGTGGATGGGCTGGATTAGTGGGTTTAACGG TAAAACCTACTATACCAAAACCCTTCAGGGCCGCGTCACAATGACC ATCGATACCAGTACAAGCACAGCTTACATGGATTTGAGATCCCTGA GGTCCGACGACACAGCCGTCTATTACTGCGCCCGGGGGCTGCTGCT GTCAGGAGAACTCTGGGGCTTTGACTACTGGGGTCAGGGCACCCTG GTGACCGTCTCATCTGGTGGCGGCGGATCAGGAGGCGGCGGATCCG GTGGAGGGGGAAGTGACATCCAGCTTGCGCAGAGTCCTTCTTTCCT GAGCGCGTCAGTTGGGGATCGGGTGACAATCACCTGTCGCGCATCA CAGGATATCAGTAGTTTTCTGGCCTGGTATCAACAGAAGCCAGGCA AAGCTCCCAAACTCCTTATTTTCGCTGCGAGCACCCTGCAATCCGG CGTGCCCAGCCGAATCAGCGGCTCTGGCTCTGGAACCGAGTTTACC CTTACGATCTCTTCCTTGCAGCCCGAGGATTTCGCAACCTACTACT GTCAGCAGTTTAACTCATACCCAAGGACCTTTGGCCAGGGCACCAA AGTGGAGATCAAGACCACAACACCTGCTCCAAGGCCCCCCACACCC GCTCCAACTATAGCCAGCCAACCATTGAGCCTCAGACCTGAAGCTT GCAGGCCCGCAGCAGGAGGCGCCGTCCATACGCGAGGCCTGGACTT CGCGTGTGATATTTATATTTGGGCCCCTTTGGCCGGAACATGTGGG GTGTTGCTTCTCTCCCTTGTGATCACTCTGTATTGTAAGCGCGGGA GAAAGAAGCTCCTGTACATCTTCAAGCAGCCTTTTATGCGACCTGT GCAAACCACTCAGGAAGAAGATGGGTGTTCATGCCGCTTCCCCGAG GAGGAAGAAGGAGGGTGTGAACTGAGGGTGAAATTTTCTAGAAGCG CCGATGCTCCCGCATATCAGCAGGGTCAGAATCAGCTCTACAATGA ATTGAATCTCGGCAGGCGAGAAGAGTACGATGTTCTGGACAAGAGA CGGGGCAGGGATCCCGAGATGGGGGGAAAGCCCCGGAGAAAAAATC CTCAGGAGGGGTTGTACAATGAGCTGCAGAAGGACAAGATGGCTGA | 65 |

-continued

L. SEQUENCE LISTING

| Description | Sequence | SEQ ID NO: |
|---|---|---|
| | AGCCTATAGCGAGATCGGAATGAAAGGCGAAAGACGCAGAGGCAAG GGGCATGACGGTCTGTACCAGGGTCTCTCTACAGCCACCAAGGACA CTTATGATGCGTTGCATATGCAAGCCTTGCCACCCCGCTAA | |
| Polypeptide of anti-BCMA CAR9 | MALPVTALLL PLALLLHAAR PQVQLVQSGA EVKKPGASVK VSCKASGYTF SNNGFSWVRQ APGQGLEWMG WISGFNGKTY YTKTLQGRVT MTIDTSTSTA YMDLRSLRSD DTAVYYCARG LLLSGELWGF DYWGQGTLVT VSSGGGGSGG GGSGGGGSDI QLAQSPSFLS ASVGDRVTIT CRASQDISSF LAWYQQKPGK APKLLIFAAS TLQSGVPSRI SGSGSGTEFT LTISSLQPED FATYYCQQFN SYPRTFGQGT KVEIKTTTPA PRPPTPAPTI ASQPLSLRPE ACRPAAGGAV HTRGLDFACD IYIWAPLAGT CGVLLLSLVI TLYCKRGRKK LLYIFKQPFM RPVQTTQEED GCSCRFPEEE EGGCELRVKF SRSADAPAYQ QGQNQLYNEL NLGRREEYDV LDKRRGRDPE MGGKPRRKNP QEGLYNELQK DKMAEAYSEI GMKGERRRGK GHDGLYQGLS TATKDTYDAL HMQALPPR | 66 |
| Polynucleotide of anti-BCMA CAR10 | ATGGCACTCCCAGTCACCGCCCTGCTGCTCCCACTGGCCCTCCTGC TGCATGCAGCACGCCCTGATATTCAGCTGGCGCAGAGTCCTAGTTT CCTTTCCGCGTCCGTCGGCGACCGGGTGACTATTACCTGCAGAGCC TCCCAAGATATTTCCTCATTCCTCGCTTGGTATCAGCAGAAGCCAG GCAAGGCGCCAAAACTTCTGATCTTTGCAGCCTCAACGCTGCAGTC CGGCGTCCCTTCTCGAATTTCTGGCAGCGGCAGTGGAACTGAATTC ACCCTTACGATTAGCAGCTTGCAACCAGAGGACTTTGCCACCTATT ACTGTCAGCAGTTCAACAGCTATCCACGGACCTTCGGTCAAGGCAC AAAAGTTGAGATAAAGGGGGGGGGTGGCAGCGGCGGGGGCGGTTCT GGTGGCGGCGGCAGTCAGGTACAGCTGGTGCAGTCCGGCGCTGAGG TCAAGAAGCCTGGTGCATCCGTGAAAGTCTCTTGCAAGGCCAGCGG TTACACCTTCTCTAATAATGGCTTTAGTTGGGTCCGCCAGGCCCCA GGTCAGGGACTGGAATGGATGGGGTGGATTAGTGGTTTCAATGGCA AGACGTATTACACCAAAACTCTGCAGGGTAGGGTGACTATGACTAT CGATACTAGCACCAGCACAGCGTACATGGACCTGCGGTCCTTGCGA TCCGATGACACTGCTGTCTACTATTGTGCCAGAGGACTCCTCCTGT CAGGGGAGCTGTGGGGGTTCGATTACTGGGGGCAAGGCACCCTCGT TACCGTGTCCTCTACCACAACACCTGCTCCAAGGCCCCCCACACCC GCTCCAACTATAGCCAGCCAACCATTGAGCCTCAGACCTGAAGCTT GCAGGCCCGCAGCAGGAGGCGCCGTCCATACGCGAGGCCTGGACTT CGCGTGTGATATTTATATTTGGGCCCCTTTGGCCGGAACATGTGGG GTGTTGCTTCTCTCCCTTGTGATCACTCTGTATTGTAAGCGCGGGA GAAAGAAGCTCCTGTACATCTTCAAGCAGCCTTTTATGCGACCTGT GCAAACCACTCAGGAAGAAGATGGGTGTTCATGCCGCTTCCCCGAG GAGGAAGAAGGAGGGTGTGAACTGAGGGTGAAATTTTCTAGAAGCG CCGATGCTCCCGCATATCAGCAGGGTCAGAATCAGCTCTACAATGA ATTGAATCTCGGCAGGCGAGAAGAGTACGATGTTCTGGACAAGAGA CGGGGCAGGGATCCCGAGATGGGGGGAAAGCCCCGGAGAAAAAATC CTCAGGAGGGGTTGTACAATGAGCTGCAGAAGGACAAGATGGCTGA AGCCTATAGCGAGATCGGAATGAAAGGCGAAAGACGCAGAGGCAAG GGGCATGACGGTCTGTACCAGGGTCTCTCTACAGCCACCAAGGACA CTTATGATGCGTTGCATATGCAAGCCTTGCCACCCCGCTAA | 67 |
| Polypeptide of anti-BCMA CAR10 | MALPVTALLL PLALLLHAAR PDIQLAQSPS FLSASVGDRV TITCRASQDI SSFLAWYQQK PGKAPKLLIF AASTLQSGVP SRISGSGSGT EFTLTISSLQ PEDFATYYCQ QFNSYPRTFG QGTKVEIKGG GGSGGGGSGG GGSQVQLVQS GAEVKKPGAS VKVSCKASGY TFSNNGFSWV RQAPGQGLEW MGWISGFNGK TYYTKTLQGR VTMTIDTSTS TAYMDLRSLR SDDTAVYYCA RGLLLSGELW GFDYWGQGTL VTVSSTTTPA PRPPTPAPTI ASQPLSLRPE ACRPAAGGAV HTRGLDFACD IYIWAPLAGT CGVLLLSLVI TLYCKRGRKK LLYIFKQPFM RPVQTTQEED GCSCRFPEEE EGGCELRVKF SRSADAPAYQ QGQNQLYNEL NLGRREEYDV LDKRRGRDPE MGGKPRRKNP QEGLYNELQK DKMAEAYSEI GMKGERRRGK GHDGLYQGLS TATKDTYDAL HMQALPPR | 68 |
| Human BCMA | MLQMAGQCSQ NEYFDSLLHA CIPCQLRCSS NTPPLTCQRY CNASVTNSVK GTNAILWTCL GLSLIISLAV FVLMFLLRKI NSEPLKDEFK NTGSGLLGMA NIDLEKSRTG DEIILPRGLE YTVEECTCED CIKSKPKVDS DHCFPLPAME EGATILVTTK TNDYCKSLPA ALSATEIEKS ISAR | 69 |

All publications, patent applications, and issued patents cited in this specification are herein incorporated by reference as if each individual publication, patent application, or issued patent were specifically and individually indicated to be incorporated by reference.

Although the foregoing embodiments have been described in some detail by way of illustration and example for purposes of clarity of understanding, it will be readily apparent to one of ordinary skill in the art in light of the teachings contemplated herein that certain changes and modifications may be made thereto without departing from the spirit or scope of the appended claims. The following examples are provided by way of illustration only and not by way of limitation. Those of skill in the art will readily recognize a variety of noncritical parameters that could be changed or modified to yield essentially similar results.

EXAMPLES

Example 1

Construction of Human Anti-BCMCA Cars

Lentiviral vectors comprising constructs that include a human anti-BCMA CARs were designed, constructed, and verified. Constructs comprising an MNDU3 promoter operably linked to an anti-BCMA CAR that contains a CD8α signal sequence, a human anti-BCMA scFv, a CD8a hinge and transmembrane domain, a CD137 costimulatory domain, and a CD3ζ primary signaling domain were cloned into lentiviral vectors. Anti-BCMA scFvs were designed and assessed in both VH/VL and VL/VH orientations using a polyglycine-serine linker. Exemplary anti-BCMA CAR polypeptide sequences are set forth in SEQ ID NOs: 50, 52, 54, 56, 58, 60, 62, 64, 66, and 68, and exemplary anti-BCMA CAR polynucleotide sequences are set forth in SEQ ID NOs: 49, 51, 53, 55, 57, 59, 61, 63, 65, and 67.

Example 2

Evaluation of Human Anti-BCMA Car T Cells

Figure 2B:
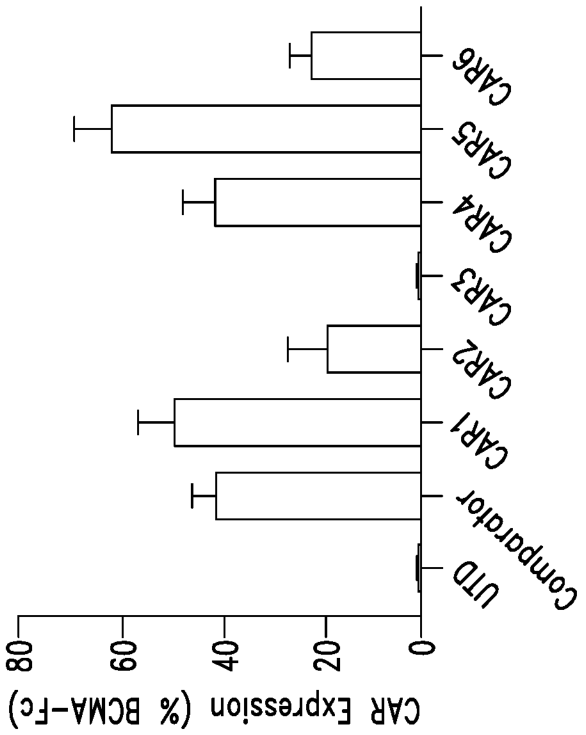
FIGS. 2A-2D show the vector copies per cell (FIGS. 2A and 2C) and expression of CAR constructs on T cells assessed by FACS (FIGS. 2B and 2D).
Figure 2A:
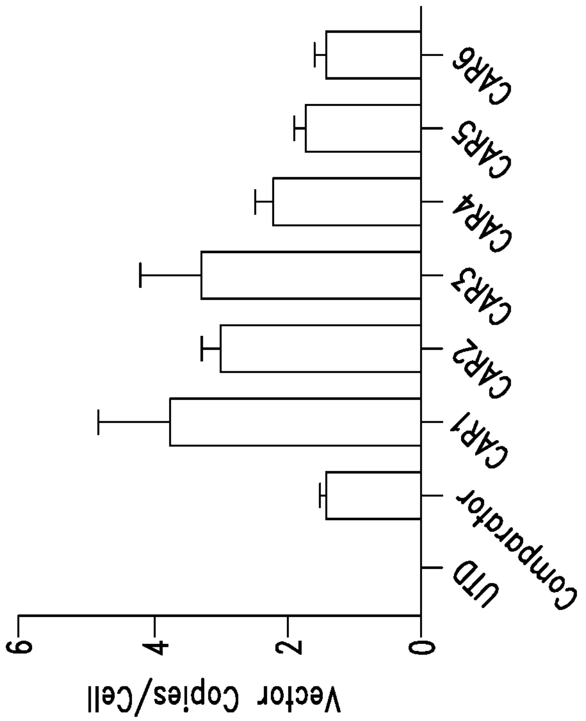
Figure 2D:
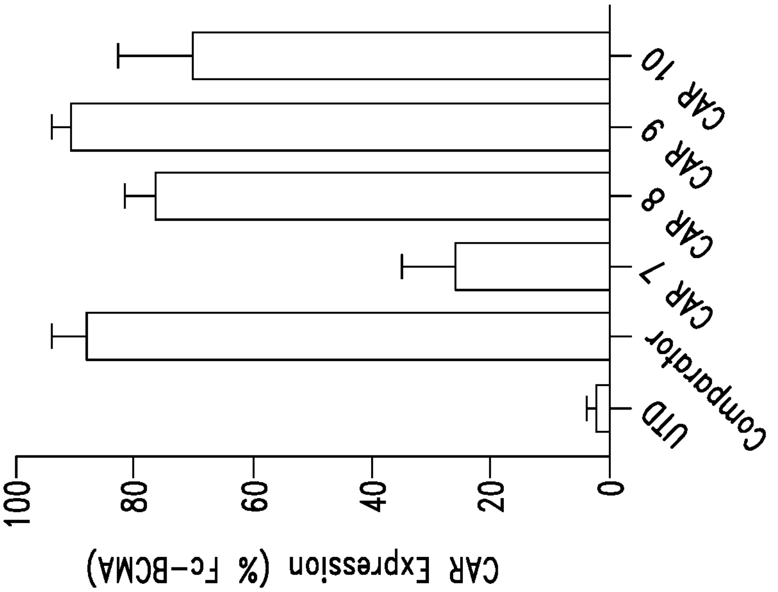
Figure 2C:
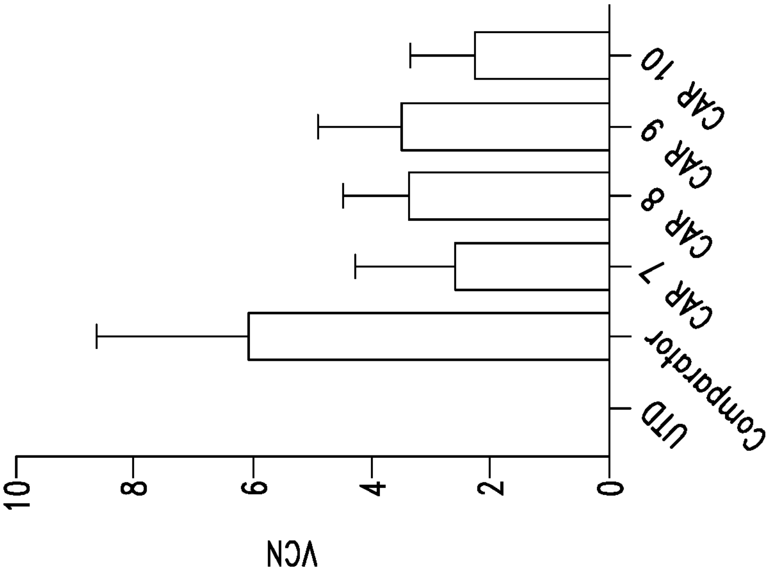

Chimeric antigen receptors (CARs) specific to BCMA and having human scFvs (e.g., SEQ ID NOs: 50, 52, 54, 56, 58, 60, 62, 64, 66, and 68) were evaluated for CAR expression and biological activity against BCMA expressing cells compared to a known anti-BCMA CAR having a murine derived scFv (the "comparator"). Anti-BCMA CAR T cells were produced in a 7 Day process using G-REX® flasks. Briefly, peripheral blood mononuclear cells (PBMC) were cultured in media containing IL-2 (CellGenix, GmbH) and antibodies specific for CD3 and CD28 (Miltenyi Biotec, Inc.). Lentiviruses encoding anti-BCMA CARs were added one day after culture initiation. On Day 4, CAR T cells were transferred from a 24 well plate, to a 24 well G-REX flask, where cells were maintained until harvest on Day 7. CAR T cells were interrogated for lentiviral vector integration into genomic DNA. Vector copies per cell ranged for transduced cells between 1 and 4 copies of transgene. As shown in FIG. 2A, all transduced cells display vector copy numbers similar to or greater than the comparator anti-BMCA CAR T cell.

CAR T cells were also analyzed for cell surface CAR expression using flow cytometry. CAR T cells were stained using a recombinant, phycoerythrin (PE) labeled, BCMA extracellular domain-FC fusion protein (Creative BioMart, Inc). Surface CAR expression by positive Fc-BCMA binding was detected for all transduced conditions at varying levels except CAR3, which had no expression. These reagents identify T cells specifically express anti-BCMA CARs. As shown in FIG. 2B, T cells transduced with CAR1, CAR4, or CAR5 have similar or greater CAR expression levels compared to the comparator anti-BMCA CAR T cell.

Figure 3B:
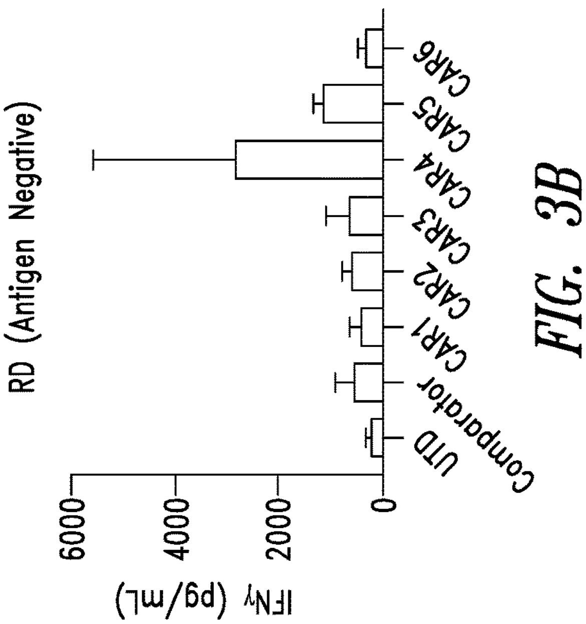
Figure 3A:
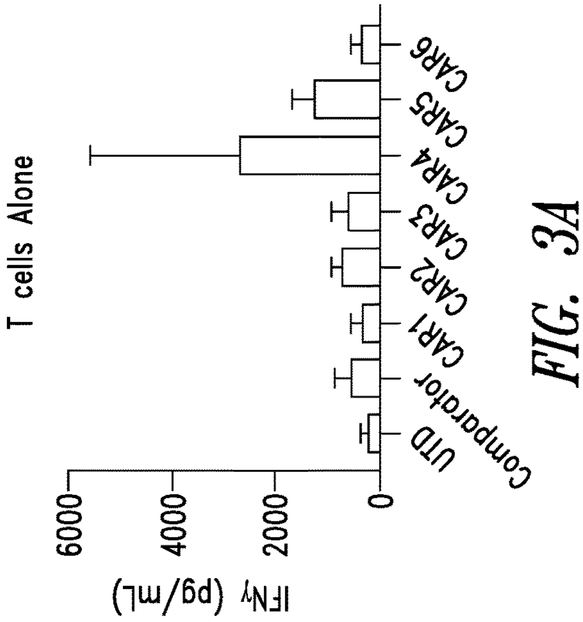
Figure 3C:
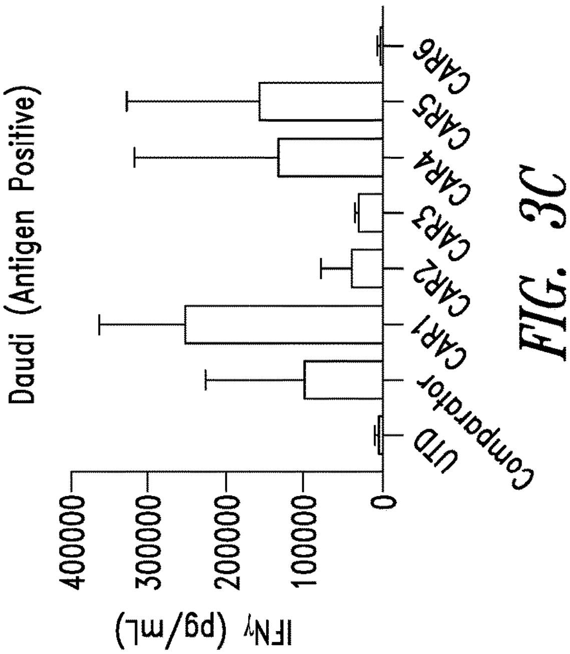
Figure 3F:
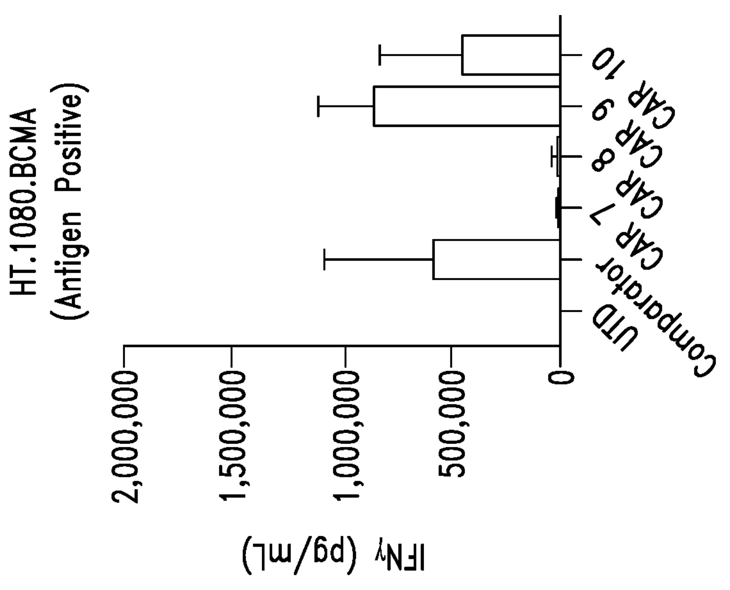
Figure 3E:
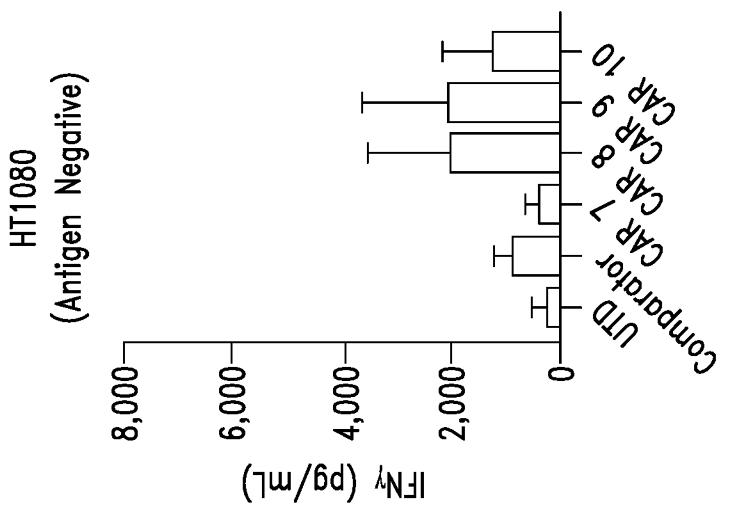
Figure 3D:
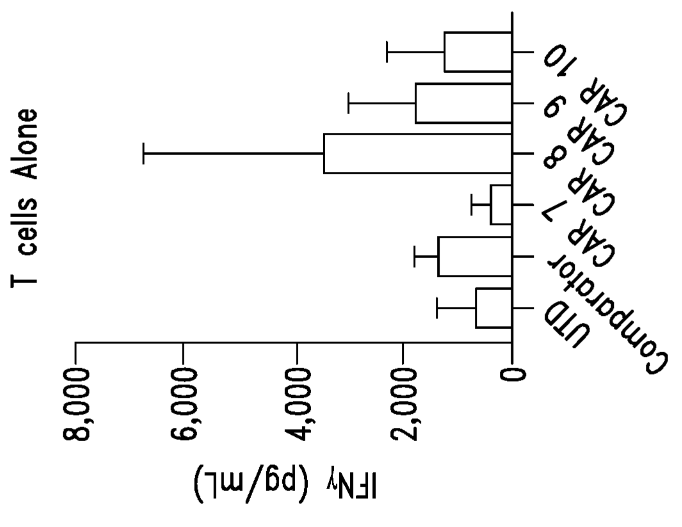
Figure 3G:
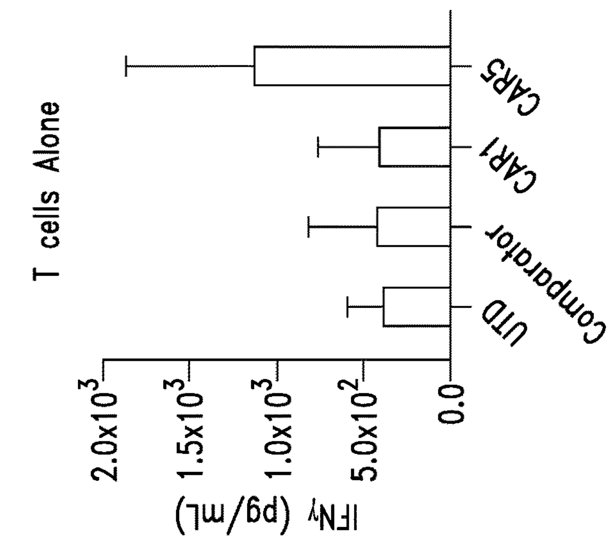
Figure 3H:
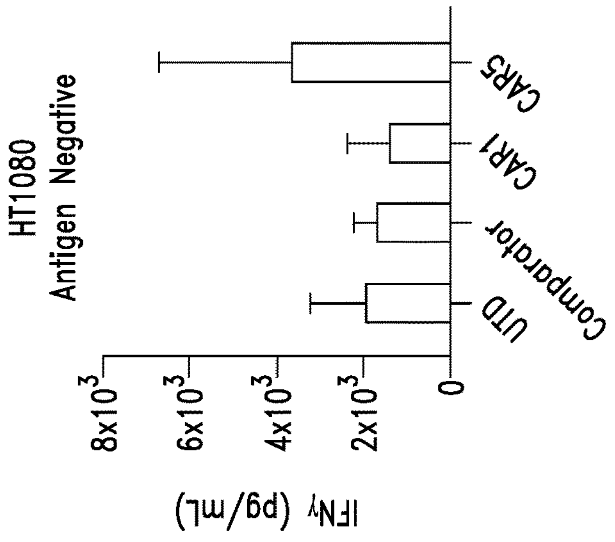
Figure 3I:
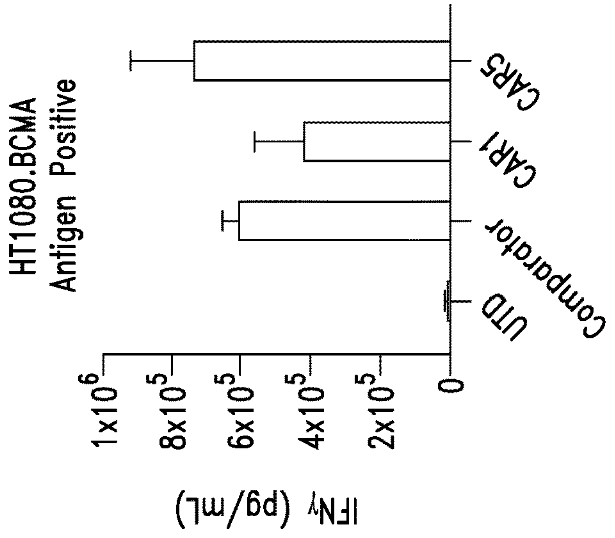

Additionally, the biological activity of the CAR T cells was assessed for interferon gamma production alone or in co-culture with tumor cell lines. Specifically, antigen-independent IFNγ production by the CAR T cells alone or in co-culture with the RD cell line or HT1080 cells that do not express BCMA was evaluated. As shown in FIGS. 3A and 3B, all CARs, except for CAR4, produce minimal IFNγ independent of antigen. Similar results are seen with CARs 7-10 in FIGS. 3D and 3E. Moreover, interferon gamma production after co-culture of CAR T cells with Burkitt's lymphoma cells (Daudi cells) or HT.1080.BCMA cells which express BCMA was measured. As shown in FIGS. 3C and 3F, CAR1, CAR4 CAR5, CAR9, and CAR10 produced similar or more IFNγ than the comparator anti-BCMA CAR. Similarly, when CAR1 or CAR5 were assessed for IFNγ production alone or in co-culture with antigen negative (HT1080) or antigen positive (HT1080.BCMA) tumor cell lines, CAR1 and CAR5 demonstrated minimal antigen independent IFNγ (as shown in FIGS. 3G and 3H), while also producing similar or more amounts of IFNγ in an antigen-dependent manner, as shown in FIG. 3I.

Figure 3J:
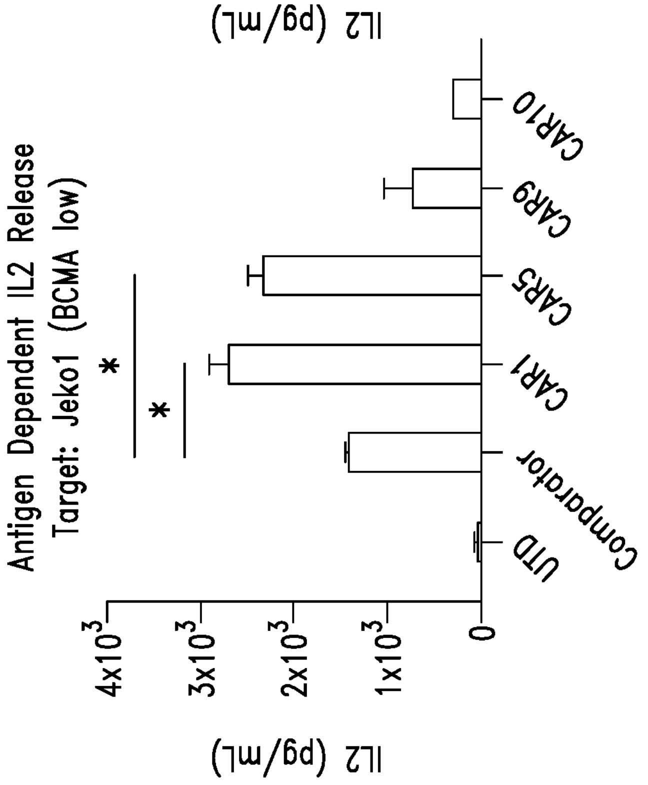
FIGS. 3J and 3*k* show the amount of IL2 released from anti-BCMA CAR T cells in co-culture with BCMA-low Jekol cells (FIG. 3J) or BCMA-high RPMI8226 cells (FIG. 3K).
Figure 3K:
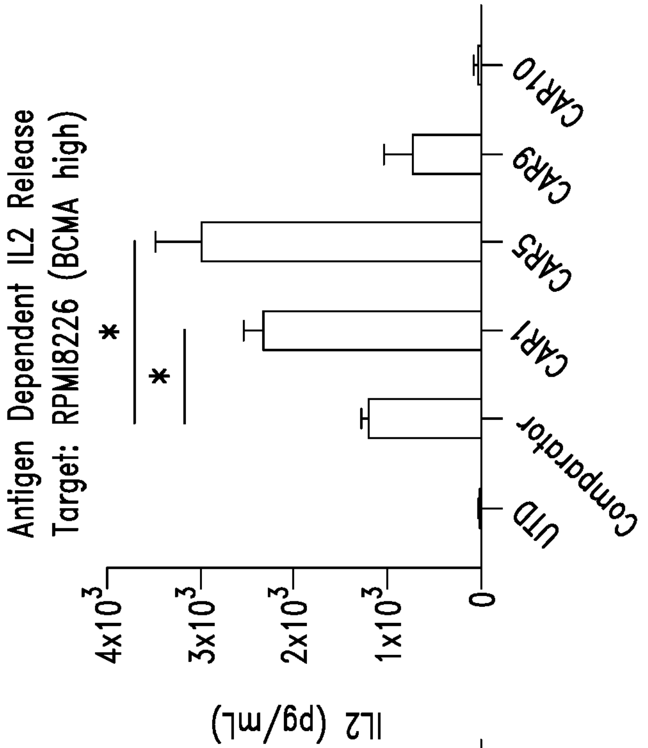

Additionally, when CAR1, CAR5, CAR9 and CAR10 were assessed for IL2 cytokine production in co-culture with antigen low (Jeko1) or antigen high (RPMI8336) tumor cell lines, CAR1 and CAR5 produced more IL2 than the comparator CAR, as shown in FIGS. 3J and 3K.

Example 3

Evaluation of Human Anti-BCMA Car T Cell Activation Against Low and High Antigen-Expressing Tumor Cells In another experiment, anti-BCMA CAR T cells were produced using a system directly scalable to large clinical manufacturing processes. Briefly, peripheral blood mononuclear cells (PBMC) were cultured in media containing IL-2 (CellGenix, GmbH) and antibodies specific for CD3 and CD28 (Miltenyi Biotec, Inc.). Lentiviruses encoding anti-BCMA CARs were added one day after culture initiation at a specified multiplicity of infection (MOI). CAR T cells were maintained in log-phase by adding fresh media containing IL-2 for a total of 10 days of culture. Anti-BCMA CAR T cells were analyzed for surface CAR expression by flow cytometry analysis of bound BCMA-Fc antigen and a normalized number CAR-positive CAR T cells were added to cultures alone or with tumor cells of varying antigen density. B cell Lymphoma cell lines RL and Toledo have low BCMA antigen expression compared to the Burkett's Lymphoma cell line (Daudi) and an engineered cell line HT1080.BCMA.

Figure 4A:
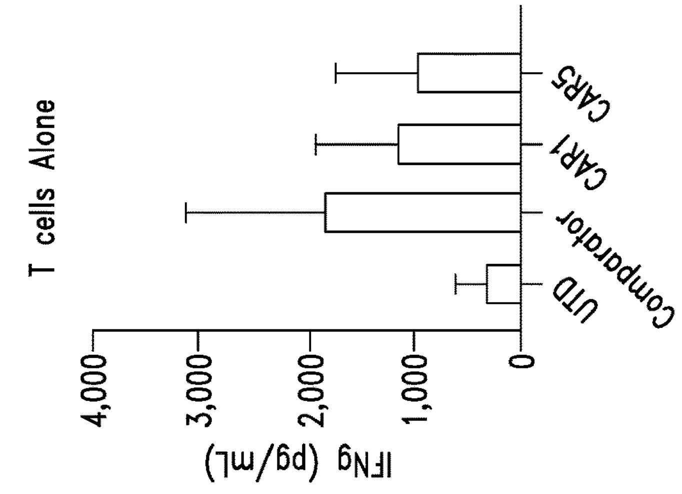
FIGS. 4A-4C show the amount of IFNγ released from anti-BCMA CAR T cells expressing a comparator CAR, CAR1 or CAR5 either alone (FIG. 4A) or in co-culture with cancer cells (FIGS. 4B and 4C). Cells were co-cultured for 24 hours with antigen-low cell lines RL and Toledo (FIG. 4B), and antigen-high cell lines Daudi and HT1080.BCMA (FIG. 4C).
Figure 4B:
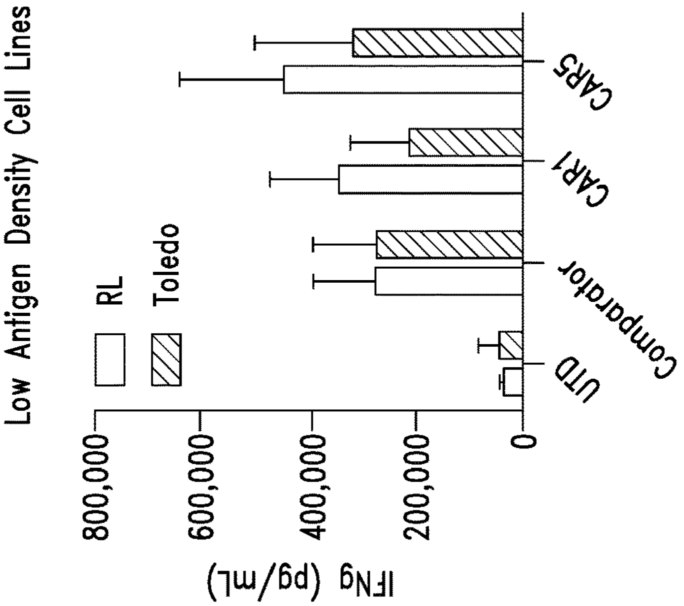
Figure 4C:
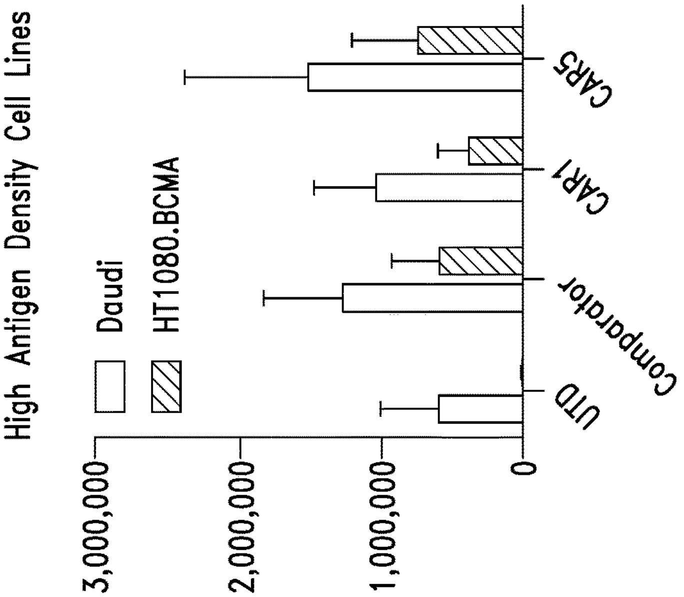

As shown in FIG. 4A, both CAR1 and CAR5 produce minimal IFNγ independent of antigen, and less than the comparator anti-BCMA CAR T cell. However, IFNγ production produced from co-cultures with low BCMA density cell lines suggest that CAR1 and CAR5 IFNγ production is higher than the comparator (FIG. 4B). Additionally, IFNγ production produced from co-cultures with high BCMA density cell lines suggest that CAR1 and CAR5 IFNγ production is similar to the comparator (FIG. 4C). This data suggests that the human CAR1 and CAR5 T cells are 1) potentially more potent than the comparator CAR against low antigen density cells, 2) at least as potent against high antigen density cells compared to the comparator CAR, and 3) display low antigen independent IFNγ release.

Example 4

Evaluation of Human Anti-BCMA Car T Cell Cytotoxicity Against Antigen-Expressing Tumor Cells To assess the ability of anti-BCMA CAR T cells to kill BCMA-expressing cancer cells, anti-BCMA CAR T cells were first produced using a system directly scalable to large clinical manufacturing processes as described above in Example 3. After 10 days in culture, an equal number of anti-BCMA expressing CAR T cells were cultured with an HT.1080 cell line expressing a nuclear red fluorescent protein (HT1080-nucRed) or a derivative line engineered to express BCMA (HT.1080-nucRed.BCMA) at various effector to target cell ratios (E:T).

Figure 5:
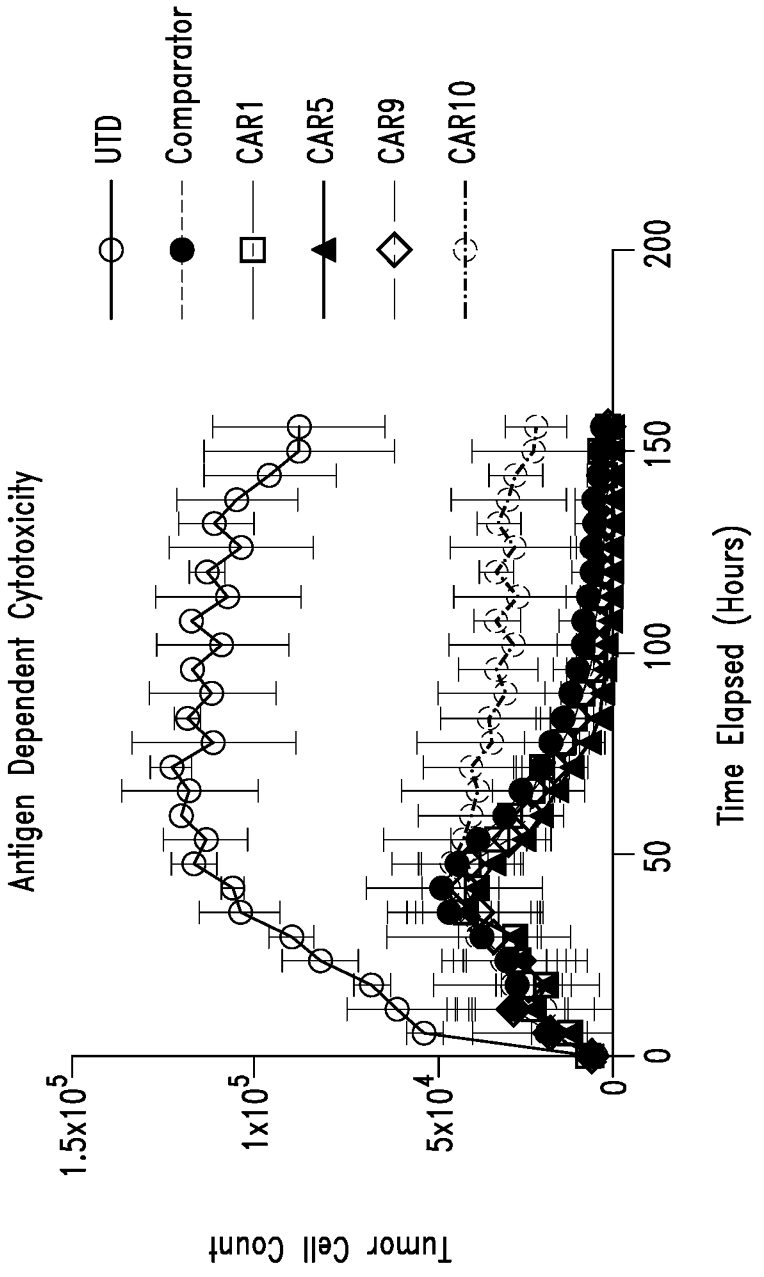

As show in FIG. 5, varying degrees of antigen-dependent cytotoxicity were observed over time in co-cultures with CAR1, CAR5, CAR9 and CAR10 and BCMA expressing HT.1080-nucRed.BCMA cell line.

Example 5

BCMA Antigen Density on Endogenous and Engineered Cell Lines

Figure 6:
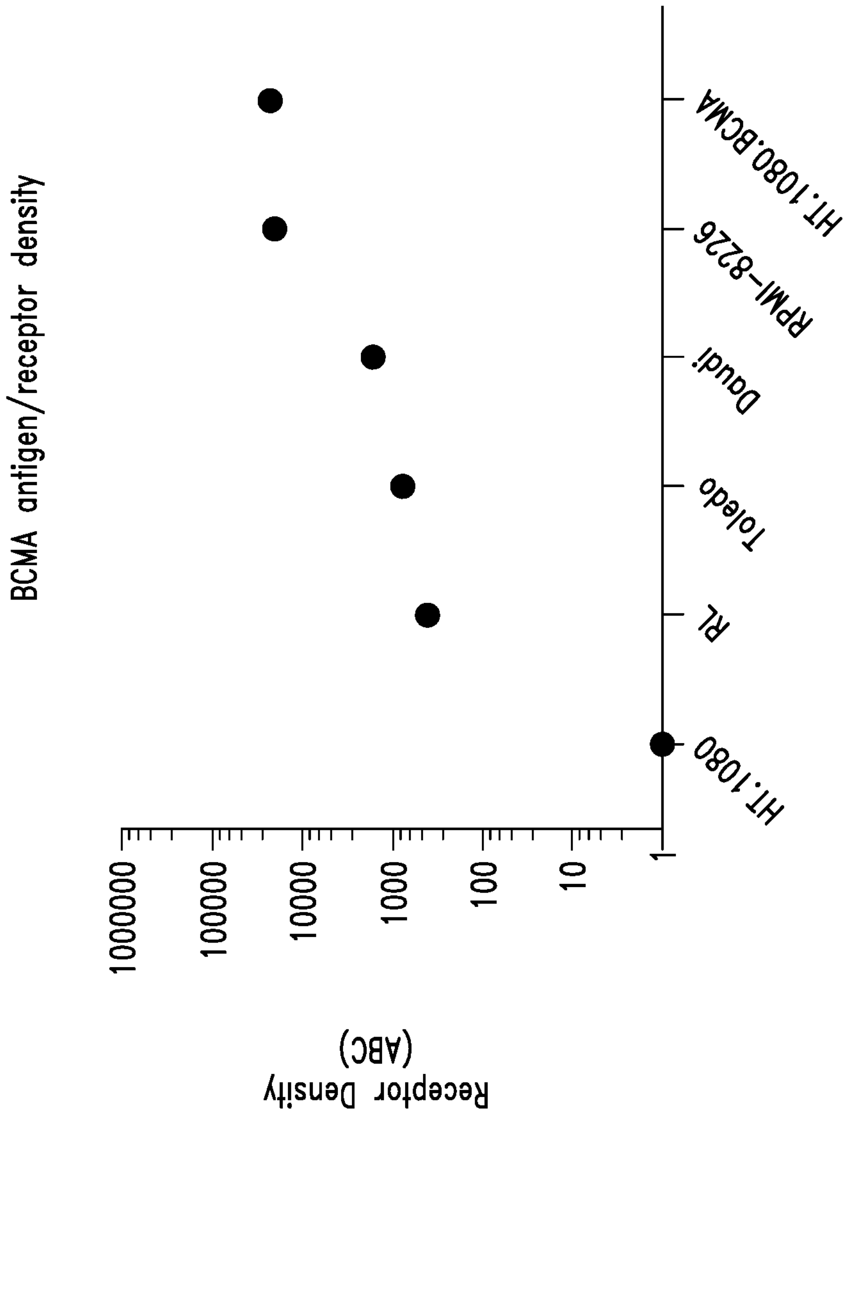

In another experiment, BCMA receptor density was assessed on a variety of cell lines, both endogenously expressing BCMA (e.g., RL, Toledo, Daudi, and RPMI-8226) and some engineered to express BCMA (e.g., HT.1080.BCMA). BCMA density was assessed using anti-BCMA antibody clone 19F2 (Biolegend) using the Quantum™ Simply Cellular® Assay (Bangs Laboratories, Inc). As shown in FIG. 6, the engineered cell line HT.1080.BCMA and multiple myeloma cell line RPMI-8226 expressed the highest amount of BCMA with an average of 20,000 receptors. Lymphoma lines Daudi, Toledo and RL express 10-50 fold less BCMA antigen than HT.1080.BCMA or RPMI-8226.

Example 6

Evaluation of Human Anti-BCMA Car T Cell Antigen-Dependent Proliferation

To assess the ability of anti-BCMA CAR T cells to proliferate in the presence of BCMA-expressing cancer cells, anti-BCMA CAR T cells were first produced using a system similar to the one described in Example 2. After 10 days in culture, an equal number of anti-BCMA expressing CAR T cells were cultured with an HT.1080 cell line expressing a nuclear red fluorescent protein (HT1080-nucRed) or a derivative line engineered to express BCMA (HT.1080-nucRed.BCMA) starting at 5E3 of each cell type per condition.

Figure 7B:
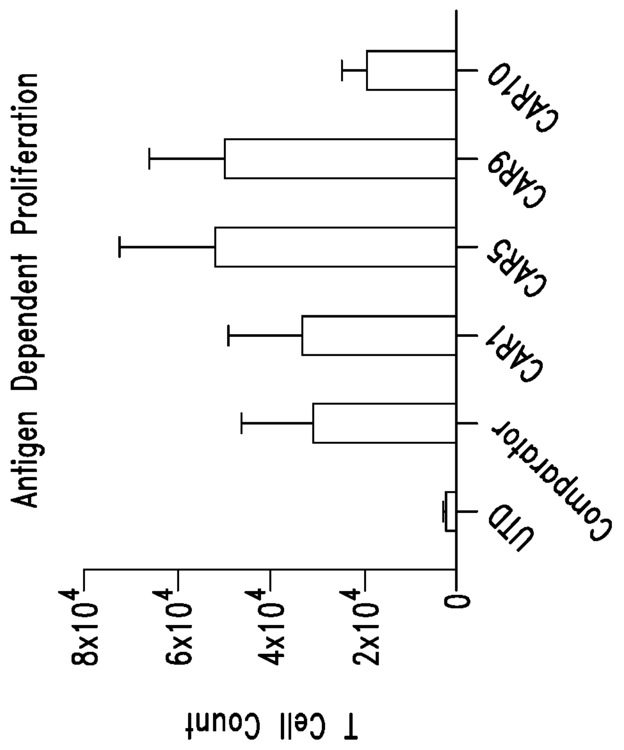
FIGS. 7A and 7B show proliferation of CAR T cells co-cultured with HT1080-nucRed cells which do not express BCMA (antigen independent proliferation.
Figure 7A:
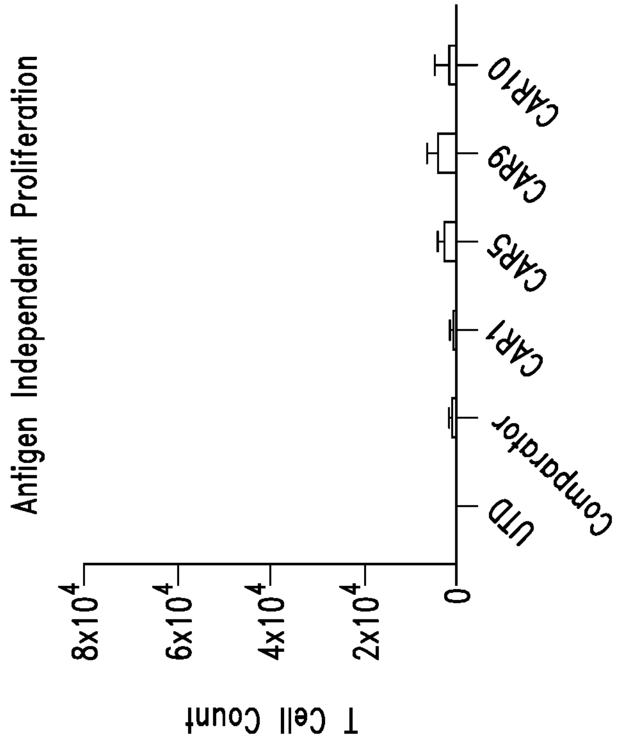

As show in FIG. 7A, minimal to no proliferation was observed against the HT.1080-nucRed cell line 6 days after CAR T cell addition. However, proliferation was observed in co-cultures with the BCMA expressing HT.1080-nucRed.BCMA cell line (FIG. 7B).

In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A chimeric antigen receptor (CAR) comprising:

a) an extracellular domain comprising an anti-BCMA (B cell maturation antigen) antibody or antigen binding fragment thereof that binds one or more epitopes of a human BCMA polypeptide comprising variable light chain CDRL1, CDRL2, and CDRL3 regions within a variable light chain amino acid sequence and variable heavy chain CDRH1, CDRH2, and CDRH3 regions within a variable heavy chain amino acid sequence as set forth in any one of:

SEQ ID NOs: 7 and 8, respectively;
SEQ ID NOs: 15 and 16, respectively;
SEQ ID NOs: 23 and 24, respectively;
SEQ ID NOs: 31 and 32, respectively;
SEQ ID NOs: 39 and 40, respectively; and
SEQ ID NOs: 47 and 48, respectively;

b) a transmembrane domain;

c) one or more intracellular signaling domains.

2. The CAR of claim 1, wherein the one or more intracellular signaling domains comprises an intracellular co-stimulatory signaling domain and a primary signaling domain.

3. The CAR of claim 1, wherein the anti-BCMA antibody or antigen binding fragment is an scFv.

4. The CAR of claim 1, wherein the anti-BCMA antibody or antigen binding fragment thereof comprises the variable light chain CDRL1, CDRL2, and CDRL3 regions as set forth in SEQ ID NOs: 1-3, and the variable heavy chain CDRH1, CDRH2, and CDRH3 regions as set forth in SEQ ID NOs: 4-6.

5. The CAR of claim 1, wherein the anti-BCMA antibody or antigen binding fragment thereof comprises the variable light chain CDRL1, CDRL2, and CDRL3 regions as set forth in SEQ ID NOs: 9-11, and the variable heavy chain CDRH1, CDRH2, and CDRH3 regions as set forth in SEQ ID NOs: 12-14.

6. The CAR of claim 1, wherein the anti-BCMA antibody or antigen binding fragment thereof comprises the variable light chain CDRL1, CDRL2, and CDRL3 regions as set forth in SEQ ID NOs: 17-19, and the variable heavy chain CDRH1, CDRH2, and CDRH3 regions as set forth in SEQ ID NOs: 20-22.

7. The CAR of claim 1, wherein the anti-BCMA antibody or antigen binding fragment thereof comprises the variable light chain CDRL1, CDRL2, and CDRL3 regions as set forth in SEQ ID NOs: 25-27, and the variable heavy chain CDRH1, CDRH2, and CDRH3 regions as set forth in SEQ ID NOs: 28-30.

8. The CAR of claim 1, wherein the anti-BCMA antibody or antigen binding fragment thereof comprises the variable light chain CDRL1, CDRL2, and CDRL3 regions as set forth in SEQ ID NOs: 33-35, and the variable heavy chain CDRH1, CDRH2, and CDRH3 regions as set forth in SEQ ID NOs: 36-38.

9. The CAR of claim 1, wherein the anti-BCMA antibody or antigen binding fragment thereof comprises the variable light chain CDRL1, CDRL2, and CDRL3 regions as set forth in SEQ ID NOs: 41-43, and the variable heavy chain CDRH1, CDRH2, and CDRH3 regions as set forth in SEQ ID NOs: 44-46.

10. The CAR of claim 1, wherein the anti-BCMA antibody or antigen binding fragment thereof comprises a variable light chain comprising an amino acid sequence having at least 85%, 90%, 95%, 96%, 97%, 98%, or 99% identity to a variable light chain amino acid sequence and a variable heavy chain comprising an amino acid sequence having at least 85%, 90%, 95%, 96%, 97%, 98%, or 99% identity to a variable heavy chain amino acid sequence as set forth in any one of:

SEQ ID NOs: 7 and 8, respectively;
SEQ ID NOs: 15 and 16, respectively;
SEQ ID NOs: 23 and 24, respectively;
SEQ ID NOs: 31 and 32, respectively;
SEQ ID NOs: 39 and 40, respectively; and
SEQ ID NOs: 47 and 48, respectively.

11. The CAR of claim 1, wherein the anti-BCMA antibody or antigen binding fragment thereof comprises a variable light chain sequence and a variable heavy chain sequence selected from the group consisting of:

a) a variable light chain sequence as set forth in SEQ ID NO: 7 and a variable heavy chain sequence as set forth in SEQ ID NO: 8,
b) a variable light chain sequence as set forth in SEQ ID NO: 15 and a variable heavy chain sequence as set forth in SEQ ID NO: 16,
c) a variable light chain sequence as set forth in SEQ ID NO: 23 and a variable heavy chain sequence as set forth in SEQ ID NO: 24,
d) a variable light chain sequence as set forth in SEQ ID NO: 31 and a variable heavy chain sequence as set forth in SEQ ID NO: 32,
e) a variable light chain sequence as set forth in SEQ ID NO: 39 and a variable heavy chain sequence as set forth in SEQ ID NO: 40; and
f) a variable light chain sequence as set forth in SEQ ID NO: 47 and a variable heavy chain sequence as set forth in SEQ ID NO: 48.

12. The CAR of claim 1, wherein the transmembrane domain is isolated from a polypeptide selected from the group consisting of: alpha or beta chain of the T-cell receptor, CDδ, CD3ε, CDγ, CD3ζ, CD4, CD5, CD8α, CD9, CD 16, CD22, CD27, CD28, CD33, CD37, CD45, CD64, CD80, CD86, CD 134, CD137, CD152, CD154, and PD1.

13. The CAR of claim 2, wherein the one or more co-stimulatory signaling domains are isolated from a co-stimulatory molecule selected from the group consisting of: TLR1, TLR2, TLR3, TLR4, TLR5, TLR6, TLR7, TLR8, TLR9, TLR10, CARD11, CD2, CD7, CD27, CD28, CD30, CD40, CD54 (ICAM), CD83, CD134 (OX40), CD137 (4-1BB), CD278 (ICOS), DAP10, LAT, NKD2C, SLP76, TRIM, and ZAP70.

14. The CAR of claim 2, wherein the primary signaling domain is isolated from a polypeptide selected from the group consisting of: FcRγ, FcRβ, CD3γ, CD3δ, CD3ε, CD3ζ, CD22, CD79a, CD79b, and CD66d.

15. The CAR of claim 1, further comprising a hinge region polypeptide and/or a signal peptide.

16. A polynucleotide encoding a CAR of claim 1.

17. A vector comprising the polynucleotide of claim 16.

18. The vector of claim 17, wherein the vector is a lentiviral vector.

19. A cell that expresses the CAR of claim 1.

20. The cell of claim 19, wherein the cell is selected from the group consisting of:

a) an immune effector cell,
b) a T-cell,
c) a cytotoxic T lymphocytes (CTLs),
d) a tumor infiltrating lymphocytes (TILs),
e) a natural killer (NK) cell or natural killer T (NKT) cell, and
f) a macrophage.

21. A composition comprising the cell of claim 20 and a physiologically acceptable excipient.

22. A method of treating a B cell related condition in a subject in need thereof, comprising administering to the subject a therapeutically effect amount of the composition of claim 21.

23. The method of claim 22, wherein the B cell related condition is a cancer or autoimmune disease.

24. The method of claim 23, wherein the B cell related condition is multiple myeloma (MM) or non-Hodgkin's lymphoma (NHL).

* * * * *

SEQUENCE LISTING

```
<160> NUMBER OF SEQ ID NOS: 111

<210> SEQ ID NO 1
<211> LENGTH: 12
<212> TYPE: PRT
<213> ORGANISM: Artificial Sequence
<220> FEATURE:
<223> OTHER INFORMATION: Made in Lab - light chain CDR1

<400> SEQUENCE: 1

Gly Ala Ser Gln Ser Val Thr Ser Ser Tyr Leu Ala
1               5                   10


<210> SEQ ID NO 2
<211> LENGTH: 7
<212> TYPE: PRT
<213> ORGANISM: Artificial Sequence
<220> FEATURE:
<223> OTHER INFORMATION: Made in Lab - light chain CDR2

<400> SEQUENCE: 2

Asp Ala Ser Gly Arg Ala Thr
1               5


<210> SEQ ID NO 3
<211> LENGTH: 9
<212> TYPE: PRT
<213> ORGANISM: Artificial Sequence
```

<220> FEATURE:
<223> OTHER INFORMATION: Made in Lab - light chain CDR3

<400> SEQUENCE: 3

Gln Gln Tyr Gly Ser Ser Pro Phe Thr
1 5

<210> SEQ ID NO 4
<211> LENGTH: 12
<212> TYPE: PRT
<213> ORGANISM: Artificial Sequence
<220> FEATURE:
<223> OTHER INFORMATION: Made in Lab - heavy chain CDR1

<400> SEQUENCE: 4

Gly Gly Ser Ile Ser Ser Ser Arg Tyr Tyr Trp Asp
1 5 10

<210> SEQ ID NO 5
<211> LENGTH: 9
<212> TYPE: PRT
<213> ORGANISM: Artificial Sequence
<220> FEATURE:
<223> OTHER INFORMATION: Made in Lab - heavy chain CDR2

<400> SEQUENCE: 5

Ser Leu Tyr Tyr Ser Gly Asn Thr Tyr
1 5

<210> SEQ ID NO 6
<211> LENGTH: 9
<212> TYPE: PRT
<213> ORGANISM: Artificial Sequence
<220> FEATURE:
<223> OTHER INFORMATION: Made in Lab - heavy chain CDR3

<400> SEQUENCE: 6

Gln Gly Ala Thr His Ala Leu Asp Leu
1 5

<210> SEQ ID NO 7
<211> LENGTH: 108
<212> TYPE: PRT
<213> ORGANISM: Artificial Sequence
<220> FEATURE:
<223> OTHER INFORMATION: Made in Lab - variable light chain sequence

<400> SEQUENCE: 7

Glu Ile Val Leu Thr Gln Ser Pro Ala Thr Leu Ser Leu Ser Pro Gly
1 5 10 15

Glu Arg Ala Thr Leu Ser Cys Gly Ala Ser Gln Ser Val Thr Ser Ser
20 25 30

Tyr Leu Ala Trp Tyr Gln Gln Lys Pro Gly Leu Ala Pro Arg Leu Leu
35 40 45

Ile Tyr Asp Ala Ser Gly Arg Ala Thr Gly Ile Pro Asp Arg Phe Ser
50 55 60

Gly Ser Gly Ser Gly Thr Asp Phe Ser Leu Thr Ile Ser Arg Leu Glu
65 70 75 80

Pro Glu Asp Phe Ala Val Tyr Tyr Cys Gln Gln Tyr Gly Ser Ser Pro
85 90 95

Phe Thr Phe Gly Pro Gly Thr Lys Val Asp Ile Lys
100 105

<210> SEQ ID NO 8
<211> LENGTH: 119
<212> TYPE: PRT
<213> ORGANISM: Artificial Sequene
<220> FEATURE:
<223> OTHER INFORMATION: Made in Lab - variable heavy chain sequence

<400> SEQUENCE: 8

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Arg Tyr Tyr Trp Asp Trp Ile Arg Gln Pro Pro Gly Lys Gly Leu Glu
        35                  40                  45

Trp Ile Gly Ser Leu Tyr Tyr Ser Gly Asn Thr Tyr Tyr Lys Pro Ser
    50                  55                  60

Leu Lys Ser Arg Val Thr Ile Ser Val Asp Thr Ser Lys Asn Gln Phe
65                  70                  75                  80

Ser Leu Lys Leu Thr Ser Val Thr Ala Ala Asp Thr Ala Val Tyr Tyr
                85                  90                  95

Cys Ala Arg Gln Gly Ala Thr His Ala Leu Asp Leu Trp Gly Pro Gly
            100                 105                 110

Thr Met Val Thr Val Ser Ser
        115

<210> SEQ ID NO 9
<211> LENGTH: 11
<212> TYPE: PRT
<213> ORGANISM: Artificial Sequence
<220> FEATURE:
<223> OTHER INFORMATION: Made in Lab - light chain CDR1

<400> SEQUENCE: 9

Arg Ala Ser Gln Asp Ile Ser Ser Phe Leu Ala
1               5                   10

<210> SEQ ID NO 10
<211> LENGTH: 7
<212> TYPE: PRT
<213> ORGANISM: Artificial Sequence
<220> FEATURE:
<223> OTHER INFORMATION: Made in Lab - light chain CDR2

<400> SEQUENCE: 10

Ala Ala Ser Thr Leu Gln Ser
1               5

<210> SEQ ID NO 11
<211> LENGTH: 9
<212> TYPE: PRT
<213> ORGANISM: Artificial Sequence
<220> FEATURE:
<223> OTHER INFORMATION: Made in Lab - light chain CDR3

<400> SEQUENCE: 11

Gln Gln Phe Asn Ser Tyr Pro Arg Thr
1               5

<210> SEQ ID NO 12
<211> LENGTH: 10
<212> TYPE: PRT
<213> ORGANISM: Artificial Sequence
<220> FEATURE:
<223> OTHER INFORMATION: Made in Lab - heavy chain CDR1

<400> SEQUENCE: 12

Gly Tyr Thr Phe Ser Asn Asn Gly Phe Ser
1 5 10

<210> SEQ ID NO 13
<211> LENGTH: 10
<212> TYPE: PRT
<213> ORGANISM: Artificial Sequence
<220> FEATURE:
<223> OTHER INFORMATION: Made in Lab - heavy chain CDR2

<400> SEQUENCE: 13

Trp Ile Ser Gly Phe Asn Gly Lys Thr Tyr
1 5 10

<210> SEQ ID NO 14
<211> LENGTH: 13
<212> TYPE: PRT
<213> ORGANISM: Artificial Sequence
<220> FEATURE:
<223> OTHER INFORMATION: Made in Lab - heavy chain CDR3

<400> SEQUENCE: 14

Gly Leu Leu Leu Ser Gly Glu Leu Trp Gly Phe Asp Tyr
1 5 10

<210> SEQ ID NO 15
<211> LENGTH: 107
<212> TYPE: PRT
<213> ORGANISM: Artificial Sequence
<220> FEATURE:
<223> OTHER INFORMATION: Made in Lab - variable light chain sequence

<400> SEQUENCE: 15

Asp Ile Gln Leu Thr Gln Ser Pro Ser Phe Leu Ser Ala Ser Val Gly
1 5 10 15

Asp Arg Val Thr Ile Thr Cys Arg Ala Ser Gln Asp Ile Ser Ser Phe
20 25 30

Leu Ala Trp Tyr Gln Gln Lys Pro Gly Lys Ala Pro Lys Leu Leu Ile
35 40 45

Phe Ala Ala Ser Thr Leu Gln Ser Gly Val Pro Ser Arg Ile Ser Gly
50 55 60

Ser Gly Ser Gly Thr Glu Phe Thr Leu Thr Ile Ser Ser Leu Gln Pro
65 70 75 80

Glu Asp Phe Ala Thr Tyr Tyr Cys Gln Gln Phe Asn Ser Tyr Pro Arg
85 90 95

Thr Phe Gly Gln Gly Thr Lys Val Glu Ile Lys
100 105

<210> SEQ ID NO 16
<211> LENGTH: 122
<212> TYPE: PRT
<213> ORGANISM: Artificial Sequene
<220> FEATURE:
<223> OTHER INFORMATION: Made in Lab - variable heavy chain sequence

<400> SEQUENCE: 16

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Ser Asn Asn
20 25 30

```
Gly Phe Ser Trp Val Arg Gln Ala Pro Gly Gln Gly Leu Glu Trp Met
        35                  40                  45

Gly Trp Ile Ser Gly Phe Asn Gly Lys Thr Tyr Tyr Thr Lys Thr Leu
    50                  55                  60

Gln Gly Arg Val Thr Met Thr Ile Asp Thr Ser Thr Ser Thr Ala Tyr
65                  70                  75                  80

Met Asp Leu Arg Ser Leu Arg Ser Asp Asp Thr Ala Val Tyr Tyr Cys
                85                  90                  95

Ala Arg Gly Leu Leu Leu Ser Gly Glu Leu Trp Gly Phe Asp Tyr Trp
            100                 105                 110

Gly Gln Gly Thr Leu Val Thr Val Ser Ser
        115                 120


<210> SEQ ID NO 17
<211> LENGTH: 11
<212> TYPE: PRT
<213> ORGANISM: Artificial Sequence
<220> FEATURE:
<223> OTHER INFORMATION: Made in Lab - light chain CDR1

<400> SEQUENCE: 17

Arg Ala Ser Gln Asp Ile Arg Asn Tyr Leu Gly
1               5                   10


<210> SEQ ID NO 18
<211> LENGTH: 7
<212> TYPE: PRT
<213> ORGANISM: Artificial Sequence
<220> FEATURE:
<223> OTHER INFORMATION: Made in Lab - light chain CDR2

<400> SEQUENCE: 18

Ala Ala Ser Ser Leu Gln Ser
1               5


<210> SEQ ID NO 19
<211> LENGTH: 9
<212> TYPE: PRT
<213> ORGANISM: Artificial Sequence
<220> FEATURE:
<223> OTHER INFORMATION: Made in Lab - light chain CDR3

<400> SEQUENCE: 19

Leu Gln Asp Tyr Ile Tyr Pro Trp Thr
1               5


<210> SEQ ID NO 20
<211> LENGTH: 10
<212> TYPE: PRT
<213> ORGANISM: Artificial Sequence
<220> FEATURE:
<223> OTHER INFORMATION: Made in Lab - heavy chain CDR1

<400> SEQUENCE: 20

Gly Phe Thr Phe Ser Ser Tyr Gly Met His
1               5                   10


<210> SEQ ID NO 21
<211> LENGTH: 10
<212> TYPE: PRT
<213> ORGANISM: Artificial Sequence
<220> FEATURE:
<223> OTHER INFORMATION: Made in Lab - heavy chain CDR2

<400> SEQUENCE: 21
```

```
Val Ile Ser Tyr Asp Gly Arg Asn Lys Asn
1               5                   10


<210> SEQ ID NO 22
<211> LENGTH: 16
<212> TYPE: PRT
<213> ORGANISM: Artificial Sequence
<220> FEATURE:
<223> OTHER INFORMATION: Made in Lab - heavy chain CDR3

<400> SEQUENCE: 22

Glu Gly Glu Ala Thr Tyr Tyr Asp Ile Leu Thr Gly Pro Phe Asp Tyr
1               5                   10                  15


<210> SEQ ID NO 23
<211> LENGTH: 107
<212> TYPE: PRT
<213> ORGANISM: Artificial Sequence
<220> FEATURE:
<223> OTHER INFORMATION: Made in Lab - variable light chain sequence

<400> SEQUENCE: 23

Asp Ile Gln Met Thr Gln Ser Pro Ser Ser Leu Ser Ala Ser Val Gly
1               5                   10                  15

Asp Arg Ile Thr Ile Thr Cys Arg Ala Ser Gln Asp Ile Arg Asn Tyr
            20                  25                  30

Leu Gly Trp Tyr Gln Gln Lys Pro Gly Lys Ala Pro Lys Val Leu Ile
        35                  40                  45

Phe Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Tyr Ile Tyr Pro Trp
                85                  90                  95

Thr Phe Ala Gln Gly Thr Lys Val Glu Ile Lys
            100                 105


<210> SEQ ID NO 24
<211> LENGTH: 125
<212> TYPE: PRT
<213> ORGANISM: Artificial Sequene
<220> FEATURE:
<223> OTHER INFORMATION: Made in Lab - variable heavy chain sequence

<400> SEQUENCE: 24

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Arg Asn Lys Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Glu Ala Thr Tyr Tyr Asp Ile Leu Thr Gly Pro Phe
            100                 105                 110
```

```
Asp Tyr Trp Gly Gln Gly Thr Leu Val Thr Val Ser Ser
        115                 120                 125


<210> SEQ ID NO 25
<211> LENGTH: 11
<212> TYPE: PRT
<213> ORGANISM: Artificial Sequence
<220> FEATURE:
<223> OTHER INFORMATION: Made in Lab - light chain CDR1

<400> SEQUENCE: 25

Arg Ala Ser Gln Gly Ile Ser Ser Tyr Leu Ala
1               5                   10


<210> SEQ ID NO 26
<211> LENGTH: 7
<212> TYPE: PRT
<213> ORGANISM: Artificial Sequence
<220> FEATURE:
<223> OTHER INFORMATION: Made in Lab - light chain CDR2

<400> SEQUENCE: 26

Val Ala Ser Thr Leu Gln Ser
1               5


<210> SEQ ID NO 27
<211> LENGTH: 9
<212> TYPE: PRT
<213> ORGANISM: Artificial Sequence
<220> FEATURE:
<223> OTHER INFORMATION: Made in Lab - light chain CDR3

<400> SEQUENCE: 27

Gln Gln Leu Tyr Ser Tyr Pro Arg Ala
1               5


<210> SEQ ID NO 28
<211> LENGTH: 10
<212> TYPE: PRT
<213> ORGANISM: Artificial Sequence
<220> FEATURE:
<223> OTHER INFORMATION: Made in Lab - heavy chain CDR1

<400> SEQUENCE: 28

Gly Phe Thr Phe Ser Ser Tyr Gly Met His
1               5                   10


<210> SEQ ID NO 29
<211> LENGTH: 10
<212> TYPE: PRT
<213> ORGANISM: Artificial Sequence
<220> FEATURE:
<223> OTHER INFORMATION: Made in Lab - heavy chain CDR2

<400> SEQUENCE: 29

Val Ile Ser Tyr Asp Gly Arg Asn Lys Asn
1               5                   10


<210> SEQ ID NO 30
<211> LENGTH: 16
<212> TYPE: PRT
<213> ORGANISM: Artificial Sequence
<220> FEATURE:
<223> OTHER INFORMATION: Made in Lab - heavy chain CDR3

<400> SEQUENCE: 30

Glu Gly Glu Ala Thr Tyr Tyr Asp Ile Leu Thr Gly Pro Phe Asp Tyr
```

```
1               5                   10                  15


<210> SEQ ID NO 31
<211> LENGTH: 107
<212> TYPE: PRT
<213> ORGANISM: Artificial Sequence
<220> FEATURE:
<223> OTHER INFORMATION: Made in Lab - variable light chain sequence

<400> SEQUENCE: 31

Asp Ile Gln Leu Thr Gln Ser Pro Ser Phe Leu Ser Ala Ser Val Gly
1               5                   10                  15

Asp Arg Val Ser Ile Thr Cys Arg Ala Ser Gln Gly Ile Ser Ser Tyr
            20                  25                  30

Leu Ala Trp Tyr Gln Gln Lys Pro Gly Lys Ala Pro Lys Val Leu Ile
        35                  40                  45

Tyr Val Ala Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Leu Tyr Ser Tyr Pro Arg
                85                  90                  95

Ala Phe Gly Gln Gly Thr Lys Val Glu Ile Lys
            100                 105


<210> SEQ ID NO 32
<211> LENGTH: 125
<212> TYPE: PRT
<213> ORGANISM: Artificial Sequene
<220> FEATURE:
<223> OTHER INFORMATION: Made in Lab - variable heavy chain sequence

<400> SEQUENCE: 32

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Arg Asn Lys Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Glu Ala Thr Tyr Tyr Asp Ile Leu Thr Gly Pro Phe
            100                 105                 110

Asp Tyr Trp Gly Gln Gly Thr Leu Val Thr Val Ser Ser
        115                 120                 125


<210> SEQ ID NO 33
<211> LENGTH: 16
<212> TYPE: PRT
<213> ORGANISM: Artificial Sequence
<220> FEATURE:
<223> OTHER INFORMATION: Made in Lab - light chain CDR1

<400> SEQUENCE: 33

Lys Ser Ser Gln Ser Leu Leu Tyr Ser Asp Gly Lys Thr Phe Leu Tyr
1               5                   10                  15
```

<210> SEQ ID NO 34
<211> LENGTH: 7
<212> TYPE: PRT
<213> ORGANISM: Artificial Sequence
<220> FEATURE:
<223> OTHER INFORMATION: Made in Lab - light chain CDR2

<400> SEQUENCE: 34

Glu Gly Ser Asn Arg Phe Ser
1               5

<210> SEQ ID NO 35
<211> LENGTH: 9
<212> TYPE: PRT
<213> ORGANISM: Artificial Sequence
<220> FEATURE:
<223> OTHER INFORMATION: Made in Lab - light chain CDR3

<400> SEQUENCE: 35

Met Gln Ser Ile Gln Leu Pro Asn Thr
1               5

<210> SEQ ID NO 36
<211> LENGTH: 10
<212> TYPE: PRT
<213> ORGANISM: Artificial Sequence
<220> FEATURE:
<223> OTHER INFORMATION: Made in Lab - heavy chain CDR1

<400> SEQUENCE: 36

Gly Tyr Thr Phe Ser Thr Tyr Gly Ile Gly
1               5                   10

<210> SEQ ID NO 37
<211> LENGTH: 10
<212> TYPE: PRT
<213> ORGANISM: Artificial Sequence
<220> FEATURE:
<223> OTHER INFORMATION: Made in Lab - heavy chain CDR2

<400> SEQUENCE: 37

Trp Ile Ser Ala Tyr Ser Gly Lys Thr Asn
1               5                   10

<210> SEQ ID NO 38
<211> LENGTH: 14
<212> TYPE: PRT
<213> ORGANISM: Artificial Sequence
<220> FEATURE:
<223> OTHER INFORMATION: Made in Lab - heavy chain CDR3

<400> SEQUENCE: 38

Asp Asp Gly Ala Gly Thr Asp Tyr Tyr Tyr Gly Met Asp Val
1               5                   10

<210> SEQ ID NO 39
<211> LENGTH: 112
<212> TYPE: PRT
<213> ORGANISM: Artificial Sequence
<220> FEATURE:
<223> OTHER INFORMATION: Made in Lab - variable light chain sequence

<400> SEQUENCE: 39

Asp Ile Val Met Thr Gln Thr Pro Leu Ser Leu Ser Val Thr Pro Gly
1               5                   10                  15

```
Gln Pro Ala Ser Ile Ser Cys Lys Ser Ser Gln Ser Leu Leu Tyr Ser
            20                  25                  30

Asp Gly Lys Thr Phe Leu Tyr Trp Tyr Leu Gln Lys Pro Gly Gln Pro
        35                  40                  45

Pro Gln Leu Leu Ile Tyr Glu Gly Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Phe Tyr Cys Met Gln Ser
                85                  90                  95

Ile Gln Leu Pro Asn Thr Phe Gly Gln Gly Thr Lys Leu Glu Ile Lys
            100                 105                 110


<210> SEQ ID NO 40
<211> LENGTH: 122
<212> TYPE: PRT
<213> ORGANISM: Artificial Sequene
<220> FEATURE:
<223> OTHER INFORMATION: Made in Lab - variable heavy chain sequence

<400> SEQUENCE: 40

Gln Val Gln Leu Val Gln Ser Gly Ala Glu Val Lys Lys Pro Gly Ala
1               5                   10                  15

Ser Val Lys Val Ser Cys Lys Gly Ser Gly Tyr Thr Phe Ser Thr Tyr
            20                  25                  30

Gly Ile Gly Trp Val Arg Gln Ala Pro Gly Gln Gly Leu Glu Trp Leu
        35                  40                  45

Ala Trp Ile Ser Ala Tyr Ser Gly Lys Thr Asn Tyr Ala Gln Lys Val
    50                  55                  60

Gln Gly Arg Val Thr Leu Thr Thr Asp Thr Ser Thr Asn Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Asp Gly Ala Gly Thr Asp Tyr Tyr Tyr Gly Met Asp Val
            100                 105                 110

Trp Gly Gln Gly Thr Thr Val Thr Val Ser
        115                 120


<210> SEQ ID NO 41
<211> LENGTH: 11
<212> TYPE: PRT
<213> ORGANISM: Artificial Sequence
<220> FEATURE:
<223> OTHER INFORMATION: Made in Lab - light chain CDR1

<400> SEQUENCE: 41

Arg Ala Ser Gln Asp Ile Ser Ser Phe Leu Ala
1               5                   10


<210> SEQ ID NO 42
<211> LENGTH: 7
<212> TYPE: PRT
<213> ORGANISM: Artificial Sequence
<220> FEATURE:
<223> OTHER INFORMATION: Made in Lab - light chain CDR2

<400> SEQUENCE: 42

Ala Ala Ser Thr Leu Gln Ser
1               5
```

<210> SEQ ID NO 43
<211> LENGTH: 9
<212> TYPE: PRT
<213> ORGANISM: Artificial Sequence
<220> FEATURE:
<223> OTHER INFORMATION: Made in Lab - light chain CDR3

<400> SEQUENCE: 43

Gln Gln Phe Asn Ser Tyr Pro Arg Thr
1 5

<210> SEQ ID NO 44
<211> LENGTH: 10
<212> TYPE: PRT
<213> ORGANISM: Artificial Sequence
<220> FEATURE:
<223> OTHER INFORMATION: Made in Lab - heavy chain CDR1

<400> SEQUENCE: 44

Gly Tyr Thr Phe Ser Asn Asn Gly Phe Ser
1 5 10

<210> SEQ ID NO 45
<211> LENGTH: 10
<212> TYPE: PRT
<213> ORGANISM: Artificial Sequence
<220> FEATURE:
<223> OTHER INFORMATION: Made in Lab - heavy chain CDR2

<400> SEQUENCE: 45

Trp Ile Ser Gly Phe Asn Gly Lys Thr Tyr
1 5 10

<210> SEQ ID NO 46
<211> LENGTH: 13
<212> TYPE: PRT
<213> ORGANISM: Artificial Sequence
<220> FEATURE:
<223> OTHER INFORMATION: Made in Lab - heavy chain CDR3

<400> SEQUENCE: 46

Gly Leu Leu Leu Ser Gly Glu Leu Trp Gly Phe Asp Tyr
1 5 10

<210> SEQ ID NO 47
<211> LENGTH: 107
<212> TYPE: PRT
<213> ORGANISM: Artificial Sequence
<220> FEATURE:
<223> OTHER INFORMATION: Made in Lab - variable light chain sequence

<400> SEQUENCE: 47

Asp Ile Gln Leu Ala Gln Ser Pro Ser Phe Leu Ser Ala Ser Val Gly
1 5 10 15

Asp Arg Val Thr Ile Thr Cys Arg Ala Ser Gln Asp Ile Ser Ser Phe
20 25 30

Leu Ala Trp Tyr Gln Gln Lys Pro Gly Lys Ala Pro Lys Leu Leu Ile
35 40 45

Phe Ala Ala Ser Thr Leu Gln Ser Gly Val Pro Ser Arg Ile Ser Gly
50 55 60

Ser Gly Ser Gly Thr Glu Phe Thr Leu Thr Ile Ser Ser Leu Gln Pro
65 70 75 80

Glu Asp Phe Ala Thr Tyr Tyr Cys Gln Gln Phe Asn Ser Tyr Pro Arg
85 90 95

```
Thr Phe Gly Gln Gly Thr Lys Val Glu Ile Lys
            100                 105


<210> SEQ ID NO 48
<211> LENGTH: 122
<212> TYPE: PRT
<213> ORGANISM: Artificial Sequene
<220> FEATURE:
<223> OTHER INFORMATION: Made in Lab - variable heavy chain sequence

<400> SEQUENCE: 48

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Asn Asn
            20                  25                  30

Gly Phe Ser Trp Val Arg Gln Ala Pro Gly Gln Gly Leu Glu Trp Met
        35                  40                  45

Gly Trp Ile Ser Gly Phe Asn Gly Lys Thr Tyr Tyr Thr Lys Thr Leu
    50                  55                  60

Gln Gly Arg Val Thr Met Thr Ile Asp Thr Ser Thr Ser Thr Ala Tyr
65                  70                  75                  80

Met Asp Leu Arg Ser Leu Arg Ser Asp Asp Thr Ala Val Tyr Tyr Cys
                85                  90                  95

Ala Arg Gly Leu Leu Leu Ser Gly Glu Leu Trp Gly Phe Asp Tyr Trp
            100                 105                 110

Gly Gln Gly Thr Leu Val Thr Val Ser Ser
        115                 120


<210> SEQ ID NO 49
<211> LENGTH: 1461
<212> TYPE: DNA
<213> ORGANISM: Artificial Sequence
<220> FEATURE:
<223> OTHER INFORMATION: Made in Lab - polynucleotide of anti-BCMA CAR1
      construct

<400> SEQUENCE: 49

atggccctgc ctgtgaccgc ccttctcctg ccccttgctc tgctcctcca tgccgccagg      60

cctcaactgc agctgcagga gagtggcccc ggcttggtga agcctagtga aacactcagc     120

cttacgtgca ctgtttctgg gggcagtata tcctccagcc gctattactg ggattggatc     180

cggcagccgc ccgggaaggg acttgaatgg attggaagcc tctactactc cggaaatact     240

tactataaac catccctgaa gagtagagtt acaattagcg tagacaccag caagaatcaa     300

ttttctctta aactgacatc agtgactgcc gcagatactg ctgtgtacta ctgtgcacgg     360

cagggagcta ctcacgccct ggacctctgg ggacctggta ctatggtcac ggtctcttct     420

ggaggaggag ggtcaggcgg aggaggttcc gggggcggag ggtccgaaat tgttcttacg     480

cagtcacccg ccacactttc tctgtccccg ggggaacggg ctactctgtc ctgtggggct     540

tcccaatccg tgaccagctc ctaccttgcc tggtatcaac agaaacctgg tctcgcccca     600

cggctgctta tctacgatgc atctggcaga gctaccggta taccagacag gttttctggt     660

tccggtagcg gaaccgattt tagtctgact atctcacggc tggagcccga ggatttcgcg     720

gtgtattact gtcagcagta cgggagcagt ccatttacct ttggacctgg cacgaaggtg     780

gatataaaga ccacaacacc tgctccaagg ccccccacac ccgctccaac tatagccagc     840

caaccattga gcctcagacc tgaagcttgc aggcccgcag caggaggcgc cgtccatacg     900

cgaggcctgg acttcgcgtg tgatatttat atttgggccc ctttggccgg aacatgtggg     960
```

```
gtgttgcttc tctcccttgt gatcactctg tattgtaagc gcgggagaaa gaagctcctg   1020

tacatcttca agcagccttt tatgcgacct gtgcaaacca ctcaggaaga agatgggtgt   1080

tcatgccgct tccccgagga ggaagaagga gggtgtgaac tgagggtgaa attttctaga   1140

agcgccgatg ctcccgcata tcagcagggt cagaatcagc tctacaatga attgaatctc   1200

ggcaggcgag aagagtacga tgttctggac aagagacggg gcagggatcc cgagatgggg   1260

ggaaagcccc ggagaaaaaa tcctcaggag gggttgtaca atgagctgca gaaggacaag   1320

atggctgaag cctatagcga gatcggaatg aaaggcgaaa gacgcagagg caaggggcat   1380

gacggtctgt accagggtct ctctacagcc accaaggaca cttatgatgc gttgcatatg   1440

caagccttgc caccccgcta a                                             1461
```

```
<210> SEQ ID NO 50
<211> LENGTH: 486
<212> TYPE: PRT
<213> ORGANISM: Artificial Sequence
<220> FEATURE:
<223> OTHER INFORMATION: Made in Lab - polypeptide of anti-BCMA CAR1
      construct

<400> SEQUENCE: 50

Met Ala Leu Pro Val Thr Ala Leu Leu Leu Pro Leu Ala Leu Leu Leu
1               5                   10                  15

His Ala Ala Arg Pro Gln Leu Gln Leu Gln Glu Ser Gly Pro Gly Leu
            20                  25                  30

Val Lys Pro Ser Glu Thr Leu Ser Leu Thr Cys Thr Val Ser Gly Gly
        35                  40                  45

Ser Ile Ser Ser Ser Arg Tyr Tyr Trp Asp Trp Ile Arg Gln Pro Pro
    50                  55                  60

Gly Lys Gly Leu Glu Trp Ile Gly Ser Leu Tyr Tyr Ser Gly Asn Thr
65                  70                  75                  80

Tyr Tyr Lys Pro Ser Leu Lys Ser Arg Val Thr Ile Ser Val Asp Thr
                85                  90                  95

Ser Lys Asn Gln Phe Ser Leu Lys Leu Thr Ser Val Thr Ala Ala Asp
            100                 105                 110

Thr Ala Val Tyr Tyr Cys Ala Arg Gln Gly Ala Thr His Ala Leu Asp
        115                 120                 125

Leu Trp Gly Pro Gly Thr Met Val Thr Val Ser Ser Gly Gly Gly Gly
    130                 135                 140

Ser Gly Gly Gly Gly Ser Gly Gly Gly Gly Ser Glu Ile Val Leu Thr
145                 150                 155                 160

Gln Ser Pro Ala Thr Leu Ser Leu Ser Pro Gly Glu Arg Ala Thr Leu
                165                 170                 175

Ser Cys Gly Ala Ser Gln Ser Val Thr Ser Ser Tyr Leu Ala Trp Tyr
            180                 185                 190

Gln Gln Lys Pro Gly Leu Ala Pro Arg Leu Leu Ile Tyr Asp Ala Ser
        195                 200                 205

Gly Arg Ala Thr Gly Ile Pro Asp Arg Phe Ser Gly Ser Gly Ser Gly
    210                 215                 220

Thr Asp Phe Ser Leu Thr Ile Ser Arg Leu Glu Pro Glu Asp Phe Ala
225                 230                 235                 240

Val Tyr Tyr Cys Gln Gln Tyr Gly Ser Ser Pro Phe Thr Phe Gly Pro
                245                 250                 255

Gly Thr Lys Val Asp Ile Lys Thr Thr Thr Pro Ala Pro Arg Pro Pro
```

```
            260                 265                 270

Thr Pro Ala Pro Thr Ile Ala Ser Gln Pro Leu Ser Leu Arg Pro Glu
        275                 280                 285

Ala Cys Arg Pro Ala Ala Gly Gly Ala Val His Thr Arg Gly Leu Asp
    290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Lys Arg Gly Arg
                325                 330                 335

Lys Lys Leu Leu Tyr Ile Phe Lys Gln Pro Phe Met Arg Pro Val Gln
            340                 345                 350

Thr Thr Gln Glu Glu Asp Gly Cys Ser Cys Arg Phe Pro Glu Glu Glu
        355                 360                 365

Glu Gly Gly Cys Glu Leu Arg Val Lys Phe Ser Arg Ser Ala Asp Ala
    370                 375                 380

Pro Ala Tyr Gln Gln Gly Gln Asn Gln Leu Tyr Asn Glu Leu Asn Leu
385                 390                 395                 400

Gly Arg Arg Glu Glu Tyr Asp Val Leu Asp Lys Arg Arg Gly Arg Asp
                405                 410                 415

Pro Glu Met Gly Gly Lys Pro Arg Arg Lys Asn Pro Gln Glu Gly Leu
            420                 425                 430

Tyr Asn Glu Leu Gln Lys Asp Lys Met Ala Glu Ala Tyr Ser Glu Ile
        435                 440                 445

Gly Met Lys Gly Glu Arg Arg Arg Gly Lys Gly His Asp Gly Leu Tyr
    450                 455                 460

Gln Gly Leu Ser Thr Ala Thr Lys Asp Thr Tyr Asp Ala Leu His Met
465                 470                 475                 480

Gln Ala Leu Pro Pro Arg
                485
```

<210> SEQ ID NO 51
<211> LENGTH: 1467
<212> TYPE: DNA
<213> ORGANISM: Artificial Sequence
<220> FEATURE:
<223> OTHER INFORMATION: Made in Lab - polynucleotide of anti-BCMA CAR2 construct

<400> SEQUENCE: 51

```
atggcgcttc ccgttaccgc tctcctcctg cccctggccc tgctgctgca cgcagcccgc     60

ccacaggtcc agctcgttca gtctggagcc gaagtaaaga agcccggggc atcagtaaag    120

gtctcttgta aggctagcgg gtacacattt agtaacaatg gcttctcttg ggtgaggcag    180

gctcccggac agggcctgga gtggatgggg tggatcagcg ggttcaacgg gaaaacatat    240

tacaccaaaa cactgcaggg acgggtcact atgacaatcg acacatccac cagcacagcc    300

tacatggacc ttagatcctt gagatcagat gataccgccg tgtactactg cgcaagagga    360

ctcctcttga gtggagaact ttggggattc gattattggg gacagggcac cctcgtgact    420

gtttcaagcg gtggaggcgg cagcggcggg ggcggatctg gaggaggagg aagtgacatt    480

cagctcacac agtcccctag cttcctctct gcatcagtgg gcgaccgcgt tactattacc    540

tgcagggcca gccaggatat ttctagcttc cttgcctggt atcaacagaa gccagggaaa    600

gcacctaaac ttctgatttt cgctgcatcc accctgcaat caggagtccc atctcgaata    660

agcggctccg gatcaggaac agagtttacg ctcacaataa gtagtctgca gcccgaggac    720
```

```
ttcgctacct attactgcca gcagttcaat agctatcccc gcaccttcgg gcagggtacg    780

aaggtcgaga ttaagaccac aacacctgct ccaaggcccc ccacacccgc tccaactata    840

gccagccaac cattgagcct cagacctgaa gcttgcaggc ccgcagcagg aggcgccgtc    900

catacgcgag gcctggactt cgcgtgtgat atttatattt gggcccettt ggccggaaca    960

tgtggggtgt tgcttctctc ccttgtgatc actctgtatt gtaagcgcgg gagaaagaag   1020

ctcctgtaca tcttcaagca gccttttatg cgacctgtgc aaaccactca ggaagaagat   1080

gggtgttcat gccgcttccc cgaggaggaa gaaggagggt gtgaactgag ggtgaaattt   1140

tctagaagcg ccgatgctcc cgcatatcag cagggtcaga atcagctcta caatgaattg   1200

aatctcggca ggcgagaaga gtacgatgtt ctggacaaga gacggggcag ggatcccgag   1260

atggggggaa agccccggag aaaaaatcct caggaggggt tgtacaatga gctgcagaag   1320

gacaagatgg ctgaagccta tagcgagatc ggaatgaaag gcgaaagacg cagaggcaag   1380

gggcatgacg gtctgtacca gggtctctct acagccacca aggacactta tgatgcgttg   1440

catatgcaag ccttgccacc ccgctaa                                       1467
```

```
<210> SEQ ID NO 52
<211> LENGTH: 488
<212> TYPE: PRT
<213> ORGANISM: Artificial Sequence
<220> FEATURE:
<223> OTHER INFORMATION: Made in Lab - polypeptide of anti-BCMA CAR2
      construct

<400> SEQUENCE: 52

Met Ala Leu Pro Val Thr Ala Leu Leu Leu Pro Leu Ala Leu Leu Leu
1               5                   10                  15

His Ala Ala Arg Pro Gln Val Gln Leu Val Gln Ser Gly Ala Glu Val
            20                  25                  30

Lys Lys Pro Gly Ala Ser Val Lys Val Ser Cys Lys Ala Ser Gly Tyr
        35                  40                  45

Thr Phe Ser Asn Asn Gly Phe Ser Trp Val Arg Gln Ala Pro Gly Gln
    50                  55                  60

Gly Leu Glu Trp Met Gly Trp Ile Ser Gly Phe Asn Gly Lys Thr Tyr
65                  70                  75                  80

Tyr Thr Lys Thr Leu Gln Gly Arg Val Thr Met Thr Ile Asp Thr Ser
                85                  90                  95

Thr Ser Thr Ala Tyr Met Asp Leu Arg Ser Leu Arg Ser Asp Asp Thr
            100                 105                 110

Ala Val Tyr Tyr Cys Ala Arg Gly Leu Leu Leu Ser Gly Glu Leu Trp
        115                 120                 125

Gly Phe Asp Tyr Trp Gly Gln Gly Thr Leu Val Thr Val Ser Ser Gly
    130                 135                 140

Gly Gly Gly Ser Gly Gly Gly Gly Ser Gly Gly Gly Gly Ser Asp Ile
145                 150                 155                 160

Gln Leu Thr Gln Ser Pro Ser Phe Leu Ser Ala Ser Val Gly Asp Arg
                165                 170                 175

Val Thr Ile Thr Cys Arg Ala Ser Gln Asp Ile Ser Ser Phe Leu Ala
            180                 185                 190

Trp Tyr Gln Gln Lys Pro Gly Lys Ala Pro Lys Leu Leu Ile Phe Ala
        195                 200                 205

Ala Ser Thr Leu Gln Ser Gly Val Pro Ser Arg Ile Ser Gly Ser Gly
    210                 215                 220
```

```
Ser Gly Thr Glu Phe Thr Leu Thr Ile Ser Ser Leu Gln Pro Glu Asp
225                 230                 235                 240

Phe Ala Thr Tyr Tyr Cys Gln Gln Phe Asn Ser Tyr Pro Arg Thr Phe
                245                 250                 255

Gly Gln Gly Thr Lys Val Glu Ile Lys Thr Thr Thr Pro Ala Pro Arg
            260                 265                 270

Pro Pro Thr Pro Ala Pro Thr Ile Ala Ser Gln Pro Leu Ser Leu Arg
        275                 280                 285

Pro Glu Ala Cys Arg Pro Ala Ala Gly Gly Ala Val His Thr Arg Gly
    290                 295                 300

Leu Asp Phe Ala Cys Asp Ile Tyr Ile Trp Ala Pro Leu Ala Gly Thr
305                 310                 315                 320

Cys Gly Val Leu Leu Leu Ser Leu Val Ile Thr Leu Tyr Cys Lys Arg
                325                 330                 335

Gly Arg Lys Lys Leu Leu Tyr Ile Phe Lys Gln Pro Phe Met Arg Pro
            340                 345                 350

Val Gln Thr Thr Gln Glu Glu Asp Gly Cys Ser Cys Arg Phe Pro Glu
        355                 360                 365

Glu Glu Glu Gly Gly Cys Glu Leu Arg Val Lys Phe Ser Arg Ser Ala
    370                 375                 380

Asp Ala Pro Ala Tyr Gln Gln Gly Gln Asn Gln Leu Tyr Asn Glu Leu
385                 390                 395                 400

Asn Leu Gly Arg Arg Glu Glu Tyr Asp Val Leu Asp Lys Arg Arg Gly
                405                 410                 415

Arg Asp Pro Glu Met Gly Gly Lys Pro Arg Arg Lys Asn Pro Gln Glu
            420                 425                 430

Gly Leu Tyr Asn Glu Leu Gln Lys Asp Lys Met Ala Glu Ala Tyr Ser
        435                 440                 445

Glu Ile Gly Met Lys Gly Glu Arg Arg Arg Gly Lys Gly His Asp Gly
    450                 455                 460

Leu Tyr Gln Gly Leu Ser Thr Ala Thr Lys Asp Thr Tyr Asp Ala Leu
465                 470                 475                 480

His Met Gln Ala Leu Pro Pro Arg
                485


<210> SEQ ID NO 53
<211> LENGTH: 1467
<212> TYPE: DNA
<213> ORGANISM: Artificial Sequence
<220> FEATURE:
<223> OTHER INFORMATION: Made in Lab - polynucleotide of anti-BCMA CAR3
      construct

<400> SEQUENCE: 53

atggccctgc ccgttacagc cttgcttctg cccctcgcgc tgcttttgca cgctgcgagg      60

ccagacatcc agttgacaca atcaccatcc tttcttagtg cctctgtggg agatagagtc     120

accatcacgt gccgagcatc tcaggatatc agtagcttct tggcatggta tcagcagaaa     180

cctggcaagg cccctaaact gctcatcttc gctgcgtcca ctctgcagtc cggagtccca     240

agcagaatca gtggttccgg atcaggaact gagtttaccc tcacaattag cagtttgcag     300

cccgaagatt tcgccaccta ttactgtcag cagtttaact cataccctag gactttcgga     360

caggggacca aggtcgagat caagggcggt gggggctccg gcggaggcgg atcaggtggt     420

ggaggttctc aggtacagct tgtccagtca ggcgccgagg tgaaaaaacc tggggcctca     480

gtgaaggtct cctgcaaagc aagcggttat acgttctcca acaacgggtt ctcatgggta     540
```

```
aggcaagctc ctggacaggg gctcgaatgg atggggtgga tcagcggctt caatggcaag    600

acctattaca ccaagaccct tcaaggcaga gtaacgatga ctatcgatac tagtacaagc    660

accgcctata tggaccttag gtccctccgc tctgatgata ccgccgtcta ttactgcgcc    720

cgcggcctgc tgttgagcgg cgagctgtgg ggattcgatt actgggggca aggcaccctg    780

gtcactgtgt cctctaccac aacacctgct ccaaggcccc ccacacccgc tccaactata    840

gccagccaac cattgagcct cagacctgaa gcttgcaggc ccgcagcagg aggcgccgtc    900

catacgcgag gcctggactt cgcgtgtgat atttatattt gggccccttt ggccggaaca    960

tgtggggtgt tgcttctctc ccttgtgatc actctgtatt gtaagcgcgg gagaaagaag   1020

ctcctgtaca tcttcaagca gccttttatg cgacctgtgc aaaccactca ggaagaagat   1080

gggtgttcat gccgcttccc cgaggaggaa gaaggagggt gtgaactgag ggtgaaattt   1140

tctagaagcg ccgatgctcc cgcatatcag cagggtcaga atcagctcta caatgaattg   1200

aatctcggca ggcgagaaga gtacgatgtt ctggacaaga gacggggcag ggatcccgag   1260

atggggggaa agccccggag aaaaaatcct caggaggggt tgtacaatga gctgcagaag   1320

gacaagatgg ctgaagccta tagcgagatc ggaatgaaag gcgaaagacg cagaggcaag   1380

gggcatgacg gtctgtacca gggtctctct acagccacca aggacactta tgatgcgttg   1440

catatgcaag ccttgccacc ccgctaa                                       1467
```

```
<210> SEQ ID NO 54
<211> LENGTH: 488
<212> TYPE: PRT
<213> ORGANISM: Artificial Sequence
<220> FEATURE:
<223> OTHER INFORMATION: Made in Lab - polypeptide of anti-BCMA CAR3
      construct

<400> SEQUENCE: 54

Met Ala Leu Pro Val Thr Ala Leu Leu Leu Pro Leu Ala Leu Leu Leu
1               5                   10                  15

His Ala Ala Arg Pro Asp Ile Gln Leu Thr Gln Ser Pro Ser Phe Leu
            20                  25                  30

Ser Ala Ser Val Gly Asp Arg Val Thr Ile Thr Cys Arg Ala Ser Gln
        35                  40                  45

Asp Ile Ser Ser Phe Leu Ala Trp Tyr Gln Gln Lys Pro Gly Lys Ala
    50                  55                  60

Pro Lys Leu Leu Ile Phe Ala Ala Ser Thr Leu Gln Ser Gly Val Pro
65                  70                  75                  80

Ser Arg Ile Ser Gly Ser Gly Ser Gly Thr Glu Phe Thr Leu Thr Ile
                85                  90                  95

Ser Ser Leu Gln Pro Glu Asp Phe Ala Thr Tyr Tyr Cys Gln Gln Phe
            100                 105                 110

Asn Ser Tyr Pro Arg Thr Phe Gly Gln Gly Thr Lys Val Glu Ile Lys
        115                 120                 125

Gly Gly Gly Gly Ser Gly Gly Gly Gly Ser Gly Gly Gly Gly Ser Gln
    130                 135                 140

Val Gln Leu Val Gln Ser Gly Ala Glu Val Lys Lys Pro Gly Ala Ser
145                 150                 155                 160

Val Lys Val Ser Cys Lys Ala Ser Gly Tyr Thr Phe Ser Asn Asn Gly
                165                 170                 175

Phe Ser Trp Val Arg Gln Ala Pro Gly Gln Gly Leu Glu Trp Met Gly
            180                 185                 190
```

Trp Ile Ser Gly Phe Asn Gly Lys Thr Tyr Tyr Thr Lys Thr Leu Gln
195 200 205

Gly Arg Val Thr Met Thr Ile Asp Thr Ser Thr Ser Thr Ala Tyr Met
210 215 220

Asp Leu Arg Ser Leu Arg Ser Asp Asp Thr Ala Val Tyr Tyr Cys Ala
225 230 235 240

Arg Gly Leu Leu Leu Ser Gly Glu Leu Trp Gly Phe Asp Tyr Trp Gly
245 250 255

Gln Gly Thr Leu Val Thr Val Ser Ser Thr Thr Thr Pro Ala Pro Arg
260 265 270

Pro Pro Thr Pro Ala Pro Thr Ile Ala Ser Gln Pro Leu Ser Leu Arg
275 280 285

Pro Glu Ala Cys Arg Pro Ala Ala Gly Gly Ala Val His Thr Arg Gly
290 295 300

Leu Asp Phe Ala Cys Asp Ile Tyr Ile Trp Ala Pro Leu Ala Gly Thr
305 310 315 320

Cys Gly Val Leu Leu Leu Ser Leu Val Ile Thr Leu Tyr Cys Lys Arg
325 330 335

Gly Arg Lys Lys Leu Leu Tyr Ile Phe Lys Gln Pro Phe Met Arg Pro
340 345 350

Val Gln Thr Thr Gln Glu Glu Asp Gly Cys Ser Cys Arg Phe Pro Glu
355 360 365

Glu Glu Glu Gly Gly Cys Glu Leu Arg Val Lys Phe Ser Arg Ser Ala
370 375 380

Asp Ala Pro Ala Tyr Gln Gln Gly Gln Asn Gln Leu Tyr Asn Glu Leu
385 390 395 400

Asn Leu Gly Arg Arg Glu Glu Tyr Asp Val Leu Asp Lys Arg Arg Gly
405 410 415

Arg Asp Pro Glu Met Gly Gly Lys Pro Arg Arg Lys Asn Pro Gln Glu
420 425 430

Gly Leu Tyr Asn Glu Leu Gln Lys Asp Lys Met Ala Glu Ala Tyr Ser
435 440 445

Glu Ile Gly Met Lys Gly Glu Arg Arg Arg Gly Lys Gly His Asp Gly
450 455 460

Leu Tyr Gln Gly Leu Ser Thr Ala Thr Lys Asp Thr Tyr Asp Ala Leu
465 470 475 480

His Met Gln Ala Leu Pro Pro Arg
485

<210> SEQ ID NO 55
<211> LENGTH: 1476
<212> TYPE: DNA
<213> ORGANISM: Artificial Sequence
<220> FEATURE:
<223> OTHER INFORMATION: Made in Lab - polynucleotide of anti-BCMA CAR4 construct

<400> SEQUENCE: 55
atggcgctgc cagtcacagc attgctgctg cctctggcac tcctgttgca tgcagcccgc 60
ccacaggtgc agctggtgga aagcggtggg ggggtggtgc agcccggcag aagtctgaga 120
ctcagctgtg cagcaagtgg cttcacattc agttcttacg gcatgcactg ggtgcgacag 180
gctcccggga agggactgga gtgggtggca gtgatatcat acgatggtag gaataagaat 240
tacgctgatt cagtcaaggg acgattcaca atcagtcgcg acaattccaa gaacaccctt 300

```
tacctgcaga tgaatagcct cagggcggag gatactgcag tctactattg cgcaagagag    360

ggagaagcta cctactacga catactgact gggccatttg attattgggg ccaaggaact    420

cttgtcactg tgagcagcgg cggcggaggc tctggaggag ggggatcagg cgggggagga    480

tccgacatcc agatgaccca gagcccttct tctctgtcag ctagtgtagg cgatcgaatc    540

actatcactt gcagggcctc ccaggacatc cgcaactacc tgggatggta tcagcagaag    600

ccaggcaaag ctccgaaggt tctcattttt gccgcctctt ccctccagtc aggggtgccc    660

tctaggttta gcggcagcgg tagcggaaca gacttcaccc ttaccatctc atctctccag    720

cccgaggact tcgctaccta ttattgcctc caagattata tatatccttg gaccttcgca    780

caaggcacta aagttgagat caaaaccaca acacctgctc caaggccccc cacacccgct    840

ccaactatag ccagccaacc attgagcctc agacctgaag cttgcaggcc cgcagcagga    900

ggcgccgtcc atacgcgagg cctggacttc gcgtgtgata tttatatttg ggcccctttg    960

gccggaacat gtggggtgtt gcttctctcc cttgtgatca ctctgtattg taagcgcggg   1020

agaaagaagc tcctgtacat cttcaagcag ccttttatgc gacctgtgca aaccactcag   1080

gaagaagatg ggtgttcatg ccgcttcccc gaggaggaag aaggagggtg tgaactgagg   1140

gtgaaatttt ctagaagcgc cgatgctccc gcatatcagc agggtcagaa tcagctctac   1200

aatgaattga atctcggcag gcgagaagag tacgatgttc tggacaagag acggggcagg   1260

gatcccgaga tgggggggaaa gccccggaga aaaaatcctc aggaggggtt gtacaatgag   1320

ctgcagaagg acaagatggc tgaagcctat agcgagatcg gaatgaaagg cgaaagacgc   1380

agaggcaagg ggcatgacgg tctgtaccag ggtctctcta cagccaccaa ggacacttat   1440

gatgcgttgc atatgcaagc cttgccaccc cgctaa                              1476
```

<210> SEQ ID NO 56
<211> LENGTH: 491
<212> TYPE: PRT
<213> ORGANISM: Artificial Sequence
<220> FEATURE:
<223> OTHER INFORMATION: Made in Lab - polypeptide of anti-BCMA CAR4
construct

<400> SEQUENCE: 56

```
Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Gly Val
            20                  25                  30

Val Gln Pro Gly Arg Ser Leu Arg Leu Ser Cys Ala Ala Ser Gly Phe
        35                  40                  45

Thr Phe Ser Ser Tyr Gly Met His Trp Val Arg Gln Ala Pro Gly Lys
    50                  55                  60

Gly Leu Glu Trp Val Ala Val Ile Ser Tyr Asp Gly Arg Asn Lys Asn
65                  70                  75                  80

Tyr Ala Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Ala Arg Glu Gly Glu Ala Thr Tyr Tyr Asp Ile
        115                 120                 125

Leu Thr Gly Pro Phe Asp Tyr Trp Gly Gln Gly Thr Leu Val Thr Val
    130                 135                 140

Ser Ser Gly Gly Gly Gly Ser Gly Gly Gly Gly Ser Gly Gly Gly Gly
```

```
145                 150                 155                 160

Ser Asp Ile Gln Met Thr Gln Ser Pro Ser Ser Leu Ser Ala Ser Val
                165                 170                 175

Gly Asp Arg Ile Thr Ile Thr Cys Arg Ala Ser Gln Asp Ile Arg Asn
            180                 185                 190

Tyr Leu Gly Trp Tyr Gln Gln Lys Pro Gly Lys Ala Pro Lys Val Leu
        195                 200                 205

Ile Phe Ala Ala Ser Ser Leu Gln Ser Gly Val Pro Ser Arg Phe Ser
    210                 215                 220

Gly Ser Gly Ser Gly Thr Asp Phe Thr Leu Thr Ile Ser Ser Leu Gln
225                 230                 235                 240

Pro Glu Asp Phe Ala Thr Tyr Tyr Cys Leu Gln Asp Tyr Ile Tyr Pro
                245                 250                 255

Trp Thr Phe Ala Gln Gly Thr Lys Val Glu Ile Lys Thr Thr Thr Pro
            260                 265                 270

Ala Pro Arg Pro Pro Thr Pro Ala Pro Thr Ile Ala Ser Gln Pro Leu
        275                 280                 285

Ser Leu Arg Pro Glu Ala Cys Arg Pro Ala Ala Gly Gly Ala Val His
    290                 295                 300

Thr Arg Gly Leu Asp Phe Ala Cys Asp Ile Tyr Ile Trp Ala Pro Leu
305                 310                 315                 320

Ala Gly Thr Cys Gly Val Leu Leu Leu Ser Leu Val Ile Thr Leu Tyr
                325                 330                 335

Cys Lys Arg Gly Arg Lys Lys Leu Leu Tyr Ile Phe Lys Gln Pro Phe
            340                 345                 350

Met Arg Pro Val Gln Thr Thr Gln Glu Glu Asp Gly Cys Ser Cys Arg
        355                 360                 365

Phe Pro Glu Glu Glu Glu Gly Gly Cys Glu Leu Arg Val Lys Phe Ser
    370                 375                 380

Arg Ser Ala Asp Ala Pro Ala Tyr Gln Gln Gly Gln Asn Gln Leu Tyr
385                 390                 395                 400

Asn Glu Leu Asn Leu Gly Arg Arg Glu Glu Tyr Asp Val Leu Asp Lys
                405                 410                 415

Arg Arg Gly Arg Asp Pro Glu Met Gly Gly Lys Pro Arg Arg Lys Asn
            420                 425                 430

Pro Gln Glu Gly Leu Tyr Asn Glu Leu Gln Lys Asp Lys Met Ala Glu
        435                 440                 445

Ala Tyr Ser Glu Ile Gly Met Lys Gly Glu Arg Arg Arg Gly Lys Gly
    450                 455                 460

His Asp Gly Leu Tyr Gln Gly Leu Ser Thr Ala Thr Lys Asp Thr Tyr
465                 470                 475                 480

Asp Ala Leu His Met Gln Ala Leu Pro Pro Arg
                485                 490
```

<210> SEQ ID NO 57
<211> LENGTH: 1476
<212> TYPE: DNA
<213> ORGANISM: Artificial Sequence
<220> FEATURE:
<223> OTHER INFORMATION: Made in Lab - polynucleotide of anti-BCMA CAR5
      construct

<400> SEQUENCE: 57

```
atggcactcc ccgtgactgc cctgcttctt ccactggcac tgctgctcca tgcagccagg      60

cccgatattc aaatgactca gagtcccagc tcactcagcg ctagcgtcgg agataggata     120
```

-continued

```
accatcacat gtcgggccag ccaagacatc cggaactatc ttggatggta tcagcaaaaa    180

cccgggaagg ctcctaaagt gctgattttc gccgctagct cactgcagtc cggggtgccg    240

agtaggtttt ccggctctgg tagtggcacc gacttcaccc ttacaatatc aagcctccag    300

ccagaggact tcgcgactta ctattgtctg caggattaca tctacccgtg gaccttcgcc    360

cagggaacta aggtcgagat taagggtggt ggtggcagcg gcgggggcgg ttccggggga    420

ggaggatccc aggtccaact cgtggagtcc ggtggtggcg tggtgcagcc tggaagatcc    480

ctgcggctct cttgtgccgc tagcggattt acattcagta gctatgggat gcattgggtt    540

cgccaggctc cgggcaaagg attggagtgg gtggcggtca tatcatatga cggccggaac    600

aaaaattatg ctgattctgt gaaggggagg ttcactatta gtagagacaa tagtaagaat    660

acgctgtact tgcagatgaa ctctcttcga gcagaagata ctgccgtgta ctattgtgcg    720

cgcgaggggg aagccactta ctacgacatt ctgacagggc ctttcgatta ttggggacag    780

ggtactctcg ttacagtgtc ctcaaccaca acacctgctc caaggccccc cacacccgct    840

ccaactatag ccagccaacc attgagcctc agacctgaag cttgcaggcc cgcagcagga    900

ggcgccgtcc atacgcgagg cctggacttc gcgtgtgata tttatatttg ggcccctttg    960

gccggaacat gtggggtgtt gcttctctcc cttgtgatca ctctgtattg taagcgcggg   1020

agaaagaagc tcctgtacat cttcaagcag ccttttatgc gacctgtgca aaccactcag   1080

gaagaagatg ggtgttcatg ccgcttcccc gaggaggaag aaggagggtg tgaactgagg   1140

gtgaaatttt ctagaagcgc cgatgctccc gcatatcagc agggtcagaa tcagctctac   1200

aatgaattga atctcggcag gcgagaagag tacgatgttc tggacaagag acggggcagg   1260

gatcccgaga tgggggggaaa gccccggaga aaaaatcctc aggaggggtt gtacaatgag   1320

ctgcagaagg acaagatggc tgaagcctat agcgagatcg gaatgaaagg cgaaagacgc   1380

agaggcaagg ggcatgacgg tctgtaccag ggtctctcta cagccaccaa ggacacttat   1440

gatgcgttgc atatgcaagc cttgccaccc cgctaa                             1476
```

<210> SEQ ID NO 58
<211> LENGTH: 491
<212> TYPE: PRT
<213> ORGANISM: Artificial Sequence
<220> FEATURE:
<223> OTHER INFORMATION: Made in Lab - polypeptide of anti-BCMA CAR5 construct

<400> SEQUENCE: 58

```
Met Ala Leu Pro Val Thr Ala Leu Leu Leu Pro Leu Ala Leu Leu Leu
1               5                   10                  15

His Ala Ala Arg Pro Asp Ile Gln Met Thr Gln Ser Pro Ser Ser Leu
            20                  25                  30

Ser Ala Ser Val Gly Asp Arg Ile Thr Ile Thr Cys Arg Ala Ser Gln
        35                  40                  45

Asp Ile Arg Asn Tyr Leu Gly Trp Tyr Gln Gln Lys Pro Gly Lys Ala
    50                  55                  60

Pro Lys Val Leu Ile Phe Ala Ala Ser Ser Leu Gln Ser Gly Val Pro
65                  70                  75                  80

Ser Arg Phe Ser Gly Ser Gly Ser Gly Thr Asp Phe Thr Leu Thr Ile
                85                  90                  95

Ser Ser Leu Gln Pro Glu Asp Phe Ala Thr Tyr Tyr Cys Leu Gln Asp
            100                 105                 110
```

```
Tyr Ile Tyr Pro Trp Thr Phe Ala Gln Gly Thr Lys Val Glu Ile Lys
        115                 120                 125

Gly Gly Gly Gly Ser Gly Gly Gly Gly Ser Gly Gly Gly Gly Ser Gln
    130                 135                 140

Val Gln Leu Val Glu Ser Gly Gly Gly Val Val Gln Pro Gly Arg Ser
145                 150                 155                 160

Leu Arg Leu Ser Cys Ala Ala Ser Gly Phe Thr Phe Ser Ser Tyr Gly
                165                 170                 175

Met His Trp Val Arg Gln Ala Pro Gly Lys Gly Leu Glu Trp Val Ala
            180                 185                 190

Val Ile Ser Tyr Asp Gly Arg Asn Lys Asn Tyr Ala Asp Ser Val Lys
        195                 200                 205

Gly Arg Phe Thr Ile Ser Arg Asp Asn Ser Lys Asn Thr Leu Tyr Leu
    210                 215                 220

Gln Met Asn Ser Leu Arg Ala Glu Asp Thr Ala Val Tyr Tyr Cys Ala
225                 230                 235                 240

Arg Glu Gly Glu Ala Thr Tyr Tyr Asp Ile Leu Thr Gly Pro Phe Asp
                245                 250                 255

Tyr Trp Gly Gln Gly Thr Leu Val Thr Val Ser Ser Thr Thr Thr Pro
            260                 265                 270

Ala Pro Arg Pro Pro Thr Pro Ala Pro Thr Ile Ala Ser Gln Pro Leu
        275                 280                 285

Ser Leu Arg Pro Glu Ala Cys Arg Pro Ala Ala Gly Gly Ala Val His
    290                 295                 300

Thr Arg Gly Leu Asp Phe Ala Cys Asp Ile Tyr Ile Trp Ala Pro Leu
305                 310                 315                 320

Ala Gly Thr Cys Gly Val Leu Leu Leu Ser Leu Val Ile Thr Leu Tyr
                325                 330                 335

Cys Lys Arg Gly Arg Lys Lys Leu Leu Tyr Ile Phe Lys Gln Pro Phe
            340                 345                 350

Met Arg Pro Val Gln Thr Thr Gln Glu Glu Asp Gly Cys Ser Cys Arg
        355                 360                 365

Phe Pro Glu Glu Glu Glu Gly Gly Cys Glu Leu Arg Val Lys Phe Ser
    370                 375                 380

Arg Ser Ala Asp Ala Pro Ala Tyr Gln Gln Gly Gln Asn Gln Leu Tyr
385                 390                 395                 400

Asn Glu Leu Asn Leu Gly Arg Arg Glu Glu Tyr Asp Val Leu Asp Lys
                405                 410                 415

Arg Arg Gly Arg Asp Pro Glu Met Gly Gly Lys Pro Arg Arg Lys Asn
            420                 425                 430

Pro Gln Glu Gly Leu Tyr Asn Glu Leu Gln Lys Asp Lys Met Ala Glu
        435                 440                 445

Ala Tyr Ser Glu Ile Gly Met Lys Gly Glu Arg Arg Arg Gly Lys Gly
    450                 455                 460

His Asp Gly Leu Tyr Gln Gly Leu Ser Thr Ala Thr Lys Asp Thr Tyr
465                 470                 475                 480

Asp Ala Leu His Met Gln Ala Leu Pro Pro Arg
                485                 490
```

<210> SEQ ID NO 59
<211> LENGTH: 1476
<212> TYPE: DNA
<213> ORGANISM: Artificial Sequence
<220> FEATURE:
<223> OTHER INFORMATION: Made in Lab - polynucleotide of anti-BCMA CAR6 construct

<400> SEQUENCE: 59

```
atggccctgc cagtaacagc cctcttgctc cccctggcac ttctgctgca cgccgcgcgg      60
ccccaggtgc agcttgtgga gagcggaggc ggcgtggtgc agccagggag gagcttgaga     120
ctctcttgtg ctgcctcagg attcactttt agtagttacg gtatgcactg ggtgcgccag     180
gctcccggaa aaggactgga gtgggtggca gtgatcagct acgatgggag gaacaagaat     240
tatgctgaca gtgtgaaagg gaggttcacg atatctcgag ataattcaaa gaacaccctg     300
tacctgcaga tgaacagtct tagagctgag gatactgctg tgtactactg cgctagagaa     360
ggggaagcca cgtactacga cattctgaca ggcccttttg actactgggg ccaaggcaca     420
ctcgttactg tgagcagtgg tggagggggc agtggaggcg gaggttctgg tggagggggt     480
agtgatatcc aactgacgca gagcccaagc ttcttgagtg cgtctgtggg ggaccgggtc     540
tctatcacct gtcgggcttc tcaggggatc agttcctatc tggcatggta tcagcagaag     600
cctggcaaag ccccaaaggt attgatctac gtcgcatcaa cgctgcagtc cggggtgcct     660
tctcggttca gcgggtctgg tagtggaact gagtttacac tgaccataag cagtctgcaa     720
cccgatgatt tcgccactta ttactgccaa cagctttact cttatccgcg cgcatttggc     780
caggggacta aagtagagat taaaaccaca acacctgctc caaggccccc cacacccgct     840
ccaactatag ccagccaacc attgagcctc agacctgaag cttgcaggcc cgcagcagga     900
ggcgccgtcc atacgcgagg cctggacttc gcgtgtgata tttatatttg ggcccctttg     960
gccggaacat gtggggtgtt gcttctctcc cttgtgatca ctctgtattg taagcgcggg    1020
agaaagaagc tcctgtacat cttcaagcag ccttttatgc gacctgtgca aaccactcag    1080
gaagaagatg ggtgttcatg ccgcttcccc gaggaggaag aaggagggtg tgaactgagg    1140
gtgaaatttt ctagaagcgc cgatgctccc gcatatcagc agggtcagaa tcagctctac    1200
aatgaattga atctcggcag gcgagaagag tacgatgttc tggacaagag acggggcagg    1260
gatcccgaga tgggggggaaa gccccggaga aaaaatcctc aggaggggtt gtacaatgag    1320
ctgcagaagg acaagatggc tgaagcctat agcgagatcg gaatgaaagg cgaaagacgc    1380
agaggcaagg ggcatgacgg tctgtaccag ggtctctcta cagccaccaa ggacacttat    1440
gatgcgttgc atatgcaagc cttgccaccc cgctaa                               1476
```

<210> SEQ ID NO 60
<211> LENGTH: 491
<212> TYPE: PRT
<213> ORGANISM: Artificial Sequence
<220> FEATURE:
<223> OTHER INFORMATION: Made in Lab - polypeptide of anti-BCMA CAR6
construct

<400> SEQUENCE: 60

```
Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Gly Val
            20                  25                  30

Val Gln Pro Gly Arg Ser Leu Arg Leu Ser Cys Ala Ala Ser Gly Phe
        35                  40                  45

Thr Phe Ser Ser Tyr Gly Met His Trp Val Arg Gln Ala Pro Gly Lys
    50                  55                  60

Gly Leu Glu Trp Val Ala Val Ile Ser Tyr Asp Gly Arg Asn Lys Asn
65                  70                  75                  80
```

```
Tyr Ala Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Ala Arg Glu Gly Glu Ala Thr Tyr Tyr Asp Ile
        115                 120                 125

Leu Thr Gly Pro Phe Asp Tyr Trp Gly Gln Gly Thr Leu Val Thr Val
    130                 135                 140

Ser Ser Gly Gly Gly Gly Ser Gly Gly Gly Gly Ser Gly Gly Gly Gly
145                 150                 155                 160

Ser Asp Ile Gln Leu Thr Gln Ser Pro Ser Phe Leu Ser Ala Ser Val
                165                 170                 175

Gly Asp Arg Val Ser Ile Thr Cys Arg Ala Ser Gln Gly Ile Ser Ser
            180                 185                 190

Tyr Leu Ala Trp Tyr Gln Gln Lys Pro Gly Lys Ala Pro Lys Val Leu
        195                 200                 205

Ile Tyr Val Ala Ser Thr Leu Gln Ser Gly Val Pro Ser Arg Phe Ser
    210                 215                 220

Gly Ser Gly Ser Gly Thr Glu Phe Thr Leu Thr Ile Ser Ser Leu Gln
225                 230                 235                 240

Pro Asp Asp Phe Ala Thr Tyr Tyr Cys Gln Gln Leu Tyr Ser Tyr Pro
                245                 250                 255

Arg Ala Phe Gly Gln Gly Thr Lys Val Glu Ile Lys Thr Thr Thr Pro
            260                 265                 270

Ala Pro Arg Pro Pro Thr Pro Ala Pro Thr Ile Ala Ser Gln Pro Leu
        275                 280                 285

Ser Leu Arg Pro Glu Ala Cys Arg Pro Ala Ala Gly Gly Ala Val His
    290                 295                 300

Thr Arg Gly Leu Asp Phe Ala Cys Asp Ile Tyr Ile Trp Ala Pro Leu
305                 310                 315                 320

Ala Gly Thr Cys Gly Val Leu Leu Leu Ser Leu Val Ile Thr Leu Tyr
                325                 330                 335

Cys Lys Arg Gly Arg Lys Lys Leu Leu Tyr Ile Phe Lys Gln Pro Phe
            340                 345                 350

Met Arg Pro Val Gln Thr Thr Gln Glu Glu Asp Gly Cys Ser Cys Arg
        355                 360                 365

Phe Pro Glu Glu Glu Glu Gly Gly Cys Glu Leu Arg Val Lys Phe Ser
    370                 375                 380

Arg Ser Ala Asp Ala Pro Ala Tyr Gln Gln Gly Gln Asn Gln Leu Tyr
385                 390                 395                 400

Asn Glu Leu Asn Leu Gly Arg Arg Glu Glu Tyr Asp Val Leu Asp Lys
                405                 410                 415

Arg Arg Gly Arg Asp Pro Glu Met Gly Gly Lys Pro Arg Arg Lys Asn
            420                 425                 430

Pro Gln Glu Gly Leu Tyr Asn Glu Leu Gln Lys Asp Lys Met Ala Glu
        435                 440                 445

Ala Tyr Ser Glu Ile Gly Met Lys Gly Glu Arg Arg Arg Gly Lys Gly
    450                 455                 460

His Asp Gly Leu Tyr Gln Gly Leu Ser Thr Ala Thr Lys Asp Thr Tyr
465                 470                 475                 480

Asp Ala Leu His Met Gln Ala Leu Pro Pro Arg
                485                 490
```

<210> SEQ ID NO 61
<211> LENGTH: 1485
<212> TYPE: DNA
<213> ORGANISM: Artificial Sequence
<220> FEATURE:
<223> OTHER INFORMATION: Made in Lab - polynucleotide of anti-BCMA CAR7
construct

<400> SEQUENCE: 61
atggccctgc ccgtaaccgc ccttctgctg cctctggctc tgcttctcca cgcagcaagg 60
cctcaggtcc agctggtgca atctggagcc gaggtcaaga aacctggcgc aagcgtgaag 120
gtgtcttgta aagggagcgg ctatacgttt tccacgtacg gcattggctg ggttagacaa 180
gcgcctggcc aaggcctgga gtggctggca tggatttccg cttacagtgg taagacgaac 240
tacgcacaga aggtccaggg cagagtgacc ctcacaactg atactagcac caacaccgcg 300
tatatggagc ttcggtccct gcggtctgat gacacagccg tctattattg cgccagggac 360
gacggtgcgg gcacagatta ttattatggc atggacgttt gggggcaggg caccacagtc 420
actgtcagca gcgggggggg aggatccggg ggaggcggat ctggtggggg aggatccgac 480
attgtgatga cccagacccc actgtcactg tctgtgaccc cgggtcagcc agcttctatt 540
agctgtaagt cctcacaaag cctcctttat agcgacggga aaacatttct ttattggtat 600
ctgcagaaac ccggccagcc tccccagttg ctcatttacg agggttccaa ccgattcagc 660
ggagttcctg acagattctc tggatctggc tcaggaactg atttcactct gaagatttca 720
agggttgagg cagaggatgt gggcgtgttc tactgcatgc aatctatcca gttgcccaat 780
acattcgggc aggggacaaa gctcgagatt aaaaccacaa cacctgctcc aaggcccccc 840
acacccgctc caactatagc cagccaacca ttgagcctca gacctgaagc ttgcaggccc 900
gcagcaggag gcgccgtcca tacgcgaggc ctggacttcg cgtgtgatat ttatatttgg 960
gcccctttgg ccggaacatg tggggtgttg cttctctccc ttgtgatcac tctgtattgt 1020
aagcgcggga gaaagaagct cctgtacatc ttcaagcagc cttttatgcg acctgtgcaa 1080
accactcagg aagaagatgg gtgttcatgc cgcttccccg aggaggaaga aggagggtgt 1140
gaactgaggg tgaaattttc tagaagcgcc gatgctcccg catatcagca gggtcagaat 1200
cagctctaca atgaattgaa tctcggcagg cgagaagagt acgatgttct ggacaagaga 1260
cggggcaggg atcccgagat gggggggaaag ccccggagaa aaaatcctca ggaggggttg 1320
tacaatgagc tgcagaagga caagatggct gaagcctata gcgagatcgg aatgaaaggc 1380
gaaagacgca gaggcaaggg gcatgacggt ctgtaccagg gtctctctac agccaccaag 1440
gacacttatg atgcgttgca tatgcaagcc ttgccacccc gctaa 1485

<210> SEQ ID NO 62
<211> LENGTH: 494
<212> TYPE: PRT
<213> ORGANISM: Artificial Sequence
<220> FEATURE:
<223> OTHER INFORMATION: Made in Lab - polypeptide of anti-BCMA CAR7
construct

<400> SEQUENCE: 62

Met Ala Leu Pro Val Thr Ala Leu Leu Leu Pro Leu Ala Leu Leu Leu
1 5 10 15

His Ala Ala Arg Pro Gln Val Gln Leu Val Gln Ser Gly Ala Glu Val
20 25 30

Lys Lys Pro Gly Ala Ser Val Lys Val Ser Cys Lys Gly Ser Gly Tyr

-continued

```
        35                  40                  45

Thr Phe Ser Thr Tyr Gly Ile Gly Trp Val Arg Gln Ala Pro Gly Gln
    50                  55                  60

Gly Leu Glu Trp Leu Ala Trp Ile Ser Ala Tyr Ser Gly Lys Thr Asn
65                  70                  75                  80

Tyr Ala Gln Lys Val Gln Gly Arg Val Thr Leu Thr Thr Asp Thr Ser
                85                  90                  95

Thr Asn Thr Ala Tyr Met Glu Leu Arg Ser Leu Arg Ser Asp Asp Thr
            100                 105                 110

Ala Val Tyr Tyr Cys Ala Arg Asp Asp Gly Ala Gly Thr Asp Tyr Tyr
        115                 120                 125

Tyr Gly Met Asp Val Trp Gly Gln Gly Thr Thr Val Thr Val Ser Ser
    130                 135                 140

Gly Gly Gly Gly Ser Gly Gly Gly Gly Ser Gly Gly Gly Gly Ser Asp
145                 150                 155                 160

Ile Val Met Thr Gln Thr Pro Leu Ser Leu Ser Val Thr Pro Gly Gln
                165                 170                 175

Pro Ala Ser Ile Ser Cys Lys Ser Ser Gln Ser Leu Leu Tyr Ser Asp
            180                 185                 190

Gly Lys Thr Phe Leu Tyr Trp Tyr Leu Gln Lys Pro Gly Gln Pro Pro
        195                 200                 205

Gln Leu Leu Ile Tyr Glu Gly Ser Asn Arg Phe Ser Gly Val Pro Asp
    210                 215                 220

Arg Phe Ser Gly Ser Gly Ser Gly Thr Asp Phe Thr Leu Lys Ile Ser
225                 230                 235                 240

Arg Val Glu Ala Glu Asp Val Gly Val Phe Tyr Cys Met Gln Ser Ile
                245                 250                 255

Gln Leu Pro Asn Thr Phe Gly Gln Gly Thr Lys Leu Glu Ile Lys Thr
            260                 265                 270

Thr Thr Pro Ala Pro Arg Pro Pro Thr Pro Ala Pro Thr Ile Ala Ser
        275                 280                 285

Gln Pro Leu Ser Leu Arg Pro Glu Ala Cys Arg Pro Ala Ala Gly Gly
    290                 295                 300

Ala Val His Thr Arg Gly Leu Asp Phe Ala Cys Asp Ile Tyr Ile Trp
305                 310                 315                 320

Ala Pro Leu Ala Gly Thr Cys Gly Val Leu Leu Leu Ser Leu Val Ile
                325                 330                 335

Thr Leu Tyr Cys Lys Arg Gly Arg Lys Lys Leu Leu Tyr Ile Phe Lys
            340                 345                 350

Gln Pro Phe Met Arg Pro Val Gln Thr Thr Gln Glu Glu Asp Gly Cys
        355                 360                 365

Ser Cys Arg Phe Pro Glu Glu Glu Glu Gly Gly Cys Glu Leu Arg Val
    370                 375                 380

Lys Phe Ser Arg Ser Ala Asp Ala Pro Ala Tyr Gln Gln Gly Gln Asn
385                 390                 395                 400

Gln Leu Tyr Asn Glu Leu Asn Leu Gly Arg Arg Glu Glu Tyr Asp Val
                405                 410                 415

Leu Asp Lys Arg Arg Gly Arg Asp Pro Glu Met Gly Gly Lys Pro Arg
            420                 425                 430

Arg Lys Asn Pro Gln Glu Gly Leu Tyr Asn Glu Leu Gln Lys Asp Lys
        435                 440                 445

Met Ala Glu Ala Tyr Ser Glu Ile Gly Met Lys Gly Glu Arg Arg Arg
    450                 455                 460
```

Gly Lys Gly His Asp Gly Leu Tyr Gln Gly Leu Ser Thr Ala Thr Lys
465 470 475 480

Asp Thr Tyr Asp Ala Leu His Met Gln Ala Leu Pro Pro Arg
485 490

<210> SEQ ID NO 63
<211> LENGTH: 1485
<212> TYPE: DNA
<213> ORGANISM: Artificial Sequence
<220> FEATURE:
<223> OTHER INFORMATION: Made in Lab - polynucleotide of anti-BCMA CAR8 construct

<400> SEQUENCE: 63
atggctctcc ctgtcactgc tctgctcctt cctctggcgc ttctgctgca tgctgcccga 60
cccgatattg tgatgacgca gaccccccctg tctctgtccg tcaccccagg gcagccggcg 120
tccatctcct gtaagagcag ccagtctctt ctgtactctg atggaaagac atttttgtac 180
tggtacttgc agaagcctgg gcaacctccg cagctcttga tttacgaagg atccaataga 240
ttcagcggag tgcccgatag atttagcggt tctggatctg gtacggactt cacactgaaa 300
atctcacggg ttgaggctga agatgtgggc gtgttttact gcatgcaaag catacaactg 360
ccgaacacct tcggccaagg aactaagctg gagattaagg gaggaggagg gagcggtggc 420
ggcggttctg gtggcggcgg atcccaggtc cagttggtac aatctggggc cgaagttaag 480
aaaccggggg ctagcgtgaa ggtatcttgc aaaggcagtg gctacacatt ctctacttac 540
ggaatcggat gggtgagaca ggctcctggt cagggtctgg aatggctcgc gtggatcagt 600
gcgtattcag gaaaaaccaa ttacgctcag aaggtgcaag gccgcgtgac actgaccact 660
gacacctcca ccaacacagc ttacatggag ctgcgatctc tcagatctga cgatactgca 720
gtgtattact gtgcccgcga tgacggggct ggcacggact actattatgg gatggatgtg 780
tggggacaag gcaccacagt aactgtgagc agtaccacaa cacctgctcc aaggcccccc 840
acacccgctc caactatagc cagccaacca ttgagcctca gacctgaagc ttgcaggccc 900
gcagcaggag gcgccgtcca tacgcgaggc ctggacttcg cgtgtgatat ttatatttgg 960 gccccttttgg ccggaacatg tggggtgttg cttctctccc ttgtgatcac tctgtattgt 1020
aagcgcggga gaaagaagct cctgtacatc ttcaagcagc cttttatgcg acctgtgcaa 1080
accactcagg aagaagatgg gtgttcatgc cgcttccccg aggaggaaga aggagggtgt 1140
gaactgaggg tgaaattttc tagaagcgcc gatgctcccg catatcagca gggtcagaat 1200
cagctctaca atgaattgaa tctcggcagg cgagaagagt acgatgttct ggacaagaga 1260
cggggcaggg atcccgagat gggggggaaag ccccggagaa aaaatcctca ggaggggttg 1320
tacaatgagc tgcagaagga caagatggct gaagcctata gcgagatcgg aatgaaaggc 1380
gaaagacgca gaggcaaggg gcatgacggt ctgtaccagg gtctctctac agccaccaag 1440
gacacttatg atgcgttgca tatgcaagcc ttgccacccc gctaa 1485

<210> SEQ ID NO 64
<211> LENGTH: 494
<212> TYPE: PRT
<213> ORGANISM: Artificial Sequence
<220> FEATURE:
<223> OTHER INFORMATION: Made in Lab - polypeptide of anti-BCMA CAR8 construct

<400> SEQUENCE: 64

```
Met Ala Leu Pro Val Thr Ala Leu Leu Leu Pro Leu Ala Leu Leu Leu
1               5                   10                  15

His Ala Ala Arg Pro Asp Ile Val Met Thr Gln Thr Pro Leu Ser Leu
            20                  25                  30

Ser Val Thr Pro Gly Gln Pro Ala Ser Ile Ser Cys Lys Ser Ser Gln
        35                  40                  45

Ser Leu Leu Tyr Ser Asp Gly Lys Thr Phe Leu Tyr Trp Tyr Leu Gln
    50                  55                  60

Lys Pro Gly Gln Pro Pro Gln Leu Leu Ile Tyr Glu Gly Ser Asn Arg
65                  70                  75                  80

Phe Ser Gly Val Pro Asp Arg Phe Ser Gly Ser Gly Ser Gly Thr Asp
                85                  90                  95

Phe Thr Leu Lys Ile Ser Arg Val Glu Ala Glu Asp Val Gly Val Phe
            100                 105                 110

Tyr Cys Met Gln Ser Ile Gln Leu Pro Asn Thr Phe Gly Gln Gly Thr
        115                 120                 125

Lys Leu Glu Ile Lys Gly Gly Gly Gly Ser Gly Gly Gly Gly Ser Gly
    130                 135                 140

Gly Gly Gly Ser Gln Val Gln Leu Val Gln Ser Gly Ala Glu Val Lys
145                 150                 155                 160

Lys Pro Gly Ala Ser Val Lys Val Ser Cys Lys Gly Ser Gly Tyr Thr
                165                 170                 175

Phe Ser Thr Tyr Gly Ile Gly Trp Val Arg Gln Ala Pro Gly Gln Gly
            180                 185                 190

Leu Glu Trp Leu Ala Trp Ile Ser Ala Tyr Ser Gly Lys Thr Asn Tyr
        195                 200                 205

Ala Gln Lys Val Gln Gly Arg Val Thr Leu Thr Thr Asp Thr Ser Thr
    210                 215                 220

Asn Thr Ala Tyr Met Glu Leu Arg Ser Leu Arg Ser Asp Asp Thr Ala
225                 230                 235                 240

Val Tyr Tyr Cys Ala Arg Asp Asp Gly Ala Gly Thr Asp Tyr Tyr Tyr
                245                 250                 255

Gly Met Asp Val Trp Gly Gln Gly Thr Thr Val Thr Val Ser Ser Thr
            260                 265                 270

Thr Thr Pro Ala Pro Arg Pro Pro Thr Pro Ala Pro Thr Ile Ala Ser
        275                 280                 285

Gln Pro Leu Ser Leu Arg Pro Glu Ala Cys Arg Pro Ala Ala Gly Gly
    290                 295                 300

Ala Val His Thr Arg Gly Leu Asp Phe Ala Cys Asp Ile Tyr Ile Trp
305                 310                 315                 320

Ala Pro Leu Ala Gly Thr Cys Gly Val Leu Leu Leu Ser Leu Val Ile
                325                 330                 335

Thr Leu Tyr Cys Lys Arg Gly Arg Lys Lys Leu Leu Tyr Ile Phe Lys
            340                 345                 350

Gln Pro Phe Met Arg Pro Val Gln Thr Thr Gln Glu Glu Asp Gly Cys
        355                 360                 365

Ser Cys Arg Phe Pro Glu Glu Glu Glu Gly Gly Cys Glu Leu Arg Val
    370                 375                 380

Lys Phe Ser Arg Ser Ala Asp Ala Pro Ala Tyr Gln Gln Gly Gln Asn
385                 390                 395                 400

Gln Leu Tyr Asn Glu Leu Asn Leu Gly Arg Arg Glu Glu Tyr Asp Val
                405                 410                 415

Leu Asp Lys Arg Arg Gly Arg Asp Pro Glu Met Gly Gly Lys Pro Arg
```

```
            420                 425                 430

Arg Lys Asn Pro Gln Glu Gly Leu Tyr Asn Glu Leu Gln Lys Asp Lys
        435                 440                 445

Met Ala Glu Ala Tyr Ser Glu Ile Gly Met Lys Gly Glu Arg Arg Arg
    450                 455                 460

Gly Lys Gly His Asp Gly Leu Tyr Gln Gly Leu Ser Thr Ala Thr Lys
465                 470                 475                 480

Asp Thr Tyr Asp Ala Leu His Met Gln Ala Leu Pro Pro Arg
                485                 490


<210> SEQ ID NO 65
<211> LENGTH: 1467
<212> TYPE: DNA
<213> ORGANISM: Artificial Sequence
<220> FEATURE:
<223> OTHER INFORMATION: Made in Lab - polynucleotide of anti-BCMA CAR9
      construct

<400> SEQUENCE: 65

atggctctgc ccgtgactgc cctgctgctg ccgttggcac tgcttttgca cgctgcacgg     60

ccgcaggtgc aattggtcca gtccggcgcc gaggtcaaaa agcctggagc ctctgtgaag    120

gtgtcctgta aagcttctgg atacacattc tccaacaacg gcttctcctg ggtgcggcaa    180

gctccagggc aaggactgga gtggatgggc tggattagtg ggtttaacgg taaaacctac    240

tataccaaaa cccttcaggg ccgcgtcaca atgaccatcg ataccagtac aagcacagct    300

tacatggatt tgagatccct gaggtccgac gacacagccg tctattactg cgcccggggg    360

ctgctgctgt caggagaact ctggggcttt gactactggg gtcagggcac cctggtgacc    420

gtctcatctg gtggcggcgg atcaggaggc ggcggatccg gtggaggggg aagtgacatc    480

cagcttgcgc agagtccttc tttcctgagc gcgtcagttg ggatcgggt gacaatcacc     540

tgtcgcgcat cacaggatat cagtagtttt ctggcctggt atcaacagaa gccaggcaaa    600

gctcccaaac tccttatttt cgctgcgagc accctgcaat ccggcgtgcc cagccgaatc    660

agcggctctg gctctggaac cgagtttacc cttacgatct cttccttgca gcccgaggat    720

ttcgcaacct actactgtca gcagtttaac tcatacccaa ggacctttgg ccagggcacc    780

aaagtggaga tcaagaccac aacacctgct ccaaggcccc ccacacccgc tccaactata    840

gccagccaac cattgagcct cagacctgaa gcttgcaggc ccgcagcagg aggcgccgtc    900

catacgcgag gcctggactt cgcgtgtgat atttatattt gggcccctt ggccggaaca     960

tgtggggtgt tgcttctctc ccttgtgatc actctgtatt gtaagcgcgg gagaaagaag   1020

ctcctgtaca tcttcaagca gccttttatg cgacctgtgc aaaccactca ggaagaagat   1080

gggtgttcat gccgcttccc cgaggaggaa gaaggagggt gtgaactgag ggtgaaattt   1140

tctagaagcg ccgatgctcc cgcatatcag cagggtcaga atcagctcta caatgaattg   1200

aatctcggca ggcgagaaga gtacgatgtt ctggacaaga gacggggcag ggatcccgag   1260

atgggggaa agccccggag aaaaaatcct caggaggggt tgtacaatga gctgcagaag    1320

gacaagatgg ctgaagccta tagcgagatc ggaatgaaag gcgaaagacg cagaggcaag   1380

gggcatgacg gtctgtacca gggtctctct acagccacca aggacactta tgatgcgttg   1440

catatgcaag ccttgccacc ccgctaa                                       1467


<210> SEQ ID NO 66
<211> LENGTH: 488
<212> TYPE: PRT
```

<213> ORGANISM: Artificial Sequence
<220> FEATURE:
<223> OTHER INFORMATION: Made in Lab - polypeptide of anti-BCMA CAR9 construct

<400> SEQUENCE: 66

```
Met Ala Leu Pro Val Thr Ala Leu Leu Leu Pro Leu Ala Leu Leu Leu
1               5                   10                  15

His Ala Ala Arg Pro Gln Val Gln Leu Val Gln Ser Gly Ala Glu Val
            20                  25                  30

Lys Lys Pro Gly Ala Ser Val Lys Val Ser Cys Lys Ala Ser Gly Tyr
        35                  40                  45

Thr Phe Ser Asn Asn Gly Phe Ser Trp Val Arg Gln Ala Pro Gly Gln
    50                  55                  60

Gly Leu Glu Trp Met Gly Trp Ile Ser Gly Phe Asn Gly Lys Thr Tyr
65                  70                  75                  80

Tyr Thr Lys Thr Leu Gln Gly Arg Val Thr Met Thr Ile Asp Thr Ser
                85                  90                  95

Thr Ser Thr Ala Tyr Met Asp Leu Arg Ser Leu Arg Ser Asp Asp Thr
            100                 105                 110

Ala Val Tyr Tyr Cys Ala Arg Gly Leu Leu Leu Ser Gly Glu Leu Trp
        115                 120                 125

Gly Phe Asp Tyr Trp Gly Gln Gly Thr Leu Val Thr Val Ser Ser Gly
    130                 135                 140

Gly Gly Gly Ser Gly Gly Gly Gly Ser Gly Gly Gly Gly Ser Asp Ile
145                 150                 155                 160

Gln Leu Ala Gln Ser Pro Ser Phe Leu Ser Ala Ser Val Gly Asp Arg
                165                 170                 175

Val Thr Ile Thr Cys Arg Ala Ser Gln Asp Ile Ser Ser Phe Leu Ala
            180                 185                 190

Trp Tyr Gln Gln Lys Pro Gly Lys Ala Pro Lys Leu Leu Ile Phe Ala
        195                 200                 205

Ala Ser Thr Leu Gln Ser Gly Val Pro Ser Arg Ile Ser Gly Ser Gly
    210                 215                 220

Ser Gly Thr Glu Phe Thr Leu Thr Ile Ser Ser Leu Gln Pro Glu Asp
225                 230                 235                 240

Phe Ala Thr Tyr Tyr Cys Gln Gln Phe Asn Ser Tyr Pro Arg Thr Phe
                245                 250                 255

Gly Gln Gly Thr Lys Val Glu Ile Lys Thr Thr Thr Pro Ala Pro Arg
            260                 265                 270

Pro Pro Thr Pro Ala Pro Thr Ile Ala Ser Gln Pro Leu Ser Leu Arg
        275                 280                 285

Pro Glu Ala Cys Arg Pro Ala Ala Gly Gly Ala Val His Thr Arg Gly
    290                 295                 300

Leu Asp Phe Ala Cys Asp Ile Tyr Ile Trp Ala Pro Leu Ala Gly Thr
305                 310                 315                 320

Cys Gly Val Leu Leu Leu Ser Leu Val Ile Thr Leu Tyr Cys Lys Arg
                325                 330                 335

Gly Arg Lys Lys Leu Leu Tyr Ile Phe Lys Gln Pro Phe Met Arg Pro
            340                 345                 350

Val Gln Thr Thr Gln Glu Glu Asp Gly Cys Ser Cys Arg Phe Pro Glu
        355                 360                 365

Glu Glu Glu Gly Gly Cys Glu Leu Arg Val Lys Phe Ser Arg Ser Ala
    370                 375                 380
```

```
Asp Ala Pro Ala Tyr Gln Gln Gly Gln Asn Gln Leu Tyr Asn Glu Leu
385                 390                 395                 400

Asn Leu Gly Arg Arg Glu Glu Tyr Asp Val Leu Asp Lys Arg Arg Gly
                405                 410                 415

Arg Asp Pro Glu Met Gly Gly Lys Pro Arg Arg Lys Asn Pro Gln Glu
            420                 425                 430

Gly Leu Tyr Asn Glu Leu Gln Lys Asp Lys Met Ala Glu Ala Tyr Ser
        435                 440                 445

Glu Ile Gly Met Lys Gly Glu Arg Arg Arg Gly Lys Gly His Asp Gly
    450                 455                 460

Leu Tyr Gln Gly Leu Ser Thr Ala Thr Lys Asp Thr Tyr Asp Ala Leu
465                 470                 475                 480

His Met Gln Ala Leu Pro Pro Arg
                485


<210> SEQ ID NO 67
<211> LENGTH: 1467
<212> TYPE: DNA
<213> ORGANISM: Artificial Sequence
<220> FEATURE:
<223> OTHER INFORMATION: Made in Lab - polynucleotide of anti-BCMA CAR10
      construct

<400> SEQUENCE: 67

atggcactcc cagtcaccgc cctgctgctc ccactggccc tcctgctgca tgcagcacgc     60

cctgatattc agctggcgca gagtcctagt ttcctttccg cgtccgtcgg cgaccgggtg    120

actattacct gcagagcctc ccaagatatt tcctcattcc tcgcttggta tcagcagaag    180

ccaggcaagg cgccaaaact tctgatcttt gcagcctcaa cgctgcagtc cggcgtccct    240

tctcgaattt ctggcagcgg cagtggaact gaattcaccc ttacgattag cagcttgcaa    300

ccagaggact ttgccaccta ttactgtcag cagttcaaca gctatccacg gaccttcggt    360

caaggcacaa aagttgagat aaaggggggg ggtggcagcg gcgggggcgg ttctggtggc    420

ggcggcagtc aggtacagct ggtgcagtcc ggcgctgagg tcaagaagcc tggtgcatcc    480

gtgaaagtct cttgcaaggc cagcggttac accttctcta ataatggctt tagttgggtc    540

cgccaggccc caggtcaggg actggaatgg atggggtgga ttagtggttt caatggcaag    600

acgtattaca ccaaaactct gcagggtagg gtgactatga ctatcgatac tagcaccagc    660

acagcgtaca tggacctgcg gtccttgcga tccgatgaca ctgctgtcta ctattgtgcc    720

agaggactcc tcctgtcagg ggagctgtgg gggttcgatt actgggggca aggcaccctc    780

gttaccgtgt cctctaccac aacacctgct ccaaggcccc ccacacccgc tccaactata    840

gccagccaac cattgagcct cagacctgaa gcttgcaggc ccgcagcagg aggcgccgtc    900

catacgcgag gcctggactt cgcgtgtgat atttatattt gggcccccttt ggccggaaca    960

tgtggggtgt tgcttctctc ccttgtgatc actctgtatt gtaagcgcgg gagaaagaag   1020

ctcctgtaca tcttcaagca gccttttatg cgacctgtgc aaaccactca ggaagaagat   1080

gggtgttcat gccgcttccc cgaggaggaa gaaggagggt gtgaactgag ggtgaaattt   1140

tctagaagcg ccgatgctcc cgcatatcag cagggtcaga atcagctcta caatgaattg   1200

aatctcggca ggcgagaaga gtacgatgtt ctggacaaga gacggggcag ggatcccgag   1260

atgggggggaa agccccggag aaaaaatcct caggaggggt tgtacaatga gctgcagaag   1320

gacaagatgg ctgaagccta tagcgagatc ggaatgaaag gcgaaagacg cagaggcaag   1380

gggcatgacg gtctgtacca gggtctctct acagccacca aggacactta tgatgcgttg   1440
```

catatgcaag ccttgccacc ccgctaa 1467

<210> SEQ ID NO 68
<211> LENGTH: 488
<212> TYPE: PRT
<213> ORGANISM: Artificial Sequence
<220> FEATURE:
<223> OTHER INFORMATION: Made in Lab - polypeptide of anti-BCMA CAR10 construct

<400> SEQUENCE: 68

Met Ala Leu Pro Val Thr Ala Leu Leu Leu Pro Leu Ala Leu Leu Leu
1 5 10 15

His Ala Ala Arg Pro Asp Ile Gln Leu Ala Gln Ser Pro Ser Phe Leu
20 25 30

Ser Ala Ser Val Gly Asp Arg Val Thr Ile Thr Cys Arg Ala Ser Gln
35 40 45

Asp Ile Ser Ser Phe Leu Ala Trp Tyr Gln Gln Lys Pro Gly Lys Ala
50 55 60

Pro Lys Leu Leu Ile Phe Ala Ala Ser Thr Leu Gln Ser Gly Val Pro
65 70 75 80

Ser Arg Ile Ser Gly Ser Gly Ser Gly Thr Glu Phe Thr Leu Thr Ile
85 90 95

Ser Ser Leu Gln Pro Glu Asp Phe Ala Thr Tyr Tyr Cys Gln Gln Phe
100 105 110

Asn Ser Tyr Pro Arg Thr Phe Gly Gln Gly Thr Lys Val Glu Ile Lys
115 120 125

Gly Gly Gly Gly Ser Gly Gly Gly Gly Ser Gly Gly Gly Gly Ser Gln
130 135 140

Val Gln Leu Val Gln Ser Gly Ala Glu Val Lys Lys Pro Gly Ala Ser
145 150 155 160

Val Lys Val Ser Cys Lys Ala Ser Gly Tyr Thr Phe Ser Asn Asn Gly
165 170 175

Phe Ser Trp Val Arg Gln Ala Pro Gly Gln Gly Leu Glu Trp Met Gly
180 185 190

Trp Ile Ser Gly Phe Asn Gly Lys Thr Tyr Tyr Thr Lys Thr Leu Gln
195 200 205

Gly Arg Val Thr Met Thr Ile Asp Thr Ser Thr Ser Thr Ala Tyr Met
210 215 220

Asp Leu Arg Ser Leu Arg Ser Asp Asp Thr Ala Val Tyr Tyr Cys Ala
225 230 235 240

Arg Gly Leu Leu Leu Ser Gly Glu Leu Trp Gly Phe Asp Tyr Trp Gly
245 250 255

Gln Gly Thr Leu Val Thr Val Ser Ser Thr Thr Thr Pro Ala Pro Arg
260 265 270

Pro Pro Thr Pro Ala Pro Thr Ile Ala Ser Gln Pro Leu Ser Leu Arg
275 280 285

Pro Glu Ala Cys Arg Pro Ala Ala Gly Gly Ala Val His Thr Arg Gly
290 295 300

Leu Asp Phe Ala Cys Asp Ile Tyr Ile Trp Ala Pro Leu Ala Gly Thr
305 310 315 320

Cys Gly Val Leu Leu Leu Ser Leu Val Ile Thr Leu Tyr Cys Lys Arg
325 330 335

Gly Arg Lys Lys Leu Leu Tyr Ile Phe Lys Gln Pro Phe Met Arg Pro
340 345 350

```
Val Gln Thr Thr Gln Glu Glu Asp Gly Cys Ser Cys Arg Phe Pro Glu
        355                 360                 365

Glu Glu Glu Gly Gly Cys Glu Leu Arg Val Lys Phe Ser Arg Ser Ala
    370                 375                 380

Asp Ala Pro Ala Tyr Gln Gln Gly Gln Asn Gln Leu Tyr Asn Glu Leu
385                 390                 395                 400

Asn Leu Gly Arg Arg Glu Glu Tyr Asp Val Leu Asp Lys Arg Arg Gly
                405                 410                 415

Arg Asp Pro Glu Met Gly Gly Lys Pro Arg Arg Lys Asn Pro Gln Glu
            420                 425                 430

Gly Leu Tyr Asn Glu Leu Gln Lys Asp Lys Met Ala Glu Ala Tyr Ser
        435                 440                 445

Glu Ile Gly Met Lys Gly Glu Arg Arg Arg Gly Lys Gly His Asp Gly
    450                 455                 460

Leu Tyr Gln Gly Leu Ser Thr Ala Thr Lys Asp Thr Tyr Asp Ala Leu
465                 470                 475                 480

His Met Gln Ala Leu Pro Pro Arg
                485


<210> SEQ ID NO 69
<211> LENGTH: 184
<212> TYPE: PRT
<213> ORGANISM: Homo sapiens

<400> SEQUENCE: 69

Met Leu Gln Met Ala Gly Gln Cys Ser Gln Asn Glu Tyr Phe Asp Ser
1               5                   10                  15

Leu Leu His Ala Cys Ile Pro Cys Gln Leu Arg Cys Ser Ser Asn Thr
            20                  25                  30

Pro Pro Leu Thr Cys Gln Arg Tyr Cys Asn Ala Ser Val Thr Asn Ser
        35                  40                  45

Val Lys Gly Thr Asn Ala Ile Leu Trp Thr Cys Leu Gly Leu Ser Leu
    50                  55                  60

Ile Ile Ser Leu Ala Val Phe Val Leu Met Phe Leu Leu Arg Lys Ile
65                  70                  75                  80

Asn Ser Glu Pro Leu Lys Asp Glu Phe Lys Asn Thr Gly Ser Gly Leu
                85                  90                  95

Leu Gly Met Ala Asn Ile Asp Leu Glu Lys Ser Arg Thr Gly Asp Glu
            100                 105                 110

Ile Ile Leu Pro Arg Gly Leu Glu Tyr Thr Val Glu Glu Cys Thr Cys
        115                 120                 125

Glu Asp Cys Ile Lys Ser Lys Pro Lys Val Asp Ser Asp His Cys Phe
    130                 135                 140

Pro Leu Pro Ala Met Glu Glu Gly Ala Thr Ile Leu Val Thr Thr Lys
145                 150                 155                 160

Thr Asn Asp Tyr Cys Lys Ser Leu Pro Ala Ala Leu Ser Ala Thr Glu
                165                 170                 175

Ile Glu Lys Ser Ile Ser Ala Arg
            180


<210> SEQ ID NO 70

<400> SEQUENCE: 70

000
```

```
<210> SEQ ID NO 71
<211> LENGTH: 5
<212> TYPE: PRT
<213> ORGANISM: Artificial Sequence
<220> FEATURE:
<223> OTHER INFORMATION: Synthesized - linker sequence

<400> SEQUENCE: 71

Asp Gly Gly Gly Ser
1               5


<210> SEQ ID NO 72
<211> LENGTH: 5
<212> TYPE: PRT
<213> ORGANISM: Artificial Sequence
<220> FEATURE:
<223> OTHER INFORMATION: Synthesized - linker sequence

<400> SEQUENCE: 72

Thr Gly Glu Lys Pro
1               5


<210> SEQ ID NO 73
<211> LENGTH: 4
<212> TYPE: PRT
<213> ORGANISM: Artificial Sequence
<220> FEATURE:
<223> OTHER INFORMATION: Synthesized - linker sequence

<400> SEQUENCE: 73

Gly Gly Arg Arg
1


<210> SEQ ID NO 74
<211> LENGTH: 5
<212> TYPE: PRT
<213> ORGANISM: Artificial Sequence
<220> FEATURE:
<223> OTHER INFORMATION: Synthesized - linker sequence

<400> SEQUENCE: 74

Gly Gly Gly Gly Ser
1               5


<210> SEQ ID NO 75
<211> LENGTH: 14
<212> TYPE: PRT
<213> ORGANISM: Artificial Sequence
<220> FEATURE:
<223> OTHER INFORMATION: Synthesized - linker sequence

<400> SEQUENCE: 75

Glu Gly Lys Ser Ser Gly Ser Gly Ser Glu Ser Lys Val Asp
1               5                   10


<210> SEQ ID NO 76
<211> LENGTH: 18
<212> TYPE: PRT
<213> ORGANISM: Artificial Sequence
<220> FEATURE:
<223> OTHER INFORMATION: Synthesized - linker sequence

<400> SEQUENCE: 76

Lys Glu Ser Gly Ser Val Ser Ser Glu Gln Leu Ala Gln Phe Arg Ser
1               5                   10                  15

Leu Asp
```

<210> SEQ ID NO 77
<211> LENGTH: 8
<212> TYPE: PRT
<213> ORGANISM: Artificial Sequence
<220> FEATURE:
<223> OTHER INFORMATION: Synthesized - linker sequence

<400> SEQUENCE: 77

Gly Gly Arg Arg Gly Gly Gly Ser
1               5

<210> SEQ ID NO 78
<211> LENGTH: 9
<212> TYPE: PRT
<213> ORGANISM: Artificial Sequence
<220> FEATURE:
<223> OTHER INFORMATION: Synthesized - linker sequence

<400> SEQUENCE: 78

Leu Arg Gln Arg Asp Gly Glu Arg Pro
1               5

<210> SEQ ID NO 79
<211> LENGTH: 12
<212> TYPE: PRT
<213> ORGANISM: Artificial Sequence
<220> FEATURE:
<223> OTHER INFORMATION: Synthesized - linker sequence

<400> SEQUENCE: 79

Leu Arg Gln Lys Asp Gly Gly Gly Ser Glu Arg Pro
1               5                   10

<210> SEQ ID NO 80
<211> LENGTH: 13
<212> TYPE: PRT
<213> ORGANISM: Artificial Sequence
<220> FEATURE:
<223> OTHER INFORMATION: Synthesized - linker sequence

<400> SEQUENCE: 80

Leu Arg Gln Lys Asp Gly Gly Gly Ser Gly Gly Gly Ser
1               5                   10

<210> SEQ ID NO 81
<211> LENGTH: 18
<212> TYPE: PRT
<213> ORGANISM: Artificial Sequence
<220> FEATURE:
<223> OTHER INFORMATION: Synthesized - linker sequence

<400> SEQUENCE: 81

Gly Ser Thr Ser Gly Ser Gly Lys Pro Gly Ser Gly Glu Gly Ser Thr
1               5                   10                  15

Lys Gly

<210> SEQ ID NO 82
<211> LENGTH: 7
<212> TYPE: PRT
<213> ORGANISM: Artificial Sequence
<220> FEATURE:
<223> OTHER INFORMATION: Cleavage sequence by TEV protease
<220> FEATURE:
<221> NAME/KEY: misc_feature
<222> LOCATION: (2)..(3)
<223> OTHER INFORMATION: Xaa is any amino acid
<220> FEATURE:
<221> NAME/KEY: misc_feature
<222> LOCATION: (5)..(5)
<223> OTHER INFORMATION: Xaa is any amino acid
<220> FEATURE:
<221> NAME/KEY: MISC_FEATURE
<222> LOCATION: (7)..(7)
<223> OTHER INFORMATION: Xaa = Gly or Ser

<400> SEQUENCE: 82

Glu Xaa Xaa Tyr Xaa Gln Xaa
1 5

<210> SEQ ID NO 83
<211> LENGTH: 7
<212> TYPE: PRT
<213> ORGANISM: Artificial Sequence
<220> FEATURE:
<223> OTHER INFORMATION: Cleavage sequence by TEV protease

<400> SEQUENCE: 83

Glu Asn Leu Tyr Phe Gln Gly
1 5

<210> SEQ ID NO 84
<211> LENGTH: 7
<212> TYPE: PRT
<213> ORGANISM: Artificial Sequence
<220> FEATURE:
<223> OTHER INFORMATION: Cleavage sequence by TEV protease

<400> SEQUENCE: 84

Glu Asn Leu Tyr Phe Gln Ser
1 5

<210> SEQ ID NO 85
<211> LENGTH: 22
<212> TYPE: PRT
<213> ORGANISM: Artificial Sequence
<220> FEATURE:
<223> OTHER INFORMATION: Self-cleaving polypeptide comprising 2A site

<400> SEQUENCE: 85

Gly Ser Gly Ala Thr Asn Phe Ser Leu Leu Lys Gln Ala Gly Asp Val
1 5 10 15

Glu Glu Asn Pro Gly Pro
20

<210> SEQ ID NO 86
<211> LENGTH: 19
<212> TYPE: PRT
<213> ORGANISM: Artificial Sequence
<220> FEATURE:
<223> OTHER INFORMATION: Self-cleaving polypeptide comprising 2A site

<400> SEQUENCE: 86

Ala Thr Asn Phe Ser Leu Leu Lys Gln Ala Gly Asp Val Glu Glu Asn
1 5 10 15

Pro Gly Pro

<210> SEQ ID NO 87
<211> LENGTH: 14
<212> TYPE: PRT
<213> ORGANISM: Artificial Sequence
<220> FEATURE:
<223> OTHER INFORMATION: Self-cleaving polypeptide comprising 2A site

<400> SEQUENCE: 87

Leu Leu Lys Gln Ala Gly Asp Val Glu Glu Asn Pro Gly Pro
1 5 10

<210> SEQ ID NO 88
<211> LENGTH: 21
<212> TYPE: PRT
<213> ORGANISM: Artificial Sequence
<220> FEATURE:
<223> OTHER INFORMATION: Self-cleaving polypeptide comprising 2A site

<400> SEQUENCE: 88

Gly Ser Gly Glu Gly Arg Gly Ser Leu Leu Thr Cys Gly Asp Val Glu
1 5 10 15

Glu Asn Pro Gly Pro
20

<210> SEQ ID NO 89
<211> LENGTH: 18
<212> TYPE: PRT
<213> ORGANISM: Artificial Sequence
<220> FEATURE:
<223> OTHER INFORMATION: Self-cleaving polypeptide comprising 2A site

<400> SEQUENCE: 89

Glu Gly Arg Gly Ser Leu Leu Thr Cys Gly Asp Val Glu Glu Asn Pro
1 5 10 15

Gly Pro

<210> SEQ ID NO 90
<211> LENGTH: 13
<212> TYPE: PRT
<213> ORGANISM: Artificial Sequence
<220> FEATURE:
<223> OTHER INFORMATION: Self-cleaving polypeptide comprising 2A site

<400> SEQUENCE: 90

Leu Leu Thr Cys Gly Asp Val Glu Glu Asn Pro Gly Pro
1 5 10

<210> SEQ ID NO 91
<211> LENGTH: 23
<212> TYPE: PRT
<213> ORGANISM: Artificial Sequence
<220> FEATURE:
<223> OTHER INFORMATION: Self-cleaving polypeptide comprising 2A site

<400> SEQUENCE: 91

Gly Ser Gly Gln Cys Thr Asn Tyr Ala Leu Leu Lys Leu Ala Gly Asp
1 5 10 15

Val Glu Ser Asn Pro Gly Pro
20

<210> SEQ ID NO 92
<211> LENGTH: 20
<212> TYPE: PRT
<213> ORGANISM: Artificial Sequence
<220> FEATURE:
<223> OTHER INFORMATION: Self-cleaving polypeptide comprising 2A site

<400> SEQUENCE: 92

Gln Cys Thr Asn Tyr Ala Leu Leu Lys Leu Ala Gly Asp Val Glu Ser
1 5 10 15

Asn Pro Gly Pro

20

<210> SEQ ID NO 93
<211> LENGTH: 14
<212> TYPE: PRT
<213> ORGANISM: Artificial Sequence
<220> FEATURE:
<223> OTHER INFORMATION: Self-cleaving polypeptide comprising 2A site

<400> SEQUENCE: 93

Leu Leu Lys Leu Ala Gly Asp Val Glu Ser Asn Pro Gly Pro
1 5 10

<210> SEQ ID NO 94
<211> LENGTH: 25
<212> TYPE: PRT
<213> ORGANISM: Artificial Sequence
<220> FEATURE:
<223> OTHER INFORMATION: Self-cleaving polypeptide comprising 2A site

<400> SEQUENCE: 94

Gly Ser Gly Val Lys Gln Thr Leu Asn Phe Asp Leu Leu Lys Leu Ala
1 5 10 15

Gly Asp Val Glu Ser Asn Pro Gly Pro
20 25

<210> SEQ ID NO 95
<211> LENGTH: 22
<212> TYPE: PRT
<213> ORGANISM: Artificial Sequence
<220> FEATURE:
<223> OTHER INFORMATION: Self-cleaving polypeptide comprising 2A site

<400> SEQUENCE: 95

Val Lys Gln Thr Leu Asn Phe Asp Leu Leu Lys Leu Ala Gly Asp Val
1 5 10 15

Glu Ser Asn Pro Gly Pro
20

<210> SEQ ID NO 96
<211> LENGTH: 14
<212> TYPE: PRT
<213> ORGANISM: Artificial Sequence
<220> FEATURE:
<223> OTHER INFORMATION: Self-cleaving polypeptide comprising 2A site

<400> SEQUENCE: 96

Leu Leu Lys Leu Ala Gly Asp Val Glu Ser Asn Pro Gly Pro
1 5 10

<210> SEQ ID NO 97
<211> LENGTH: 19
<212> TYPE: PRT
<213> ORGANISM: Artificial Sequence
<220> FEATURE:
<223> OTHER INFORMATION: Self-cleaving polypeptide comprising 2A site

<400> SEQUENCE: 97

Leu Leu Asn Phe Asp Leu Leu Lys Leu Ala Gly Asp Val Glu Ser Asn
1 5 10 15

Pro Gly Pro

<210> SEQ ID NO 98
<211> LENGTH: 19
<212> TYPE: PRT

<213> ORGANISM: Artificial Sequence
<220> FEATURE:
<223> OTHER INFORMATION: Self-cleaving polypeptide comprising 2A site

<400> SEQUENCE: 98

Thr Leu Asn Phe Asp Leu Leu Lys Leu Ala Gly Asp Val Glu Ser Asn
1               5                   10                  15

Pro Gly Pro

<210> SEQ ID NO 99
<211> LENGTH: 14
<212> TYPE: PRT
<213> ORGANISM: Artificial Sequence
<220> FEATURE:
<223> OTHER INFORMATION: Self-cleaving polypeptide comprising 2A site

<400> SEQUENCE: 99

Leu Leu Lys Leu Ala Gly Asp Val Glu Ser Asn Pro Gly Pro
1               5                   10

<210> SEQ ID NO 100
<211> LENGTH: 17
<212> TYPE: PRT
<213> ORGANISM: Artificial Sequence
<220> FEATURE:
<223> OTHER INFORMATION: Self-cleaving polypeptide comprising 2A site

<400> SEQUENCE: 100

Asn Phe Asp Leu Leu Lys Leu Ala Gly Asp Val Glu Ser Asn Pro Gly
1               5                   10                  15

Pro

<210> SEQ ID NO 101
<211> LENGTH: 20
<212> TYPE: PRT
<213> ORGANISM: Artificial Sequence
<220> FEATURE:
<223> OTHER INFORMATION: Self-cleaving polypeptide comprising 2A site

<400> SEQUENCE: 101

Gln Leu Leu Asn Phe Asp Leu Leu Lys Leu Ala Gly Asp Val Glu Ser
1               5                   10                  15

Asn Pro Gly Pro
            20

<210> SEQ ID NO 102
<211> LENGTH: 24
<212> TYPE: PRT
<213> ORGANISM: Artificial Sequence
<220> FEATURE:
<223> OTHER INFORMATION: Self-cleaving polypeptide comprising 2A site

<400> SEQUENCE: 102

Ala Pro Val Lys Gln Thr Leu Asn Phe Asp Leu Leu Lys Leu Ala Gly
1               5                   10                  15

Asp Val Glu Ser Asn Pro Gly Pro
            20

<210> SEQ ID NO 103
<211> LENGTH: 40
<212> TYPE: PRT
<213> ORGANISM: Artificial Sequence
<220> FEATURE:
<223> OTHER INFORMATION: Self-cleaving polypeptide comprising 2A site

<400> SEQUENCE: 103

Val Thr Glu Leu Leu Tyr Arg Met Lys Arg Ala Glu Thr Tyr Cys Pro
1 5 10 15

Arg Pro Leu Leu Ala Ile His Pro Thr Glu Ala Arg His Lys Gln Lys
20 25 30

Ile Val Ala Pro Val Lys Gln Thr
35 40

<210> SEQ ID NO 104
<211> LENGTH: 18
<212> TYPE: PRT
<213> ORGANISM: Artificial Sequence
<220> FEATURE:
<223> OTHER INFORMATION: Self-cleaving polypeptide comprising 2A site

<400> SEQUENCE: 104

Leu Asn Phe Asp Leu Leu Lys Leu Ala Gly Asp Val Glu Ser Asn Pro
1 5 10 15

Gly Pro

<210> SEQ ID NO 105
<211> LENGTH: 40
<212> TYPE: PRT
<213> ORGANISM: Artificial Sequence
<220> FEATURE:
<223> OTHER INFORMATION: Self-cleaving polypeptide comprising 2A site

<400> SEQUENCE: 105

Leu Leu Ala Ile His Pro Thr Glu Ala Arg His Lys Gln Lys Ile Val
1 5 10 15

Ala Pro Val Lys Gln Thr Leu Asn Phe Asp Leu Leu Lys Leu Ala Gly
20 25 30

Asp Val Glu Ser Asn Pro Gly Pro
35 40

<210> SEQ ID NO 106
<211> LENGTH: 33
<212> TYPE: PRT
<213> ORGANISM: Artificial Sequence
<220> FEATURE:
<223> OTHER INFORMATION: Self-cleaving polypeptide comprising 2A site

<400> SEQUENCE: 106

Glu Ala Arg His Lys Gln Lys Ile Val Ala Pro Val Lys Gln Thr Leu
1 5 10 15

Asn Phe Asp Leu Leu Lys Leu Ala Gly Asp Val Glu Ser Asn Pro Gly
20 25 30

Pro

<210> SEQ ID NO 107
<211> LENGTH: 10
<212> TYPE: DNA
<213> ORGANISM: Artificial Sequence
<220> FEATURE:
<223> OTHER INFORMATION: Consensus Kozak sequence

<400> SEQUENCE: 107 gccrccatgg 10

<210> SEQ ID NO 108
<211> LENGTH: 4
<212> TYPE: PRT

```
<213> ORGANISM: Artificial Sequence
<220> FEATURE:
<223> OTHER INFORMATION: Exemplary rule for determining light chain
      CDR-L3 motif
<220> FEATURE:
<221> NAME/KEY: MOD_RES
<222> LOCATION: (3)..(3)
<223> OTHER INFORMATION: Xaa is any amino acid

<400> SEQUENCE: 108

Phe Gly Xaa Gly
1


<210> SEQ ID NO 109
<211> LENGTH: 4
<212> TYPE: PRT
<213> ORGANISM: Artificial Sequence
<220> FEATURE:
<223> OTHER INFORMATION: Exemplary rule for determining heavy chain
      CDR-H1 motif
<220> FEATURE:
<221> NAME/KEY: MOD_RES
<222> LOCATION: (2)..(4)
<223> OTHER INFORMATION: Xaa is any amino acid

<400> SEQUENCE: 109

Cys Xaa Xaa Xaa
1


<210> SEQ ID NO 110
<211> LENGTH: 5
<212> TYPE: PRT
<213> ORGANISM: Artificial Sequence
<220> FEATURE:
<223> OTHER INFORMATION: Exemplary rule for determining heavy chain
      CDR-H2 motif

<400> SEQUENCE: 110

Leu Glu Trp Ile Gly
1               5


<210> SEQ ID NO 111
<211> LENGTH: 4
<212> TYPE: PRT
<213> ORGANISM: Artificial Sequence
<220> FEATURE:
<223> OTHER INFORMATION: Exemplary rule for determining heavy chain
      CDR-H3 motif
<220> FEATURE:
<221> NAME/KEY: MOD_RES
<222> LOCATION: (3)..(3)
<223> OTHER INFORMATION: Xaa is any amino acd

<400> SEQUENCE: 111

Trp Gly Xaa Gly
1
```